United States Patent
Hewitt et al.

(10) Patent No.: US 10,233,428 B2
(45) Date of Patent: Mar. 19, 2019

(54) RESTRICTIVE INVERTED TERMINAL REPEATS FOR VIRAL VECTORS

(71) Applicant: The University of North Carolina at Chapel Hill, Chapel Hill, NC (US)

(72) Inventors: Curtis Hewitt, Austin, TX (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/922,935

(22) Filed: Oct. 26, 2015

(65) Prior Publication Data

US 2016/0102297 A1    Apr. 14, 2016

Related U.S. Application Data

(62) Division of application No. 13/521,448, filed as application No. PCT/US2011/020939 on Jan. 12, 2011, now Pat. No. 9,169,494.

(60) Provisional application No. 61/294,191, filed on Jan. 12, 2010.

(51) Int. Cl.
| | |
|---|---|
| *C12N 7/00* | (2006.01) |
| *C07K 14/005* | (2006.01) |
| *C12N 15/86* | (2006.01) |
| *C12N 15/864* | (2006.01) |

(52) U.S. Cl.
CPC .............. *C12N 7/00* (2013.01); *C07K 14/005* (2013.01); *C12N 15/86* (2013.01); *C12N 15/8645* (2013.01); *C12N 2750/14122* (2013.01); *C12N 2750/14143* (2013.01); *C12N 2750/14162* (2013.01); *C12N 2750/14322* (2013.01); *C12N 2750/14352* (2013.01); *C12N 2820/60* (2013.01)

(58) Field of Classification Search
None
See application file for complete search history.

(56) References Cited

U.S. PATENT DOCUMENTS

| | | |
|---|---|---|
| 6,984,517 B1 | 1/2006 | Chiorini et al. |
| 2003/0129203 A1 | 7/2003 | Vega et al. |
| 2604/0197895 | 10/2004 | Kotin et al. |
| 2005/0002908 A1 | 1/2005 | Horer et al. |

OTHER PUBLICATIONS

Hewitt et al. Creating a Novel Origin of Replication through Modulating DNA-Protein Interfaces. PLoS ONE 5(1): e8850.*
Walker et al. Mutational analysis of the adeno-associated virus Rep68 protein: identification of critical residues necessary for site-specific endonuclease activity. J Virol. Apr. 1997;71(4):2722-30.*
Chiorini et al. Adeno-associated virus (AAV) type 5 Rep protein cleaves a unique terminal resolution site compared with other AAV serotypes. J Virol. May 1999;73(5):4293-8.*
Office Action corresponding to European Application No. 11733293.2 dated Apr. 1, 2016.
Hewitt "Toward a recombinant adeno-associated virus origin of replication", (2009) https://cdr.lib.unc.edu/indexablecontent/uuid Retrieved Mar. 3, 2016 (152 pages).
Brister, J.R. et al., "Mechanism of Rep-Mediated Adeno-Associated Virus Origin Nicking", *Journal of Virology*, Sep. 2000, vol. 74, No. 17, p. 7762-7771.
Cathomen, T. et al., "A Chimeric Protein Containing the N Terminus of the Adeno-Associated Virus Rep Protein Recognizes Its Target Site in an In Vivo Assay", *Journal of Virology*, Mar. 2000, vol. 74, No. 5, p. 2372-2382.
Farkas, S.L. et al., "A parvovirus isolated from royal python (*Python regius*) is a member of the genus *Dependovirus*", *Journal of General Virology* (2004), vol. 85, p. 555-561.
Hewitt, F.C. et al., "Creating a Novel Origin of Replication through Modulating DNA-Protein Interfaces", *PLoS ONE*, Jan. 22, 2010, vol. 5, Issue 1, pp. 1-13.
Hewitt, F.C. et al., "Reducing the Risk of Adeno-Associated Virus (AAV) Vector Mobilization with AAV Type 5 Vectors", *Journal of Virology*, Apr. 2009, vol. 83, No. 8, p. 3919-3929, Published Feb. 11, 2009.
Hewitt, F.C. et al., "Replication Specificity of Adeno-Associated Virus Genomes", *2008 DNA Replication and Genome Integrity Meeting*, Salk Institute, Jul. 20, 2008, 1 page.
International Preliminary Report on Patentability Corresponding to International Application No. PCT/US2011/020939; dated Jul. 26, 2012; 8 Pages.
Rabinowitz, J.E. et al., "Cross-Packaging of a Single Adeno-Associated Virus (AAV) Type 2 Vector Genome into Multiple AAV Serotypes Enables Transduction with Broad Specificity", *Journal of Virology*, Jan. 2002, vol. 76, No. 2, p. 791-801.
International Preliminary Report on Patentability Corresponding to International Application No. PCT/US2011/036215; dated Nov. 29, 2012; 7 Pages.
Extended European Search Report for EP Application No. 11733293. 2; dated Jan. 9, 2014; 10 Pages.
Yoon et al., "Amino-terminal domain exchange redirects origin-specific interactions of adeno-associated virus Rep78 in vitro," J. Virol. 75:3230-3239 (2001).
European Application No. 11733293.2; Summons to Attend Oral Proceedings dated Mar. 3, 2017

* cited by examiner

*Primary Examiner* — Nianxiang Zou
(74) *Attorney, Agent, or Firm* — Myers Bigel, P.A.

(57) ABSTRACT

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that limits vector mobilization, increasing the safety of viral vectors.

11 Claims, 65 Drawing Sheets

Specification includes a Sequence Listing.

```
            '                     '         +
REP5 MATFYEVIVRVPFDVEEHLPGISDSFVDWVTGQIWELPPESDLNLTLVEQ   50
REP2 MPGFYEIVIKVPSDLDGHLPGISDSFVNWVAEKEWELPPDSDMDLNLIEQ   50
     *. ***:::.** *:: **********:**: : *****:**::*.*:**

+   +   ++                    '        '  '
REP5 PQLTVADRIRRVFLYEWNKFSKQ-ESKFFVQFEKGSEYFHLHTLVETSGI   99
REP2 APLTVAEKLQRDFLTEWRRVSKAPEALFFVQFEKGESYFHMHVLVETTGV  100
     ****::::* ** **..:.** *: ********..***:*.****.*:

^^  ^^  ^^   +      + +         ^ ^^  ^  ^
REP5 SSMVLGRYVSQIRAQLVKVVFQGIEPQINDWVAITKVKK--GGANKVVDS  147
REP2 KSMVLGRFLSQIREKLIQRIYRGIEPTLPNWFAVTKTRNGAGGGNKVVDE  159
     .******::**** :*:: :::*** : :*.*:**.:: **.*****.

'         '
REP5 GYIPAYLLPKVQPELQWAWTNLDEYKLAALNLEERKRLVAQFLAESSQRS  197
REP2 CYIPNYLLPKTQPELQWAWTNMEQYLSACLNLTERKRLVAQHLTHVSQTQ  200
     ***.*****.*********:::* *.*** *******.*:. **  .

REP5 -QEASQREFSADPVIKSKTSQKYM 222
REP2 EQNKENQNPNSDAPVIRSKTSARYM 225
     *: .*. *  ***:****  :**
```

*FIG. 5A*

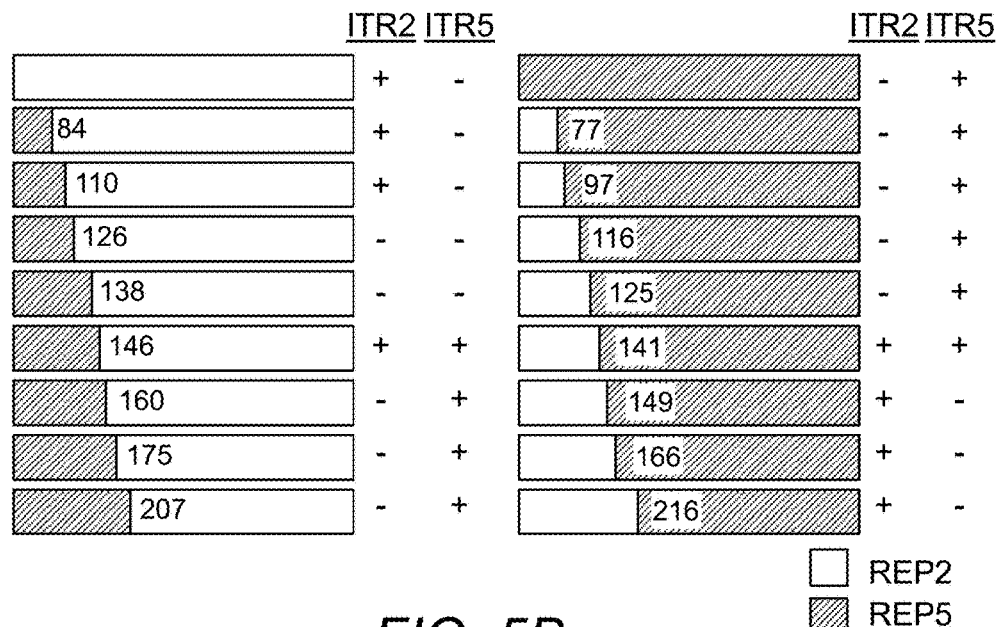

*FIG. 5B*

AAV-1, COMPLETE SEQUENCE, GENBANK ACCESSION NO. NC_002077 AND XIAO ET
AL. (1999) *J. VIROL.* 73:3994
TTGCCCACTCCCTCTCTGCGCGCTCGCTCGCTCGGTGGGGCCTGCGGACCAAAGGTCCGCAGACGGCA
GAGCTCTGCTCTGCCGGCCCCACCGAGCGAGCGAGCGCGCAGAGAGGGAGTGGGCAACTCCATCACTA
GGGGTAATCGCGAAGCGCCTCCCACGCTGCCGCGTCAGCGCTGACGTAAATTACGTCATAGGGGAGTG
GTCCTGTATTAGCTGTCACGTGAGTGCTTTTGCGACATTTTGCGACACCACGTGGCCCATTTAGGGTAT
ATATGGCCGAGTGAGCGAGCAGGATCTCCATTTTGACCGCGAAATTTGAACGAGCAGCAGCCATGCCG
GGCTTCTACGAGATCGTGATCAAGGTGCCGAGCGACCTGGACGAGCACCTGCCGGGCATTTCTGACTC
GTTTGTGAGCTGGGTGGCCGAGAAGGAATGGGAGCTGCCCCCGGATTCTGACATGGATCTGAATCTGA
TTGAGCAGGCACCCCTGACCGTGGCCGAGAAGCTGCAGCGCGACTTCCTGGTCCAATGGCGCCGCGTG
AGTAAGGCCCCGGAGGCCCTCTTCTTTGTTCAGTTCGAGAAGGGCGAGTCCTACTTCCACCTCCATAT
TCTGGTGGAGACCACGGGGGTCAAATCCATGGTGCTGGGCCGCTTCCTGAGTCAGATTAGGGACAAGC
TGGTGCAGACCATCTACCGCGGGATCGAGCCGACCCTGCCCAACTGGTTCGCGGTGACCAAGACGCGT
AATGGCGCCGAGGGGGGAACAAGGTGGTGGACGAGTGCTACATCCCCAACTACCTCCTGCCCAAGAC
TCAGCCCGAGCTGCAGTGGGCGTGGACTAACATGGAGGAGTATATAAGCGCCTGTTTGAACCTGGCCG
AGCGCAAACGGCTCGTGGCGCAGCACCTGACCCACGTCAGCCAGACCCAGGAGCAGAACAAGGAGAAT
CTGAACCCCAATTCTGACGCGCCTGTCATCCGGTCAAAAACCTCCGCGCGCTACATGGAGCTGGTCGG
GTGGCTGGTGGACCGGGGCATCACCTCCGAGAAGCAGTGGATCCAGGAGGACCAGGCCTCGTACATCT
CCTTCAACGCCGCTTCCAACTCGCGGTCCCAGATCAAGGCCGCTCTGGACAATGCCGGCAAGATCATG
GCGCTGACCAAATCCGCGCCCGACTACCTGGTAGGCCCCGCTCCGCCCGCGGACATTAAAACCAACCG
CATCTACCGCATCCTGGAGCTGAACGGCTACGAACCTGCCTACGCCGGCTCCGTCTTTCTCGGCTGGG
CCCAGAAAAGGTTCGGGAAGCGCAACACCATCTGGCTGTTTGGGCCGGCCACCACAGGGCAAGACCAAC
ATCGCGGAAGCCATCGCCCACGCCGTGCCCTTCTACGGCTGCGTCAACTGGACCAATGAGAACTTTCC
CTTCAATGATTGCGTCGACAAGATGGTGATCTGGTGGGAGGAGGGCAAGATGACGGCCAAGGTCGTGG
AGTCCGCCAAGGCCATTCTCGGCGGCAGCAAGGTGCGCGTGGACCAAAAGTGCAAGTCGTCCGCCCAG
ATCGACCCCACCCCCGTGATCGTCACCTCCAACACCAACATGTGCGCCGTTGACGGGAACAGCAC
CACCTTCGAGCACCAGCAGCCGTTGCAGGACCGGATGTTCAAATTTGAACTCACCCGCCGTCTGGAGC
ATGACTTTGGCAAGGTGACAAAGCAGGAAGTCAAAGAGTTCTTCCGCTGGGCGCAGGATCACGTGACC
GAGGTGGCGCATGAGTTCTACGTCAGAAAGGGTGGAGCCAACAAAAGACCCGCCCCCGATGACGCGGA
TAAAAGCGAGCCCAAGCGGGCCTGCCCCTCAGTCGCGGATCCATCGACGTCAGACGCGGAAGGAGCTC
CGGTGGACTTTGCCGACAGGTACCAAAACAAATGTTCTCGTCACGCGGGCATGCTTCAGATGCTGTTT
CCCTGCAAGACATGCGAGAGAATGAATCAGAATTTCAACATTTGCTTCACGCACGGGACGAGAGACTG
TTCAGAGTGCTTCCCCGGCGTGTCAGAATCTCAACCGGTCGTCAGAAAGAGGACGTATCGGAAACTCT
GTGCCATTCATCATCTGCTGGGGCGGGCTCCCGAGATTGCTTGCTCGGCCTGCGATCTGGTCAACGTG
GACCTGGATGACTGTGTTTCTGAGCAATAAATGACTTAAACCAGGTATGGCTCCGATGGTTATCTTC
CAGATTGGCTCGAGGACAACCTCTCTGAGGGCATTCGCGAGTGGTGGGACTTGAAACCTGGAGCCCCG
AAGCCCAAAGCCAACCAGCAAAAGCAGGACGACGGCCGGGGTCTGGTGCTTCCTGGCTACAAGTACCT
CGGACCCTTCAACGGACTCGACAAGGGGGAGCCCGTCAACGCCGGCGGACGCAGCGGCCCTCGAGCACG
ACAAGGCCTACGACCAGCAGCTCAAAGCGGGTGACAATCCGTACCTGCGGTATAACCACGCCGACGCC
GAGTTTCAGGAGCGTCTGCAAGAAGATACGTCTTTTGGGGCAACCTCGGGCGAGCAGTCTTCCAGGC
CAAGAAGCGGGTTCTCGAACCTCTCGGTCTGGTTGAGGAAGGCGCTAAGACGGCTCCTGGAAAGAAAC
GTCCGGTAGAGCAGTCGCCGCACAAGAGCCAGACTCCTCCTCGGGCATCGGCAAGACAGGCCAGCAGCCC
GCTAAAAAGAGACTCAATTTTGGTCAGACTGGCGACTCAGAGTCAGTCCCCGATCCACAACCTCTCGG
AGAACCTCCAGCAACCCCCGCTGCTGTGGGACCTACTACAATGGCTTCAGGCGGTGGCGCACCAATGG
CAGACAATAACGAAGGCGCCGACGGAGTGGGTAATGCCTCAGGAAATTGGCATTGCGATTCCACATGG
CTGGGCGACAGAGTCATCACCACCAGCACCCGCACCTGGGCCTTGCCCACCTACAATAACCACCTCTA
CAAGCAAATCTCCAGTGCTTCAACGGGGGCCGACAACAACAACACCACTACTTCGGCTACAGCACCCCCT
GGGGGTATTTTGATTTCAACAGATTCCACTGCCACTTTTCACCACGTGACTGGCAGCGACTCATCAAC
AACAATTGGGGATTCCGGCCCAAGAGACTCAACTTCAAACTCTTCAACATCCAAGTCAAGGAGGTCAC
GACGAATGATGGCGTCACAACCATCGCTAATAACCTTACCAGCACGGTTCAAGTCTTCTCGGACTCGG
AGTACCAGCTTCCGTACGTCCTCGGCTCTGCGCACCAGGGCTGCCTCCCTCCGTTCCCGGCCGACGTG
TTCATGATTCCGCAATACGGCTACCTGACGCTCAACAATGGCAGCCAAGCCGTGGGACGTTCATCCTT
TTACTGCCTGGAATATTTCCCTTCTCAGATGCTGAGAACGGGCAACAACTTTACCTTCAGCTACACCT
TTGAGGAAGTGCCTTTCCACAGCAGCTACGCGCACAGCCAGAGCCTGGACCGGCTGATGAATCCTCTC
ATCGACCAATACCTGTATTACCTGAACAGAACTCAAATCAGTTGCCCAAAACAAGGACTT
GCTGTTTAGCCGTGGGTCTCCAGCTGGCATGTCTGTTCAGCCCAAAAACTGGCTACCTGGACCCTGTT
ATCGGCAGCAGCGCGTTTCTAAAACAAAAACAGACAACAACAACAGCAATTTTACCTGGACTGGTGCT
TCAAAATATAACCTCAATGGGCGTGAATCCATCATCAACCCTGGCACTGCTATGGCCTCACACAAAGA
CGACGAAGACAAGTTCTTTCCCATGAGCGGTGTCATGATTTTTGGAAAAGAGAGCGCCGGAGCTTCAA
ACACTGCATTGGACAATGTCATGATTACAGACGAAGAGGAAATTAAAGCCACTAACCCTGTGGCCACC
GAAAGATTTGGGACCGTGGCAGTCAATTTCCAGAGCAGCAGCACAGACCCTGCGACCGGAGATGTGCA
TGCTATGGGAGCATTACCTGGCATGGTGTGGCAAGATAGAGACGTGTACCTGCAGGGTCCCATTTGGG
CCAAAATTCCTCACACAGATGGACACTTTCACCCGTCTCCTCTTATGGGCGGCTTTGGACTCAAGAAC
CCGCCTCCTCAGATCCTCATCAAAAACACGCCTGTTCCTGCGAATCCTCCGGCGGAGTTTTCAGCTAC
AAAGTTTGCTTCATTCATCACCCAATACTCCACAGGACAAGTGAGTGTGGAAATTGAATGGGAGCTGC
AGAAAGAAAACAGCAAGCGCTGGAATCCCGAAGTGCAGTACACATCCAATTATGCAAATCTGCCAAC
GTTGATTTTACTGTGGACAACAATGGACTTTATACTGAGCCTCGCCCCATTGGCACCCGTTACCTTAC
CCGTCCCCTGTAATTACGTGTTAATCAATAAACCGGTTGATTCGTTTCAGTTGAACTTTGGTCTCCTG
TCCTTCTTATCTTATCGGTTACCATGGTTATAGCTTACACATTAACTGCTTGGTTGCGCTTCGCGATA
AAAGACTTACGTCATCGGGTTACCCCTAGTGATGGAGTTGCCCACTCCCTCTCTGCGCGCTCGCTCGC
TCGGTGGGGCCTGCGGACCAAAGGTCCGCAGACGGCAGAGCTCTGCTCTGCCGGCCCCACCGAGCGAG
CGAGCGCGCAGAGAGGGAGTGGGCAA

*FIG. 8*

```
AAV-2, COMPLETE SEQUENCE, GENBANK ACCESSION NO. NC_001401 AND
CHIORINI ET AL. (1999) J. VIROL. 73:1309
TTGGCCACTCCCTCTCTGCGCGCTCGCTCGCTCACTGAGGCCGGGCGACCAAAGGTCGCCCGACGCCC
GGGCTTTGCCCGGGCGGCCTCAGTGAGCGAGCGAGCGCGCAGAGAGGGAGTGGCCAACTCCATCACTA
GGGGTTCCTGGAGGGGTGGAGTCGTGACGTGAATTACGTCATAGGGTTAGGGAGGTCCTGTATTAGAG
GTCACGTGAGTGTTTTGCGACATTTTGCGACACCATGTGGTCACGCTGGGTATTTAAGCCCGAGTGAG
CACGCAGGGTCTCCATTTTGAAGCGGGAGGTTTGAACGCGCAGCCGCCATGCCGGGGTTTTACGAGAT
TGTGATTAAGGTCCCCAGCGACCTTGACGGGCATCTGCCCGGCATTTCTGACAGCTTTGTGAACTGGG
TGGCCGAGAAGGAATGGGAGTTGCCGCCAGATTCTGACATGGATCTGAATCTGATTGAGCAGGCACCC
CTGACCGTGGCCGAGAAGCTGCAGCCGGACTTTCTGACGGAATGGCGCCGTGTGAGTAAGGCCCCGGA
GGCCCTTTTCTTTGTGCAATTTGAGAAGGGAGAGAGCTACTTCCACATGCACGTGCTCGTGGAAACCA
CCGGGGTGAAATCCATGGTTTTGGGACGTTTCCTGAGTCAGATTCGCGAAAAACTGATTCAGAGAATT
TACCGCGGGATCGAGCCGACTTTGCCAAACTGGTTCGCGGTCACAAAGACCAGAAATGGCGCCGGAGG
CGGGAACAAGGTGGTGGATGAGTGCTACATCCCCAATTACTTGCTCCCCAAAAACCCAGCCTGAGCTCC
AGTGGGCGTGGACTAATATGGAACAGTATTTAAGCGCCTGTTTGAATCTCACGGAGCGTAAACGGTTG
GTGGCGCAGCATCTGACGCACGTGTCGCAGACGCAGGAGCAGAACAAAGAGAATCAGAATCCCAATTC
TGATGCGCCGGTGATCAGATCAAAAACTTCAGCCAGGTACATGGAGCTGGTCGGGTGGCTCGTGGACA
AGGGGATTACCTCGGAGAAGCAGTGGATCCAGGAGGACCAGGCCTCATACATCTCCTTCAATGCGGCC
TCCAACTCGCGGTCCCAAATCAAGGCTGCCTTGGACAATGCGGGAAAGATTATGAGCCTGACTAAAAC
CGCCCCCGACTACCTGGTGGGCCAGCAGCCCGTGGAGGACATTTCCAGCAATCGGATTTATAAAATTT
TGGAACTAAACGGGTACGATCCCCAATATGCGGCTTCCGTCTTTCTGGGATGGGCCACGAAAAAGTTC
GGCAAGAGGAACACCATCTGGCTGTTTGGGCCTGCAACTACCGGGAAGACCAACATCGCGGAGGCCAT
AGCCCACACTGTGCCCTTCTACGGGTGCGTAAACTGGACCAATGAGAACTTTCCCTTCAACGACTGTG
TCGACAAGATGGTGATCTGGTGGGAGGAGGGGAAGATGACCGCCAAGGTCGTGGAGTCGGCCAAAGCC
ATTCTCGGAGGAAGCAAGGTGCGCGTGGACCAGAAATGCAAGTCCTCGGCCCAGATAGACCCGACTCC
CGTGATCGTCACCTCCAACACCAACATGTGCGCCGTGATTGACGGGAACTCAACGACCTTCGAACACC
AGCAGCCGTTGCAAGACCGGATGTTCAAATTTGAACTCACCCGCCGTCTGGATCATGACTTTGGGAAG
GTCACCAAGCAGGAAGTCAAAGACTTTTTCCGGTGGGCAAAGGATCACGTGGTTGAGGTGGAGCATGA
ATTCTACGTCAAAAAGGGTGGAGCCAAGAAAAGACCCGCCCCCAGTGACGCAGATATAAGTGAGCCCA
AACGGGTGCGCGAGTCAGTTGCGCAGCCATCGACGTCAGACGCGGAAGCTTCGATCAACTACGCAGAC
AGGTACCAAAACAAATGTTCTCGTCACGTGGGCATGAATCTGATGCTGTTTCCCTGCAGACAATGCGA
GAGAATGAATCAGAATTCAAATATCTGCTTCACTCACGGACAGAAAGACTGTTTAGAGTGCTTTCCCG
TGTCAGAATCTCAACCCGTTTCTGTCGTCAAAAAGGCGTATCAGAAACTGTGCTACATTCATCATATC
ATGGGAAAGGTGCCAGACGCTTGCACTGCCTGCGATCTGGTCAATGTGGATTTGGATGACTGCATCTT
TGAACAATAAATGATTTAAATCAGGTATGCTGCGATGGTTATCTTCCAGATTGGCTCGAGGACACT
CTCTCTGAAGGAATAAGACAGTGGTGGAAGCTCAAACCTGGCCCACCACCACCAAAGCCCGCAGAGCG
GCATAAGGACGACAGCAGGGGTCTTGTGCTTCCTGGGTACAAGTACCTCGGACCCTTCAACGGACTCG
ACAAGGGAGAGCCGGTCAACGAGGCAGACGCCGCGGCCCTCGAGCACGACAAAGCCTACGACCGGCAG
CTCGACAGCGGAGACAACCCGTACCTCAAGTACAACCACGCCGACGCGGAGTTTCAGGAGCGCCTTAA
AGAAGATACGTCTTTTGGGGGCAACCTCGGACGAGCAGTCTTCCAGGCGAAAAAGAGGGTTCTTGAAC
CTCTGGGCCTGGTTGAGGAACCTGTTAAGACGGCTCCGGGAAAAAAGAGGCCGGTAGAGCACTCTCCT
GTGGAGCCAGACTCCTCCTCGGGAACCGGAAAGGCGGGCCAGCAGCCTGCAAGAAAAAGATTGAATTT
TGGTCAGACTGGAGACGCAGACTCAGTACCTGACCCCCAGCCTCTCGGACAGCCACCAGCAGCCCCCT
CTGGTCTGGGAACTAATACGATGGCTACAGGCAGTGGCGCACCAATGGCAGACAATAGCAGGGGCGCC
GACGGAGTGGGTAATTCCTCCGGAAATTGGCATTGCGATTCCACATGGATGGGCGACAGAGTCATCAC
CACCAGCACCCGAACCTGGGCCCTGCCCACCTACAACAACCACCTCTACAAACAAATTTCCAGCCAAT
CAGGAGCCTCGAACGACAATCACTACTTTGGCTACAGCACCCCTTGGGGGTATTTTGACTTCAACAGA
TTCCACTGCCACTTTTCACCACGTGACTGGCAAAAGACTCATCAACAACAACAACTGGGGGATTCCGACCCAA
GAGACTCAACTTCAAGCTCTTTAACATTCAAGTCAAAGAGGTCACGCAGAATGACGGTACGACGACGA
TTGCCAATAACCTTACCAGCACGGTTCAGGTGTTTACTGACTCGGAGTACCAGCTCCCGTACGTCCTC
GGCTCGGCGCATCAAGGATGCCTCCCGCCGTTCCCAGCAGACGTCTTCATGGTGCCACAGTATGGATA
CCTCACCCTGAACAACGGGAGTCAGGCAGTAGGACGCTCTTCATTTTACTGCCTGGAGTACTTTCCTT
CTCAGATGCTGCGTACCGGAAACAACTTTACCTTCAGCTACACTTTTGAGGACGTTCCTTTCCACAGC
AGCTACGCTCACAGCCAGAGTCTGGACCGTCTCATGAATCCTCTCATCGACCAGTACCTGTATTACTT
GAGCAGAACAAACACTCCAAGTGGAACCACCAGCGCAAGCAGGCTTCAGTTTTCTCAGGCCGGGAGCGA
GTGACATTCGGGACCAGTCTAGGAACTGGCTTCCTGGACCCTGTTACCGCCAGCAGCGAGTATCAAAG
ACATCTGCGGATAACAACAACAGTGAATACTCGTGGACTGGAGCTACCAAGTACCACCTCAATGGCAG
AGACTCTCTGGTGAATCCGGGCCCGGCCATGGCAAGCCACAAGGACGATGAAGAAAAGTTTTTTCCTC
AGAGCGGGGTTCTCATCTTTGGGAAGCAAGGCTCAGAGAAAACAAATGTGGACATTGAAAAGGTCATG
ATTACAGACGAAGAGGAAATCCGGACAACCAATCCCGTGGCTACGGAGCAGTATGGTTCTGTATCTAC
CAACCTCCAGAGAGGCAACAGACAAGCAGCTACCGCAGATGTCAACACACAAGGCGTTCTTCCAGGCA
TGGTCTGGCAGGACAGAGATGTGTACCTTCAGGGGCCCATCTGGGCAAAGATTCCACACACGGACGGA
CATTTTCACCCCTCTCCCTCATGGGTGGATTCGGACTTAAACACCCTCCTCACAGATTCTCATCAA
GAACACCCCGTACCTGGAATCCTTCGACCACCTTCAGTGCGGCAAAGTTTGCTTCCTTCATCACAC
AGTACTCCACGGGACAGGTCAGCGTGGAGATCGAGTGGGAGCTGCAGAAGGAAAACAGCAAACGCTGG
AATCCCGAAATTCAGTACACTTCCAACTACAACAAGTCTGTTAATCGTGGACTTACCGTGGATACTAA
TGGCGTGTATTCAGAGCCTCGCCCCATTGGCACCAGATACCTGACTCGTAATCTGTAATTGCTTGTTA
ATCAATAAACCGTTTAATTCGTTTCAGTTGAACTTTGGTCTCTGCGTATTTCTTTCTTATCTAGTTTC
CATGGCTACGTAGATAAGTAGCATGGCGGGTTAATCATTAACTACAAGGAACCCCTAGTGATGGAGTT
GGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGAGAGGGAGTGGCCAA
```

FIG. 9

```
AAV-3A, COMPLETE SEQUENCE, GENBANK ACCESSION NO. NC_001729 AND
MURAMATSU ET AL. (1996) VIROLOGY 221:208
TTGGCCACTCCCTCTATGCGCACTCGCTCGCTCGGTGGGGCCTGGCGACCAAAGGTCGCCCAGACGGACG
TGCTTTTGCACGTCCGGCCCCACCGAGCGAGCGAGTGCGCATAGAGGGAGTGGCCAACTCCATCACTAGA
GGTATGGCAGTGACGTAACGCGAAGCGCGCGAAGCGAGACCACGCCTACCAGCTGCGTCAGCAGTCAGG
TGACCCTTTTGCGACAGTTTGCGACACCACGTGGCCGCTGAGGGTATATATTCTCGAGTGAGCGAACCA
GGAGCTCCATTTTGACCGCGAAATTTGAACGAGCAGCAGCCATGCCGGGGTTCTACGAGATTGTCCTGA
AGGTCCCGAGTGACCTGGACGAGCGCCTGCCGGGCATTTCTAACTCGTTTGTTAACTGGGTGGCCGAGA
AGGAATGGGACGTGCCGCCGGATTCTGACATGGATCCGAATCTGATTGAGCAGGCACCCCTGACCGTGG
CCGAAAAGCTTCAGCGCGAGTTCCTGGTGGAGTGGCGCCGCGTGAGTAAGGCCCCGGAGGCCCTCTTTT
TTGTCCAGTTCGAAAAGGGGGAGACCTACTTCCACCTGCACGTGCTGATTGAGACCATCGGGGTCAAAT
CCATGGTGGTCGGCCGCTACGTGAGCCAGATTAAAGAGAAGCTGGTGACCCGCATCTACCGCGGGGTCG
AGCCGCAGCTTCCGAACTGGTTCGCGGTGACCAAAACGCGAAATGGCGCCGGGGCGGGAACAAGGTGG
TGGACGACTGCTACATCCCCAACTACCTGCTCCCAAGACCCAGCCCGAGCTCCAGTGGGCGTGGACTA
ACATGGACCAGTATTTAAGCGCCTGTTTGAATCTCGCGGAGCGTAAACGGCTGGTGGCGCAGCATCTGA
CGCACGTGTCGCAGACGCAGGAGCAGAACAAAGAGAATCAGAACCCCAATTCTGACGCGCCGGTCATCA
GGTCAAAAACCTCAGCCAGGTACATGGAGCTGGTCGGGTGGCTGGTGGACCGCGGGATCACGTCAGAAA
AGCAATGGATTCAGGAGGACCAGGCCTCGTACATCTCCTTCAACGCCGCCTCCAACTCGCGGTCCCAGA
TCAAGGCCGCGCTGGACAATGCCTCCAAGATCATGAGCCTGACAAAGACGGCTCCGGACTACCTGGTGG
GCAGCAACCCGCCGGAGGACATTACCAAAAATCGGACTCTACCAAATCCTGGAGCTGAACGGGTACGATC
CGCAGTACGCGGCCTCCGTCTTCCTGGGCTGGGCGCAAAAGAAGTTCGGGAAGAGGAACACCATCTGGC
TCTTTGGGCCGGCCACGACGGGTAAAACCAACATCGCGGAAGCCATCGCCCACGCCGTGCCCTTCTACG
GCTGCGTAAACTGGACCAATGAGAACTTTCCCTTCAACGATTGCGTCGACAAGATGGTGATCTGGTGGG
AGGAGGGCAAGATGACGGCCAAGGTCGTGGAGAGCGCCAAGGCCATTCTGGGCGGAAGCAAGGTGCGCG
TGGACCAAAAGTGCAAGTCATCGGCCCAGATCGTCACCACTCCCGTGATCGTCACCTCCAACACCAACA
TGTGCGCCGTGATTGACGGGAACAGCACCACCTTCGAGCATCAGCAGCCGCTGCAGGACCGGATGTTTG
AATTTGAACTTACCCGCCGTTTGGACCATGACTTTGGGAAGGTCACCAAACAGGAAGTAAAGGACTTTT
TCCGGTGGGCTTCCGATCACGTGACTGACGTGGCTCATGAGTTCTACGTCAGAAAGGGTGGAGCTAAGA
AACGCCCCGCCTCCAATGACGCGGATGTAAGCGAGCCAAAACGGGAGTGCACGTCACTTGCGCAGCCGA
CAACGTCAGACGCGGAAGCACCGGCGGACTACGCGGACAGGTACCAAAACAAATGTTCTCGTCACGTGG
GCATGAATCTGATGCTTTTCTCCCTGTAAAACATGCGAGAGAATGAATCAAATTTCCAATGTCTGTTTTA
CGCATGGTCAAAGAGACTGTGGGGAATGCTTCCCTGGAATGTCAGAATCTCAACCCGTTTCTGTCGTCA
AAAAGAAGACTTATCAGAAACTGTGTCCAATTCATCATATCCTGGGAAGGGCACCCGAGATTGCCTGTT
CGGCCTGCGATTTGGCCAATGTGGACTTGGATGACTGTGTTTCTGAGCAATAAATGACTTAAACCAGGT
ATGGCTGCTGACGGTTATCTTCCAGATTGGCTCGAGGACAACCTTTCTGAAGGCATTCGTGAGTGGTGG
GCTCTGAAACCTGGAGTCCCTCAACCCAAAGCGAACCAACAACACCAGGACAACCGTCGGGGTCTTGTG
CTTCCGGGTTACAAATACCTCGGACCCGGTAACGGACTCGACAAAGGAGAGCCGGTCAACGAGGCGGAC
GCGGCAGCCCTCGAACACGACAAAGCTTACGACCAGCAGCTCAAGGCCGGTGACAACCCGTACCTCAAG
TACAACCACGCCGACGCCGAGTTTCAGGAGCGTCTTCAAGAAGATACGTCTTTTGGGGGCAACCTTGGC
AGAGCAGTCTTCCAGGCCAAAAAGAGGATCCTTGAGCCTCTTGGTCTGGTTGAGGAAGCAGCTAAAACG
GCTCCTGGAAAGAAGGGGGCTGTAGATCAGTCTCCTCAGGAACCGGACTCATCATCTGGTGTTGGCAAA
TCGGGCAAACAGCCTGCCAGAAAAAGACTAAATTTCGGTCAGACTGGAGACTACAGAGTCAGTCCCAGAC
CCTCAACCTCTCGGAGAACCACCAGCAGCCCCCACAAGTTTGGGATCTAATACAATGGCTTCAGGCGGT
GGCGCACCAATGGCAGACAATAACGAGGGTGCCGATGGAGTGGGTAATTCCTCAGGAAATTGGCATTGC
GATTCCCAATGGCTGGGCGACAGAGTCATCACCACCAGCACCAGAACCTGGGCCCTGCCCACTTACAAC
AACCATCTCTACAAGCAAATCTCCAGCCAATCCAAGGACTTCAAACGACAAACCACTACTTTGGCTACAGC
ACCCCTTGGGGGTATTTTGACTTTAACAGATTCCACTGCCACTTCTCACCACGTGACTGGCAGCGACTC
ATTAACAACAACTGGGGATTCCGGCCCAAGAAACTCAGCTTCAAGCTCTTCAACATCCAAGTTAGAGGG
GTCACGCAGAACGATGGCACGACGACTATTGCCAATAACCTTACCAGCACGGTTCAAGTGTTTACGGAC
TCGGAGTATCAGCTCCCGTACGTGCTCGGGTCGGCGCACCAAGGCTGTCTCCCGCCGTTTCCAGCGGAC
GTCTTCATGGTCCCTCAGTATGGATACCTCACCCTGAACAACGGAAGTCAAGCGGTGGGACGCTCATCC
TTTTACTGCCTGGAGTACTTCCCTTCGCAGATGCTAAGGACTGGAAATAACTTCCAATTCAGCTATACC
TTCGAGGATGTACCTTTTCACAGCAGCTACGCTCACAGCCAGAGTTTGGATCGCTTGATGAATCCTCTT
ATTGATCAGTATCTGTACTACCTGAACAGAACCCAAAACCTCTGGAACAACCAACCAATCACGGG
CTGCTTTTTAGCCAGGCTGGGCCTCAGTCTATGTCTTTGCAGGCCAGAAATTGGCTACCTGGGCCCTGC
TACCGGCAACAGAGACTTTCAAAGACTGCTAACGACAACAACAACAGTAACTTTCCTTGGACAGCGGCC
AGCAAATATCATCTCAATGGCCGCGACTCGCTGGTGAATCCAGGACCAGCTATGGCCAGTCACAAGGAC
GATGAAGAAAATTTTTCCCTATGCACGGCAATCTAATATTTGGCAAAGAAGGGACAACGGCAAGTAAC
GCAGAATTAGATAATGTAATGATTACGGATGAAGAAGATATTCGTACCACCAATCCTGTGGCAACAGAG
CAGTATGGAACTGTGGCAAATAACTTGCAGAGCTCAAATACAGCTCCCACGACTGGAACTGTCAATCAT
CAGGGGGCCTTACCTGGCATGGTGTGGCAAGATCGTGACGTGTACCTTCAAGGACCTATCTGGGCAAAG
ATTCCTCACACGGATGGACACTTTCATCCTTCTCCTCTGATGGGAGGCTTTGGACTGAAACATCCGCCT
CCTCAAATCATGATCAAAAATACTCCGGTACCGGCAAATCCTCCGACGACTTTCAGCCCCGGCAAGTTT
GCTTCATTTATCACTCAGTACTCCACTGGACAGGTCAGCGTGGAAATTGAGTGGGAGCTACAGAAAGAA
AACAGCAAACGTTGGAATCCAGAGATTCAGTACACTTCCAACTACAACAAGTCTGTTAATGTGGACTTT
ACTGTAGACACTAATGGTGTTTATAGTGAACCTCGCCCTATTGGAACCCGGTATCTCACACGAAACTTG
TGAATCCTGGTTAATCAAAACCGTTTAATTCGTTTCAGTTGAACTTTGGCTCTTGTGCACTTCTTTA
TCTTTATCTTGTTTCCATGGCTACTGCGTAGATAAGCAGCGGCCTGCGGCGCTTGCGCTTCGCGGTTTA
CAACTGCTGGTTAATATTTAACTCTCGCCATACCTCTAGTGATGGAGTTGGCCACTCCCTCTATGCGCA
CTCGCTCGCTCGGTGGGCCTGGCGACCAAAGGTCGCCAGACGGACGTGCTTTGCACGTCCGGCCCCAC
CGAGCGAGCGAGTGCGCATAGAGGGAGTGGCCAA
```

*FIG. 10*

AAV-3B, COMPLETE SEQUENCE, GENBANK ACCESSION NO. NC_001863
TGGCCACTCCCTCTATGCGCACTCGCTCGCTCGGTGGGGCCTGGCGACCAAAGGTCGCCAGACGGACGT
GCTTTGCACGTCCGGCCCCACCGAGCGAGCGAGTGCGCATAGAGGGAGTGGCCAACTCCATCACTAGAG
GTATGGCAGTGACGTAACGCGAAGCGCGCGAAGCGAGACCACGCCTACCAGCTGCGTCAGCAGTCAGGT
GACCCTTTTGCGACAGTTTGCGACACCACGTGGCCGCTGAGGGTATATATTCTCGAGTGAGCGAACCAG
GAGCTCCATTTTGACCGCGAAATTTGAACGAGCAGCAGCCATGCCGGGGTTCTACGAGATTGTCCTGAA
GGTCCCGAGTGACCTGGACGAGCACCTGCCGGGCATTTCTAACTCGTTTGTTAACTGGGTGGCCGAGAA
GGAATGGGAGCTGCCGCCGGATTCTGACATGGATCCGAATCTGATTGAGCAGGCACCCCTGACCGTGGC
CGAAAAGCTTCAGCGCGAGTTCCTGGTGGAGTGGCGCCGCGTGAGTAAGGCCCCGGAGGCCCTCTTTTT
TGTCCAGTTCGAAAAGGGGGAGACCTACTTCCACCTGCACGTGCTGATTGAGACCATCGGGGTCAAATC
CATGGTGGTCGGCCGCTACGTGAGCCAGATTAAAGAGAAGCTGGTGACCCGCATCTACCGCGGGGTCGA
GCCGCAGCTTCCGAACTGGTTCGCGGTGACCAAAACGCGAAATGGCGCCGGGGGCGGGAACAAGGTGGT
GGACGACTGCTACATCCCCAACTACCTGCTCCCCAAGACCCAGCCCGAGCTCCAGTGGGCGTGGACTAA
CATGGACCAGTATTTAAGCGCCTGTTTGAATCTCGCGGAGCGTAAACGGCTGGTGGCGCAGCATCTGAC
GCACGTGTCGCAGACGCAGGAGCAGAACAAAGAGAATCAGAACCCCAATTCTGACGCGCCGGTCATCAG
GTCAAAAACCTCAGCCAGGTACATGGAGCTGGTCGGGTGGCTGGTGGACCGCGGGATCACGTCAGAAAA
GCAATGGATTCAGGAGGACCAGGCCTCGTACATCTCCTTCAACGCCGCCTCCAACTCGCCGGTCCCAGAT
CAAGGCCGCGCTGGACAATGCCTCCAAGATCATGAGCCTGACAAAGACGGCTCCGGACTACCTGGTGGG
CAGCAACCCGCCGGAGGACATTACCAAAAATCGGATCTACCAAATCCTGGAGCTGAACGGGTACGATCC
GCAGTACGCGGCCTCCGTCTTCCTGGGCTGGGCGCAAAAGAAGTTCGGGAAGAGGAACACCATCTGGCT
CTTTGGGCCGGCCACGACGGGTAAAACCAACATCGCGGAAGCCATCGCCCACGCCGTGCCCTTCTACGG
CTGCGTAAACTGGACCAATGAGAACTTTCCCTTCAACGATTGCGTCGACAAGATGGTGATCTGGTGGGA
GGAGGGCAAGATGACGGCCAAGGTCGTGGAGAGCGCCAAGGCCATTCTGGGCGGAAGCAAGGTGCGCGT
GGACCAAAAGTGCAAGTCATCGGCCCAGATCGAACCCACTCCCGTGATCGTCACCTCCAACACCAACAT
GTGCGCCGTGATTGACGGGAACAGCACCACCTTCGAGCATCAGCAGCCGCTGCAGGACCGGATGTTTAA
ATTTGAACTTACCCGCCGTTTGGACCATGACTTTGGGAAGGTCACCAAACAGGAAGTAAAGGACTTTTT
CCGGTGGGCTTCCGATCACGTGACTGACGTGGCTCATGAGTTCTACGTCAGAAAGGGTGGAGCTAAGAA
ACGCCCCGCCTCCAATGACGCGGATGTAAGCGAGCCAAAACGGCAGTGCACGTCACTTGCGCAGCCGAC
AACGTCAGACGCGGAAGCACCGGCGGACTACGCGGACAGGTACCAAAACAAATGTTCTCGTCACGTGGG
CATGAATGCTGATTGCTTTTTCCCTGTAAAACATGCAGAGAATGAATCAAATTTCAATGTCTGTTTTAC
GCATGGTCAAAGAGACTGTGGGGAATGCTTCCCTGGAATGTCAGAATCTCAACCCGTTTCTGTCGTCAA
AAAGAAGACTTATCAGAAACTGTGTCCAATTCATCATATCCTGGGAAGGGCACCCGAGATTGCCTGTTC
GGCCTGCGATTTGGCCAATGTGGACTTGGATGACTGTGTTTCTGAGCAATAAATGACTTAAACCAGGTA
TGGCTGCTGACGGTTATCTTCCAGATTGGCTCGAGGACAACCTTTCTGAAGGCATTCGTGAGTGGTGGG
CTCTGAAACCTGGAGTCCCTCAACCCAAAGCGAACCAACAACACCAGGACAACCGTCGGGGTCTTGTGC
TTCCGGGTTACAAATACCTCGGACCCGGTAACGGACTCGACAAAGGAGAGCCGGTCAACGAGGCGGACG
CGGCAGCCCTCGAACACGACAAAGCTTACGACCAGCAGCTCAAGGCCGGTGACAACCCGTACCTCAAGT
ACAACCACGCCGACGCCGAGTTTCAGGAGCGTCTTCAAGAAGATACGTCTTTTGGGGGCAACCTTGGCA
GAGCAGTCTTCCAGGCCAAAAAGAGGGATCCTTGAGCCTCTTGGTCTGGTTGAGGAAGCAGCTAAAACGG
CTCCTGGAAAGAAGAGGCCTGTAGATCAGTCTCCTCAGGAACCGGACTCATCATCTGGTGTTGGCAAAT
CGGGCAAACAGCCTGCCAGAAAAAGACTAAATTTCGGTCAGACTGGCGACTCAGAGTCAGTCCCAGACC
CTCAAGCTCTCCGGAGAACCACCAGCAGCCCCCACAAGTTTGGGATCTAATCAAATGGCTTCAGGCGGTG
GCGCACCAATGGCAGACAATAACGAGGGTGCCGATGGAGTGGGTAATTCCTCAGGAAATTGGCATTGCG
ATTCCCAATGGCTGGGCGACAGAGTCATCACCACCAGCACCAGAACCTGGGCCCTGCCCACTTACAACA
ACCATCTCTACAAGCAAATCTCCAGCCAATCAGGAGCTTCAAACGACAACCACTACTTTGGCTACAGCA
CCCCTTGGGGTATTTTGACTTTAACAGATTCCACTGCCACTTCTCACCACGTGACTGGCAGCGACTCA
TTAACAACAACTGGGGATTCCGGCCCAAGAAACTCAGCTTCAAGCTCTTCAACATCCAAGTTAAAGAGG
TCACGCAGAACGATGGCACGACGACTATTGCCAATAACCTTACCAGCACGGTTCAAGTGTTTACGGACT
CGGAGTATCAGCTCCCGTACGTGCTCGGGTCGGCGCACCAAGGCTGTCTCCCGCCGTTTCCAGCGGACG
TCTTCATGGTCCCTCAGTATGGATACCTCACCCTGAACAACGGAAGTCAAGCGGTGGGACGCTCATCCT
TTTACTGCCTGGAGTACTTCCCTTCGCAGATGCTAAGGACTGGAAATAACTTCCAATTCAGCTATACCT
TCGAGGATGTACCTTTTCACAGCAGCTACGCTCACAGCCAGAGTTTGGATCGCTTGATGAATCCTCTTA
TTGATCAGTATCTGTACTACCTGAACAGAACGCAAGGAACAACCTCTGGAACAACCAACCAATCACGGC
TGCTTTTTAGCCAGCTGGGCCTCAGTCTATGTCTTTGCAGGCCAGAAATTGGCTACCTGGGCCCTGCT
ACCGGCAACAGAGACTTTCAAAGACTGCTAACGACAACAACAGTACTTTCCTTGGACAGCGGCCA
GCAAATATCATCTCAATGGCCGCGACTCGCTGGTGAATCCAGGACCAGCTATGGCCAGTCACAAGGACG
ATGAAGAAAATTTTTCCCTATGCACGGCAATCTAATATTTGGCAAAGAAGGGACAACGGCAAGTAACG
CAGAATTAGATAATGTAATGATTACGGATGAAGAAGAGATTCGTACCACCAATCCTGTGGCAACAGAGC
AGTATGGAACTGTGGCAAATAACTTGCAGAGCTCAAATACAGCTCCCACGACTAGAACTGTCAATGATC
AGGGGGCCTTACCTGGCATGGTGTGGCAAGATCGTGACGTGTACCTTCAAGGACCTATCTGGGCAAAGA
TTCCTCACACGGATGGACACTTTCATCCTTCTCCTCTGATGGGAGGCTTTGGACTGAAACATCCGCCTC
CTCAAATCATGATCAAAAATACTCCGGTACCGGCAAATCCTCCGACGACTTTCAGCCCGGCCAAGTTTG
CTTCATTTATCACTCAGTCTGCCAGCAGGTGGCTGGTGAAATTGAGTGGGAGCTACAGAAAGAA
ACAGCAAACGTTGGAATCCAGAGATTCAGTACACTTCCAACTACAACAAGTCTGTTAATGTGGACTTTA
CTGTAGACACTAATGGTGTTTATAGTGAACCTCGCCCTATTGGAACCCGGTATCTCACACGAAACTTGT
AATCCTGGTTAATCAATAAACCGTTTAATTCGTTTCAGTTGAACTTTGGCTCTTGTGCACTTCTTATCT
TATCTTGTTTCCATGGCTACTGCGTAGATAAGCAGCGGCCTCGCGGCGCTTCGCCGGTTTACAAC
TGCTGGTTAATATTTAACTCTCGCCATACCTCTAGTGATGGAGTTGGCCACTCCCTCTATGCGCACTCG
CTCGCTCGGTGGGGCCGGACGTGCAAAGCACGTCCGTCGGCGACCTTTGGTCGCCAGGCCCCACCGAG
CGAGCGAGTGCGCATAGAGGGAGTGGCCAA
```

*FIG. 11*

AAV-4, COMPLETE SEQUENCE, GENBANK ACCESSION NO. NC_001829 AND
CHIORINI AT AL. (1997) J. VIROL. 71:6823
TTGGCCACTCCCTCTATGCGCGCTCGCTCACTCACTCGGCCCTGGAGACCAAAGGTCTCCAGACTGCCG
GCCTCTGGCCGGCAGGGCCGAGTGAGTGAGCGAGCGCGCATAGAGGGAGTGGCCAACTCCATCATCTAG
GTTTGCCCACTGACGTCAATGTGACGTCCTAGGGTTAGGGAGGTCCCTGTATTAGCAGTCACGTGAGTG
TCGTATTTCGCGGAGCGTAGCGGAGCGCATACCAAGCTGCCACGTCACAGCCACGTGGTCCGTTTGCGA
CAGTTTGCGACACCATGTGGTCAGGAGGGTATATAACCGCGAGTGAGCCAGCGAGGAGCTCCATTTTGC
CCGCGAATTTTGAACGAGCAGCAGCCATGCCGGGGTTCTACGAGATCGTGCTGAAGGTGCCCAGCGACC
TGGACGAGCACCTGCCCGGCATTTCTGACTCTTTTGTGAGCTGGGTGGCCGAGAAGGAATGGGAGCTGC
CGCCGGATTCTGACATGGACTTGAATCTGATTGAGCAGGCACCCCTGACCGTGGCCGAAAAGCTGCAAC
GCGAGTTCCTGGTCGAGTGGCGCCGCGTGAGTAAGGCCCCGGAGGCCCTCTTCTTTGTCCAGTTCGAGA
AGGGGGACAGCTACTTCCACCTGCACATCCTGGTGGAGACCGTGGGCGTCAAATCCATGGTGGTGGGCC
GCTACGTGAGCCAGATTAAAGAGAAGCTGGTGACCCGCATCTACCGCGGGGTCGAGCCGCAGCTTCCGA
ACTGGTTCGCGGTGACCAAGACGCGTAATGCGCCGGAGGCGGGAACAAGGTGGTGGACGACTGCTACA
TCCCCAACTACCTGCTCCCCAAGACCCAGCCCGAGCTCCAGTGGGCGTGGACTAACATGGACCAGTATA
TAAGCGCCTGTTTGAATCTCGCGGAGCGTAAACGGCTGGTGGCGCAGCATCTGACGCACGTGTCGCAGA
CGCAGGAGCAGAACAAGGAAAACCAGAACCCCAATTCTGACGCGCCGGTCATCAGGTCAAAAACCTCCG
CCAGGTACATGGAGCTGGTCGGGTGGCTGGTGGGCACGGGGATCACGTCAGAAAAGCAATGGATCCAGG
AGGACCAGGCGTCCTACATCTCCTTCAACGCCGCCTCCAACTCGCGGTCACAAATCAAGGCCGCGCTGG
ACAATGCCTCCAAAATCATGAGCCTGACAAAGACGGCTCCGGACTACCTGGTGGGCCAGAACCCGCCGG
AGGACATTTCCAGCAACCGCATCTACCGAATCCTCGAGATGAACGGGTACGATCCGCAGTACGCGGCCT
CCGTCTTCCTGGGCTGGGCGCAAAAGAAGTTCGGCAAGAGGAACACCATCTGGCTCTTTGGGCCGGCCA
CGACGGGTAAAACCAACATCGCGGAAGCCATCGCCCACGGCCGTGCCCTTCTACGGCTGCGTGAACTGGA
CCAATGAGAACTTTCCGTTCAACGATTGCGTCGACAAGATGGTGATCTGGTGGGAGGAGGGCAAGATGA
CGGCCAAGGTCGTAGAGAGCGCCAAGGCCATCCTGGGCGGAAGCAAGGTGCGCGTGGACCAAAAGTGCA
AGTCATCGGCCCAGATCGACCCAACTCCCGTGATCGTCACCTCCAACACCAACATGTGCGCGGTCATCG
ACGGAAACTCGACCACCTTCGAGCACCAACAACCACTCAGGACCGGATGTTCAAGTTCGAGCTCACCA
AGCGCCTGGAGCACGACTTTGGCAAGGTCACCAAGCAGGAAGTCAAAGACTTTTTCCGGTGGGCGTCAG
ATCACGTGACCGAGGTGACTCACGAGTTTTACGTCAGAAAGGGTGGAGCTAGAAAGAGGCCCGCCCCA
ATGACGCAGATATAAGTGAGCCCAAGCGGGCCTGTCCGTCAGTTGCGCAGCCATCGACGTCAGACGCGG
AAGCTCCGGTGGACTACGCGGACAGGTACCAAAACAAATGTTCTCGTCACGTGGGTATGAATCTGATGC
TTTTTCCCTGCCGGCAATGCGAGAGAATGAATCAGAATGTGGACATTTGCTTCACGCACGGGGTCATGG
ACTGTGCCGAGTGCTTCCCCGTGTCAGAATCTCAACCCGTGTCTGTCGTCAGAAAGCGGACGTATCAGA
AACTGTGTCCGATTCATCACATCATGGGGAGGGCCCCGAGGTGGCCTGCTCGGCCTGCGAACTGGCCA
ATGTGGACTTGGATGACTGTGACATGGAACAATAAATGACTCAAACCAGATATGACTGACGGTTACCTT
CCAGATTGGCTAGAGGACAACCTCTCTGAAGGCGTTCGAGAGTGGTGGGCGCTGCAACCTGGAGCCCCT
AAACCCAAGGCAAATCAACAACATCAGGACAACGCTCGGGGTCTTGTGCTTCCGGGTTACAAATACCTC
GGACCCGGCAACGGACTCGACAAGGGGGAACCCGTCAACGCAGCGGACGCGGCAGCCCTCGAGCACGAC
AAGGCCTACGACCAGCAGCTCAAGGCCGGTGACAACCCCTACCTCAAGTACAACCACGCCGACGCGGAG
TTCCAGCAGCGGCTTCAGGGCGACACATCGTTTGGGGGCAACCTCGGCAGAGCAGTCTTCCAGGCCAAA
AAGAGGGTTCTTGAACCTCTTGGTCTGGTTGAGCAAGCGGGTGAGACGGCTCCTGGAAAGAAGAGACCG
TTGATTGAATCCCCCCAGCAGCCCGACTCCTCACGGGTATCGGCAAAAAAGGCAAGCAGCCGGCTAAA
AAGAAGCTCGTTTTCGAAGACGAAACTGGAGCAGGCGACGGACCCCCTGAGGGATCAACTTCCGGAGCC
ATGTCTGATGACAGTGAGATGCGTGCAGCAGCTGGCGGAGCTGCCGTCGAGGGCGGACAAGGTGCCGAT
GGAGTGGGTAATGCCTCGGGGTGATTGGCATTGCGATTCCACCTGGTCTGAGGGCCCACGTCACGACCACC
AGCACCAGAACCTGGGTCTTGCCCACCTACAACAACCACCTCTACAAGCGACTCGGAGAGAGCCTGCAG
TCCAACACCTACAACGGATTCTCCACCCCCTGGGGATACTTTGACTTCAACCGCTTCCACTGCCACTTC
TCACCACGTGACTGGCAGCGACTCATCAACAACAACTGGGGCATGCGACCCAAAGCCATGCGGGTCAAA
ATCTTCAACATCCAGGTCAAGGAGGTCACGACGTCGAACGGCGAGACAACGGTGGCTAATAACCTTACC
AGCACGGTTCAGATCTTTGCGGACTCGTCGTACGAACTGCCGTACGTGATGGATGCGGGTCAAGAGGGC
AGCCTGCCTCCTTTTCCCAACGACGTCTTTATGGTGCCCCAGTACGGCTACTGTGGACTGGTGACCGGC
AACACTTCGCAGCAACAGACTGACAGAAATGCCTTCTACTGCCTGGAGTACTTTCCTTCGCAGATGCTG
CGGACTGGCAACAACTTTGAAATTACGTACAGTTTTGAGAAGGTGCCTTTCCACTCGATGTACGCGCAC
AGCCAGAGCCTGGACCGGCTGATGAACCCTCTCATCGACCAGTACCTGTGGGGACTGCAATCGACCACC
ACCGGAACCACCCTGAATGCCGGGACTGCCACCACCAACTTTACCAAGCTGCGGCCTACCAACTTTTCC
AACTTTAAAAAGAACTGGCTGCCCGGGCCTTCATCAACAGCAGGGCTTCTCAAAGACTGCCAATCAA
AACTACAAGATCCCTGCCACCGGGTCAGACAGTCTCATCAAATACGAGACGCACAGCACTCTGGACGGA
AGATGGAGTGCCCTGACCCCGGACCTCCAATGGCCACGGCTGGACCTGCGGACAGCAAGTTCAGCAAC
AGCCAGCTCATCTTTGCGGGGCCTAAACAGAACGGCAACACGGCCACCGTACCCGGGACTCTGATCTTC
ACCTCTGAGGAGGAGCTGGCAGCCACCAACGCCACCGATACGGACATGTGGGGCAACCTACCTGGCGGT
GACCAGAGCAACAGCAACCTGCCGACCGTGGACAGACTGACAGCCTTGGGAGCCGTGCCTGGAATGGTC
TGGCAAAACAGAGACATTTACTACCAGGGTCCCATTTGGGCAAGATTCCTCATACCGATGGACACTTT
CACCCCTCACCGCTGATTGGTGGGTTTGGGCTGAAACACCCGCCTCCTCAAATTTTTATCAAGAACACC
CCGGTACCTGCGAATCCTGCAACGACCTTCAGCTCTACTCCGGTAAACTCCTTCATTACTCAGTACAGC
ACTGGCCAGGTGTCGGTCGAGATTGACTGGGAGATCCAGAAGGAGCGGTCCAAACGCTGGAACCCCGAG
GTCCAGTTTACCTCCAACTACGGACAGCAAAACTCTCTGTTGTGGGCTCCCGATGCGGCTGGGAAATAC
ACTGAGCCTAGGGCTATCGGTACCCGCTACCTCACCCACCACCTGTAATAACCTGTAATAACCC
GGTTTATTCGTTTCAGTTGAACTTTGGTCTCCGTGTCCTTCTTATCTTATCTGTTTCCATGGCTACTG
CGTACATAAGCAGCGGCCTGCGGCGCTTGCGCTTCGCGGTTTACAACTGCCGGTTAATCAGTAACTTCT
GGCAAACCAGATGATGGAGTTGGCCACATTAGCTATGCGCGCTCGCTCACTCACTCGGCCCTGGAGACC
AAAGGTCTCCAGACTGCCGGCCTCTGGCCGGCAGGGCCGAGTGAGTGAGCGAGCGCGCATAGAGGGAGT
GGCCAA

FIG. 12

AAV-5, COMPLETE SEQUENCE, GENBANK ACCESSION NO. NC_006152 AND CIORINI
ET AL. (1999) J. VIROL. 73:1309
CTCTCCCCCTGTCGCGTTCGCTCGCTCGCTGGCTCGTTTGGGGGGGTGGCAGCTCAAAGAGCTGCCAG
ACGACGGCCCTCTGGCCGTCGCCCCCCCAAACGAGCCAGCGAGCGAGCGAACGCGACAGGGGGGAGAGT
GCCACACTCTCAAGCAAGGAGGTTTTGTAAGCAGTGATGTCATAATGATGTAATGCTTATTGTCACGCG
ATAGTTAATGATTAACAGTCATGTGATGTGTTTTATCCAATAGGAAGAAAGCGCGCGTATGAGTTCTCG
CGAGACTTCCGGGGTATAAAAGACCGAGTGAACGAGCCCGCCGCCATTCTTTGCTCTGGACTGCTAGAG
GACCCTCGCTGCCATGGCTACCTTCTATGAAGTCATTGTTCGCGTCCCATTTGACGTGGAGGAACATCT
GCCTGGAATTTCTGACAGCTTTGTGGACTGGGTAACTGGTCAAATTTGGGAGCTGCCTCCAGAGTCAGA
TTTAAATTTGACTCTGGTTGAACAGCCTCAGTTGACGGTGGCTGATAGAATTCGCCGCGTGTTCCTGTA
CGAGTGGAACAAATTTTCCAAGCAGGAGTCCAAATTCTTTGTGCAGTTTGAAAAGGGATCTGAATATTT
TCATCTGCACACGCTTGTGGAGACCTCCGGCATCTCTTCCATGGTCCTCGGCCGCTACGTGAGTCAGAT
TCGCGCCCAGCTGGTGAAAGTGGTCTTCCAGGGAATTGAACCCCAGATCAACGACTGGGTCGCCATCAC
CAAGGTAAAGAAGGGCGGAGCCAATAAGGTGGTGGATTCTGGGTATATTCCCGCCTACCTGCTGCCGAA
GGTCCAACCGGAGCTTCAGTGGGCGTGGACAAACCTGGACGAGTATAAATTGGCCGCCCTGAATCTGGA
GGAGCGCAAACGGCTCGTCGCGCAGTTTCTGGCAGAATCCTCGCAGCGCTCGCAGGAGGCGGCTTCGCA
GCGTGAGTTCTCGGCTGACCCGGTCATCAAAAGCAAGACTTCCCAGAAATACATGGCGCTCGTCAACTG
GCTCGTGGAGCACGGCATCACTTCCGAGAAGCAGTGGATCCAGGAAAATCAGGAGAGCTACCTCTCCTT
CAACTCCACCGGCAACTCTCGGAGCCAGATCAAGGCCCGCTCGACAACGCGACCAAAATTATGAGTCT
GACAAAAAGCGCGGTGGACTACCTCGTGGGGAGCTCCGTTCCCGAGGACATTTCAAAAAACAGAATCTG
GCAAATTTTTGAGATGAATGGCTACGACCCGGCCTACGCGGGATCCATCCTCTACGGCTGGTGTCAGCG
CTCCTTCAACAAGAGGAACACCGTCTGGCTCTACGGACCCGCCACGACCGGCAAGACCAACATCGCGGA
GGCCATCGCCCACACTGTGCCCTTTTACGGCTGCGTGAACTGGACCAATGAAAACTTTCCCTTTAATGA
CTGTGTGGACAAAATGCTCATTTGGTGGGAGGAGGGAAAGATGACCAACAAGGTGGTTGAATCCGCCAA
GGCCATCCTGGGGGGCTCAAAGGTGCGGGTCGATCAGAAATGTAAATCCTCTGTTCAAATTGATTCTAC
CCCTGTCATTGTAACTTCCAATACAAACATGTGTGTGGTGGTGGATGGGAATTCCACGACCTTTGAACA
CCAGCAGCCGCTGGAGGACCGCATGTTCAAATTTGAACTGACTAAGCGGCTCCCGCCAGATTTTGGCAA
GATTACTAAGCAGGAAGTCAAGGACTTTTTTGCTTGGGCAAAGGTCAATCAGGTGCCGGTGACTCACGA
GTTTAAAGTTCCCAGGGAATTGGCGGGAACTAAAGGGGCGGAGAAATCTCTAAAACGCCCACTGGGTGA
CGTCACCAATACTAGCTATAAAAGTCTGGAGAAGCGGGCCAGGCTCTCATTTGTTCCCGAGACGCCTCG
CAGTTCAGACGTGACTGTTGATCCCGCTCCTCTGCGACCGCTCAATTGGAATTCAAGGTATGATTGCAA
ATGTGACTATCATGCTCAATTTGACAACATTTCTAACAAATGTGATGAATGTGAATATTTGAATCGGGG
CAAAAATGGATGTATCTGTCACAATGTAACTCACTGTCAAATTTGTCATGGGATTCCCCCTGGGAAAA
GGAAAACTTGTCAGATTTTGGGGATTTTGACGATGCCAATAAAGAACAGTAAATAAAGCGAGTAGTCAT
GTCTTTTGTTGATCACCCTCCAGATTGGTTGGAAGAAGTTGGTGAAGGTCTTCGCGAGTTTTTGGGCCT
TGAAGCGGGCCCACCGAAACCAAAACCCAATCAGCAGCATCAAGATCAAGCCCGTGGTCTTGTGCTGCC
TGGTTATAACTATCTCGGACCCGGAAACGGTCTCGATCGAGGAGAGCCTGTCAACAGGGCAGACGAGGT
CGCGCGAGAGCACGACATCTCGTACAACGAGCAGCTTGAGGCGGGAGACAACCCCTACCTCAAGTACAA
CCACGCGGACGCCGAGTTTCAGGAGAAGCTCGCCGACAACATCCTTCGGGGAGGCGAACCTCGGAAAGGC
AGTCTTTCAGGCCAGAAAAGGGGTTCTCGAACCTTTTGGCCTGGTTGAAGAGGGTGCTAAGACGGCCCC
TACCGGAAAGCGGATAGACGACCACTTTCCAAAAAGAAAGAAGGCTCGGACCGAAGAGGACTCCAAGCC
TTCCACCTCGTCAGACGCCGAAGCTGGACCCAGCGGATCCCAGCAGCTGCAAATCCCAGCCCAACCAGC
CTCAAGTTTGGGAGCTGATACAATGTCTGCGGGAGGTGGCGGCCCCATTGGGCGACAATAACCAAGGTGC
CGATGGAGTGGGCAATGCCTCGGGAGATTGGCATTGCGATTCCACGTGGATGGGGACAGAGTCGTCAC
CAAGTCCACCCGAACCTGGGTGCTGCCCAGCTACAACAACCACCAGTACCGAGAGATCAAAAGCGGCTC
CGTCGACGGAAGCAACGCCAACGCCTACTTTGGATACAGCACCCCCTGGGGGTACTTTGACTTTAACCG
CTTCCACAGCCACTGGAGCCCCCGAGACTGGCAAAGACTCATCAACAACTACTGGGGCTTCAGACCCCG
GTCCCTCAGAGTCAAAATCTTCAACATTCAAGTCAAAGAGGTCACGGTGCAGGACTCCACCACCACCAT
CGCCAACAACCTCACCTCCACCGTCCAAGTGTTTACGGACGACGACTACCAGCTGCCCTACGTCGTCGG
CAACGGGACCGAGGGATGCCTGCCGGCCTTCCCTCCGCAGGTCTTTACGCTGCCGCAGTACGGTTACGC
GACGCTGAACCGCGACAACACAGAGAAAATCCCACCGAGGAGCAGCTTCTTCTGCCTAGAGTACTTTCC
CAGCAAGATGCTGAGAACGGGCAACAACTTTGAGTTTACCTACAACTTTGAGGAGGTGCCCTTCCACTC
CAGCTTCGCTCCCAGTCAGAACCTCTTCAAGCTGGCCAACCCGCTGGTGGACCAGTACTTGTACCGCTT
CGTGAGCACAAATAACACTGGCGGAGTCCAGTTCAACAAGAACCTGGCCGGGAGATACGCCAACACCTA
CAAAAACTGGTTCCCGGGGCCCATGGGCCGAACCCAGGGCTGGAACCTGGGCTCCGGGGTCAACCGCGC
CAGTGTCAGCGCCTTCGCCACGACCAATAGGATGGAGCTCGAGGGCGCGAGTTACCAGGTGCCCCCGCA
GCCGAACGGCATGACCAACAACCTCCAGGGCAGCAACACCTATGCCCTGGAGAACACTATGATCTTCAA
CAGCCAGCCGGCGAACCCGGGCACCACCGCCACGTACCTCGAGGGCAACATGCTCATCACCAGCGAGAG
CGAGACGCAGCCGGTGAACCGCGTGGCGTACAACGTGGGCGGACAGATGGCCACCAACAACCAGAGCTC
CACCACTGCCCCCGCGACGGGCACGTACAACCTCCAGGAAATCGTGCCCGGCAGCGTGTGGATGGAGAG
GGACGTGTACCTCCAAGGACCCATCTGGGCCAAGATCCCAGAGACGGGGGCGCACTTTCACCCCTCTCC
GGCCATGGGCGGATTCGGACTCAAACACCCACCGCCCATGATGCTCATCAAGAACACGCCTGTGCCCGG
AAATATCACCAGCTTCTCGGACGTGCCCGTCAGCAGCTTCATCACCCAGTACAGCACCGGGCAGGTCAC
CGTGGAGATGGAGTGGGAGCTCAAGAAGGAAAACTCCAAGAGGTGGAACCCAGAGATCCAGTACACAAA
CAACTACAACGACCCCAGTTTGTGGACTTTGCCCGGACAGCACCGGGGAATACAGAACCACCAGACC
TATCGGAACCCGATACCTTACCCGACCCCTTTAACCCATTCATGTCGCATACCCTCAATAAACCGTGTA
TTCGTGTCAGTAAAAATACTGCCTCTTGTGGTCATTCAATGAATAACAGCTTACAACATTTACAAAACCT
CCTTGCTTGAGAGTGTGGCACTCTCCCCCCTGTCGCGTTCGCTCGCTCGCTGGCTCGTTTGGGGGGGCG
ACGGCCAGAGGGCCGTCGTCTGGCAGCTCTTTGAGCTGCCACCCCCCAAACGAGCCAGCGAGCGAGCG
AACGCGACAGGGGGGAGAG

FIG. 13

```
AAV-6, COMPLETE SEQUENCE, GENBANK ACCESSION NO. NC_001862
TTGGCCACTCCCTCTCTGCGCGCTCGCTCGCTCACTGAGGCCGGGCGACCAAAGGTCGCCCGACGCCCG
GGCTTTGCCCGGGCGGCCTCAGTGAGCGAGCGAGCGCGCAGAGAGGGAGTGGCCAACTCCATCACTAGG
GGTTCCTGGAGGGGTGGAGTCGTGACGTGAATTCATAGGGTTAGGGAGGTCCTGTATTAGAGGTC
ACGTGAGTGTTTTGCGACATTTTGCGACACCATGTGGTCACGCTGGGTATTTAAGCCCGAGTGAGCACG
CAGGGTCTCCATTTTGAAGCGGGAGGTTTGAACGCGCAGCGCCATGCCGGGGTTTTACGAGATTGTGAT
TAAGGTCCCCAGCGACCTTGACGAGCATCTGCCCGGCATTTCTGACAGCTTTGTGAACTGGGTGGCCGA
GAAGGAATGGGAGTTGCCGCCAGATTCTGACATGGATCTGAATCTGATTGAGCAGGCACCCCTGACCGT
GGCCGAGAAGCTGCAGCGCGACTTCCTGGTCCAGTGGCCGCGCGTGAGTAAGGCCCCGGAGGCCCTCTT
CTTTGTTCAGTTCGAGAAGGGCGAGTCCTACTTCCACCTCCATATTCTGGTGGAGACCACGGGGGTCAA
ATCCATGGTGCTGGGCCGCTTCCTGAGTCAGATTAGGGACAAGCTGGTGCAGACCATCTACCGCGGGAT
CGAGCCGACCCTGCCCAACTGGTTCGCGGTGACCAAGACGCGTAATGGCGCCGGAGGGGGGAACAAGGT
GGTGGACGAGTGCTACATCCCCAACTACCTCCTGCCCAAGACTCAGCCCGAGCTGCAGTGGGCGTGGAC
TAACATGGAGGAGTATATAAGCGCGTGTTTAAACCTGGCCGAGCGCAAACGGCTCGTGGCGCACGACCT
GACCCACGTCAGCCAGACCCAGGAGCAGAACAAGGAGAATCTGAACCCCAATTCTGACGCGCCTGTCAT
CCGGTCAAAAACCTCCGCACGCTACATGGAGCTGGTCGGGTGGCTGGTGGACCGGGGCATCACCTCCGA
GAAGCAGTGGATCCAGGAGGACCAGGCCTCGTACATCTCCTTCAACGCCGCCTCCAACTCGCGGTCCCA
GATCAAGGCCGCTCTGGACAATGCCGGCAAGATCATGGCGCTGACCAAATCCGCGCCCGACTACCTGGT
AGGCCCCGCTCCGCCCGCCGACATTAAAACCAACCGCATTTACCGCATCCTGGAGCTGAACGGCTACGA
CCCTGCCTACGCCGGCTCCGTCTTTCTCGGCTGGGCCCAGAAAAGGTTCGGAAAACGCAACACCATCTG
GCTGTTTGGGCCGGCCACCACGGGCAAGACCAACATCGCGGAAGCCATCGCCCACGCCGTGCCCTTCTA
CGGCTGCGTCAACTGGACCAATGAGAACTTTCCCTTCAACGATTGCGTCGACAAGATGGTGATCTGGTG
GGAGGAGGGCAAGATGACGGCCAAGGTCGTGGAGTCCGCCAAGGCCATTCTCGGCGGCAGCAAGGTGCG
CGTGGACCAAAAAGTGCAAGTCGTCCGCCCAGATCGATCCCACCCCCGTGATCGTCACCTCCAACACCAA
CATGTGCGCCGTGATTGACGGGGAACAGCAGCACCTTGCGAGCACCAGCAGCCGTTGCAGGACCGGATGTT
CAAATTTGAACTCACCCGCCGTCTGGAGCATGACTTTGGCAAGGTGACAAAGCAGGAAGTCAAAGAGTT
CTTCCGCTGGGCGCAGGATCACGTGACCGAGGTGGCGCATGAGTTCTACGTCAGAAAGGGTGGAGCCAA
CAAGAGACCCGCCCCCGATGACGCGGATAAAAGCGAGCCCAAGCGGGCCTGCCCCTCAGTCGCGGATCC
ATCGACGTCAGACGCGGAAGGAGCTCCGGTGGACTTTGCCGACAGGTACCAAAACAAATGTTCTCGTCA
CGCGGGCATGCTTCAGATGCTGTTTCCCTGCAAAACATGCGAGAGAATGAATCAGAATTTCAACATTTG
CTTCACGCACGGGACCAGAGACTGTTCAGAATGTTTCCCGGCGTGTCAGAATCTCAACCGGTCGTCAG
AAAGAGGACGTATCGGAAACTCTGTGCCATTCATCATCTGCTGGGGCGGGCTCCCGAGATTGCTTGCTC
GGCCTGCGATCTGGTCAACGCTGGATCTGGATGACTGTGTTTCTGAGCAATAAATGACTTAAACCAGGTA
TGGCTGCCGATGGTTATCTTCCAGATTGGCTCGAGGACAACCTCTCTGAGGGCATTCGCGAGTGGTGGG
ACTTGAAACCTGGAGCCCCGAAACCCAAAGCCAACCAGCAAAGCAGGACGACGGCCGGGGTCTGGTGC
TTCCTGGCTACAAGTACCTCGGACCCTTCAACGGACTCGACAAGGGGGAGCCCGTCAACGCGGCGGATG
CAGCGGCCCTCGAGCACGACAAGGCCTACGACCAGCAGCTCAAAGCGGGTGACAATCCGTACCTGCGGT
ATAACCACGCCGACGCCGAGTTTCAGGAGCGTCTGCAAGAAGATACGTCTTTTGGGGGCAACCTCGGCG
GAGCAGTCTTCCAGGCCAAGAAGAGGGTTCTCGAACCTTTTGGTCTGGTTGAGGAAGGTGCTAAGACGG
CTCCTGGAAAGAAACGTCCGGTAGAGCAGTCGCCACAAGAGCCAGACTCCTCCTCGGGCATTGGCAAGA
CAGGCCAGCAGCCCGCTAAAAAGAGACTCAATTTTGGTCAGACTGGCGACTCAGAGTCAGTCCCCGACC
CACAACCTCTCGGAGAACCTCCAGCAACCCCCGCTGCTGTGGGACCTACTACAATGGCTTCAGGCGGTG
GCGCACCAATGGCAGACAATAACGAAGGCGCCGACGGAGTGGGTAATGCCTCAGGAAATTGGCATTGCG
ATTCCACATGGCTGGGCGACAGAGTCATCACCACCAGCACCCGAACATGGGCCTTGCCCACCTATAACA
ACCACCTCTACAAGCAAATCTCCAGTGCTTCAACGGGGGCCAGCAACGACAACCACTACTTCGGCTACA
GCACCCCCTGGGGGTATTTTGATTTCAACAGATTCCACTGCCATTTCTCACCACGTGACTGGCAGCGAC
TCATCAACAACAATTGGGGATTCCGGCCCAAGAGACTCAACTTCAAGCTCTTCAACATCCAAGTCAAGG
AGGTCACGACGAATGATGGCGTCACGACCATCGCTAATAACCTTACCAGCACGGTTCAAGTCTTCTCGG
ACTCGGAGTACCAGTTGCCGTACGTCCTCGGCTCTGCGCACCAGGGCTGCCTCCCTCCGTTCCCGGCGG
ACGTGTTCATGATTCCGCAGTACGGCTACCTAACGCTCAACAATGGCAGCCAGGCAGTGGGACGGTCAT
CCTTTTACTGCCTGGAATATTTCCCATCGCAGATGCTGAGAACGGCAATAACTTTACCTTCAGCTACA
CCTTCGAGGACGTGCCTTTCCACAGCAGCTACGCGCACAGCCAGAGCCTGGACCGGCTGATGAATCCTC
TCATCGACCAGTACCTGTATTACCTGAACAGAACTCAGAATCAGTCCGGAAGTGCCCAAAACAAGGACT
TGCTGTTTAGCCGGGGGTCTCCAGCTGGCATGTCTGTTCAGCCCAAAAACTGGCTACCTGGACCCTGTT
ACCGGCAGCAGCGCGTTTCTAAAACAAAAACAGACAACAACAACACAGCCAACTTTACCTGGACTGGCTT
CAAAATATAACCTTAATGGGCGTGAATCTATAATCAACCCTGGCACTGCTATGGCCTCACACAAAGACG
ACAAAGACAAGTTCTTTCCCATGAGCGGTGTCATGATTTTTGGAAAGGAGAGCGCCGGAGCTTCAAACA
CTGCATTGGACAATGTCATGATCACAGACGAAGAGGAAATCAAAGCCACTAACCCCGTGGCCACCGAAA
GATTTGGGACTGTGGCAGTCAATCTCCAGAGCAGCAGCACACCCTGCGACCGGAGATGTGCATGTTA
TGGGAGCCTTACCTGGAATGGTGTGGCAAGACAGAGACGTATACCTGCAGGGTCCTATTTGGGCCAAAA
TTCCTCACACGGATGGCACTTTCACCCGTCTCCTCTCATGGGCGGCTTTGGACTTAAGCACCCGCCTC
CTCAGATCCTCATCAAAAACACGCCTGTTCCTGCGAATCCTCCGGCAGAGTTTTCGGCTACAAAGTTTG
CTTCATTCATCACCAGTATTCCACAGGACAAGTGAGCGTGGAGATTGAATGGGAGCTGCAGAAAGAAA
ACAGCAAACGCTGGAATCCCGAAGTGCAGTATACATCTAACTATGCAAAATCTGCCAACGTTGATTTCA
CTGTGGACAACAATGGACTTTATACTGAGCCTCGCCCCATTGGCACCCGTTACCTCACCCGTCCCCTGT
AATTGTGTGTTAATCAATAAACCGGTTAATTCGTGTCAGTTGAACTTTGGTCTCATGTCGTTATTATCT
TATCTGGTCACCATAGCAACCGGTTACACATTAACTGCTTAGTTGCGCTTCGCGAATACCCCTAGTGAT
GGAGTTGCCCACTCCCTCTATGCGCGCTCGCTCGCTCGGTGGGGCCGGCAGAGCAGAGCTCTGCCGTCT
GCGGACCTTTGGTCCGCAGGCCCCACCGAGCGAGCGAGCGCGCATAGAGGGAGTGGGCAA
```

*FIG. 14*

AAV-7, COMPLETE SEQUENCE, GENBANK ACCESSION NO. AF513851 AND GAO ET
AL. (2002) PNAS 99:11854
TTGGCCACTCCCTCTATGCGCGCTCGCTCGCTCGGTGGGGCCTGCGGACCAAAGGTCCGCAGACGGCAG
AGCTCTGCTCTGCCGGCCCCACCGAGCGAGCGAGCGCGCATAGAGGGAGTGGCCAACTCCATCACTAGG
GGTACCGCGAAGCGCCTCCCACGCTGCCGCGTCAGCGCTGACGTAAATCACGTCATAGGGGAGTGGTCC
TGTATTAGCTGTCACGTGAGTGCTTTTGCGACATTTTGCGACACCACGTGGCCATTTGAGGTATATATG
GCCGAGTGAGCGAGCAGGATCTCCATTTTGACCGCGAAATTTGAACGAGCAGCAGCCATGCCGGGTTTC
TACGAGATCGTGATCAAGGTGCCGAGCGACCTGGACGAGCACCTGCCGGGCATTTCTGACTCGTTTGTG
AACTGGGTGGCCGAGAAGGAATGGGAGCTGCCCCCGGATTCTGACATGGATCTGAATCTGATCGAGCAG
GCACCCCTGACCGTGGCCGAGAAGCTGCAGCGCGACTTCCTGGTCCAATGGCGCCGCGTGAGTAAGGCC
CCGGAGGCCCTGTTCTTTGTTCAGTTCGAGAAGGGCGAGAGCTACTTCCACCTTCACGTTCTGGTGGAG
ACCACGGGGGTCAAGTCCATGGTGCTAGGCCGCTTCCTGAGTCAGATTCGGGAGAAGCTGGTCCAGACC
ATCTACCGCGGGGTCGAGCCCACGCTGCCCAACTGGTTCGCGGTGACCAAGACGCGTAATGGCGCCGGC
GGGGGGAACAAGGTGGTTGGACGAGTGCTACATCCCCAACTACCTCCTGCCCAAGACCCAGCCCGAGCTG
CAGTGGGCGTGGACTAACATGGAGGAGTATATAAGCGCGTGTTTGAACCTGGCCGAACGCAAACGGCTC
GTGGCGCAGCACCTGACCCACGTCAGCCAGACGCAGGAGCAGAACAAGGAGAATCTGAACCCCAATTCT
GACGCGCCCGTGATCAGGTCAAAAACCTCCGCGCGCTACATGGAGCTGGTCGGGTGGCTGGTGGACCGG
GGCATCACCTCCGAGAAGCAGTGGATCCAGGAGGACCAGGCCTCGTACATCTCCTTCAACGCCGCCTCC
AACTCGCGGTCCCAGATCAAGGCCGCGCTGGACAATGCCGGCAAGATCATGGCGCTGACCAAATCCGCG
CCCGACTACCTGGTGGGGCCCTCGCTGCCCGCGGACATTAAAACCAACCGCATCTACCGCATCCTGGAG
CTGAACGGGTACGATCCTGCCTACGCCGGCTCCGTCTTTCTCGGCTGGGCCCAGAAAAAGTTCGGGAAG
CGCAACACCATCTGGCTGTTTGGGCCCGCCACCACCGGCAAGACCAACATTGCGGAAGCCATCGCCCAC
GCCGTGCCCTTCTACGGCTGCGTCAACTGGACCAATGAGAACTTTCCCTTCAACGATTCGTCGACAAG
ATGGTGATCTGGTGGGAGGAGGGCAAGATGACGGCCAAGGTCGTGGAGTCCGCCAAGGCCATTCTCGGC
GGCAGCAAGGTGCGCGTGGACCAAAAGTGCAAGTCGTCCGCCCAGATCGACCCCACCCCCGTGATCGTC
ACCTCCAACACCAACATGTGCGCCGTGATTGACGGGAACAGCACCACCTTCGAGCACCAGCAGCCGTTG
CAGGACCGGATGTTCAAATTTGAACTCACCCGCCGTCTGGAGCACGACTTTGGCAAGGTGACGAAGCAG
GAAGTCAAAGAGTTCTTCCGCTGGGCCAGTGATCACGTGACCGAGGTGGCGCATGAGTTCTACGTCAGA
AAGGGCGGAGCCAGCAAAAGACCCGCCCCGATGACGCGGATATAAGCGAGCCCAAGCGGGCCTGCCCC
TCAGTCGCCGATCCATCGACGTCAGACGCGGAAGGAGCTCCGGTGGACTTTGCCGACAGGTACCAAAAC
AAAATGTTCTCGTCACGCGGGCATGATTCAGATGCTGTTTCCCTGCAAAACGTGCGAGAGAATGAATCAG
AATTTCAACATTTGCTTCACACACGGGGTCAGAGACTGTTTAGAGTGTTTCCCCGGCGTGTCAGAATCT
CAACCGGTCGTCAGAAAAAAGACGTATCGGAAACTCTGCGCGATTCATCATCTGCTGGGGCGGGCGCCC
GAGATTGCTTGCTCCGGCCCTGCGACCCAGCGGCCTGGACGACTGCGTTCTGAGCAATAAATG
ACTTAAACCAGGTATGGCTGCCGATGGTTATCTTCCAGATTGGCTCGAGGACAACCTCTCTGAGGGCAT
TCGCGAGTGGTGGGACCTGAAACCTGGAGCCCCGAAACCCAAAGCCAACCAGCAAAAGCAGGACAACGG
CCGGGGTCTGGTGCTTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCTCAAAGCGGGTGACAA
TCCGTACCTGCGGTATAACCACGCCGACGCCGAGTTTCAGGAGCGTCTGCAAGAAGATACGTCATTTGG
GGGCAACCTCGGGCGAGCAGTCTTCCAGGCCAAGAAGCGGGTTCTCGAACCTCTCGGTCTGGTTGAGGA
AGGCGCTAAGACGGCTCCTGCAAAGAAGAGACCGGTAGAGCCGTCACCTCAGCGTTCCCCCGACTCCTC
CACGGGCATCGGCAAGAAAGGCCAGCAGCCGCCGCAGAAAAGGACTCAATTTCGGTCAGACTGGCGACTC
AGAGTCAGTCCCCGACCCTCAACCTCTCGGAGAACCTCCAGCAGCGCCCTCTAGTGTGGGATCTGGTAC
AGTGGCTGCAGGCGGTGGCGCACCAATGGCAGACAATAACGAAGGTGCCGACGGAGTGGGTAATGCCTC
AGGAAATTGGCATTGCGATTCCACATGGCTGGGCGACAGAGTCATTACCACCAGCACCCGAACCTGGGC
CCTGCCCACCTACAACAACCACCTCTACAAGCAAATCTCCAGTGAAACTGCAGGTAGTACCAACGACAA
CACCTACTTCGGCTACAGCACCCCTTGGGGTATTTTGACTTTAACAGATTCCACTGCCACTTCTCACC
ACGTGACTGGCAGCGACTCATCAACAACAACTGGGGATTCCGGCCCAAGAAGCTGCGGTTCAAGCTCTT
CAACATCCAGGTCAAGGAGGTCACGACGAATGACGGCGTTACGACCATCGCTAATAACCTTACCAGCAC
GATTCAGGTATTCTCGGACTCGGAATACCAGCTGCCGTACGTCCTCGGCTCTGCGCACCAGGGCTGCCT
GCCTCCGTTCCCGGCGGACGTCTTCATGATTCCTCAGTACGGCTACCTGACTCTCAACAATGGCAGTCA
GTCTGTGGGACGTTCCTCCTTCTACTGCCTGGAGTACTTCCCCTCTCAGATGCTGAGAACGGGCAACAA
CTTTGAGTTCAGCTACAGCTTCGAGGACGTGCCTTTCCACAGCAGCTACGCACACAGCCAGAGCCTGGA
CCGGCTGATGAATCCCCTCATCGACCAGTACTTGTACTACCTGGCCAGAACACAGAGTAACCAGGAGG
CACAGCTGGCAATCGGGAACTGCAGTTTTACCAGGCGGCCCTTCAACTATGGCCGAACAAGCCAAGAA
TTGGTTACCTGGACCTTGCTTCCGGCAACAAAGAGTCTCCAAAACGCTGGATCAAAACAACAACAGCAA
CTTTGCTTGGACTGGTGCCACCAAATATCACCTGAACGGCAGAAACTCGTTGGTTAATCCCGGCGTCGC
CATGGCAACTCACAAGGACGACGAGGACCGCTTTTTCCCATCCAGCGGAGTTCTCATGTTTGGAAAAAC
TGGAGCAACTAACAAAACTACATTGGAAAATGTGTTAATGCAAATGAAGAAGAAATTCGTCCTACTAA
TCCTGTAGCCACGGAAGAATACGGGATAGTCAGCAGCAACTTACAAGCGGCTAATACTGCAGCCCAGAC
ACAAGTTGTCAACAACCAGGGAGCCTTACCTGGCATGGTCTGGCAGAACCGGGACGTGTACCTGCAGGG
TCCCATCTGGGCCAAGATTCCTCACACGGATGGACAACTTTCACCCGTCTCCTTTGATGGGCGGCTTTGG
ACTTAAACATCCGCCTCCTCAGATCCTGATCAAGAACACTCCCGTTCCCGCTAATCCTCCGGAGGTGTT
TACTCCTGCCAAGTTTGCTTCGTTCATCACACAGTACAGCACCGGACAAGTCAGCGTGGAAATCGAGTG
GGAGCTGCAGAAGGAAAACAGCAAGCGCTGGAACCCCGAGATTCAGTACACCTCCAACTTTGAAAAGCA
GACTGGTGTGGACTTTGCCGTTGACGCCAGGGTGTTTACTCTGAGCCTCGCCTATTGCGACTCGTTA
CCTCACCCGTAATCTGTAATTGCATGTTAATCAATAAACCGGTTGATTCGTTTCAGTTGAACTTTGGTC
TCCTGTGCTTCTTATCTTATCGGTTTCCATAGCAACTGGTTACACATTAACTGCTTGGGTGCGCTTCAC
GATAAGAACACTGACGTCACCGCGGTACCCCTAGTGATGGAGTTGGCCACTCCCTCTATGCGCGCTCGC
TCGCTCGGTGGGGCCTGCGGACCAAAGGTCCGCAGACGGCAGAGCTCTGCTCTGCCGGCCCCACCGAGC
GAGCGAGCGCGCATAGAGGGAGTGGCCAA
```

FIG. 15

```
AAV-8, COMPLETE SEQUENCE, GENBANK ACCESSION NO. AF513852 AND GAO ET
AL. (2002) PNAS 99:11854
CAGAGAGGGAGTGGCCAACTCCATCACTAGGGGTAGCGCGAAGCGCCTCCCACGCTGCCGCGTCAGC
GCTGACGTAAATTACGTCATAGGGGAGTGGTCCTGTATTAGCTGTCACGTGAGTGCTTTTGCGGCAT
TTTGCGACACCACGTGGCCATTTGAGGTATATATGGCCGAGTGAGCGAGCAGGATCTCCATTTTGAC
CGCGAAATTTGAACGAGCAGCAGCCATGCCGGGCTTCTACGAGATCGTGATCAAGGTGCCGAGCGAC
CTGGACGAGCACCTGCCGGGCATTTCTGACTCGTTTGTGAACTGGGTGGCCGAGAAGGAATGGGAGC
TGCCCCCGGATTCTGACATGGATCGGAATCTGATCGAGCAGGCACCCCTGACCGTGGCCGAGAAGCT
GCAGCGCGACTTCCTGGTCCAATGGCGCCGCGTGAGTAAGGCCCCGGAGGCCCTCTTCTTTGTTCAG
TTCGAGAAGGGCGAGAGCTACTTTCACCTGCACGTTCTGGTCGAGACCACGGGGGTCAAGTCCATGG
TGCTAGGCCGCTTCCTGAGTCAGATTCGGGAAAAGCTTGGTCCAGACCATCTACCCGCGGGGTCGAG
CCCCACCTTGCCCAACTGGTTCGCGGTGACCAAAGACGCGGTAATGGCGCCGGCGGGGGGGAACAAG
GTGGTGGACGAGTGCTACATCCCCAACTACCTCCTGCCCAAGACTCAGCCCGAGCTGCAGTGGGCGT
GGACTAACATGGAGGAGTATATAAGCGCGTGCTTGACCTGGCCGAGCGCAAACGGCTCGTGGCGCA
GCACCTGACCCACGTCAGCCAGACGCAGGAGCAGAACAAGGAGAATCTGAACCCCAATTCTGACGCG
CCCGTGATCAGGTCAAAAACCTCCGCGCGCTATATGGAGCTGGTCGGGTGGCTGGTGGACCGGGGCA
TCACCTCCGAGAAGCAGTGGATCCAGGAGGACCAGGCCTCGTACATCTCCTTCAACGCCGCCTCCAA
CTCGCGGTCCCAGATCAAGGCCGCGCTGGACAATGCCGGCAAGATCATGGCGCTGACCAAATCCGCG
CCCGACTACCTGGTGGGGCCCTCGCTGCCCGCGGACATTACCCAGAACCGCATCTACCGCATCCTCG
CTCTCAACGGCTACGACCCTGCCTACGCCGGCTCCGTCTTTCTCGGCTGGGCTCAGAAAAAGTTCGG
GAAACGCAACACCATCTGGCTGTTTGGACCCGCCACCACCGGCAAGACCAACATTGCGGAAGCCATC
GCCCACGCCGTGCCCTTCTACGGCTGCGTCAACTGGACCAATGAGAACTTTCCCTTCAATGATTGCG
TCGACAAGATGGTGATCTGGTGGGAGGAGGGCAAGATGACGGCCAAGGTCGTGGAGTCCGCCAAGGC
CATTCTCGGCGGCAGCAAGGTGCGCGTGGACCAAAAGTGCAAGTCGTCCGCCCAGATCGACCCCACC
CCCGTGATCGTCACCTCCAACACCAACATGTGCGCCGTGATTGACGGGAACAGCACCACCTTCGAGC
ACCAGCAGCCTCTCCAGGACCGGATGTTTAAGTTCGAACTCACCCGCCGTCTGGAGCACGACTTTGG
CAAGGTGACAAAGCAGGAAGTCAAAGAGTTCTTCCGCTGGGCCAGTGATCACGTGACCGAGGTGGCG
CATGAGTTTTACGTCAGAAAGGGCGGAGCCAGCAAAAGACCCGCCCCGATGACGCGGATAAAAGCG
AGCCCAAGCGGGCCTGCCCCTCAGTCGCGGATCCATCGACGTCAGACGCGGAAGGAGCTCCGGTGGA
CTTTGCCGACAGGGTACCAAAACAAATGTTCTCGTCACGCGGGCATGCTTCAGATGCTGTTTCCCTGC
AAAACGTGCGAGAGAATGAATCAGAATTTCAACATTTGCTTCACACACGGGGTCAGAGACTGCTCAG
AGTGTTTCCCCGGCGTGTCAGAATCTCAACCGGTCGTCAGAAAGAGGACGTATCGGAAACTCTGTGC
GATTCATCATCTGCTGGGGCGGGCTCCCGAGATTGCTTGCTCGGCCTGCGATCTGGTCAACGTGGAC
CTGGATGACTGTGTTTCTGAGCAATAAATGACTTAACCAGGTATGGCTGCCGATGGTTATCTTCCA
GATTGGCTCGAGGACAACCTCTCTGAGGGCATTCGCGAGTGGTGGCGCTGAAACCTGGAGCCCCGA
AGCCCAAAGCCAACCAGCAAAAGCAGGACGACGGCCGGGGTCTGGTGCTTCCTGGCTACAAGTACCT
CGGACCCTTCAACGGACTCGACAAGGGGGAGCCCGTCAACGCGGCGGACGCAGCGGCCCTCGAGCAC
GACAAGGCCTACGACCAGCAGCTGCAGGCGGGAGCAATCCGTACCTGCCGTATAACCACGCCGACG
CCGAGTTTCAGGAGCGTCTGCAAGAAGATACGTCTTTTGGGGCGCAACCTCGGGCGAGCAGTCTTCCA
GGCCAAGAAGCGGGTTCTCGAACCTCTCGGTCTGGTTGAGGAAGGCGCTAAGACGGCTCCTGGAAAG
AAGAGACCGGTAGAGCCATCACCCCAGCGTTCTCCAGACTCCTCTACGGGCATCGGCAAGAAAGGCC
AACAGCCCGCCAGAAAAAGACTCAATTTTGGTCAGACTGGCGACTCAGAGTCAGTTCCAGACCCTCA
ACCTCTCGGAGAACCTCCAGCAGCGCCCTCTGGTGTGGGACCTAATACAATGGCTGCAGGCGGTGGC
GCACCAATGGCAGACAATAACGAAGGCGCCGACGGAGTGGGTAGTTCCTCGGGAAATTGGCATTGCG
ATTCCACATGGCTGGGCGACAGAGTCATCACCACCAGCACCCGAACCTGGGCCCTGCCCACCTACAA
CAACCACCTCTACAAGCAAATCTCCAACGGGACATCGGGAGGAGCCCACCAACGACAACACCTACTTC
GGCTACAGCACCCCCTGGGGGTATTTTGACTTTAACAGATTCCACTGCCACTTTTCACCACGTGACT
GGCAGCGACTCATCAACAACAACTGGGGATTCCGGCCCAAGAGACTCAGCTTCAAGCTCTTCAACAT
CCAGGTCAAGGAGGTCACGCAGAATGAAGGCACCAAGACCATCGCCAATAACCTCACCAGCACCATC
CAGGTGTTTACGGACTCGGAGTACCAGCTGCCGTACGTTCTCGGCTCTGCCCACCAGGGCTGCCTGC
CTCCGTTCCCGGCGGACGTGTTCATGATTCCCCAGTACGGCTACCTAACACTCAACAACGGTAGTCA
GGCCGTGGGACGCTCCTCCTTCTACTGCCTGGAATACTTTCCTTCGCAGATGCTGAGAACCGGCAAC
AACTTCCAGTTTACTTACACCTTCGAGGACGTGCCTTTCCACAGCAGCTACGCCCACAGCCAGAGCT
TGGACCGGCTGATGAATCCTCTGATTGACCAGTACCTGTACTACTTGTCTCGGACTCAAACAACAGG
AGGCACGGCAAATACGCAGACTCTGGGCTTCAGCCAAGGTGGGCCTAATACAATGGCCAATCAGGCA
AAGAACTGGCTGCCAGGACCCTGTTACCGCCAACAACGCGTCTCAACGACAACCGGGCAAAACAACA
ATAGCAACTTTGCCTGGACTGCTGGGACCAAATACCATCTGAATGGAAGAAATTCATTGGCTAATCC
TGGCATCGCTATGGCAACACACAAAGACGACGAGGCGCGTTTTTTCCCAGTAACGGGATCCTGATT
TTTGGCAAACAAAATGCTGCCAGAGACAATGCGGATTACAGCGATGTCATGCTCACCAGCGAGGAAG
AAATCAAAACCACTAACCCTGTGGCTACAGAGGAATACGGTATCGTGGCAGATAACTTGCAGCAGCA
AAACACGGCTCCTCAAATTGGAACTGTCAACAGCCAGGGGGCCTTACCCGGTATGGTCTGGCAGAAC
CGGGACGTGTACCTGCAGGGTCCCATCTGGGCCAAGATTCCTCACACGGACGGCAACTTCCACCCGT
CTCCGCTGATGGGCGGCTTTGGCCTGAAACATCCTCCGCCTCAGATCCTGATCAAGAACACGCCTGT
ACCTGCGGATCCTCCGACCACCTTCAACCAGTCAAAGCTGAACTCTTTCATCACGCAATACAGCACC
GGACAGGTCAGCGTGGAAATTGAATGGGAGCTGCAGAAGGAAAACAGCAAGCGCTGGAACCCCGAGA
TCCAGTACACCTCCAACTACTACAAATCTACAAGTGTGGACTTTGCTGTTAATACAGAAGGCGTGTA
CTCTGAACCCCGCCCCATTGGCACCCGTTACCTCACCCGTAATCTGTAATTGCCTGTTAATCAATAA
ACCGGTTGATTCGTTTCAGTTGAACTTTGGTCTCTGCG
```

FIG. 16

AAV-9, GENBANK ACCESSION NO. AX753250 AND GAO ET AL. (MAY 14, 2003)
EP1310571
CAGAGAGGGAGTGGCCAACTCCATCACTAGGGGTAATCGCGAAGCGCCTCCCACGCTGCCGCGTC
AGCGCTGACGTAGATTACGTCATAGGGGAGTGGTCCTGTATTAGCTGTCACGTGAGTGCTTTTGC
GACATTTTGCGACACCACATGGCCATTTGAGGTATATATGGCCGAGTGAGCGAGCAGGATCTCCA
TTTTGACCGCGAAATTTGAACGAGCAGCAGCCATGCCGGGCTTCTACGAGATTGTGATCAAGGTG
CCGAGCGACCTGGACGAGCACCTGCCGGGCATTTCTGACTCTTTTGTGAACTGGGTGGCCGAGAA
GGAATGGGAGCTGCCCCCGGATTCTGACATGGATCGGAATCTGATCGAGCAGGCACCCCTGACCG
TGGCCGAGAAGCTGCAGCGCGACTTCCTGGTCCAATGGCGCCGCGTGAGTAAGGCCCCGGAGGCC
CTCTTCTTTGTTCAGTTCGAGAAGGGCGAGAGCTACTTTCACCTGCACGTTCTGGTCGAGACCAC
GGGGGTCAAGTCCATGGTGCTAGGCCGCTTCCTGAGTCAGATTCGGGAGAAGCTGGTCCAGACCA
TCTACCGCGGGATCGAGCCGACCCTGCCCAACTGGTTCGCGGTGACCAAGACGCGTAATGGCGCC
GGCGGGGGGAACAAGGTGGTGGACGAGTGCTACATCCCCAACTACCTCCTGCCCAAGACTCAGCC
CGAGCTGCAGTGGGCGTGGACTAACATGGAGGAGTATATAAGCGCGTGCTTGAACCTGGCCGAGC
GCAAACGGCTCGTGGCGCAGCACCTGACCCACGTCAGCCAGACGCAGGAGCAGAACAAGGAGAAT
CTGAACCCCAATTCTGACGCGCCCGTGATCAGGTCAAAAACCTCCGCGCGCTACATGGAGCTGGT
CGGGTGGCTGGTGGACCGGGGCATCATCTCCGAGAAGCAGTGGATCCAGGAGGACCAGGCCTCGT
ACATCTCCTTCAACGCCGCCTCCAACTCGCGGTCCCAGATCAAGGCCGCTGGACAATGCCGGC
AAGATCATGGCGCTGACCAAATCCGCGCCCGACTACCTGGTAGGCCCTTCACTTCCGGTGGACAT
TACGCAGAACCGCATCTACCGCATCCTGCAGCTCAACGGCTACGACCCTGCCTACGCCGGCTCCG
TCTTTCTCGGCTGGGCACAAAAGAAGTTCGGGAAACGCAACACCATCTGGCTGTTTGGGCCGGCC
ACCACGGGAAAGACCAACATCGCAGAAGCATTGCCCACGCCGTGCCCTTCTACGGCTGCGTCAA
CTGGACCAATGAGAACTTTCCCTTCAACGATTGCGTCGACAAGATGGTGATCTGGTGGGAGGAGG
GCAAGATGACGGCCAAGGTCGTGGAGTCCGCCAAGGCCATTCTCGGCGGCAGCAAGGTGCGCGTG
GACCAAAAGTGCAAGTCGTCTCCGCCCAGATCGACCCCACTCCCGTGATCGTCACCTCCAACACAA
CATGTGCGCCGTGATTGACGGGAACAGCACCACCTTCGAGCACCAGCAGCCTCTCCAGGACCGGA
TGTTTAAGTTCGAACTCACCCGCCGTCTGGAGCACGACTTTGGCAAGGTGACAAAGCAGGAAGTC
AAAGAGTTCTTCCGCTGGCGCCAGTGATCACGTGACCGAGGTGGCGCATGAGTTTTACGTCAGAAA
GGGCGGAGCCAGCAAAAGACCCGCCCCCGATGACGCGGATAAAAGCGAGCCCAAGCGGGCCTGCC
CCTCAGTCGCGGATCCATCGACGTCAGACGCGGAAGGAGCTCCGGTGGACTTTGCCGACAGGTAC
CAAAACAAATGTTCTCGTCACGCGGGCATGCTTCAGATGCTGCTTCCCTGCAAAACGTGCGAGAG
AATGAATCAGAATTTCAACATTTGCTTCACACACCGGGTCAGAGACTGCTCAGAGTGTTTCCCCG
GCGTGTCAGAATCTCAACCGGTCGTCAGAAAGAGGACGTATCGGAAACTCTGTGCGATTCATCAT
CTGCTGGGGCGGGCTCCCGAGATTGCTTGCTCGGCCTGCGATCGGTCAACGTGGACCTGGATGA
CTGTGTTTCTGAGCAATAAATGACTTAAACCAGGTATGGCTGCCGATGGTTATCTTCCAGATTGG
CTCGAGGACAACCTCTCTGAGGGCATTCGCGAGTGGTGGGCGCTGAAACCTGGAGCCCCGAAGCC
CAAAGCCAACCAGCAAAAGCAGGACGACGGCGGGGTCTGGTGCTTCCTGGCTACAAGTACCTCG
GACCCTTCAACGGACTCGACAAGGGGGAGCCCGTCAACGCGGCGGACGCAGCGGCCCTCGAGCAC
GGCAAGGCCTACGACCAGCAGCTGCAGGCGGGTGACAATCCGTACCTGCGGTATAACCACGCCGA
CGCCGAGTTTCAGGAGCGTCTGCAAGAAGATACGTCTTTTGGGGGCAACCTCGGGCGAGCAGTCT
TCCAGGCCAAGAAGCGGGTTCTCGAACCTCTCGGTCTGGTTGAGGAAGGCGCTAAGACGGCTCCT
GGAAAGAAGAGACCGGTAGAGCCATCACCCCAGCGTTCTCCAGACTCCTCTACGGGCATCGGCAA
GAAAGGCCAACAGCCCGCCCAGAAAAAGACTCAATTTTGGTCAGACTGGCGACTCAGAGTCAGTTC
CAGACCCTCAACCTCTCGGAGAACCTCCAGCAGCGCCCTCTGGTGTGGGACCTAATACAATGGCT
GCAGGCGGTGGCGCACCAATGGCAGACAATAACGAAGGCGCCGACGGAGTGGGTAATTCCTCGGG
AAATTGGCATTGCGATTCCACATGGCTGGGGGACAGAGTCATCACCACCAGCACCCGAACCTGGG
CATTGCCCACCTACAACAACCACCTCTACAAGCAAATCTCCAATGGACATCGGGAGGAAGCACC
AACGACAACACCTACTTTGGCTACAGCACCCCCTGGGGGTATTTTGACTTCAACAGATTCCACTG
CCACTTCTCACCACGTGACTGGCAGCGACTCATCAACAACAACTGGGGATTCCGGCCAAAGAGAC
TCAACTTCAAGCTGTTCAACATCCAGGTCAAGGAGGTTACGACGAACGAAGGCACCAAGACCATC
GCCAATAACCTTACCAGCACCGTCCAGGTCTTTACGGACTCGGAGTACCAGCTACCGTACGTCCT
AGGCTCTGCCCACCAAGGATGCCTGCCACCGTTTCCTGCAGACGTCTTCATGGTTCCTCAGTACG
GCTACCTGACGCTCAACAATGGAAGTCAAGCGTTAGGACGTTCTTCTTTCTACTGTCTGGAATAC
TTCCCTTCTCAGATGCTGAGAACCGGCAACAACTTTCAGTTCAGCTACACACTTTCGAGGACGTGCC
TTTCCACAGCAGCTACGCACACAGCCAGAGTCTAGATCGACTGATGAACCCCCTCATCGACCAGT
ACCTATACTACCTGGTCAGAACACAGACAACTGGAACTGGGGGAACTCAAACTTTGGCATTCAGC
CAAGCAGGCCCTAGCTCAATGGCCAATCAGGCTAGAACTGGGTACCCGGGCCCTTGCTACCGTCA
GCAGCGCGTCTCCACAACCACCAACCAAAATAACAACAGCAACTTTGCGTGGACGGGAGCTGCTA
AATTCAAGCTGAACGGGAGAGACTCGCTAATGAATCCTGGCGTGGCTATGGCATCGCACAAAGAC
GACGAGGACCGCTTCTTTCCATCAAGTGGCGTTCTCATATTTGGCAAGCAAGGAGCCGGGAACGA
TGGAGTCGACAGCCAGGTGCTGATTACAGATGAGGAAGAAATTAAAGCCACCAACCCTGTAG
CCACAGAGGAATACGGAGCAGTGGCCATCAACAACCAGGCCGCTAACACGCAGGCGCAAACTGGA
CTTGTGCATAACCAGGGAGTTATTCCTGGTATGGTCTGGCAGAACCGGGACGTGTACCTGCAGGG
CCCTATTTGGGCTAAAATACCTCACACAGATCGGCAACTTTCACCCGTCTCCTCTGATGGGTGGAT
TTGGACTGAAACACCCACCTCCACAGATTCTAATTAAAAATACACCAGTGCCGGCAGATCCTCCT
CTTACCTTCAATCAAGCCAAGCTGAACTCTTTCATCACGCAGTACAGCACGGGACAAGTCAGCGT
GGAAATCGAGTGGGAGCTGCAGAAAGAAAACAGCAAGCGCTGGAATCCAGAGATCCAGTATACTT
CAAACTACTACAAATCTACAAATGTGGACTTTGCTGTCAATACCAAAGGTGTTTACTCTGAGCCT
CGCCCCATTGGTACTCGTTACCTCACCCGTAATTTGTAATTGCCTGTTAATCAATAAACCGGTTA
ATTCGTTTCAGTTGAACTTTGGTCTCTGCG

*FIG. 17*

AAV-11, NONSTRUCTURAL PROTEIN AND CAPSID PROTEIN GENES, COMPLETE CDS,
GENBANK ACCESSION NO. AY631966 AND MORI ET AL. (2004) VIROL. 330:375
ATGCCGGGCTTCTACGAGATCGTGATCAAGGTGCCGAGCGACCTGGACGAGCACCTGCCGGGC
ATTTCTGACTCGTTTGTGAACTGGGTGGCCGAGAAGGAATGGGAGCTGCCCCCGGATTCTGAC
ATGGATCGGAATCTGATCGAGCAGGCACCCCTGACCGTGGCCGAGAAGCTGCAGCGCGACTTC
CTGGTCCACTGGCGCCGCGTGAGTAAGGCCCCGGAGGCCCTCTTCTTTGTTCAGTTCGAGAAG
GGCGAGTCCTACTTCCACCTCCACGTTCTCGTCGAGACCACGGGGGTCAAGTCCATGGTCCTG
GGCCGCTTCCTGAGTCAGATCAGAGACAGGCTGGTGCAGACCATCTACCGCGGGGTCGAGCCC
ACGCTGCCCAACTGGTTCGCGGTGACCAAGACGCGAAATGGCGCCGGCGGGGGGAACAAGGTG
GTGGACGAGTGCTACATCCCCAACTACCTCCTGCCCAAGACCCAGCCCGAGCTGCAGTGGGCG
TGGACTAACATGGAGGAGTATATAAGCGCGTGTCTAAACCTCGCGGAGCGTAAACGGCTCGTG
GCGCAGCACCTGACCCACGTCAGCCAGACGCAGGAGCAGAACAAGGAGAATCTGAACCCGAAT
TCTGACCGCCCGTGATCAGGTCAAAAACCTCCGCGCGCTACATGGAGCTGGTCGGGTGGCTG
GTGGACCGGGGCATCACCTCCGAGAAGCAGTGGATCCAGGAGGACCAGGCCTCGTACATCTCC
TTCAACGCCGCCTCCAACTCGCGGTCCCAGATCAAGGCCGCGCTGGACAATGCCGGAAAGATC
ATGGCGCTGACCAAATCCGCGCCCGACTACCTGGTAGGCCCGTCCTTACCCGCGGACATTAAG
GCCAACCGCATCTACCGCATCCTGGAGCTCAACGGCTACGACCCCGCCTACGCCGGCTCCGTC
TTCCTGGGCTGGGCGCAGAAAAAGTTCGGTAAACGCAACACCATCTGGCTGTTTGGGCCCGCC
ACCACCGGCAAGACCAACATCGCGGAAGCCATAGCCCACGCCGTGCCCTTCTACGGCTGCGTG
AACTGGACCAATGAGAACTTTCCCTTCAACGATTGCGTCGACAAGATGGTGATCTGGTGGGAG
GAGGGCAAGATGACCGCCAAGGTCGTGGAGTCCGCCAAGGCCATTCTGGGCGGAAGCAAGGTG
CGCGTGGACCAAAAGTGCAAGTCCTCGGCCCAGATCGACCCCACGCCCGTGATCGTCACCTCC
AACACCAACATGTGCGCCGTGATCGACGGGAACAGCACCACCTTCGAGCACCAGCAGCCGCTG
CAGGACCGCATGTTCAAGTTCGAGCTCACCCGCCGTCTGGAGCACGACTTTGGCAAGGTGACC
AAGCAGGAAGTCAAAGAGTTCTTCCGCTGGGCTCAGGATCACGTGACTGAGGTGGCGCATGAG
TTCTACGTCAGAAAGGGCGGAGCCACCAAAAGACCCGCCCCAGTGACGCGGATATAAGCGAG
CCCAAGCGGGCCTGCCCCTCAGTTCCGGAGCCATCGACGTCAGACGCGGAAGCACCGGTGGAC
TTTGCGGACAGGTACCAAAACAAATGTTCTCGTCACGCGGGCATGCTTCAGATGCTGTTTCCC
TGCAAGACATGCGAGAGAATGAATCAGAATTTCAACGTCTGCTTCACGCACGGGGTCAGAGAC
TGCTCAGAGTGCTTCCCCGGCGCGTCAGAATCTCAACCCGTCGTCAGAAAAAAGACGTATCAG
AAACTGTGCGCGATTCATCATCTGCTGGGGCGGGCACCCGAGATTGCGTGTTCGGCCTGCGAT
CTCGTCAACGTGGACTTGGATGACTGTGTTTCTGAGCAATAAATGACTTAAACCAGGTATGGC
TGCTGACGGTTATCTTCCAGATTGGCTCGAGGACAACCTCTCTGAGGGCATTCGCGAGTGGTG
GGACCTGAAACCTGGAGCCCCGAAGCCCAAGGCCAACAGCAGAAGCAGGACGACGGCCGGGG
TCTGGTGCTTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCTCAAAGCGGG
TGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTTCAGGGCCAAGAAGAGGGTACTCGAACC
TCTGGGCCTGGTTGAAGAAGGTGCTAAAACGGCTCCTGGAAAGAAGAGACCGTTAGAGTCACC
ACAAGAGCCCGACTCCTCCTCGGGCATCGGCAAAAAAGGCAAACAACCAGCCAGAAAGAGGCT
CAACTTTGAAGAGGACACTGGAGCCGGAGACGGACCCCCTGAAGGATCAGATACCAGCGCCAT
GTCTTCAGACATTGAAATGCGTGCAGCACCGGGCGAAATGCTGTCGATGCGGGACAAGGTTC
CGATGGAGTGGGTAATGCCTCGGGTGATTGGCATTGCGATTCCACCTGGTCTGAGGGCAAGGT
CACAACAACCTCGACCAGAACCTGGGTCTTGCCCACCTACAACAACCACTTGTACCTGCGTCT
CGGAACAACATCAAGCAGCAACACCTACAACGGATTCTCCACCCCCTGGGGATATTTTGACTT
CAACAGATTCCACTGTCACTTCTCACCACGTGACTGGCAAAGACTCATCAACAACAACTGGGG
ACTACGACCAAAAGCCATGCGCGTTAAAATCTTCAATATCCAAGTTAAGGAGGTCACAACGTC
GAACGGCGAGACTACGGTCGCTAATAACCTTACCAGCACGGTTCAGATATTTGCGGACTCGTT
GTATGAGCTCCCGTACGTGATGGACGCGTGGACAAGAGGGGAGGCCTGCCTCCTTTCCCCAATGA
CGTGTTCATGGTGCCTCAATATGGCTACTGTGGCATCGTGACTGGCGAGAATCAGAACCAAAC
GGACAGAAACGCTTTCTACTGCCTGGAGTATTTCCTTCGCAAATGTTGAGAACTGGCAACAA
CTTTGAAATGGCTTACAACTTTGAGAAGGTGCCGTTCCACTCAATGTATGCTCACAGCCAGAG
CCTGGACAGACTGATGAATCCCCTCCTGGACCCAGTACCTGTGGCACTTACAGTCGACTACCTC
TGGAGAGACTCTGAATCAAGGCAATGCAGCAACCACATTTGGAAAAATCAGGAGTGGAGACTT
TGCCTTTTACAGAAAGAACTGGCTGCCTGGGCCTTGTGTTAAACAGCAGAGATTCTCAAAAAC
TGCCAGTCAAAATTACAAGATTCCTGCCAGCGGGGGCAACGCTCTGTTAAAGTATGACACCCA
CTATACCTTAAACAACCGCTGGAGCAACATCAGCGCCCGGACCTCCAATGGCCACAGCCGGACC
TTCGGATGGGGACTTCAGTAACGCCCAGCTTATATTCCCTGGACCATCTGTTACCGGAAATAC
AACAACTTCAGCCAACAATCTGTTGTTTACATCAGAAGAAGAAATTGCTGCCACCAACCCAAG
AGACACGGACATGTTTGGCCAGATTGCTGACAATAATCAGAATGCTACAACTGCTCCCATAAC
CGGCAACGTGACTGCTATGGGCGACTGCTGGCATGGTGTGGCAAAACAGAGACATTTACTA
CCAAGGGCCAATTTGGGCCAAGATCCCACACGCGGGACATTTTCATCCTTCACCGCTGAT
TGGTGGGTTTGGACTGAAACACCCGCCTCCCAGATATTCATCAAGAACACTCCCGTACCTGC
CAATCCTGCGACAACCTTCACTGCAGCCAGAGTGGACTCTTTCATCACACAATACAGCACCGG
CCAGGTCGCTGTTCAGATTGAATGGGAAATTGAAAAGGAACGCTCCAAACGCTGGAATCCTGA
AGTGCAGTTTACTTCAAACTATGGGAACCAGTCTTCTATGTTGTGGGCTCCTGATACAACTGG
GAAGTATACAGAGCCGCGGGTTATTGGCTCTCGTTATTTGACTAATCATTTGTAA

FIG. 18

AAV-13, NONSTRUCTURAL PROTEIN AND CAPSID PROTEIN GENES, COMPLETE CDS, GENBANK ACCESSION NO. EU285562 AND SCHMIDT ET AL. (2008) J. VIROL. 82:8911

```
CCGCGAGTGAGCGAACCAGGAGCTCCATTTTGCCCGCGAATTTTGAACGAGCAGCAGCCATGC
CGGGATTCTACGAGATTGTCCTGAAGGTGCCCAGCGACCTGGACGAGCACCTGCCTGGCATTT
CTGACTCTTTTGTAAACTGGGTGGCGGAGAAGGAATGGGAGCTGCCGCCGGATTCTGACATGG
ATCTGAATCTGATTGAGCAGGCACCCCTAACCGTGGCCGAAAAGCTGCAACGCGAATTCCTGG
TCGAGTGGCGCCGCGTGAGTAAGGCCCCGGAGGCCCTCTTCTTTGTTCAGTTCGAGAAGGGGG
ACAGCTACTTCCACCTACACATTCTGGTGGAGACCGTGGGCGTGAAATCCATGGTGGTGGGCC
GCTACGTGAGCCAGATTAAAGAGAAGCTGGTGACCCGCATCTACCGCGGGGTCGAGCCGCAGC
TTCCGAACTGGTTCGCGGTGACCAAGACGCGTAATGGCGCCGGAGGCGGGAACAAGGTGGTGG
ACGACTGCTACATCCCCAACTACCTGCTCCCCAAGACCCAGCCCGAGCTCCAGTGGGCGTGGA
CTAATATGGACCAGTATTTAAGCGCCTGTTTGAATCTCGCGGAGCGTAAACGGCTGGTGGCGC
AGCATCTGACGCACGTGTCGCAGACGCAGGAGCAGAACAAAGAGAACCAGAATCCCAATTCTG
ACGCGCCGGTGATCAGATCAAAAACCTCCGCGAGGTACATGGAGCTGGTCGGGTGGCTGGTGG
ACCGCGGGATCACGTCAGAAAAGCAATGGATCCAGGAGGACCAGGCCTCTTACATCTCCTTCA
ACGCCGCCTCCAACTCGCGGTCACAAATCAAGGCCGCACTGGACAATGCCTCCAAATTTATGA
GCCTGACAAAAACGGCTCCGGACTACCTGGTGGGAAACAACCCGCCGGAGGACATTACCAGCA
ACCGGATCTACAAAATCCTCGAGATGAACGGGTACGATCCGCAGTACGGGCCTCCGTCTTCC
TGGGCTGGGCGCAAAAGAAGTTCGGGAAGAGGAACACCATCTGGCTCTTTGGGCCGGCCACGA
CGGGTAAAACCAACATCGCTGAAGCTATCGCCCACGCCGTGCCCTTTTACGGCTGCGTGAACT
GGACCAATGAGAACTTTCCGTTCAACGATTGCGTCGACAAGATGGTGATCTGGTGGGAGGAGG
GCAAGATGACGGCCAAGGTCGTGGAGTCCGCCAAGGCCATTCTGGGCGGAAGCAAGGTGCGCG
TGGACCAAAAGTGCAAGTCATCGGCCCAGATCGACCCAACTCCCGTCATCGTCACCTCCAACA
CCAACATGTGCGCGGTCATCGACGGAAATTCCACCACCTTCGAGCACCAACAACCACTCCAAG
ACCGGATGTTCAAGTTCGAGCTCACCAAGCGCCTGGAGCACGACTTTGGCAAGGTCACCAAGC
AGGAAGTCAAGGACTTTTTTCCGGTGGGCGTCAGATCACGTGACTGAGGTGTCTCACGAGTTTT
ACGTCAGAAAGGGTGGAGCTAGAAGAGGCCCGCCCCAATGACGCAGATATAAGTGAGCCCA
AGCGGGCCTGTCCGTCAGTTGCGCAGCCATCGACGTCAGACGCGGAAGCTCCGGTGGACTACG
CGGACAGGTACCAAAACAAATGTTCTCGTCACGGTGGGCATGAATCTGATGCTTTTTTCCCTGCC
GGCAATGCGAGAGAATGAATCAGAATGTGGACATTTGCTTCACGCACGGGTCATGGACTGTG
CCGAGTGCTTCCCCGTGTCAGAATCTCAACCCGTGTCTGTCGTCAGAAAGCGGACATATCAGA
AACTGTGTCCGATTCATCACATCATGGGGAGGGCGCCCGAGGTGGCTTGTTCGGCCTGCGATC
TGGCCAATGTGGACTTGGATGACTGTGACATGGACATGAATAAATGACTCAAACCAGATATGACT
GACGGTTACCTTCCAGATTGGCTAGAGGACAACCTCTCTGAAGGCGTTCGAGAGTGGTGGGCG
CTGCAACCTGGAGCCCCTAAACCCAAGGCAAATCAACAACATCAGGACAACGCTCGGGGTCTT
GTGCTTCCGGGTTACAAATACCTCGGACCCGGCAACGGACTTGACAAGGGGGAACCCGTCAAC
GCAGCGGACGCGGCAGCCCTCGAACACGACAGGCCTACGACCAGCAGCTCAAGGCCGGTGAC
AACCCCTACCTCAAGTACAACCACGCGACGCCGAGTTTCAGGAGCGTCTTCAAGAAGATACG
TCTTTTGGGGGCAACCTCGGACGAGCAGTCTTCCAGGCCAAAAAGAGGATCCTTGAGCCTCTG
GGTCTGGTTGAGGAAGCGGCTAAGACGGCTCCTGGAAAAAAGAGACCTGTAGAGCAATCTCCA
GCAGAACCGGACTCCTCTTCCGGGCATCGGCAAATCAGGCCAGCAGCCCGCTAGAAAAAGACTG
AATTTTGGTCAGACTGGCACACAGAGTCAGTCCCAGACCCTCAACCACTCGGACAACCTCCC
GCAGCCCCTCTGGTGTGGGATCTACTACAATGGCTTCAGGCGGTGGCGCACCAATGGCAGAC
AATAACGAGGGTGCCGATGGAGTGGGTAATTCCTCAGGAAATTGGCATTGCGATTCCCAATGG
CTGGGCGACAGAGTCATCACCACCAGCACCCGCACCTGGGCCCTGCCCACCTACAACAATCAC
CTCTACAAGCAAATCTCCAGCCAATCAGGAGCCACCAACGACAACCACTACTTTGGCTACAGC
ACCCCCTGGGGGTATTTTGACTTCAACAGATTCCACTGCCACTTTTCACCACGTGACTGGCAA
AGACTCATCAACAACAACTGGGGATTCCGACCCAAGAGACTCAACTTCAAGCTCTTTAACATT
CAAGTCAAAGAGGTCACGCAGAATGACGGTACGACGACGATTGCCAATAACCTTACCAGCACG
GTTCAGGTGTTTACTGACTCCGAGTACCAGCTCCCGTACGTCCTCGGCTCGGCGCATCAGGGA
TGCCTCCCGCCGTTCCCAGCAGACGTCTTCATGGTCCCACAGTATGGATACCTCACCCTGAAC
AACGGGAGTCAGGCGGTAGGACGCTCTTCCTTTTACTGCCTGGAGTACTTTCCTTCTCAGATG
CTGCGTACTGGAAACAACTTTCAGTTTAGCTACGAGTTTGAAGACGTGCCTTTCCACAGCAGC
TACGCTCACAGCCAAAGTCTGGACCGTCTCATGAATCCTCTGATCGACCAGTACCTGTACTAT
CTGAACAGGACACAAACAGCCAGTGGAACTCAGCAGTCTCGGCTACTGTTTAGCCAAGCTGGA
CCCACCAGTATGTCTCTTCAAGCTAAAAACTGGCTGCCTGGACCTTGCTACAGACAGCAGCGT
CTGTCAAAGCAGGCAAACGACAACAACAGCAACAGCCAACTTTCCCTGGACTGGTGCCACCAAATAT
CATCTGAATGGCCGGGACTCATTGGTGAACCCGGGCCCTGCTATGGCCAGTCACAAGGATGAC
AAAGAAAAGTTTTTCCCCATGCATGGAACCCTGATATTTGGTAAAGAAGGAACAAATGCCAAC
AACGCGGATTTGGAAAATGTCATGATTACAGATGAAGAAGAAATCCGCACCACCAATCCCGTG
GCTACGGAGCAGTACGGGACTGTGTCAAATAATTTGCAAAACTCAAACGCTGGTCCAACTACT
GGAACTGTCAATCACCAAGGAGCGTTACCTGGTATGGTGTGGCAGGATCGAGACGTGTACCTG
CAGGGACCCATTTGGGCCAAGATTCCTCACACCGATGGACACTTTCATCCTTCTCCACTGATG
GGAGGTTTTGGGCTCAAACACCCGCCTCCTCAGATCATGATCAAAAACACTCCCGTTCCAGCC
AATCCTCCCACAACTTTAGTGCGGCAAAAGTTTGCTTCATCACACAGTACTCCACGGGG
CAGGTCAGCGTGGAGATCGAGTGGGAGCTGCAGAAGGAGAACAGCAAACGCTGGAATCCCGAA
ATTCAGTACACTTCCAACTACAACAAATCTGTTAATGTGGACTTTACTGTGGACACTAATGGT
GTGTATTCAGAGCCTCGCCCCATTGGCACCAGATACCTGACTCGTAATCTGTAATTGCTTGTT
AATCAATAAACCGGTTAATTCG
```

*FIG. 19*

B19 PARVOVIRUS, COMPLETE SEQUENCE, GENBANK ACCESSION NO. NC_000883 AND
SHADE ET AL. (1986) *J. VIROL.* 58:921
```
CCAAATCAGATGCCGCCGGTCGCCGCCGGTAGGCGGGACTTCCGGTACAAGATGGCGGACAATTACGTCATTT
CCTGTGACGTCATTTCCTGTGACGTCACTTCCGGTGGGCGGGACTTCCGGAATTAGGGTTGGCTCTGGGCCAG
CTTGCTTGGGGTTGCCTTGACACTAAGACAAGCGGCGCGCCGCTTGTCTTAGTGGCACGTCAACCCCAAGCGC
TGGCCCAGAGCCAACCCTAATTCCGGAAGTCCCGCCCACCGGAAGTGACGTCACAGGAAATGACGTCACAGGA
AATGACGTAATTGTCCGCCATCTTGTACCGGAAGTCCCGCCTACCGGCGGCGACCGGCGGCATCTGATTTGGT
GTCTTCTTTTAAATTTTAGCGGGCTTTTTTCCCGCCTTATGCAAATGGGCAGCCATTTTAAGTGTTTCACTAT
AATTTTATTGGTCAGTTTTGTAACGGTTAAAATGGGCGGAGCGTAGGCGGGACTACAGTATATATAGCACGG
CACTGCCGCAGCTCTTTCTTTCTGGGCTGCTTTTTCCTGGACTTTCTTGCTGTTTTTTGTGAGCTAACTAACA
GGTATTTATACTACTTGTTAACATACTAACATGGAGCTATTTAGAGGGGTGCTTCAAGTTTCTTCTAATGTTC
TGGACTGTGCTAACGATAACTGGTGGTGCTCTTTACTGGATTTAGACACTTCTGACTGGGAACCACTAACTCA
TACTAACAGACTAATGGCAATATACTTAAGCAGTGTGGCTTCTAAGCTTGACTTTACCGGGGGGCCACTAGCG
GGGTGCTTGTACTTTTTTCAAGTAGAATGTAACAAATTTGAAGAAGGCTATCATATTCATGTGGTTATTGGG
GGCCAGGGTTAAACCCCAGAAACCTCACAGTGTGTGTAGAGGGGTTATTTAATAATGTACTTTATCACCTTGT
AACTGAAAATGTAAAGCTAAAATTTTTGCCAGGAATGCTACAAAAGGCAAATACTTTAGAGATGGAGAGCAG
TTTATAGAAAACTATTTAATGAAAAAAATACCTTTAAATGTTGTATGGTGTGTTACTAATATTGATGGATATA
TAGATACCTGTATTTCTGCTACTTTTAGAAGGGGAGCTTGCCATGCCAAGAAACCCCGCATTACCACAGCCAT
AAATGCACACTAGTAGTGATGCTGGGGAGTCTAGCGGCACAGGGGCAGAGGTTGTGCCAATTAATGGGAAGGGA
ACTAAGGCTAGCATAAAGTTTCAAACTATGGTAAACTGGTTGTGTGAAAACAGAGTGTTTACAGAGGATAAGT
GGAAACTAGTTGACTTTAACCAGTACACTTTACTAAGCAGTAGTCACAGTGGAAGTTTCAAATTCAAAGTGC
ACTAAAACTAGCAATTTATAAAGCAACTAATTTAGTGCCTTACAAGCACATTTCTATTGCATACAGACTTTGAG
CAGGTTATGTGTATTAAAGACAATAAAATTGTTAAATTGTTACTTTGTCAAAACTATGACCCCCTATTAGTGG
GGCAGCATGTGTTAAAGTGGATTGATAAAAAATGTGGCAAGAAAAATACACTGTGGTTTTATGGGCCGCCAAG
TACAGGAAAAACAAACTTGGCAATGGCCATTGCTAAAAGTGTTCCAGTATATGGCATGGTTAACTGGAATAAT
GAAAACTTTCCATTTAATGATGTAGCAGGGAAAAGCTTGGTGGTCTGGGATGAAGGTATTATTAAGTCTACAA
TTGTAGAAGCTGCAAAAGCCATTTTAGGCGGGCAACCCACCAGGGTAGATCAAAAAGTGCGTGGAAGTGTAGC
TGTGCCTGGAGTACCTGTGGTTATAACCAGCAATGTGACATTACTTTTGTTGTAAGCGGAACACTACAACA
ACTGTACATGCTAAAGCCTTAAAAGAGCGAATGGTAAAGTTAAACTTTACTGTAAGATGCAGCCCTGACATGG
GGTTACTAACGAGAGGCTGATGTACAACAGTGGCTTACATGGTGTAATGCACAAAGCTGGGACCACTATGAAAA
CTGGGCAATAAACTACACTTTTGATTTCCCTGGAATTAATGCAGATGCCCTCCACCCAGACCTCCAAACCACC
CCAATTGTCACAGACACCAGTATCAGCAGCAGTGGTGGTGAAAGCTCTGAAGAACTCAGTGAAAGCAGCTTTT
TTAACCTCATCACCCCAGGCGCCTGGAACACTGAAACCCCGCCTCTAGTACGGCCCATCCCCGGGACCAGTTC
AGGAGAATCATTTGTCGGAAGCTCAGTTTCCTCCGAAGTTGTAGCTGCATCGTGGGAAGAAGCCTTCTACACA
CCTTTGGCAGACCAGTTTCGTGAACTGTTAGTTGGGGTTGATTATGTGTGGGACGGTGTAAGGGGTTTACCTG
TGTGTTGTGTGCAACATATTAACAATAGTGGGGGAGGCTTGGGACTTTGTCCCCATTGCATTAATGTAGGGGC
TTGGTATAATGGATGGAAATTTCGAGAATTTACCCCAGATTTGGTGCGGTGTAGCTGCCATGTGGGAGCTTCT
AATCCCTTTTCTGTGCTAACCTGCAAAAAATGTGCTTACCTGTCTGGATTGCAAAGCTTTGTAGATTATGAGT
AAAGAAAGTGGCAAATGGTGGGAAAGTGATGATAAATTTGCTAAAGCTGTGTATCAGCAATTTGTGGAATTTT
ATGAAAAGGTTACTGGAACAGACTTAGAGCTTATTCAAATATTAAAAGATCACTATAATATTTCTTTAGATAA
TCCCCTAGAAAACCATCCTCTCTGTTTGACTTAGTTGCTCGTATTAAAAATAACCTTAAAAACTCTCCAGAC
TTATATAGTCATCATTTTCAAAGTCATGGACAGTTATCTGACCACCCCATGCCTTATCATCCAGTAGCAGTC
ATGCAGAACCTAGAGGAGAAAATGCAGTATTATCTAGTGAAGACTTACACAAGCCTGGGCAAGTTAGCGTACA
ACTACCCGGTACTAACTATGTTGGGCCTGGCAATGAGCTACAAGCTGGGCCCCCGCAAAGTGCTGTTGACAGT
GCTGCAAGGATTCATGACTTTAGGTATAGCCAACTGGCTAAGTTGGGAATAAATCCATATACTCATTGGACTG
TAGCAGATGAAGAGCTTTTAAAAAATATAAAAAATGAAACTGGGTTTCAAGCACAAGTAGTAAAAGACTACTT
TACTTTAAAAGGTGCAGCTGCCCCTGTGGCCCATTTTCAAGGAAGTTTGCCGGAAGTTCCCGCTTACAACGCC
TCAGAAAAATACCCAAGCATGACTTCAGTTAATTCTGCAGAAGCCAGCACTGGTGCAGGAGGGGGTGGCAGTA
ATCCTGTCAAAAGCATGTGGAGTGAGGGGGCCACTTTTAGTGCCAACTCTGTAACTTGTACATTTTCCAGACA
GTTTTTAATTCCTTATGACCCAGAGCACCATTATAAAGGTGTTTTCTCCCCGCAAGCAGCTGCCACAATGCC
AGTGGAAAGGAGGCAAAAGGTTTGCACAATTAGTCCCATAATGGGATACTCAACCCCATGGAGATATTTAGATT
TTAATGCTTTAAATTTATTTTTTTCACCTTTAGAGTTTCAGCACTTAATTGAAAATTATGGAAGTATAGCTCC
TGATGCTTTAACTGTAACCATATCAGAAATTGCTGTTAAGGATGTTACAGACAAAACTGGAGGGGGGGTACAG
GTTACTGACAGCACTACAGGGCGCCTATCCATGTTAGTAGACCATGAATACAAGTACCCATATGTGTAGGAC
AAGGTCAGGATACTTTAGCCCCAGAACTTCCTATTTGGGTATACTTTCCCCCCTCAATATGCTTACTTAACAGT
AGGAGATGTTAACACAGAGGAATCTCTGGAGACAGCAAAAAATTTAGCAAGTGAAGAATCAGCATTTTATGTT
TTGGAACACAGTTCTTTCAGCTTTTAGGTACAGGAGGTACAGCAACTATGTCTTATAAGTTTCCTCCAGTGC
CCCAGAAAATTTAGAGGGCTGCAGTCAACACTTTTATGAAATGTACAATCCCTTATACGGATCCCGCTTAGG
GGTTCCTGACACATTAGGAGGTGACCCAAAATTTAGATCTTTTAACACATGAAGACCATGCAATTCAGCCCCAA
AACTTCATGCCAGGGCCACTAGTAAACTCAGTGTCTACAAAGGAGGGAGACAGCTCTAATACTGGAGCTGGAA
AAGCCTTAACAGGCCTTAGCACAGGCACCTCTTACAAATATCCTTACGCCCTGGGCCAGTGTCACA
GCCATACCACCACTGGGACACAGATAAATATGTTCCAGGAATAAATGCCATTTCTCATGGTCAGACCACTTAT
GGTAACGCTGAAGACAAAGAGTATCAGCAAGGAGTGGGTAGATTTCCAAATGAAAAGAACAGCTAAAACAGT
TACAGGGTTTAAACATGCACACCTATTTCCCCAATAAAGGAAACCCAGCAATATACAGATCAAATTGAGCGCCC
CCTAATGGTGGGTTCTGTATGGAACAGAAGAGCCCTTCACTATGAAAGCCAGCTGTGGAGTAAAATTCCAAAT
TTAGATGACAGTTTTAAAACTCAGTTTGCAGCCTTAGGAGGATGGGGTTTGCATCAGCCACCTCCTCAAATAT
TTTTAAAAATATTACCACAAAGTGGGCCAATTGGAGTGATTAAAATCAATGGGAATTACTACCTTAGTTCAGTA
TGCCGTGGGAATTATGACAGTAACTATGACATTTAAATTGGGGCCCCGTAAAGCTACGGGACGGTGGAATCCT
CAACCTGGAGTATATCCCCCGCACGCAGCAGGTCATTTACCATATGTACTATATGACCCCACAGCTACAGATG
CAAAACAACACCACAGGCCATGGATACGAAAAGCCTAGAAGATTTGTGGACAGCCAAAAGCCGTGTGCACCCATT
GTAAACACTCCCCACCGTGCCCTCAGCCAGGATGCGTAACTAAACGCCCACCAGTACCACCCAGACTGTACCT
GCCCCCCTCCTGTACCTATAAGACAGCCTAACACAAAAGATATGACAATGTAGAAATTTAAGTACTTAACCAGA
TATGACAACATGTTATTAGAATGTTAAGATTGTGTAATATGTATCAAAATTTAGAAAAATAAACATTTGTTG
TGGTTAAAAAATTATGTTGTTGCGCTTTAAAAATTTAAAAGAAGACACCAAATCAGATGCCGCCGGTCGCCGC
CGGTAGGCGGGACTTCCGGTACAAGATGGCGGACAATTACGTCATTTCCTGTGACGTCATTTCCTGTGACGTC
ACTTCCGGTGGGCGGGACTTCCGGAATTAGGGTTGGCTCTGGGCCAGCGCTTGGGGTTGACGTGCCACTAAGA
CAAGCGGCGCGCCGCTTGTCTTAGTGTCAAGGCAACCCCAAGCAAGCTGGCCCAGAGCCAACCCTAATTCCGG
AAGTCCCGCCCACCGGAAGTGACGTCACAGGAAATGACGTCACAGGAAATGACGTAATTGTCCGCCATCTTGT
ACCGGAAGTCCCGCCTACCGGCGGCGACCGGCGGCATCTGATTTGG
```

FIG. 20

MINUTE VIRUS FROM MOUSE (MVM), COMPLETE SEQUENCE, GENBANK ACCESSION
NO. NC_001510
ATTTTTAGAACTGACCAACCATGTTCACGTAAGTGACGTGATGACGCGCGCTGCGCGCGCGCCTTCGGACGTC
ACACGTCACTTACGTTTCACATGGTTGGTCAGTTCTAAAAATGATAAGCGGTTCAGGGAGTTTAAACCAAGGC
GCGAAAAGGAAGTGGGCGTGGTTTAAAGTATATAAGCAACTACTGAAGTCAGTTACTTATCTTTTCTTTCATT
CTGTGAGTCGAGACGGCACAGAAAGAGAGTAACCAACTAACCATGGCTGGAAATGCTTACTCTGATGAAGTTTT
GGGGAGCAACCAACTGGTTAAAGGAAAAAGTAACCAGGAAGTGTTCTCATTTGTTTTTAAAAATGAAAATGTT
CAACTGAATGGAAAAGATATCGGATGGAATAGTTACAAAAAAGAGCTGCAGGAGGACGAGCTGAAATCTTTAC
AACGAGGAGCGGAAACTACTTGGGACCAAAGCGAGGACATGGAATGGGAAACCACAGTGGATGAAATGACCAA
AAAGCAAGTATTCATTTTTGATTCTTTGGTTAAAAAATGTTTATTTGAAGTGCTTAACACAAAGAATATATTT
CCTGGTGATGTTAATTGGTTTGTGCAACATGAATGGGAAAAAGACCAAGGCTGGCACTGCCATGTACTAATTG
GAGGAAAGGACTTTAGTCAAGCTCAAGGGAAATGGTGGAGAAGGCAACTAAATGTTTACTGGAGCAGATGGTT
GGTAACAGCCTGTAATGTGCAACTAACACCAGCTGAAAGAATTAAACTAAGAGAAATAGCAGAAGACAATGAG
TGGGTTACTCTACTTATAAGCATAAGCAAACCAAAAAAGACTATACCAAGTGTGTTCTTTTTGGAAACA
TGATTGCTTACTATTTTTTAACTAAAAAGAAAATAAGCACTAGTCCACCAAGAGACGGAGGCTATTTTCTTAG
CAGTGACTCTGGCTGGAAAACTAACTTTTTAAAAGAAGGCGAGCGCCATCTAGTGAGCAAACTATACACTGAT
GACATGCGGCCAGAAACGGTTGAAACCACAGTAACCACTGCGCAGGAAACTAAGCGCGGCAGAATTCAAACTA
AAAAAGAAGTTTCTATTAAAACTACACTTAAAGAGCTGGTGCATAAAAGAGTAACCTCACCAGAGGACTGGAT
GATGATGCAGCCAGACAGTTACATTGAAATGATGGCTCAACCAGGTGGAGAAAACCTGCTGAAAAATACGCTA
GAGATTTGTACACTAACTCTAGCCACAACCAAAACAGCATTTGACTTAATTTTAGAAAAAGCTGAAACCAGCA
AACTAACCAACTTTTCACTGCCTGACACAAGAACCTGCAGAATTTTTGCTTTTCATGGCTGGAACTATGTTAA
AGTTTGCCATGCTATTTGCTGTGTTTTAAACAGACAAGGAGGCAAAAGAAATACTGTTTTATTTCATGGACCA
GCCAGCACAGGCAAATCTATTATTGCACAAGCCATAGCACAAGCAGTTGGCAATGTTGGTTGCTATAATGCAG
CCAATGTAAACTTTCCATTTAATGACTGTACCAACAAGAACTTGATTTGGGTAGAAGAAGCTGGTAACTTTGG
ACAGCAAGTAAACCAGTTTAAAGCCATTTGCTCTGGTCAAACTATTCGCATTGATCAAAAAGGAAAAGGCAGC
AAACAGATTGAACCAACACCAGTCATCATGACCAAAATGAGAACATTACAGTGGTCAGAATAGGCTGCGAAG
AAAGACCAGAACACACTCAACCAATCAGAGACAGAATGCTTAACATTCATCTAACACATACCTTGCCTGGTGA
CTTTGGTTTGGTTGACAAAAATGAATGGCCCATGATTTGTGCTTGGTTGGTAAAGAATGGTTACCAATCTACC
ATGGCAAGCTACTGTGCTAAATGGGGCAAAGTTCCTGATTGGTCAGAAAACTGGGGAGGCAAGGTTGGTCACTACTTTTTTAGA
ACCAAGCGCGCTTTTGCACCTAAGCTTGCTACTGACTCTGAACCTGGAACTTCTGGTGTAAGCAGAGCTGGTA
AACGCACTAGACCACCTGCTTACATTTTTATTAACCAAGCCAGAGCTAAAAAAAAACTTACTTCTTCTGCTGC
ACAGCAAAGCAGTCAAACCATGAGTGATGGCACCGCCAAACCTGACGGCAGGAAACGCTGTCCACTCAGCTGCA
AGAGTTGAACGAGCAGCTGACGGCCCTGGAGGCTCTGGGGTGGGGGCTCTGGCGGGGGTGGGGTTGGTGTTT
CTACTGGGTCTTATGATAATCAAACGCATTATAGATTCTTGGGTGACGGCTGGGTAGAAATTACTGCACTAGC
AACTAGACTAGTACATTTAAACATGCCTAAATCAGAAAACTATTGCAGAATCAGAGTTCACAATACAACAGAC
ACATCAGTCAAAGGCAACATGGCAAAAGATGATGCTCATGAGCAAATTTGGACACCATGGAGCTTGGTGGATG
CTAATGCTTGGGGAGTTTGGCTCCAGCCAAGTGACTGGCAATACATTTGCAACACCATGAGCCAGCTTAACTT
GGTATCACTTGATCAAGAAATATTCAATGTAGTGCTGAAAACTGTTACAGGACAAGACTTAGGAGGTCAAGCT
ATAAAAATATACAACAATGACCTTACAGCTTGCATGATGGTTGCAGTAGACTCAAACAACATTTTGCCATACA
CACCTGCAGCAAACTCAATGGAAACACTTGGTTTCTACCCCTGGAAACCAACCATAGCATCACCATACAGGTA
CTATTTTTGCGTTGACAGAGATCTTTCAGTGACCTACGAAAATCAAGAAGGCACAGTTGAACATAATGTGATG
GGAACACCAAAAGGAATGAATTCTCAATTTTTTACCATTGAGAACACACAAACAAATACATTGCTCAGAACAC
GGGACGAATTTGCCACAGGTACTTACTACTTTGACACAAATTCAGTTAAACTCACACACACGTGGCAAACCAA
CCGTCAACTTGGACAGCCTCCACTGCTGTCAACCTTTCCTGAAGCTGACACTGATGCAGGTACACTTACTGCT
CAAGGGAGCAGACATGGAACAACACAAATGGGGGTTAACTGGGTGAGTGAGCAATCAGAAACCAGACCTGCTC
AAGTAGGATTTTGTCAACCACACAATGACTTTGAAGCCAGCAGAGCTGGACCATTTGCTGCCCCAAAAGTTCC
AGCAGATATTACTCAAGGAGTAGACAAAGAAGCCAATGGCAGTGTTAGATACAGTTATGGCAAACAGCATGGT
GAAAATTGGGCTTCACATGGACCAGCACCAGAGCGCTACACATGGGATGAAACAAGACTTTGGTTCAGGTAGAG
ACACCAAAGATGGTTTTATTCAATCAGCACCACTAGTTGTTCCACCACCTAAATGGCATTCTTACAAATGC
AAACCCTATTGGGACTAAAAATGACATTCATTTTTCAAATGTTTTTAACAGCTATGGTCCACTAACTGCATTT
TCACACCCAAGTCCTGTATACCCTCAAGGACAAATATGGGACAAAGAACTAGATCTTGAACACAAACCTAGAC
TTCACATAACTGCTCCATTTGTTTGTAAAAACAATGCACCTGGACAAATGTTGGTTAGATTAGGACCAAACCT
AACTGACCAATATGATCCAAACGGAGCCACACTTTCTAGAATTGTTACATACGGTACATTTTCTGGAAAGGA
AAACTAACCATGAGACGAAACTTAGAGCTAACACCACCACCTTGGAAACCCAGTGTACCAAGTAAGTGCTGAAGACA
ATGGCAACTCATACATGAGTGTAACTAAATGGTTACCAACTGCTACTGGAAACATGCAGTCTGTGCCGCTTAT
AACAAGACCTGTTGCTAGAAATACTTACTAACTAACCATGCTTTTCTTTCTGTACTTCATATATTATTAAGA
CTAATAAAGATACAACATAGAAATATTATTACAGAATGATTTAAGAAATAATATTGTACTTAGTAA
CTGTTAAAAATAATAGAACCTTTGGAATAACAAGATAGTTAGTTGGTAATGTTAGATAGAATAAGAAGATCA
TGTATAATGAATAAAAGGGTGGAAGGGTGGTTGGTAGGTTAATGTTAGATAGAATAAGAAGATCATGTATAAT
GAATAAAGGGTGGAAGGGTGGTTGGTAGGTATTCCCTTAGACTTGATGTTAAGGACCAAAAAAATAATAAAA
CTTTTTTAAAACTCAACCAAGACTACTGTCTATTCAGTGAACCAACTGAACCATTAGTATTACTATGTTTTA
GGGTGGGAGGGTGGGAGATACATGTGTTCGCTATGAGCGAACTGGTACTGGTTGGTTGCTCTGCTCAACCAAC
CAGACCGGCAAAGCCGGTCTGGTTGGTTGAGCGCAACCAACCAGTACCAGTTCGCTCATAGCGAACACATGTA
TCTCCCACCCTCCCACCCTAAAAACATAGTAATACTAAT

*FIG. 21*

GOOSE PARVOVIRUS, COMPLETE SEQUENCE, GENBANK ACCESSION NO. NC_001701
CTCATTGGAGGGTTCGTTCGTTCGAACCAGCCAATCAGGGGAGGGGGAAGTGACGCAAGTTCCGGTCACATG
CTTCCGGTGACGCACATCCGGTGACGTAGTTCCGGTCACGTGCTTCCTGTCACGTGTTTCCGGTCACGTGAC
TTCCGGTCATGTGACTTCCGGTGACGTGTTTCCGGCTGTTAGGTTGACCACGCGCATGCCGCGCGGTCAGCC
CAATAGTTAAGCCGGAAACACGTCACCGGAAGTCACATGACCGGAAGTCACGTGACCGGAAACACGTGACAG
GAAGCACGTGACCGGAACTACGTCACCGGATGTGCGTCACCGGAAGCATGTGACCGGAACTTGCGTCACTTC
CCCCTCCCCTGATTGGCTGGTTCGAACGAACGAACCCTCCAATGAGACTCAAGGACAAGAGGATATTTTGCG
CGCCAGGAAGTGACGTGCAATGCCACCCTATATAAGCCAGGAAACTTCCGGTTTAGTTCATTCGTTACTCTG
CTCTCAGAGAGAACGGACCTCAGGTCGGAGAGATGGCACTTTCTAGGCCTCTTCAGATTTCTTCTGATAAAT
TCTATGAAGTTATTATTAGATTATCATCGGATATTGATCAAGATGTCCCCGGTCTGTCTCTTAACTTTGTAG
AATGGCTTTCTACCGGAGTTTGGGAGCCCACGGGCATCTGGAACATGGAGCATGTGAATCTACCGATGGTGA
CCTTGGCAGAGAAGATCAAGAACATTTTCATACAAAGATGGAATCAGTTCAACCAGGACGAAACGGACTTCT
TCTTTCAACTGGAAGAAGGCAGTGAGTACATTCATCTTCATTGCTGTATTGCCCAGGGCAATGTACGGTCTT
TTGTTCTCGGGAGATATATGTCTCAGATAAAAGACTCTATCATAAGAGATGTATATGAAGGGAAACAAATCA
AGATCCCCGATTGGTTTGCTATTACTAAAACCAAGAGGGGAGGACAGAATAAGACCGTGACTGCAGCATACA
TACTGCATTACCTTATTCCTAAAAAGCAACCTGAACTGCAATGGGCCTTTACCAATATGCCTTTATTCACTG
CTGCTGCTCTTTGTCTGCAAAAGCGGCAAGAATTGCTGGATGCATTTCAAGAAAGTGATTTGGCTGCCCCTT
TACCTGATCCTCAAGCATCAACTGTGGCACCGCTTATTTCCAACAGAGCGGCAAAGAACTATAGCAACCTTG
TTGATTGGCTCATTGAAATGGGGATAACATCTGAGAAGCAATGGCTCACTGAGAACCGAGAGAGCTACAGAA
GCTTTCAAGCAACTTCTTCAAATAATAGACAAGTGAAAGCTGCACTGGAAAATGCCCGTGCTGAAATGTTAT
TGACAAAGACTGCAACTGATTACCTGATAGGAAAAGACCCTGTCCTGGATATAACTAAGAATAGGGTCTATC
AAATTCTGAAAATGAATAACTACAACCCTCAATACATAGGAAGTATCCTGTGCGGCTGGGTGAAGAGAGAGT
TCAACAAAAGAAACGCCATATGGCTCTACGGACCTGCCACCACCGGGAAGACCAACATTGCAGAAGCTATTG
CCCATGCTGTACCCTTCTATGGCTGTGTTAACTGGACTAATGAGAACTTTCCTTTTAATGATTGTGTTGATA
AAATGCTGATTTGGTGGGAGGAGGGAAAAATGACTAATAAGGTTGTTGAATCTGCAAAAGCAATTTTGGGAG
GGTCTGCTGTCCGGGTAGACCAGAAATGTAAAGGATCTGTTTGTATTGAACCTACTCCTGTAATTATTACTA
GTAATACTGATATGTGTATGATTGTTGATGGCAACTCTACTACAATGGAACATAGAATACCATTAGAGGAGC
GTATGTTTCAAATTGTCCTATCACATAAATTGGAGCCTTCTTTTGGAAAAATTTCTAAAAAAGAAGTCAGAG
AATTTTTCAAATGGGCCAATGACAATCTAGTTCCTGTTGTGTCTGAGTTCAAAGTCCGAACTAATGAACAAA
CCAACTTGCCAGAGCCCGTTCCTGAACGAGCGAACGAGCCGGAGGAGCCTCCTAAGATCTGGGCTCCTCCTA
CTAGGGAGGAGTTAGAAGAGCTTTTAAGAGCCAGCCCAGAATTGTTCTCATCAGTCGCTCCAATTCCTGTGA
CTCCTCAGAACTCCCCTGAGCCTAAGAGAAGCAGGAACAATTACCAGGTACGCTGCGCTTTGCATACTTATG
ACAATTCTATGGATGTATTTGAATGTATGGAATGTGAGAAAGCAAACTTTCCTGAATTTCAACCTCTGGGAG
AAAATTATTGTGATGAACATGGGTGGTATGATTGTGCTATATGTAAAGAGTTGAAAAATGAACTTGCAGAAA
TTGAGCATGTGTTTGAGCTTGATGATGCTGAAAATGAACAATAAAGATGACTCAAAGCAGATATGTCTACTT
TTTTAGATTCTTTTGAAGAGTGGTATGAGACTGCAGCCGCCTCGTGGCGGAATCTGAAAGCTGGAGCCCCTC
AGCCAAAACCAAACCAGCAGTCTCAGTCTGTGTCTCCAGACAGAGAACCCGAACGAAAAGATAATAATCGGG
GCTTTGTACTTCCTGGCTATAAGTATCTTGGGCCTGGTAACGGCCTGGATAAAGGCCCACCTGTCAATAAGG
CGGACAGCGTCGCGCTTGAACACGACAAGGCCTATGACCAGCAGCTTAAAGCGGGAGACAACCCCATATATAA
AATTCAATCACGCTGACCAGGACTTTATAGATAGCCTCCAAGACGACCAGTCATTCGGAGGTAATCTTGGAA
AGGCTGTATTTCAGGCCAAAAAACGTATCTTAGAGCCATTTGGCCTAGTAGAAGATCCTGTCAACACGGCAC
CTGCAAAAAAAAATACAGGGAAGCTTACTGACCATTACCCGGTAGTTAAGAAGCCTAAACTTACCGAGGAAG
TCAGTGCGGGAGGTGGTAGCAGTGCCGTACAAGACGGAGGAGCCACCGCGGAGGGCACCGAACCTGTGGCAG
CATCTGAAATGGCAGAGGGAGGAGGCGGAGCTATGGGCGACTCTTCAGGGGGTGCCGATGGAGTGGGTAATG
CCTCGGGAAATTGGCATTGCGATTCCCAATGGATGGGAAACACAGTCATCACAAAGACCACCAGAACCTGGG
TCCTGCCAAGCTACAACAACCACATCTACAAAGCAATTACCAGCGGAACCTCTCAAGATGCAAATGTCCAGT
ATGCAGGATACAGTACCCCCTGGGGGTACTTTGATTTCAACCGCTTCCACTGCCACTTCTCCCCTAGAGACT
GGCAGAGACTTATCAACAACCATTGGGGAATCAGACCCAAGTCTCTTAAATTCAAGATCTTCAATGTCCAAG
TCAAAGAAGTCACAACGCAGGATCAGACAAAGACCATTGCAAACAATCTCACCTCAACAATTCAAGTCTTTA
CGGATGATGAGCATCAACTCCCGTATGTCCTGGGCTCGGCTACGGAAGGCACCATGCCGCCGTTCCCGTCGG
ATGTCTATGCCCTGCCGCAGTACGGGTACTGCACAATGCACACCAACCAGAATGGAGCACGGTTCAATGACC
GTAGTGCATTCTACTGCTTAGAGTACTTCCCTAGTCAGATGCTAAGAACAGGCAACAACTTTGAGTTCACAT
TTGACTTTGAAGAAGTTCCTTTCCATAGCATGTTCGCTCATTCACAGGACTTAGACAGGCTGATGAACCCCC
TAGTGGATCAATACCTCTGGAATTTCAATGAGGTAGACAGCAGCAGAAATGCTCAATTTAAAAAGGCTGTGA
AAGGGGCTTATGGCACCATGGGCCGCAATTGGCTGCCAGGACCTAAATTCCTGGATCAAAGAGTTAGGGCCT
ACACAGGAGGAACAGACAACTATGCAAACTGGAACATCTGGAGTAATGGGAACAAGGTGAATTTGAAAGACA
GACAGTATCTCCTACAACCCGGACCTGTGTCAGCTACTTACACAGAAGGGGAGGCTTCCAGCCTTCCAGCTC
AAAATATTTTAGGGATAGCTAAAGATCCATACAGATCAGGCAGCACTACAGCAGGAATAAGTGACATTATGG
TCACGGAAGAACAAGAAGTAGCACCTACAAATGGAGTAGGGTGGAAACCATATGGTAGGACTGTAACGAATG
AACAAAACACTACTACAGCTCCTACAAGTTCAGATCTGGATGTTCTTGGAGCTTTACCAGGAATGGTTTGGC
AGAACAGGGATATATATCTGCAGGGACCTATTGGGGCAAAAATACCGAAGACTGATGGTAAATTCCATCCTT
CTCCGAATCTCGGAGGATTTGGCCTGCACAATCCACCACCGCAGGTGTTCATCAAGAATACACCAGTGCCTG
CAGACCCTCCAGTAGAATACGTGCACCAGAAGTGGAATTCCTACATAACCCAGTACTCTACGGGCCAGTGTA
CAGTAGAGATGGTGTGGGAGCTGAGAAAAGAGAATTCAAAGAGATGGAACCCAGAAATCCAGTTCACCAGTA
ATTTCAGTAACAGAACAAGCATAATGTTTGCACCTAATGAAACTGGTGGATATGTAGAAGATAGATTGATTG
GAACCAGATATCTAACTCAAAATCTGTAAATTCTGTGTAAAAATTCAAATAAAGCACTTCCTGGCGCGCAAA
ATATCCTCTTGTCCTTGAGTCTCATTGGAGGGTTCGTTCGTTCGAACCAGCCAATCAGGGGAGGGGGAAGTG
ACGCAAGTTCCGGTCACATGCTTCCGGTGACGCACATCCGGTGACGTAGTTCCGGTCACGTGCTTCCTGTCA
CGTGTTTCCGGTCACGTGACTTCCGGTCATGTGACTTCCGGTGACGTGTTTCCGGCTTAACTATTGGGCTGA
CCGCGCGCATGCGCGTGGTCAACCTAACAGCCGGAAACACGTCACCGGAAGTCACATGACCGGAAGTCACGT
GACCGGAAACACGTGACAGGAAGCACGTGACCGGAACTACGTCACCGGATGTGCGTCACCGGAAGCATGTGA
CCGGAACTTGCGTCACTTCCCCCTCCCCTGATTGGCTGGTTCGAACGAACGAACCCTCCAATGAGA

FIG. 22

SNAKE PARVOVIRUS 1, COMPLETE GENOME, GENBANK ACCESSION NO. NC_006148
AND FARKAS ET AL. (2004) J. GEN. VIROL. 85:555
CGCCCCACCCCTAGTGATCGCGCGCGCTCTCTCTTGGGGCCTGACGGCCGAAGGCCGTCAGCTGCCGAGC
TTCGCTCGGCAGGCCCCAAGAGAGAGCGCGCGCGATCACTAGGGGTGGGGCGAGTGCCCTGCTCAACGGG
TTTTTTGGTGGGCGGAGCAATGACGTCAGCGGACATGTCTGGACATGTCTTTGAGCAAGTCCATATAAGG
AGTTCCGCCGGATATGCAAATGAGCAATCGCGCAAAGCATTTTGGGTAGTCACCATGAATAAAAAGGACA
GCAAGAAAGATGACGCCCCATAATTTTAATAGGAATTTTAACCATGGCGTTTTACGAGGTTGTGTTTCGT
TTGCCAAGAGACAATAACAACTTGTTGGATGAAGATAGATATCAGCCAGAGTTGAAAGAAGAAGATGACT
GGCCTGAGGAATATTTAACCAGTGAAGATGCCAGCTTTATCGGACTAGCGTATGCTGTGCTAAGTGAAAT
TCGGAGATTCTTTGGAAAGGAACTACAATGGTTTGCCCAGGTTGAATGGTGTCCTACTGCTGGTTACCAC
ATGCATGTTTTGTTGAACCATCCTAAGCTGAGTAACCAGACTTATGGAAGAAAGGTCAATGAACTGGCTT
GCCGTATAGTCGATACCTTTGGCCTAATTAATCCAGAAGAAGTCATCAGTACCCATTATGTTAAAAGCAA
CTATGGACATAAAAAGGTGAGAGTCATTCACCTAGAGTCTTATTTGAAGAACTACTTTTTCAGAAAGACT
TTAGCTCCTCCCAATTATACCGAGGAAGGAGCTATAAAAGAGGAAGAAGTCGTGCTGTGGGCATTTA
CGAATATCGTCGCTTGGAAGCCATTCGTGCGGAATCTCATCAAGAGATCGGAGCTAGCGACTGTTCCTAA
GCAACCAGAGAATCCGGCGGGAGACGGACCGGCACCTCGAGTGACTGCAGGAACCCGCCATTTTATGGAA
ACCATCGACTGGTTGGTGAAACATGGAATTACTACAGAACGAGAATTCTGCCACGCCAACCGCCCTTTGT
ACCTGTCTATGCTGGCTTCTACTTCGGGTGCTGGGCAGATTAAAAGAGCGCTGGACCAGGCGAAACACAT
GATGACCAGCACCATGTCAGCAGAGGATTACCTGACAACAGAAGAGGATGTGATCGAACCACCTACTGAA
AATAGAATCTACAAGATTATGAAACTGAATCGCTATGATCCAGAACTAGCAGCTGCTCTCTTCTACGGCT
GGACCTGCAAGAACTTTGGCAAGAGAAACACCATCTGGCTGTATGGTCCAGCTACTACCGGCAAAACCAT
CATCGCTCAAGCTATTGCACATGCTGTTAAACTGTGTTGCTGGTGTTAATTGGACTAATGAAAACTTTCCC
TTCTGTAACTGTCCAGGGAAACTGCTTATCTGGTGGGAGGAGGCAAGATGACAAACAAAATGGTGGAGA
CGGCTAAATGTATACTGGGGGGATCTGCTGTACCTGTAGACATCAAAGGCAAACCCGCTGAAATGTGTCC
TCAAACACCCTGTATTATTACTAGCAATACTGTCAAGTATATGATGGTAATAGTTCTAGCTTT
GAGCACCAAGAACCCCTAGAGGAACGCATGTTTATGTTCAGACTTAATACTAAACTGCCATCGACCTTTG
GCAAGATCACAGAAGAGGAAGTCAAACAGTTTATTACCTGGGGGAGGAGCTTAAAGGTTCAAGTTCCACA
TCAGTTCAGAGTGCCTACCACAGGAGAGTATAAAAGGCCAGCCCCGAGGCGAAAGCTCATTCTTCGGAT
GAGCCGCCAAAGAAGACTCGCGCGTATTGATGACTCTCTAACCAGGTATGTTAACAATATTGATGAGT
CAGCTACCAGTAGAGAAATGTTTCTAGAGATTGCTAATACTAATCAATGTATGTTGCATCATTGCTTTTC
TTGTACCGAATGTTATCCTGAATTGCTTGATGACATGGACAAGGAACAATAAACTTACTGATAACAGATA
TGGATTTTCTCGATGATTTCTTTGCAGATAAATATAAAGAGACTGTTAACGAACTCGGTAAACCGGTCAA
TCCTAAACCTGTAAAACACATTAGCGAAGCTCACTCGCCAACCTGGCAGCAGGAGGGGCTTTGTGGTGCCT
GGGTATCGGTATCTTGGGCCTGGTAATAGCTTGGACCGTGGAAAGCCCGTTAACAAAGCAGACGAGGCTG
CTAAAAAGCACGATCAAGAATACGATCAACAGCTTAAAGCGGGAGACAATCCCTACATAAAATATAATCA
CGCGGACGAACAGTTCCAGAAAGACCTACAAGGTGATACCAGTCTAGCCGGCAACGCGGCTAACGCTCTA
TTTCAAGGCAAAAGACTCTACTAGCGCCCCTGTCTAGTAGAACCCCTGTCGGCAAAACGTCTGAAA
AGCACAAATTAGACGAATACTATCCTAAAGCTAAAAAGGCCAAACAAGGCTTGCAGATACCAGCTCCACC
TAAAGGCGGAGAAGAAGAAGCTACATCGTCACAATCTGGAGGGAGCCCAGCAGGTTCCGATACTAGCGGC
ACATCTGTCATGGCTACAGGAGGAGGCGGTCCGATGGCAGACGATAACCAGGGCGCCGAGGGAGTGGGTA
ATTCCTCAGGTGATTGGCATTGCGATACCAAGTGGATGGGAGACCACGTCATTACAAGTCAACCAGAAC
TTGGGTGCTCCCCACTTACGGGAATCATCTCTACGGGCCTATCAACTTTGACGGCACCACAGGTTCGGGT
GCTAATGCAGCCTATGCAGGATACAAGACTCCTGGGGGTACTTTGACTTCAATCGATTCCATTGCCACT
TCTCCCCCCGAGACTGGCAAAGACTCATCAACAACCACACAGGCATCAGGCCGAAAGGACTCAAAATCAA
AGTCTTTAACGTCCAAGTCAAAGAAGTTACAACACAGATTCAACGAAACAATTGCCAACAATCTCACC
AGCACCGTACAGATCTTTGCGGACGAGAACTACACTTACCATATGTATTAGGCAGTGCTACACAAGGCA
CATTTCCTCCATTTCCCAATGATGTATTTATGTTACCACAATATGCTTATTGTACACTTCAAGGAAATTC
GGGGAAATTTGTAGATAGAAGTGCCTTTTATTGTTTAGAATATTTTCCTTCACAAATGCTGAGAACAGGA
AACAATTTTGAATTCCAGTTTAAATTTGAAGAAGTTCCCTTTCATTCTGGATGGGCACAGAGTCAAAGCC
TAGACAGATTGATGAATCCGTTGCTTGATCAATATCTGATAGGAGACTATGGAACAGATGCATCAGGAAA
CCTTATTTATCACAGAGCTGGTCCAAATGATTTGAATGAATTCTACAAGAATTGGGCACCTGCACCCTAT
GAATGTATCCAGAATATTAACACGACAGTGATAATACCAAGAATGCTAATTCTATAAATGGTTCAAATTCTA
CCAACAAATGGGGACTACAAGGAAGACAAGCATGGGATGCTCCAGGATTTGTTCAAGCTAGTACCTATGA
AGGTGCAGCAGCAGGACAATCTCTTCTTAATGGCGTACTTACTTTCGATAAAAGTTCAGCTACTACTTCA
TCTCCAGCTGCTACTGCAGTAAACAGAACAATTGAAGACGAAATACAGGGTACCAATAATTTTGGTAATG
CTAGAAATAACATTGTTGCTATCAATCAACAAACAGGAAGACAAATCCAACAACAGGTAGTACATCTCA
ATTTGAGACAATGCCAGGTATGGTGTGGTCTAATAGAGACATTTACTTACAGGGGCCTATTTGGGCTAAA
ATTCCAAATACAGATGGACATTTTCATCCTTCTCCCAGAATGGGTGGTTTTGGATTAAAACATCCTCCGC
CTATGATTCTGATCAAAAATACACCAGTTCCTGCTGATCCTCCAACTACCTTCAATCCAATGCCACAGAC
TAGTTTCATTACTGAATACAGTACAGGACAAGTACTGTTGAAATGTTGTGGGAGGTACAGAAAGAATCC
TCCAAAAGATGGAATCCAGAAGTACAGTTTACTTCCAATTTTGGAACTTCAGATCCAGCTGTTGATGAA
TACCGTTTGGAATTAATAATTTGGGTACTTATGTTGAATCTAGACCTATTGGAACTCGTTATATTTCTAA
ACACTTGTAAATAATAAAAATTGTCAAATTTGCACTAAGAATTGTTGTCACGTGGTTGTTTACATGCTTG
CTAAAACACGCCCACCAAAAACCCGTTGAGCAGGGCACTCGCCCCACCCCTAGTGATCGCGCGCGCTCT
CTCTTGGGGCCTGCCGAGCGAAGCTCGGCAGCTGACGGCCTTCGGCCGTCAGGCCCAAGAGAGAGCGCG
CGCGATCACTAGGGGTGGGGCG

FIG. 23

CHIMERIC ITRS

ITR2
```
  1 AGGAACCCCT AGTGATGGAG TTGGCCACTC CCTCTCTGCG CGCTCGCTCG CTCACTGAGG CCGGGCGACC AAAGGTCGCC CGACGCCCGG CCTTTGGGCC
101 GGGCCCCTCA GTGAGCGAGC GAGCGCGCAG AGAGGGAGTG GCCAACTCCA TCACTAGGGG TTCCT
```

ITR5
```
  1 TACAAAAACCT CCTTGCTTGA GAGTGTGGCA CTCTCCCCCC CTCTCTGCGC TGCTCGCTTC GCTCGCTCGC TGGCTCGTTT GGGGGGGCGA CGGCCCAAAG GGCCGTCGTC
101 TGGCAGCTCT TTGAGCTGCC ACCCCCCAA ACGAGCCAGC GAGCGAGAGTG CCACACTCTC AAGCAAGGAG GTTTTGTA
```

ITR5+2SNS
```
  1 AGGAACCCCT AGTGATGGAG TTGGCCACTC CCTCTCCCCC CTCTCTGCGC GTCGCTCGCT CGCTCACTGA GGGGGGGCGA CCAAAGGTCG CCCGAGCCCG
101 GCCCTTTTGG CCGGGCCCCT CAGTGAGCGA GCGAGCGCGC GAACGCGACA AGTGGCCAAC TCCATCACTA GGGGTTCCT
```

ITR2+5SNS
```
  1 TACAAAAACCT CCTTGCTTGA GAGTGTGGCA CTCTCCCCCC CTCTCCCCCT GTCGCGTTTC GCGCGCTCGC TCGCTCACTG GGGGGGGGA ACCAAAGGTC
101 GGGGCCCCCC GCCGGGCCCC TCAGTGAGCG AGCGAGCGCG AGGGGGGAGA AGTGGCCACACT CTCAAGCAAG GAGGTTTTGT A
```

ITR5+2NS
```
  1 AGGAACCCCT AGTGATGGAG TTGGCCACTC CCTCCCCCCC CTCTCTGCGC GTCGCGTTTC GCGCGCTCGC TCGCTCGTTTG GGGGGGGGAC GGCCCAAAGG GCCGTCGTCT
101 GGCAGCTCTT TGAGCTGCCA CCCCCAAA CGAGCCAGCG AGCGAGCGAA CGGCACAGGG GGCCAACTCC ATCACTAGGG GTTCCT
```

ITR2+5NS
```
  1 TACAAAAACCT CCTTGCTTGA GAGTGTGGCA CTCTCCCCCC CTCTCTCTGC GCGCTCGCTC GCTCACTGAG GCGGGGCGAC CAAAGGTCGC CCGACGCCCG GCCCTTTGGG
101 CCGGGCGGCC CTCAGTGAGC GAGCGAGCGC GCAGAGAGAG TGCCAACTC TCAAGCAAGG AGGTTTTTGTA
```

ITR2 - TA
```
  1 AGGAACCCCT AGTGATGGAG TTGGCCACTC CCTCTCTGCG CGCTCTCTGC TCTGCTCGCT CACTGAGGGC GGGCGACCAA AGGTCGCCCG ACGCCCGGGC CTTTGGGCCG
101 GGCGTCCTC AGTGAGCGAG CGAGCGCGCA GAGAGGGAGT GCCAACTCCA CACTAGGGGT TCCT
```

ITR5 + TA
```
  1 TACAAAAACCT CCTTGCTTGA GAGTGTTGGA CACTCTCCCC CCTCCCCCGT TGCTCGCGCT TTTGGGGGGGC GACGGCCCAA AGGGCCGTCG
101 TCTGGCAGCT CTTTGAGCTG CCACCCCCCC AAAACGAGCA GGGCGAGCAGC GAACGCGACA GGGGGAGAG TGTCCAACAC TCTCAAGCAA GGAGGTTTTG
201 TA
```

ITR2 -GC
```
  1 AGGAACCCCT AGTATGGAGT GGCCACTCCC CTCGCTCGCT CACTGAGGCC GGGCGACCAA AGGTCGCCCG AGCCCGGCCC TTTGGGCCGG
101 GCCCTCAGT GAGCGAGCGA GCGCGCAGAA TGGAGTGGCC AACTCCATAC TAGGGGTTCC T
```

FIG. 24

ITR5 +GC
```
  1 TACAAAACCT CCTTGCTTGG AGAGTGTGGC ACTCTCCCCC CCTGTCGCGT TCGCTCGCTC GCTGGCTCGT TTGGGGGGGC GACGGCCCAA AGGGCCGTCG
101 TCTGGCCAGCT CTTTGAGCTG CCACCCCCCC AAACGAGCCA GCGAGCGAGC GCGAGCGACA GGGGGGAGA GTGCCACACT CTCCAAGCAA GGAGGTTTTG
201 TA
```

ITR2 -2nt
```
  1 AGGAACCCCT AGTGCTGGAG TTGGCCACTC CCGGGCGCTC GCTCGCTCAC TGAGGGCGGG CGACCAAAGG TCGCCCGAGC CGGGCCCTTT GGGCCGGGCC
101 CCTCAGTGAG CGAGCGAGCG CGCGGGAGTG GCCAACTCCA GCACTAGGGG TTCCT
```

ITR2 5nt
```
  1 AGGAACCCCT AGTGCTGGAG GCCACTCCTC TGCGCGCTCG CTCGCTCACT GAGGGCGGGC GACCAAAGTC CGCCCGAGCC CGGGCCCTTTG GGCCGGGCCC
101 CTCAGTGAGC GAGCGAGCGC GCAGAGGGAGT ACTAGGGGTT CCT
```

ITR2+7
```
  1 AGGAACCCCT AGTGCTGGAG TTGGCCACTC CCTCCACGCG TTCTGCGGCG CTCGCTCGCTC ACTGAGGGCG GGCGACCAAA GGTCGCCCGA CGCCCGGCCC
101 TTTGGCCCGG GCGGCCCTCA GTGAGCGAGC AACGGTGGA GGGAGTGGCC AACTCCATCA CTAGGGGTTC CT
```

ITR2 9nt
```
  1 AGGAACCCCT AGTGGATGGA GTTGGCCACT CCCTCCTCTG CGCGCTCGCT GGCTCACTGA GGGCGGGCGA CCAAAGGTCG CCCGAGCCCG GCCCTTTGGG
101 CCGGGCCCCT CAGTGAGCGA GCGAGCGCGG AGAGGAGTGG CCAACTCCAC TAGGGGTTCC T
```

ITR2 10nt
```
  1 AGGAACCCCT AGTGATGGAG TTGGCCACTC CCTCCACGCG TTCTGCGGCG CTCGCTCGCTC ACTGAGGGCG GGCGACCAAA GGTCGCCCGA CGCCCGGCCC
101 CCGGGCGCCT GTGAGCGCGA GTGAGCGAGC AACGGTGGAA GGGAGTGGCC AACTCCATCA CTAGGGGTTC CT
```

ITR2 11nt
```
  1 AGGAACCCCT AGTGCTGATG GAGTTGGCCA CTCCCTCCTC TGCGCGCTCA CGCTCGCTCA CGACGACTAGG GTTCCT
101 TGGGCCGGGC CCCTCAGTGA GCGAGCGAGC GCGCAGAGGT GAGGGAGTGG CCAACTCCAT
```

ITR5 3nt
```
  1 TACAAAACCT CCTTGCTTGA GAGTGTGGCA CTCTTTCTGCT CGCTCGCTGG GGGGCGACGG CCCAAAGGGG CCCAAAGGGGC CCCGAGCCCG
101 AGTTGCCACC CCCCAAAACG CGAGCCAGCG GAGAGCGAGA GAGTGCCACA CTCTCAAGCA AGGAGGTTTT GTA
```

FIG. 24 (cont.)

```
ITR5 6nt
  1 TACAAAAACCT CCTTGCTTAG AGTGTGGCAC TCTCCCCCTG TCGGGTTCGC GCTCGTTTGG GGGGGCGACG GCCCAAAGGG CCGTCGTCTG
101 GCAGCTCTTT GAGCTGCCAC CCCCCCAAAC GAGCCAGGGA GCGAGCAGGG CACTCTAAGC AAGGAGGTTT TGTA

ITR5 9bp NS
  1 TACAAAAACCT CCTTGCTTGA GAGAGTGTGG CACTCTCTCC CCCCTGTCGC GTTCGCTCGC GTTTGGGGGG GCGACGGCCC AAAGGGCCGT
101 CGTCTGGCAG CTCTTTGAGC TGCCACCCCC CCAAACGAGC CAGGGGGGAG AGAGTGCCAC ACTCTCTCAA GCAAGGAGGT
201 TTTGTA

ITR5 21nt
  1 TACAAAAACCT CCTTGCTTGA GAGTGTGGCA CTCTACGCGT CCCCCCTGTC GCGTTCGCTC GGGTTCGCTC TCGTTTGGGG GGGCGACGGC CCAAAGGGCC
101 GTCGTCTGGC AGCTCTTTGA GCTGCCACCC CCCAAAACGA GCCAGCGAGC GAGCGAACGC GACAGGGGGC GGGTGGAGAG TGCCACACTC TCAAGCAAGG
201 AGGTTTTTGTA

ITR5 30nt
  1 TACAAAAACCT CCTTGCTTGA GAGTGTGGCA CTCTCACGCG TAGATTCTAGA CCCCCTGTCG CGTTCGCTCG CTGCCTGGCT CGTTTGGGGG GGCGACGGCC
101 CAAAGGGCCG TCGTCTGGCA GCTCTTGAGC CTGCCACCCC CCCAAACGAG CCAGCGAGCG AGCGAACGCG ACAGGGGGTC TAGATCTACG GTGAGAGTGC
201 CACACTCTCA AGCAAGGAGG TTTTGTA

ITR5 GAGY
  1 TACAAAAACCT CCTTGCTTGA GAGTGTGGCA CTCTCCCCGC TGGCTCGCTC GCTCGCTCGC GGGGGGGGA CGGCCCAAAG GGCCGTCGTC
101 TGGCAGCTCT TTGAGCTGCC ACCCCCCCAA ACGAGCCAGC GAGCGAGCGA GGGGAGAGTG CCACACTCTC AAGCAAGGAG GTTTTGTA

ITR5 No GAGY
  1 TACAAAAACCT CCTTGCTTGA GAGTGTGGCA CTCTCCCCAG CTAAGATGCA GCTCGCTCGC TGGCTTCGTTT GGGGGGGGGA CGGCCCAAAG GGCCGTCGTC
101 TGGCAGCTCT TTGAGCTGCC ACCCCCCCAA ACGAGCCAGC TG CATCTTAGCT GGGGAGAGTG CCACACTCTC AAGCAAGGAG GTTTTGTA

ITR2 +8nt GAGY
  1 AGGAACCCCT AGTGATGGAG TTGGCCACTC CCTCTCTGCT CGCTCGGCGG CTCGCTCGCT CACTGAGGGC GGGCGACCAA AGGTCGCCCG AGCCCGGCCC
101 TTTGGGCCGG GCCCCTCAGT GAGCGAGCGA GCGCGCAGAG ACTCCATCAC TAGGGGTTCC T

ITR5 SPACER RBE
  1 TACAAAAACCT CCTTGCTTGA GAGTGTGGCA CTCTCCGTTC GCTCAGCTAA GATTGCAGTTT GGGGGGGGA CGGCCCAAAG GGCCGTCGTC
101 TGGCAGCTCT TTGAGCTGCC ACCCCCCCAA ACTGCATCTT AGCTGAGCGA ACGGCACAGG GGGGAGAGTG CCACACTCTC AAGCAAGGAG GTTTTGTA

ITR2 +8-8 SPACER RBE
  1 AGGAACCCCT AGTGATGGAG TTGGCCACTC CCTCTCTGCT CGCTCGGCGG AGCAGAGAGG GAGTGGCCAA CTCCATCACT AGGGGTTCCT
101 TTGGGCCGGG CCCCTCAGTT GCATCTTGAG CGCGCGAGCG AGCAGAGAGG GAGTGGCCAA GTCGCCCGA GCCCGGCCCT
```

*FIG. 24 (cont.)*

ITR5 WITH ITR2 HAIRPINS

```
  1 TACAAAACCT CCTTGCTTGA GAGTGTGGCA CTTCCCCCCC TGTCGCGTTC GCTCGCTCGC TGGCTCGTTT GGGGGGGCGG GCGACCAAAG GTCGCCCGAG
101 CCCGGCCCTT TGGGCCGGGC CCCCCCCAAA CGAGCCAGCG AGCGAGCGAA CGCGACAGGG GGGAGAGTGC CACACTCTCA AGCAAGGAGG TTTTGTA
```

ITR2 NO HAIRPINS

```
  1 AGGAACCCCT AGTGATGGAG TTGGCCACTC CCTCTCTGCG CGCTCGCTCG CTCGCTCACT GAGGCCGGGC GACCAAAGGT CGCCCGACGC CCGGGCGCCT TTGGGCCGG
101 AGAGGGAGTG GCCAACTCCA TCACTAGGGG TTCCT
```

ITR2 T1

```
  1 AGGAACCCCT AGTGATGGAG TTGGGGTCTG CGCGCGCTCG CTCGCTCACT GAGGCCGGGC GACCAAAGGT CGCCCGACGC CCGGGCGACC CGGCCCTTTG GGCCGGGCCC
101 CTCAGTGAGC GAGCGAGCGC GCGCAGACCC CAACTCCATC ACTAGGGGTT CCT
```

ITR2 T2

```
  1 AGGAACCCCT AGTGATGGAG TTGGGACTCC CTCTCTGCGC GCTCGCTCGC TCACTGAGGG CGGGCGACCA AAGGTCGCCC GAGCCCCGGG CCTTTGGGCCG
101 GGCCCCCTCAG TGAGCGAGCG AGCGCGCAGA GGAGGAGTGC CCAACTCCAT CACTAGGGGT TCCT
```

ITR2 T2 #2

```
  1 AGGAACCCCT AGTGATGGAG TTGGGGTTAA CTCTGGGGGG TTTTGGTCCC TCGCTCGCTC ACTGAGGGCG GGCGACCAAA GGTCGCCCGA GCCCGGCCCT TTGGGCCGGG
101 CCCCCTCAGTG AGCGAGCGAG CGCGCAGAGT TAACCCCAAC TCCATCACTA GGGGTTCCT
```

ITR2 T3

```
  1 AGGAACCCCT AGTGATGGAG TTGGGGTTAA CTCTGGCCTC TCTGCGCGCT CGCTCGCTCA CTGAGGGCGG GCGACCAAGG GTCGCCCGAG CCCGGCCCTT TGGGCCGGGC
101 CCCTCAGTGA GCGAGCGAGC GCGCAGACAGG CATCACTAGG GGTTCCT
```

ITR2 T4

```
  1 AGGAACCCCT AGTGATGGAG TTGGGGTTAA CCCCTCTGGG CGCTCGCTCG GGCTCGCTCG CTCGTTTGGG CTCGTTTGGG GGGCGACCAA AAAGGTCGCC CGAGCCCGGC CCTTTGGGCC
101 CCCTCAGTGA GCGAGCGAGC GTGAGCGAGC AGGGGTTAAC CCCAACTCCA TCACTAGGGG TTCCT
```

ITR5+3nt SPACER & ITR5 NS

```
  1 AGGAACCCCT AGTGATGGAG TTGGCCACTC CCTCTTCGCT CGCTCGCTCG GGGAGAGGGC CCCAAAGGGC CGTGTCTGG CAGCTCTTTG
101 AGCTGCCACC CCCCAAACG CGAGCGAAGA GGGAGTGGGC CCAACTCCA TCACTAGGG CT
```

ITR2 pHpa8

```
  1 AGGAACCCCT AGTGATGGAG TTGGGGTTAA CCCCACTCCC TCTCTGCGCG CTCGCTCGCT CACTGAGGGC GGGCGACCAA AGTTCGCCCG AGCCCGGCCC
101 TTTGGGCCGG GCCCCCTCAGT GAGCGAGCGA GCGCGCAGAG AGGGAGTGGG GTTAACCCCA ACTCCATCAC TAGGGGTTCCT
```

FIG. 24 (cont.)

CHIMERIC REP PROTEINS

```
REP52AA73
  1 MATFYEVIVR VPFDVEEHLP GISDSFVDWV TGQIWELPPE SDINLTIVEQ PQLTVADRLR RVFLYEWNKF SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NLTERKRLVA QHLTHVSQTQ
201 EQNKENQNPN SDAPVIRSKT SARYMELVGM LVDKGITSEK QWIQEDQASY ISFNAASNSR SQIKAALDNA GKIMSLTKTA PDYLVGQQPV EDISSNRIYK
301 ILELNGYDPQ YAASVFLGWA TKKFGKRNTI WLFGPATTGK NSTTFEHQQP LQDRMFKFEL TRRLDHDFGK RWAKDHVVEV EHEFYVKKGG AKKRPAPSDA
401 VDQKCKSSAQ IDPTPVIVTS NTNMCAVIDG NSTTFEHQQP LQDRMFKFEL TRRLDHDFGK RWAKDHVVEV EHEFYVKKGG AKKRPAPSDA
501 DISEPKRVRE SVAQPSTSDA EASINYADRY QNKCSRHVGM NIMLFPCRQC FTHGQKDCLE CFPVSESQPV SVVKKAYQKL CYIHHIMGKV
601 PDACTACDLV NVDLDDCIFE Q*

REP52AA84
  1 MATFYEVIVR VPFDVEEHLP GISDSFVDWV TGQIWELPPE SDINLTIVEQ PQLTVADRLR RVFLYEWNKF SKQESKFFVQ FEKG ESYFH MHVLVETTGV
101 KSMVLGRFLS QIREKLIQRI YRGIEPTLPN WFAVTKTRNG AGGGNKVVDE CYIPNYLLPK TQPELQWAWT NLTERKRLVA QHLTHVSQTQ
201 EQNKENQNPN SDAPVIRSKT SARYMELVGM LVDKGITSEK QWIQEDQASY ISFNAASNSR SQIKAALDNA GKIMSLTKTA PDYLVGQQPV EDISSNRIYK
301 ILELNGYDPQ YAASVFLGWA TKKFGKRNTI WLFGPATTGK TNIAEAIAHT VPFYGCVNWT NENFPFNDCV DKMVIWEEG KMTAKVVESA KAILGGSKVR
401 VDQKCKSSAQ IDPTPVIVTS NTNMCAVIDG NSTTFEHQQP LQDRMFKFEL TRRLDHDFGK RWAKDHVVEV EHEFYVKKGG AKKRPAPSDA
501 DISEPKRVRE SVAQPSTSDA EASINYADRY QNKCSRHVGM NIMLFPCRQC FTHGQKDCLE CFPVSESQPV SVVKKAYQKL CYIHHIMGKV
601 PDACTACDLV NVDLDDCIFE Q*

REP52AA110
  1 MATFYEVIVR VPFDVEEHLP GISDSFVDWV TGQIWELPPE SDINLTIVEQ PQLTVADRLR RVFLYEWNKF SKQESKFFVQ FEKGSEYFHL HTLVETSGIS
101 SMVLGRYVSQ IREKLIQRIY RGIEPTLPNW FAVIKTRNGA GGGNKVVDEC YIPNYLLPKT QPELQWAWTN LTERKRLVAQ HLTHVSQTQE
201 QNKENQNPNS DAPVIRSKTS ARYMELVGWL VDKGITSEKQ WIQEDQASYI SFNAASNSRS QIKAALDNAG DYLVGQQPVE DISSNRIYKI
301 LELNGYDPQY AASVFLGWAT KKFGKRNTIW LFGPATTGKT NIAEAIAHTV PFYGCVNWTN ENFPFNDCVD KMVIWEEGK MTAKVVESAK AILGGSKVRV
401 DQKCKSSAQI DPTPVIVTSN TNMCAVIDGN STTFEHQQPL QDRMFKFELT RRLDHDFGKV TKQEVKDFFR WAKDHVVEVE HEFYVKKGGA KKRPAPSDAD
501 ISEPKRVRES VAQPSTSDAE ASINYADRYQ NKCSRHVGMN IMLFPCRQCE THGQKDCLEC FPVSESQPVS VVKKAYQKLC YIHHIMGKVP
601 DACTACDLVN VDLDDCIFEQ *

REP52AA126
  1 MATFYEVIVR VPFDVEEHLP GISDSFVDWV TGQIWELPPE SDINLTIVEQ PQLTVADRLR RVFLYEWNKF SKQESKFFVQ FEKGSEYFHL HTLVETSGIS
101 SMVLGRYVSQ IRAQLVKVVF QGIEPTLPNW FAVIKTRNGA GGGNKVVDEC YIPNYLLPKT QPELQWAWTN LTERKRLVAQ HLTHVSQTQE
201 QNKENQNPNS DAPVIRSKTS ARYMELVGWL VDKGITSEKQ WIQEDQASYI SFNAASNSRS QIKAALDNAG DYLVGQQPVE DISSNRIYKI
301 LELNGYDPQY AASVFLGWAT KKFGKRNTIW LFGPATTGKT NIAEAIAHTV PFYGCVNWTN ENFPFNDCVD KMVIWEEGK MTAKVVESAK AILGGSKVRV
401 DQKCKSSAQI DPTPVIVTSN TNMCAVIDGN STTFEHQQPL QDRMFKFELT RRLDHDFGKV TKQEVKDFFR WAKDHVVEVE HEFYVKKGGA KKRPAPSDAD
501 ISEPKRVRES VAQPSTSDAE ASINYADRYQ NKCSRHVGMN IMLFPCRQCE THGQKDCLEC FPVSESQPVS VVKKAYQKLC YIHHIMGKVP
601 DACTACDLVN VDLDDCIFEQ *
```

FIG. 25

```
REP52AA138
  1 MATFYEVIVR VPFDVEEHLP GISDSFVDWV TGQIWELPPE SDLNLTIVEQ PQLIVADRIR RVFLYEWNKF SKQESKFVQ FEKGSEYFHL HTLVETSGIS
101 SMVLGRYVSQ IRAQLVKVVF QGIEPQINDW YMELVGMLVD KGITSEKQWI GNKVVDECYI PNYLLPKTQP ELQWAWTNME QYLSACLNLT ERKRLVAQHL THVSQTQEQN
201 KENQNPNSDA PVIRSKTSAR SVFLGWATKK FGKRNTIWLF GPATIGKINI QEDQASYISF NAASNSRSQI YGCVAWTNEN FPFNECVDRM MSLTKIFAPDY LVGQQPVEDI SSNRIYKILE
301 LNGYDPQYAA SVFLGWATKK TPVIVTSNTN MCAVIDGNST TFEHQQPLQD RMFKFELTRR LDHDFGKVTK QEVKDFFRWA KDHVVEHEHE FYVKKGGAKK AKVVESAKAI LGGSKVRVDQ
401 KCKSSAQIDP TPVIVTSNTN MCAVIDGNST TFEHQQPLQD RMFKFELTRR LDHDFGKVTK QEVKDFFRWA KDHVVEHEHE FYVKKGGAKK RPAPSDADIS
501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
601 CTACDLVNVD LDDCIFEQ*

REP52AA160
  1 MATFYEVIVR VPFDVEEHLP GISDSFVDWV TGQIWELPPE SDLNLTIVEQ PQLIVADRIR RVFLYEWNKF SKQESKFVQ FEKGSEYFHL HTLVETSGIS
101 SMVLGRYVSQ IRAQLVKVVF QGIEPQINDW MELVGMLVDK GITSEKQWIQ ANKVVDSGYI PAYLLPKVQP ELQWAWTNME QYLSACLNLT ERKRLVAQHL THVSQTQEQN
201 KENQNPNSDA PVIRSKTARY MELVGMLVDK GITSEKQWIQ EDQASYISFN AASNSRSQIK AALLDNAGKI VGQQPVEDIS SNRIYKILEL
301 NGYDPQYAAS VFLGWATKKF GKRNTIWLFG PATTGKTNIA EAIAHTVPFY GCVAWTNENF PFNDCVDRMV IWWEEGRMTA KVVESAKAIL GGSKVRVDQK
401 CKSSAQIDPT PVIVTSNTNM CAVIDGNSTT FEHQQPLQDR MFKFELHRRL DHDFGKVTKQ EVKDFFRWAK DHVVEHEHEF YVKKGGAKKR PAPSDADISE
501 PKRVRESVAQ PSTSDAEASI NYADRYQNKC SRHVGMNLMF FPCRQCERMN QNSNICFTHG QKDCLECFPV SESQPVSVVK KAYQKLCYIH HIMGKVPDAC
601 TACDLVNVDL DDCIFEQ*

REP52AA175
  1 MATFYEVIVR VPFDVEEHLP GISDSFVDWV TGQIWELPPE SDLNLTIVEQ PQLIVADRIR RVFLYEWNKF SKQESKFVQ FEKGSEYFHL HTLVETSGIS
101 SMVLGRYVSQ IRAQLVKVVF QGIEPQINDW VAITKVKKGG VAITKVKKGG ANKVVDSGYI PAYLLPKVQP ELQWAWTNME EYKLACLNLT ERKRLVAQHL THVSQTQEQN
201 KENQNPNDAP VIRSKTARYM ITSEKQWIQE ASNSRSQIKA ALDNAGKIMS LITKIAPDYIV GQQPVEDISS NRIYKILELN
301 GYDPQYAASV FLGWATKKFG KRNTIWLFGP ATTGKTNIAE AIAHTVPFYG CVNWTNENFP FNDCVDKMVI WWEEGRMTAK VVESAKAIIG GSKVRVDQKC
401 KSSAQIDPTP VIVTSNTNMC AVIDGNSTTE EHQQPLQDRM FKFELITRLD HDFGKVTKQE VKDFFRWAKD HVVEVEHEFY VKKGGAKKRP APSDADISEP
501 KRVRESVAQP STSDAEAGIN YADRYQNKCS RHVGMNLMF PCRQCERMNQ NSNICFTHGQ KDCLECFPVS ESQPVSVVRK AYQKLCYIHH IMGKVPDACT
601 ACDLVNVDLD DCIFEQ*

REP52AA187
  1 MATFYEVIVR VPFDVEEHLP GISDSFVDWV TGQIWELPPE SDLNLTIVEQ PQLIVADRIR RVFLYEWNKF SKQESKFVQ FEKGSEYFHL HTLVETSGIS
101 SMVLGRYVSQ IRAQLVKVVF QGIEPQINDW SARYMELVGM VAITKVKKGG VAITKVKKGG LVDRGITSEK QMIQEDQASY ELQWAWTNLD EYKLAALNLE ERKRRKRLVA QHLITHVSQTQ
201 EQNKENQNPN SDAPVIRSKT SARYMELVGM LVDRGITSEK QMIQEDQASY ISFNAASNSR SQIKAALLDNA GKIMSLIKTA PDYLVGQQPV EDISSNRIYK
301 ILELNGYDPQ YAASVFLGWA TKKFGKRNTI WLFGPATTGK TNIAEAIAHT VPFYGCVNWT NENFPFNDCV RMTAKVVESA KAILLGGSKVR
401 VDQKCKSSAQ IDPTPVIVTS NTNMCAVIDG NSTTFEHQQP LQDRMFKFEL TRLDHDFGKV TKQEVKDFF RWAKDHVVEV EHEFYVKKGG AKKRPAPSDA
501 DISEPKRVRE SVAQPSTSDA EASINYADRY QNKCSRHVGM NLMLFPCRQC ERMQNSNIC FTHGQKDCLE CFPVSESQPV SVVKKAYQKL CYIHHIMGKV
601 PDACTACDLV NVDLDDCIFE Q*
```

```
REP52AA207
  1 MATFYEVIVR VPFDVEEHLP GLSDSFVNWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKG MELVGMLVDK GITSEKQWIQ EDQASYISFN ANKVVDSGYI PAYLLPKVQP ELQMAWTNLD EYKLAALNLE ERKRLVAQFL AESSQRSEQN
201 KENQNPNSDA PVIRSKSARY VFLGWATKRF GKRNTIWLFG PATTGKTNIA EAIAHTVPFY GCVNWTNENF PFNDCVDKMV IWWEEGKMTA SLTKTAPDYL VGQQPVEDIS SNRIYKILEL
301 NGYDPQYAAS VFLGWATKRF GKRNTIWLFG PATTGKTNIA EAIAHTVPFY GCVNWTNENF PFNDCVDKMV IWWEEGKMTA KVVESAKAIL GGSKVRVDQK
401 CKSSAQIDPT PVIVTSNTNM CAVIDGNSTT FEHQQPLQDR MFKFELTRRL DHDFGKVTHQ EVKDFFRWAK DHVVEVEHEF YVKKGGAKKR PAPSDADISE
501 PKRVRESVAQ PSTSDAEASI NXADRYQNKC SRHVGMNIML FPCRQCERMN QNSNICFTHG QKDCLECFPV SESQPVSVVK KAYQKLCYIH HIMGKVPDAC
601 TACDLVNVDL DDCIFEQ*

REP25AA73
  1 MPGFYEIVIK VPSDLIGHLP GISDSFVNWV AEKEWELPPD SIMDLNLIEQ APLTVAEKLQ RDFLTEWRRV SKQESKFFVQ FEKGSEYFHL HTLVETSGIS
101 SSMVLGRYVSQ IRAQLVKVVF QGIEPQINDW VAITKVKKG MALVNMLVEH GITSEKQWIQ ENQESYISFN STGNSRSQIK AALLDNATKIM SITKSAVDYL VGSSVPEDIS KNRIWQIFEM
201 ASQREFSADP VIKSKTSQKY ILYGWCQRSF NKRNTVWLYG PVIVTSNTNM CVVVDGNSTT FEHQQPLEDR MFKFELTKRL PPDFGKITKQ EVKDFFAWAK VNQVPVTHEF KVPRELAGTK GAEKSLKRPL
301 NGYDPAYAGS ILYGWCQRSF NKRNTVWLYG PVIVTSNTNM CVVVDGNSTT FEHQQPLEDR MFKFELTKRL PPDFGKITKQ EVKDFFAWAK VNQVPVTHEF KVPRELAGTK GAEKSLKRPL
401 CKSSVQIDST PVIVTSNTNM CVVVDGNSTT FEHQQPLEDR MFKFELTKRL PPDFGKITKQ EVKDFFAWAK VNQVPVTHEF KVPRELAGTK GAEKSLKRPL
501 GDVTNTSYKS LEKRARLSFV PETPRSSDVT VDPAPLRPLN WNSRYDCKCD YHAQFTDNIS KCDECEYLNR GKNGCICHNV THCQICHGIP PWEKENLSDF
601 GDFDDANKEQ *

REP25AA77
  1 MPGFYEIVIK VPSDLIGHLP GISDSFVNWV AEKEWELPPD SIMDLNLIEQ APLTVAEKLQ RDFLTEWRRV SKAPEALFFV QFEKGSEYFH LHTLVETSGI
101 SSMVLGRYVS QIRAQLVKVV FQGIEPQIND WVAITKVKKG GANKVVDSGY IPAYLLPKVQ PELQNAWTNL EERKRLVAQF LAESSQRSQE
201 AASQREFSAD PVIKSKTSQK WMALVNMLVE HGITSEKQWI QENQESYLSF NSTGNSRSQI KAALLNATKI MSLITKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELITKR QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFTDNIS NKCDECEYLN RGKNGCICHN VTHCQICHGI PPWEKENLSD
601 FGDFDDANKE Q*

REP25AA97
  1 MPGFYEIVIK VPSDLIGHLP GISDSFVNWV AEKEWELPPD SIMDLNLIEQ APLTVAEKLQ RDFLTEWRRV SKAPEALFFV QFEKGSEYFH MHVLVETSGI
101 SSMVLGRYVS QIRAQLVKVV FQGIEPQIND WVAITKVKKG GANKVVDSGY IPAYLLPKVQ PELQNAWTNL EERKRLVAQF LAESSQRSQE
201 AASQREFSAD PVIKSKTSQK WMALVNMLVE HGITSEKQWI QENQESYLSF NSTGNSRSQI KAALLNATKI MSLITKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELITKR QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFTDNIS NKCDECEYLN RGKNGCICHN VTHCQICHGI PPWEKENLSD
601 FGDFDDANKE Q*
```

```
REP25AA116
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLVKVV FQGIEPQIND WVAITKVKKG GANKVVDSGY IPAYLLPKVQ PELQWAWTNL DEYKLAAINL EERKRLVAQF LAESSQRSQE
201 AASQREFSAD PVIKSKTSQK YMALVNWLVE HGITSEKQWI QENQESYLSF NSTGNSRSQI KAALDNATKI MSLITKSAVDY LVGSSVPEDI SKNRIMQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*
REP25AA125
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPQIND WVAITKVKKG GANKVVDSGY IPAYLLPKVQ PELQWAWTNL DEYKLAAINL EERKRLVAQF LAESSQRSQE
201 AASQREFSAD PVIKSKTSQK YMALVNWLVE HGITSEKQWI QENQESYLSF NSTGNSRSQI KAALDNATKI MSLITKSAVDY LVGSSVPEDI SKNRIMQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*
REP25AA141
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGANKVVDS GYIPAYLLPK VQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLITKSAV DYLVGSSVPE DISKNRIMQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
REP25AA149
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDS GYIPAYLLPK VQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLITKSAV DYLVGSSVPE DISKNRIMQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

FIG. 25 (cont.)

REP25AA166

```
  1 MPGFYEIVIK VPSDLDGHLP GISDSFVNWV AEKEWELPPD SDMDLNLIEQ APLTVAEKLQ RDFLITEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWIN ENFPFNDCVD KMLIWWEEGK MINKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

REP25AA187

```
  1 MPGFYEIVIK VPSDLDGHLP GISDSFVNWV AEKEWELPPD SDMDLNLIEQ APLTVAEKLQ RDFLITEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLITERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWIN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

REP25AA216

```
  1 MPGFYEIVIK VPSDLDGHLP GISDSFVNWV AEKEWELPPD SDMDLNLIEQ APLTVAEKLQ RDFLITEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLITERKRLVA QHLTHVSQTQ
201 EQNKENQNPN SDAPVIKSKT SQKYMALVNW LVEHGITSEK QWIQENQESY TKIMSLTKSA VDYLVGSSVP EDISKNRIWQ
301 IFEMNGYDPA YAGSILYGWC QRSFNKRNTV WLYGPATTGK TNIAEAIAHT VPFYGCVNWT NENFPFNDCV DRMLIWWEEG KMINKVVESA KAILGGSKVR
401 VDQKCKSSVQ IDSTPVIVTS NTNMCVVVDG NSTTFEHQQP LEDRMFKFEL TKRLPPDFGK ITKQEVKDFF AWAKVNQVPV THEFKVPREL AGTKGAEKSL
501 KRPLGDVTNT SYKSLEKRAR LSFVPETPRS SDVTVDPAPL RPLNWNSRYD CKCDYHAQFD NISNKCDECE YLNRGKNGCI CHNVTHCQIC HGIPPWEKEN
601 LSDFGDFDDA NKEQ*
```

REP525AA110-148

```
  1 MATFYEVIVR VPFDVEEHLP IREKLIQRIY RGIEPTLPNW TGQIWELPPE SDINLTLVEQ PQLTVADRIR RVFLKYEMNKF SKQESKFFVQ FEKGSEYFHL HTIVETSGIS
101 SMVLGRYVSQ IREKLIQRIY RGIEPTLPNW FAVIKTRNGA GGGNKVVDSG YIPAYLLPKV QPELQWAWTN LLEYKLAALN LEERKRLVAQ FIAESSQRSQ
201 EAASQREFSA DPVIKSKTSQ KYMALVNWLV EHGITSEKQW IQENQESYLS FNSTGNSRSQ IKAALDNATK IMSLTKSAVD YLVGSSVPED ISKNRIWQIF
301 EMNGYDPAYA GSILYGWCQR SFNKRNTVWL YGPATTGKTN IAEAIAHTVP FYGCVNWTNE NFPFNDCVDK MLIWWEEGKM TNKVVESAKA ILGGSKVRVD
401 QKCKSSVQID STPVIVTSNT NMCVVVDGNS TTFEHQQPLE DRMKFELTK RLPPDFGKIT KQEVKDFFAW AKVNQVPVTH EFKVPRELAG TKGAEKSLKR
501 PLGDVTNTSY KSLEKRARLS FVPETPRSSD VTVDPAPLRP LNWNSRYDCK CDYHAQFDNI SNKCDECEYL NRGKNGCCIH NVTHCQICHG IPPWEKENLS
601 DFGDFDDANK EQ*
```

FIG. 25 (cont.)

```
REP525AA146-187
  1 MATFYEVIVR VPFDVEEHLP GISDSFVDWV TGQIWELPPE SDINLTLVEQ PQLTVADRIR RVFLYEWNKF SKQESKFFVQ FEKGSEYFHL HTLVETSGIS
101 SMVLGRYVSQ IRAQLVKVF QGIEPQINDW VAITKVKKGG ANKVVDECYI PNYLLPKTQP ELQWAWTNME QYLSACLNLT ERKRLVAQFL AESSQRSQEA
201 ASQREFSADP VIKSKTSQKY MALVNMLVEH GITSEKQMIQ ENQESYLSEN STGNSRSQIK AALDNATKIM SLTKSAVDYL VGSSVPEDIS KNRIWQIFEM
301 NGYDPAYAGS ILYGWCQRSF NKRNTWMLYG PATTGKTNIA EAIAHTVPFY GCVNWNENE PFNDCVDRWL IWWEEGKMTN KVVESAKAIL GGSKVRVDQK
401 CKSSVQIDST PVIVTSNTNM CVVVDGNSTT FEHQQPLEDR MFKFELTKRL PPDFGKITRQ EVKDFFAWAK VNQVPVTHEF KVPRELAGTK GAEKSLKRPL
501 GDVTNTSYKS LEKRARLSFV PETPRSSDVT VDPAPLRPLN WNSRYDCKCD YHAQFDNISN KCDECEYLNR GKNGCICHNV THCQICHGIP PWEKENLSDF
601 GDFDDANKEQ *
REP525AA110-187
  1 MATFYEVIVR VPFDVEEHLP GISDSFVDWV TGQIWELPPE SDINLTLVEQ PQLTVADRIR RVFLYEWNKF SKQESKFFVQ FEKGSEYFHL HTLVETSGIS
101 SMVLGRYVSQ IREKLIQRIY RGIEPTLPNW FAVTKTRNGA GGGNKVVDEC YIPNLLPKT QPELQWAWTN MEQYLSACLN LTERKRLVAQ FLAESSQRSQ
201 EAASQREFSA DPVIKSKTSQ KYMALVNMLV EHGITSEKQW IQENQESYLS FNSTGNSRSQ IKAALDNATK IMSLTKSAVD YLVGSSVPED ISKNRIWQIF
301 EMNGYDPAYA GSILYGWCQR SFNKRNTVWL YGPATTGKTN IAEAIAHTVP FYGCVNWTNE NEPFNDCVDK NFPFNDCVDK MLIWWEEGKM TNKVVESAKA ILGGSKVRVD
401 QKCKSSVQID STPVIVTSNT NMCVVVDGNS TTFEHQQPLE DRMFKFELIK RLPPDFGKIT KQEVKDFFAW AKVNQVPVTH EFKVPRELAG TKGAEKSLKR
501 PLGDVTNTSY KSLEKRARLS FVPETPRSSD VTVDPAPLRP LNWNSRYDCK CDYHAQFDNI SNKCDECEYL NRGKNGCICH NVTHCQICHG IPPWEKENLS
601 DFGFDFDDANK EQ*
REP252AA97-146
  1 MPGFYEIVIK VPSDLDGHLP GISDSFVNMV AEKEMELPPD SMDLNLIEQ APLITVAEKLQ RDFLTEWRRV SKAPEALFFV QFEKGESYFH MAVLVETSGI
101 SSMVLGRYVS QIRAQLVKVV FQGIEPQIND WWAITKVKKG IQEDQASYIS IPNYLLPKTQ PELQWAWTNM TERKRLVAQL LITHVSQTQEQ
201 NKENQNPNSD APVIRSKTSA RYMELVGMLV DKGITSEKQW FGPATTGKTN IAEAIAHTVP FYGCVNWTNE FNAASNSRSQ IMSLTKTAPD YLVGQQPVED ISSNRIYKIL
301 ELNGYDPQYA ASVFLGWATK KFGKRNTIWL NMCAVIDGNS TTFEHQQPLQ DRMFKFELIR RLDHDFGKVT TAKVVESAKA ILGGSKVRVD
401 QKCKSSAQID PTPVIVTSNT SINYADRYQN KCSRHVGMNL MLFPCRQCER MNQNSNICFT HGQKDCLECF KQEVKDFFRW AKDHVVEVEH EFYVKKGGAK KRPAPSDADI
501 SEPKRVRESV AQPSTSDAEA DRYQNKCSRH VGMNIMLFPC ROCERMNQNS NICFTHGQKD CLECFPVSES QPVSVVKRAY QKLCYIHHIM
601 ACTACDLVNV DLDDCIFEQ*
REP252AA149-187
  1 MPGFYEIVIK VPSDLDGHLP GISDSFVNMV AEKEMELPPD SMDLNLIEQ APLITVAEKLQ RDFLTEWRRV SKAPEALFFV QFEKGESYFH MAVLVETTGV
101 KSMVLGRFLS QIREKLIQRI YRGIEPTLPN WFAVTKTRNG AGGGNKVVDS GYIPAYLLPK VQPELQWAWT NLDEYKLAAL NLEERKRKR LVAQHLTHVS
201 QTQEQNKENQ NPNSDAPVIR SKTSARYMEL VGMLVDKGIT SEKQWIQEDQ ASYISFNAAS NSRSQIKAAL DNAGKIMSLT KTAPDYLVGQ QPVEDISSNR
301 IYKILELNGY DPQYAASVFL GWATKKFGKR NTIWLFGPAT TGKTNIAEAI AHTVPFYGCV NWTNENFPFN DCVDKMVIWW EEGKMTAKVV ESAKAILGGS
401 KVRVDQKCKS SAQIDPTPVI VTSNTNMCAV IDGNSTTFEH QQPLQDRMFK FELTRRLDHD FGKVTKQEVK DFFRWAKDHV VEVEHEFYVK KGGAKKRPAP
501 SDADISEPKR VRESVAQPST SDAEASINYA DRYQNKCSRH VGMNIMLFPC RQCERMNQNS NICFTHGQKD CLECFPVSES QPVSVVKRAY QKLCYIHHIM
601 GKVPDACTAC DLVNVDLDDC IFEQ*
```

*FIG. 25 (cont.)*

REP252AA97-187

```
  1 MPGFYEIVIK VPSDLDGHLP GISDSFVNWV AEKEWELPPD SIMDLNLIEQ APLTVAEKLQ RDFLTEWRRV SKAPFALFTV QFEKGESYFH MHVLVETSGI
101 SSMVLGRYVS QIRAQLVKVV FQGIEPQIND WVAITKVKKG GANKVVDSGY IPAYLLPKVQ PELQWAWTNL DEYKLAALNL EERKRRKRLV AQHLTHVSQT
201 QEQNKENQNP NSDAPVIRSK TSARYMELVG WLVDKGITSE KQMIQEDQAS YISFNAASNS RSQIKAALDN AGKIMSLTKT APDYLVGQQP VEDISSNRIY
301 KILELNGYDP QYAASVFLGW ATKKFGKRNT IWLFGPATTG GNSTTFEHQQ KTNIAEAIAH TVPFYGCVNW TNENFPFNDC VDKMVIWWEE GKMTAKVVES AKAILGGSKV
401 RVDQKCKSSA QIDPTPVIVT SNTNMCAVID PLQDRMFKFE LTRRLDHDRG KVTKQEVKDF FRWAKDHVVE VEHEFYVKKG GAKKRPAPSD
501 ADISEPKRVR ESVAQPSTSD AEASINYADR YQNKCSRHVG MNLMLFPCRQ CERMQNSNI  CFTHGQKDCL ECFPVSESQP VSVVKKAYQK LCYIHHIMGK
601 VPDACTACDL VNVDLDDCIF EQ*
```

FIG. 25 (cont.)

REP52AA146

```
   1 ATGGCTACCT TCTATGAAGT TATTGTTCGC GTCCCATTTG ACGTGGAGGA ACATCTGCCT GGAATTTCTG GGACTGGGTA ACTGGTCAAA
 101 TTTGGGAGCT GCCTCCAGAG TCAGATTTAA AGTCCAAATT CTTTGTGCAG TCTTGACTCT GGTTGAACAG CCTTGGCTGA CGGTGTTCC TGTTACGAGTG
 201 GAACAAATTT TCCAAGCAGG AGTCCGGCTA CGTGCGCTA  AITTCGCCCC AGTGGTGAA  TTTTCATCTG CACACGCTTG TGGAGACCTC CGGCATCTCT
 301 TCCATGGTCC TCGGCCGTCC TCCATGTCGG GCCAATAAGC AGTGGTCTTC AGCAGTCTGT TGCCTCCCAA AACCCAGTCT CAAGCTCAAG GTCGACCAG
 401 CCAAGTAAA  GAAGGCGGA  GCCAATAAG  TGGTGGATGA GTGCTACATC GGTTGTTGCC GCAGCATCTG ACGCACTGT  CGCAGGAAC  GGGAGCAGAC
 501 TAATATGGAA CAGTATTTAA GCGCTGTGTT GAATCTCACG GAGCGTCACG GATCAAAAAC TACATGGAGC TGGTCGGGTG GCTCGTGGAC AAGGGGATTA
 601 AAAGAGAATC AGAATCCCAA TTCTGATGCG CCGGTGATCA CATTCCCTTC AATGCGGCCT TCCAGCAATC AGCAGACATT AAGGCTGCCT TGGACAATGC
 701 CCTCGGAGAA ATGAGCCTGA CAGAACCGC  CCCGACTAC  CTGGTGGGCC TGGATGGGC  ACGAAAAAG  TTCGGCAAGA CTGTCTGTTT GGGCCTGCAA
 801 GGAAAGATT  AGAACGCGCT ATATGCGGCT TCCGTCTTTC TGTGCCCTTC TAGCCCAAC  CAATGAGAAC TCAAAGCCAT CTGGAGGAA  CCGACTGTGT
 901 CTAACGGGT  GACCAACATC GGGGAGGGGA GAAGATGACC GCCAAGCCAA TCGCGAGAA  CTCCAAGAA  ATGTGCGCG  CAAGGTGCG  CCTTCAACG
1001 CGACAAGATG GTGATCTGGT GGGAAGAGG  GATAGACCCG ACTCCCGTGA TCGTCACCTC CAACCAAC  CACCGCCAAG TGATTGACGA GAACTCAAGG
1101 AAATGCAAGT CCTCCGCCCA GATAGACCCG ACTCCCGTGA TCGTCACCTC CAACCAAC  ATGTGCGCG  GGTCACCAAG AGACCGCC   CCAGTGACGC
1201 ACCAGCAGCC GTTCAAGAC  CGGATGTTCA AATTTGAACT GGAGCAHGAA TTCTACGTCA AAAAGGTGG  AGCCAAGAAA AGATGACAC  CCAAAACAAA
1301 CGGGTGGGCA AAGGATCACG TGGTTGAGGT GGAGCAHGAA TTCTACGTCA CGTCAGAGCC GGAGTTCG   CAGACAGGTA CTTCACTCAC TGTTCTCGTC
1401 GAGCCCAAAC GGTGCGCGA  GTCAGTTGCG GCACAAATG  GCAGACAATG CGACAGAATT CAAATCAGAATT ATCAGAAACT CATCATATCA GCCAGAGCCT
1501 ACGTGGGCAT GAATCTGATG CTGTTTCCT  TTCTGTCGTC CGGAGCAATG TTTCTGCGTC CGGAGAGATG AAAAAGGCGT AAAAAGGCGT TGGGAAAAGT
1601 GTGCTTTCCC GTGTCAGAAT CTCAACCCGT CAATGTGGAT TTGGATGACT AAAAAGGCGT GCATCTTTGA TGGCAAGCGT GATGACAGGT GCCAGACGCT
1701 TGCACCGCCT GCGATCTGGT CAATGTGGAT TTGGATGACT
```

REP52AA146

```
  1 MATFYEVIVR VPFDVEEHLP GISDSFVDWV TGQIWELPPE SDLNLITIVEQ RVFLYEWNKF SKQESKFFVQ FEKGSEYFHL HTILVETSGIS
101 SMVLGRYVSQ IRAQLVKVVF QGIEPQINDW VAITKVKKGG ANKVVDSGYI PNYLLPKTOP ELQNAWTNME QYLSACLNLT ERKRLVAQHL THVSQTEQN
201 KENQNPNSDA PVIRSKTSAR YMELVGWLVD KGITSEKQWI QEDQASYISF NAASNSRSQI KAALDNAGKI MSLIKTAPDY LVGQQPVEDI SSNRIYKILE
301 LNGYDPQYAA SVFLGWATKK FGKRNTIWLF GPATTGKTNI AEAIAHTVPF YGCVWNTNEN FPFNDCVDKM VIMWEEGKMT AKVVESAKAI LGGSKVRVDQ
401 KCKSSAQIDP TPVIVTSNTN MCAVIDGNST TFEHQOPLQD RMFKFELTRR LDHDFGKVTIK QEVKDFFRWA KDHVVEVEHE FYVKKGGAKK RPAPSDADIS
501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
601 CTACDLVNVD LDDCIFEQ*
```

FIG. 26

REP52AA147

```
   1 ATGGCTACCT TCTATGAAGT CATTGTTCGC GTCCCATTTG AGTGGAGGA ACATCTGCCT GGAATTCTG ACAGCTTTGT GGACTGGGTA ACTGGTCAAA
 101 TTTGGGAGCT GCCTCCAGAG TCAGATTTAA GCTTGACTCT GGTTGAACAG CCTCAGTTGA CGGTGGCTGA TAGAATTCGC CGGTGTTCC TGTACGAGTG
 201 GAACAAATTT TCCAAGCAGG AGTCCAAATT CTTTGTTGCA GATTCGAATA TTTCATCTG CAGGGAATTG AACCCAGAGA CACACGCTTG TGGAGACCTC CGGCATCCT
 301 TCCATGGTCC TCGGCCGCTA CGTGAGTCAG ATTCGCGCCC AGTGGTCTTC CCCAATTACT TGCTCCCCAA AACCCAGCCT GAGCTCCAGT GTCGCCATCA
 401 CCAAGTAAAA GAAGGGCGGA GCCAATAAGG TTGCTACATC GAGCGTAAAC GGTTGGTGCC GCAGCATCTG ACGCACGTGT CGCAGACGCA GGAGCAGAAC
 501 TAATATGGAA CAGTATTTAA GCGCCCTGTT GAATCTCACG GAGCGTAAAC TTCCAGCCAGG TACATGGAGC TGGTCGGGTG GCTCGTGGAC AAGGGGATTA
 601 AAAGAGAATC AGAATCCCAA TTCTGATGCG CGGTGATCA CATCTCCTTC AATGCGGGCT GTCCCAAATC CCAACTCGCG AAGGCTGCCT TGGACAATGC
 701 CCTCGGAGAA GCAGTGGATC CAGGAGGAC CAGGGAGCCT CTGGTGGGCC CACGGAGACATT CGGAGGACCCGTT TCCAGCAACC CTGCTGTTT GGGCCTGCAA
 801 GGGAAAGATT ATGAGCCTGA CTAAAACCGC TGGGATGGGC GTGCCCTTC TACGGGTGCG GGAAGAAAAG TCCAGCAACC CAGCCAGAAAC TTTCCCTTCA ACGACTGTGT
 901 CTAAACGGGT ACGATCCCCA ATATGCGGCT GCGGAGGCCA GAAGATGACC GCCAAGGTCG TGGAGTCCGG CAAAGCCATT CTCGGAGGAA GCAAGGTGCG CGTTGACCAG
1001 CTACCGGGGA GACCAACATC GCCGAGGGCA GTGATCTGGT CCTCGGCCCA GATAGACCCG ACTCCACTCG TGGTCACTCC CAAACCACCAC AATGTGCCCG GAACTCAAG ACTTTCGTC
1101 CGACAAGATG GTCAAGCAGC CCTCGGCCCA GATAGACCCG ACTCCACTCG CACCGCCGGT CTGACCACAC AGGTCACCAAG CAGGAAGTCA AAGACTTTTT
1201 AAAATGCAAGT GTTGCAAGAG CGGATGTTCA AATTTGAACT GGAGCATGAA TTCTACGTCA AAAGGGTGG AGCCAAGAAA AGACCCGCCC CCAGTAGACGC AGATATAAGT
1301 ACCAGCAGCC AAGGATCACG TGGTTGAGGT GTCAGTTGCG CAGCCCATGA CGTCAGACG ATCAAGCTTCG ATCAACTACG CAGACAGGTA CCAAAACAAA TGTTCTCGTC
1401 CCGGTGGCA GGGTCGCGA GAATCTGATG CTGTTTCCCT GCAACACAATG CGAGAGAATG AATCAGAATT AATCAGAACT CAAATATCTG GGACAGAAAG ACTGTTTAGA
1501 GAGCCCAAAC GAATCTGATG CTGTTTCCCT GCAACACAATG TTCTGTCGTC AAAAGGCGT AATCAGAACT ATCAGAACT GTGCTACATT CATCATATCA TGGAAAGGTT GCCAGACGCT
1601 ACGTGGCCAT GTCAACCCGT TTCTGTCGTC CAATGTGGAT TGGATGACT GCAATCTTGA ACAATAA
1701 GTGCTTTCCC GTGTCAGAAT ACACAATCAT
1801 TGCACTGCGT GCGAATCTGGT CAATGTGGAT TGGATGACT GCAATCTTGA ACAATAA

1 MATFYEVIVR VPFWEEHLP GISDSFVDMV TGQIWELPPE SDLNLTLVEQ PQLTVADRIR RVFLYEMNKF SKQESKFFVQ FEKGSEYFHL HTLVETSGIS
 101 SMVLGRYVSQ IRAQLVKVVF QGIEPQINDW VAITKVKKGG YMELVGWLVD ANKVVDSCYI PNYLLPKYQP ELQWAWINME QYLSACINLIT ERKRLVAQHL THVSQTQEQN
 201 KENQNPNSDA PVIRSKTSAR YMELVGWLVD KGITSEKQWI QEDQASYISF NAASNSRSQI KAALLNAGKI MSLTKTAPDY LVGQQPVEDI SSNRIYKILE
 301 LNGYDPQYAA SVFLGWATKK FGKRNTIWLF GPATTGKTNI AEAIAHTVPF YGCVNWTNEN FPFNDCVDRM VIWWEELGKMI AKVVESAKAI LGGSKVRVDQ
 401 KCKSSAQIDP TPVIVTSNTN MCAVIDGNST TFEHQQPLQD RMFKFELTRR LDHDFGKVTK QEVKDFFRWA KDHVVEHE FYVKKGGAKK RPAPSDADIS
 501 EPKRVRESSVA QPSTSDAEAS INYADRYQNK CSRHVGMNIM LFPCRQCERM NQNSNICFTH GQKDCLECFP VSESQPVSVV KKAYQKLCYI HHIMGKVPDA
 601 CTACDLVNVD LDDCIFEQ*
```

FIG. 27

REP 52AA151

```
   1 ATGGCTACCT TCTATGAAGT CATTGTTCGC GTCCCATTTG AGTGTGGAGGA ACATCTGCCT GGAATTCTG ACAGCTTTGT GGACTGGGTA ACTGGTCAAA
 101 TTTGGGAGCT GCCTCCAGAG TCAGATTTAA ATTTGACTCT GGTTGAACAG CGGTTGGCTGA TAGAATTCGC CGCGTGTTCC TGTACGAGTG
 201 GAACAAATTT TCCAAGCAGG AGTCCAAATT CTTTGTGCAG GATCTGAATA TTTGAAAAGG CACACGCTTG AACCCCAGAT CGGATCTCT
 301 TCCATGGTCC TCGGCCGCTA CGTGAGTCAG ATTCCGCGCC AGTGGTGAA AGCTGGTGAA TTTTCATCTG CAGGGAATTG AACCCCAGCT GTCGGCATCA
 401 CCAAGGTAAA GAAGGGCGGA GCCAATAAGG TGGTGGATTC TGGGTATATT TGCTCCCCAA AACCCAGCCT GCAGCTCCAGT GGGGGTGGAC
 501 TAATATGGAA CAGTATTTAA GCGCCTGTTT GAATCTCACG GAGCGTAAAC GGTTGGTGGC GCAGACATGT ACGACGTGT GCAGACGCA GGAGCAGAAC
 601 AAAGAGAATC AGAATCCCAA TTCTGATGCG CCGGTGATCA CATCCCTTC AATGCGGCCT TTCAGCCAGG TACATGGAGC TGGTCGGGTG GCTCGTGGAC AAGGGGATTA
 701 CCTCGGAGAA GCAGTGGATC CAGGAGGACC CCCCGACTAC CTGGTGGGCC AGGCCCGT GTCCAAATC CCAGCAATC AAGGCTGCCT TGGACAATGC
 801 GGGAAAGATT ATGAGCCTGA CTAAAACGC CTGGTGGGGC TGGGATGGGC CACGGGTGCG AGCAGCCCGT GGAGGACCAT GGATTATTAA AATTTTGGAA
 901 CTAAACGGGT ACGATCCCA ATATGCGGCT TCCGTCTTTC TGTGCCCTTC TACGGGTGCG CACGAGAAAC TTCCCCTTCA ACGACTGTGT
1001 CTACCGGGAA GACCAACATC GCGGAGGCCA GAAGATGACC GCCAAGGTCG TGGAGTCGGC CAATGAGAAC CTCGAGGAA GCAAGGTGCG CGTGGACCAG
1101 CGACAAGATG GTGATCTGGT CCTCGGCCA GATAGACCCG TCGTCACCTC CAACCCAAAC ATGTGCGCG GAATCAACG ACCTTGAAC
1201 AAATGCAAGT CTTGCAAGAC GTTGCAAGAC CGGATGTTCA AATTTGAACT CACCCGCCGT CTGGATCAT ACTTTGGGAA CAGGAAGTCA AAGACTTTTT
1301 ACCAGCAGCC AAGGATCACG TGGTTGAGGT TCCTACGTCA CACCCGCCGT AAAAGGGTGG AGCCAAGAA AGACCCGCCC CCAGTGACGC AGATATAAGT
1401 CGGTGGGCA AAGGATCACG GGTGCGCGA GTCAGCATCGA CGTCAGACGC GGAAGCTTCG ATCAACTACG CAGACAGGTA CCAAAACAAA TGTTCTCGTC
1501 GAGCCCAAAC GAATCTGATG CTGTTTCCCT GCAGACAATG AAAAGGGCGT TTCGTGCGTC AAAAAGGCGT AATCAGAATT CAATATCTG CTTCACTCAC GGACAGAAAG ACTGTTTAGA
1601 ACGTGGCAT GTGTCAGAAT CTCAACCCGT TTCTGTCGTC TTGATGACT GCAATCTTTGA ACAATAA CAATATCA GTGCTACATT TGGGAAAGGT GCCAGACGCT
1701 GTGCTTCC GTGTCAGAAT CTCAACCCGT TTCTGTCGTC TTGATGACT GCAATCTTTGA ACAATAA
1801 TGCACTGCCT GCGATCTGGT
```

```
   1 MATFYEVIVR VPFDVEEHLP GISDSFVDMV TGQIWELPPE SDLNLILIVEQ PQLIVADRIR RVFLYEWNKF SKQESKFFVQ FEKGSEYFHL HTLVETSGIS
 101 SMVLGRYVSQ IRAQLVKVVF QGIEPQINDW VAITKVKKGG ANKVVDSGYI PNYLLPKTQP ELQWAWINME QYLSACINLF ERKRLVAQHL THVSQTQEQN
 201 KENQNPNSDA FVIRSKTSAR YMELVGWLVD KGITSEKQWI QEDQASYISF NAASNSRSQI MSLIKTAPDY LVGQQPVEDI SSNRIYKILE
 301 LNGYDPQYAA SVFLGWATKK FGKRNTIWLF GPATTGKTNI AEAIAHTVPF YGCVNWINEN FPFNDCVDKM VIMWEEGKMT AKVVESAKAI LGGSKVRVDQ
 401 KCKSSAQIDP TPVIVTSNTN MCAVIDGNST TFEHQQPLQD RMFKFELTRR QEVKDFFRWA KDHVVEVEHE FVVKKGGAKK RPAPSDADIS
 501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
 601 CTACDLVNVD LDDCIFEQ*
```

FIG. 28

```
         150        160        170        180        190        200        210        220
AAV1 REP40   VIWWEEGKMTAKVVESAKAILGGSKVRVDQKCKSSAQIDPTPVIVTSNTNMCAVIDGNSTTFEHQQPLQDRMFKF
AAV2 REP40   VIWWEEGKMTAKVVESAKAILGGSKVRVDQKCKSSAQIDPTPVIVTSNTNMCAVIDGNSTTFEHQQPLQDRMFKF
AAV3A REP40  VIWWEEGKMTAKVVESAKAILGGSKVRVDQKCKSSAQIEPTPVIVTSNTNMCAVIDGNSTTFEHQQPLQDRMFKF
AAV3B REP40  VIWWEEGKMTAKVVESAKAILGGSKVRVDQKCKSSAQIDPTPVIVTSNTNMCAVIDGNSTTFEHQQPLQDRMFKF
AAV4 REP40   VIWWEEGKMTAKVVESAKAILGGSKVRVDQKCKSSVQIDSTPVIVTSNTNMCVVVDGNSTTFEHQQPLEDRMFKF
AAV5 REP40   LIWWEEGKMTAKVVESAKAILGGSKVRVDQKCKSSAQIDPTPVIVTSNTNMCVVVDGNSTTFEHQQPLQDRMFKF
AAV6 REP40   VIWWEEGKMTAKVVESAKAILGGSKVRVDQKCKSSAQIDPTPVIVTSNTNMCAVIDGNSTTFEHQQPLQDRMFKF
AAV7 REP40   VIWWEEGKMTAKVVESAKAILGGSKVRVDQKCKSSAQIDPTPVIVTSNTNMCAVIDGNSTTFEHQQPLQDRMFKF
AAV8 REP40   VIWWEEGKMTAKVVESAKAILGGSKVRVDQKCKSSAQIDPTPVIVTSNTNMCAVIDGNSTTFEHQQPLQDRMFKF
CONSENSUS 230        240        250        260        270        280        290
AAV1 REP40   ELTRRLEHDFGKVTKQEVKEFFRWAQDHVTEVAHEFYVR------KGGAN--KRPAPDDADKSEP------KRACP
AAV2 REP40   ELTKRLEHDFGKVTKQEVKEFFRWAKDHVTEVAHEFYVK------KGGAK--KRPAPSDADISEP------KRVRE
AAV3A REP40  ELTRRLDHDFGKVTKQEVKDFFRWAKDHVTEVEHEFYVK------KGGAK--KRPASDADISEP------KRVRE
AAV3B REP40  ELTRRLDHDFGKVTKQEVKDFFRWASDHVTDVAHEFYVK------KGGAK--KRPASNDADVSEP------KRECT
AAV4 REP40   ELTKRLEHDFGKVTKQEVKDFFRWASDHVTEVAHEFYVK------KGGAK--KRPASNDADVSEP------KRQCT
AAV5 REP40   ELTRRLEHDFGKVTKQEVKDFFAWAKVNQVPVTHEFKVPRELAGTKGAEKSLKRPLGDVTNTSYKSLEKRARLSF
AAV6 REP40   ELTKRLPPDFGKITKQEVKEFFRWAKDHVTEVAHEFYVR------KGGAR--KRPAPNDADISEP------KRACP
AAV7 REP40   ELTRRLEHDFGKVTKQEVKEFFRWAQDHVTEVAHEFYVR------KGGAN--KRPAPDDADKSEP------KRACP
AAV8 REP40   ELTRRLEHDFGKVTKQEVKEFFRWASDHVTEVAHEFYVR------KGGAS--KRPAPDDADKSEP------KRACP
CONSENSUS
```

FIG. 29 (cont.)

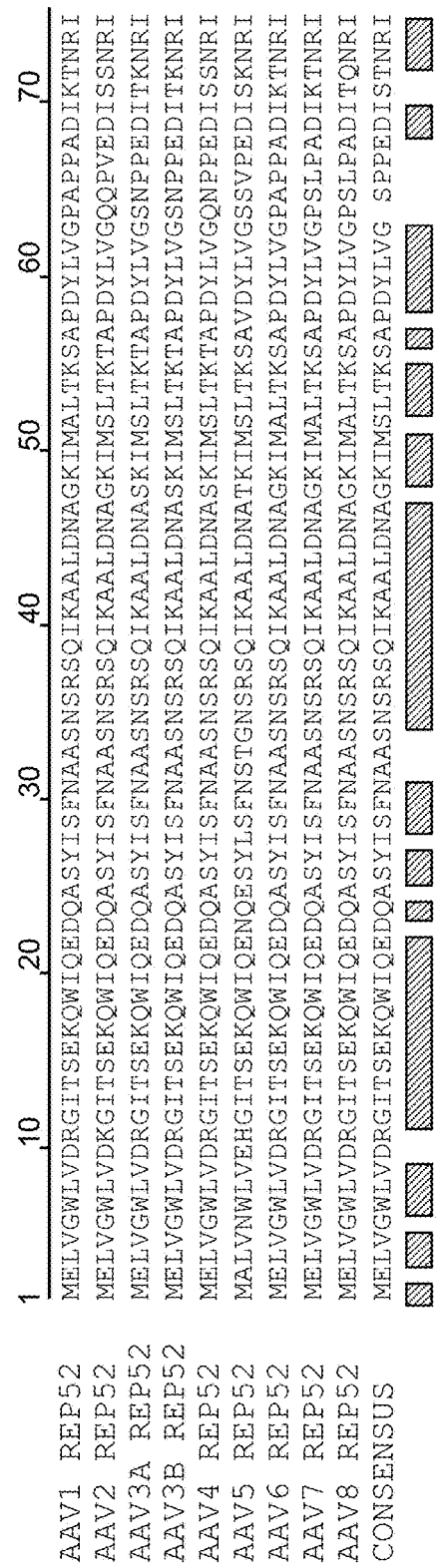

|            |                                                                    |
|------------|--------------------------------------------------------------------|
|            | 80        90        100       110       120       130       140   |
| AAV1 REP52 | YRILELNGYEPAYAGSVFLGWAQKRFGKRNTIWLFGPATTGKTNIAEAIAHAVPFYGCVNWTNENFPFNDCVDKM |
| AAV2 REP52 | YKILELNGYDPQYAASVFLGWATKKFGKRNTIWLFGPATTGKTNIAEAIAHTVPFYGCVNWTNENFPFNDCVDKM |
| AAV3A REP52| YQILELNGYDPQYAASVFLGWAQKKFGKRNTIWLFGPATTGKTNIAEAIAHAVPFYGCVNWTNENFPFNDCVDKM |
| AAV3B REP52| YQILELNGYDPQYAASVFLGWAQKKFGKRNTIWLFGPATTGKTNIAEAIAHAVPFYGCVNWTNENFPFNDCVDKM |
| AAV4 REP52 | YRILEMNGYDPQYAYAGSVFLGWAQKKFGKRNTIWLFGPATTGKTNIAEAIAHAVPFYGCVNWTNENFPFNDCVDKM |
| AAV5 REP52 | WQIFEMNGYDPAYAGSILYGWCQRSFNKRNTVWLKRNTIWLFGPATTGKTNIAEAIAHTVPFYGCVNWTNENFPFNDCVDKM |
| AAV6 REP52 | YRILELNGYDPAYAGSVFLGWAQKRFGKRNTIWLFGPATTGKTNIAEAIAHAVPFYGCVNWTNENFPFNDCVDKM |
| AAV7 REP52 | YRILELNGYDPAYAGSVFLGWAQKKFGKRNTIWLFGPATTGKTNIAEAIAHAVPFYGCVNWTNENFPFNDCVDKM |
| AAV8 REP52 | YRILALNGYDPAYAGSVFLGWAQKKFGKRNTIWLFGPATTGKTNIAEAIAHAVPFYGCVNWTNENFPFNDCVDKM |
| CONSENSUS  | YRILELNGYDPAYAGSVFLGWAQKKFGKRNTIWLFGPATTGKTNIAEAIAHAVPFYGCVNWTNENFPFNDCVDKM |

|            |                                                                    |
|------------|--------------------------------------------------------------------|
|            | 150       160       170       180       190       200       210       220 |
| AAV1 REP52 | VIWWEEGKMTAKVVESAKAILGGSKVRVDQKCKSSAQIDPTPVIVTSNTNMCAVIDGNSTTFEHQQPLQDRMFKF |
| AAV2 REP52 | VIWWEEGKMTAKVVESAKAILGGSKVRVDQKCKSSAQIDPTPVIVTSNTNMCAVIDGNSTTFEHQQPLQDRMFKF |
| AAV3A REP52| VIWWEEGKMTAKVVESAKAILGGSKVRVDQKCKSSAQIEPTPVIVTSNTNMCAVIDGNSTTFEHQQPLQDRMFKF |
| AAV3B REP52| VIWWEEGKMTAKVVESAKAILGGSKVRVDQKCKSSAQIEPTPVIVTSNTNMCAVIDGNSTTFEHQQPLQDRMFKF |
| AAV4 REP52 | VIWWEEGKMTAKVVESAKAILGGSKVRVDQKCKSSVQIDSTPVIVTSNTNMCVVDGNSTTFEHQQPLQDRMFKF |
| AAV5 REP52 | LIWWEEGKMTNKVVESAKAILGGSKVRVDQKCKSSAQIDSTPVIVTSNTNMCAVIDGNSTTFEHQQPLEDRMFKF |
| AAV6 REP52 | VIWWEEGKMTAKVVESAKAILGGSKVRVDQKCKSSAQIDPTPVIVTSNTNMCAVIDGNSTTFEHQQPLQDRMFKF |
| AAV7 REP52 | VIWWEEGKMTAKVVESAKAILGGSKVRVDQKCKSSAQIDPTPVIVTSNTNMCAVIDGNSTTFEHQQPLQDRMFKF |
| AAV8 REP52 | VIWWEEGKMTAKVVESAKAILGGSKVRVDQKCKSSAQIDPTPVIVTSNTNMCAVIDGNSTTFEHQQPLQDRMFKF |
| CONSENSUS  | VIWWEEGKMTAKVVESAKAILGGSKVRVDQKCKSSAQIDPTPVIVTSNTNMCAVIDGNSTTFEHQQPLQDRMFKF |

FIG. 30 (cont.)

| | 230 | 240 | 250 | 260 | 270 | 280 | 290 |
|---|---|---|---|---|---|---|---|
| AAV1 REP52 | ELTRRLEHDFGKVTKQEVKEFFRWAQDHVTEVAHEFYVR | | | | ----KGGAN | --KRPAPDDADKSEP | ----KRA------ |
| AAV2 REP52 | ELTRRLDHDFGKVTKQEVKDFFRWAKDHVVEVEHEFYVK | | | | ====KGGAK | --KRPAPSDADISEP | --KRV------ |
| AAV3A REP52 | ELTRRLDHDFGKVTKQEVKDFFRWASDHVTDVAHEFYVR | | | | ----KGGAK | --KRPASNDADVSEP | ---KRE------ |
| AAV3B REP52 | ELTRRLDHDFGKVTKQEVKDFFRWASDHVTDVAHEFYVR | | | | ----KGGAK | --KRPASNDADVSEP | ---KRE------ |
| AAV4 REP52 | ELTRRLEHDFGKVTKQEVKDFFRWASDHVTEVTHEFYVR | | | | ----KGGAR | --KRPAPNDADISEP | ----KRQ------ |
| AAV5 REP52 | ELTKRLPPDFGKITKQEVKDFFAWAKVNQVPVTHEFKVPRELAGTKGAEKSLKRPLGDVTNTSYKSLEKRARLSF |
| AAV6 REP52 | ELTRRLEHDFGKVTKQEVKEFFRWAQDHVTEVAHEFYVR | | | | ----KGGAN | --KRPAPDDADKSEP | ----KAR------ |
| AAV7 REP52 | ELTRRLEHDFGKVTKQEVKEFFRWASDHVTEVAHEFYVR | | | | ----KGGAS | --KRPAPDDADISEP | ----KRA------ |
| AAV8 REP52 | ELTRRLEHDFGKVTKQEVKEFFRWASDHVTEVAHEFYVR | | | | ----KGGAS | --KRPAPDDADKSEP | ----KRA------ |
| CONSENSUS | ELTRRLEHDFGKVTKQEVKDFFRWASDHVTEVAHEFYVR | | | | KGGAK | KRPAPDDADISEP | KRA |

| | 300 | 310 | 320 | 330 | 340 | 350 | 360 |
|---|---|---|---|---|---|---|---|
| AAV1 REP52 | ---CPSVADPSTSDAEGAPVDFADRYQNKCSRHAGMLQMLFPCKTCERMNQNFNICFTHGTRDCSECFPG |
| AAV2 REP52 | ---RESVAQPSTSDAE-ASINYADRYQNKCSRHVGMNLMLFPCRQCERMNQNSNICFTHGQKDCLECFPV |
| AAV3A REP52 | ---CTSLAQPTTSDAE--APADYADRYQNKCSRHVGMNLMLFPCKTCERMNQISNVCFTHGQRDCGECFPG |
| AAV3B REP52 | ---CTSLAQPTTSDAE--APADYADRYQNKCSRHVGMNLMLFPCKTCERMNQISNVCFTHGQRDCGECFPG |
| AAV4 REP52 | ---CPSVAQPSTSDAE--APVDYADRYQNKCSRHVGMNLMLFPCRQCERMNQNVDICFTHGVMDCAECFPV |
| AAV5 REP52 | VPETPRSSDVTVDPAPLRPLNWNSRYDCKCDYHAQFDNISNKCDECEYLNRGKNGCICHNVTHCQICHGI |
| AAV6 REP52 | ---CPSVADPSTSDAEGAPVDFADRYQNKCSRHAGMLQMLFPCKTCERMNQNFNICFTHGTRDCSECFPG |
| AAV7 REP52 | ---CPSVADPSTSDAEGAPVDFADRYQNKCSRHAGMLQMLFPCKTCERMNQNFNICFTHGVRDCLECFPG |
| AAV8 REP52 | ---CPSVADPSTSDAEGAPVDFADRYQNKCSRHAGMLQMLFPCKTCERMNQNFNICFTHGVRDCSECFPG |
| CONSENSUS | CPSVADPSTSDAE APVDFADRYQNKCSRHAGM QMLFPCKTCERMNQN NICFTHG RDC ECFPG |

|     |       |     80         90         100        110        120        130        140 |
| --- | ----- | --- |
| AAV1 | REP68 | EALFFVQFEKGESYFHLHILVETTGVKSMVLGRFLSQIRDKLVQTIYRG-IEPTLPNWFAVTKTRNGAGGG-NKV |
| AAV2 | REP68 | EALFFVQFEKGESYFHMHVLVETTGVKSMVLGRFLSQIREKLIQRIYRG-IEPTLPNWFAVTKTRNGAGGG-NKV |
| AAV3A | REP68 | EALFFVQFEKGETYFHLHVLIETIGVKSMVVGRYVSQIKEKLVTRIYRG-VEPQLPNWFAVTKTRNGAGGG-NKV |
| AAV3B | REP68 | EALFFVQFEKGETYFHLHVLIETIGVKSMVVGRYVSQIKEKLVTRIYRG-VEPQLPNWFAVTKTRNGAGGG-NKV |
| AAV4 | REP68 | EALFFVQFEKGDSYFHLHILVETTGVKSMVLGRYVSQIKEKLVTRIYRG-VEPQLPNWFAVTKTRNGAGGG-NKV |
| AAV5 | REP68 | ESKFFVQFEKGSEYFHLHTLVETSGISSMVLGRYVSQIRAQLVKVVFQG-IEPQINDWVAITKVKK---GGANKV |
| AAV6 | REP68 | EALFFVQFEKGESYFHLHILVETTGVKSMVLGRFLSQIRDKLVQTIYRG-IEPTLPNWFAVTKTRNGAGGG-NKV |
| AAV7 | REP68 | EALFFVQFEKGESYFHLHVLVETTGVKSMVLGRFLSQIREKLVQTIYRG-VEPTLPNWFAVTKTRNGAGGG-NKV |
| AAV8 | REP68 | EALFFVQFELGESYFHLVLVETTGVKSMVLGRFLSQIREKLGPDHLPAGSSPTLPNWFAVTKDAVMAPAGGNKV |

|     |       |     150        160        170        180        190        200        210        220 |
| --- | ----- | --- |
| AAV1 | REP68 | VDECYIPNYLLPKTQPELQWAWTNMEEYISACLNLAERKRLVAQHLTHVSQTQEQNKENLNPNSDAPVIRSKTSA |
| AAV2 | REP68 | VDECYIPNYLLPKTQPELQWAWTNMEQYLSACLNLTERKRLVAQHLTHVSQTQEQNKENQNPNSDAPVIRSKTSA |
| AAV3A | REP68 | VDDCYIPNYLLPKTQPELQWAWTNMDQYLSACLNLTERKRLVAQHLTHVSQTQEQNKENQNPNSDAPVIRSKTSA |
| AAV3B | REP68 | VDDCYIPNYLLPKTQPELQWAWTNMDQYLSACLNLTERKRLVAQHLTHVSQTQEQNKENQNPNSDAPVIRSKTSA |
| AAV4 | REP68 | VDDCYIPNYLLPKTQPELQWAWTNMDQYISACLNLAERKRLVAQHLTHVSQTQEQNKENQNPNSDAPVIRSKTSA |
| AAV5 | REP68 | VDSGYIPAYLLPKTQPELQWAWTNLDEYKLAAINLEYRKRLVAQFLAESSQRS-QEAASQREFSADPVIKSKTSQ |
| AAV6 | REP68 | VDECYIPNYLLPKTQPELQWAWTNMEEYISACLNLAERKRLVAQHLTHVSQTQEQNKENLNPNSDAPVIRSKTSA |
| AAV7 | REP68 | VDECYIPNYLLPKTQPELQWAWTNMEEYISACLNLAERKRLVAHDLTHVSQTQEQNKENLNPNSDAPVIRSKTSA |
| AAV8 | REP68 | VDECYIPNYLLPKTQPELQWAWTNMEEYISACLNLAERKRLVAQHLTHVSQTQEQNKENLNPNSDAPVIRSKTSA |

FIG. 31 (cont.)

```
           230        240        250        260        270        280        290
AAV1 REP68  RYMELVGWLVDRGITSEKQWIQEDQASYISFNAASNSRSQIKAALDNAGKIMALTKSAPDYLVGPAPPADIKTNR
AAV2 REP68  RYMELVGWLVDKGITSEKQWIQEDQASYISFNAASNSRSQIKAALDNAGKIMSLTKTAPDYLVGQQPVEDISSNR
AAV3A REP68 RYMELVGWLVDRGITSEKQWIQEDQASYISFNAASNSRSQIKAALDNAGKIMSLITKTAPDYLVGSNPPEDITKNR
AAV3B REP68 RYMELVGWLVDRGITSEKQWIQEDQASYISFNAASNSRSQIKAALDNASKIMSLTKTAPDYLVGSNPPEDITKNR
AAV4 REP68  RYMELVGWLVDRGITSEKQWIQEDQASYISFNAASNSRSQIKAALDNASKIMSLTKTAPDYLVGQNPPEDISSNR
AAV5 REP68  KYMALVNWLVEHGITSEKQWIQENQESYLSFNSTGNSRSQIKAALDNATKIMSLTKSAVDYILVGSSVPEDISKNR
AAV6 REP68  RYMELVGWLVDRGITSEKQWIQEDQASYISFNAASNSRSQIKAALDNAGKIMALTKSAPDYLVGPAPPADIKTNR
AAV7 REP68  RYM LVGWLVDRGITSEKQWIQEDQASYISFNAASNSRSQIKAALDNAGKIMALTKSAPDYLVGPSLPADIKTNR
AAV8 REP68  RYMELVGWLVDRGITSEKQWIQEDQASYISFNAASNSRSQIKAALDNAGKIMALTKSAPDYLVGPSLPADITQNR 300        310        320        330        340        350        360        370
AAV1 REP68  IYRILELNGYEPAYAGSVFLGMAQKRFGKRNTIWLFGPATTGKTNIAEAIAHAVPFYGCVNWTNENFPFNDCVDK
AAV2 REP68  IYKILELNGYDPQYAASVFLGWATKKFGKRNTIWLFGPATTGKTNIAEAIAHTVPFYGCVNWTNENFPFNDCVDK
AAV3A REP68 IYQILELNGYDPQYAASVFLGWAQKKFGKRNTIWLFGPATTGKTNIAEAIAHAVPFYGCVNWTNENFPFNDCVDK
AAV3B REP68 IYQILELNGYDPQYAASVFLGWAQKKFGKRNTIWLFGPATTGKTNIAEAIAHAVPFYGCVNWTNENFPFNDCVDK
AAV4 REP68  IYRILEMNGYDPAYAGSILYGWAQKKFGKRNTIWLFGPATTGKTNIAEAIAHAVPFYGCVNWTNENFPFNDCVDK
AAV5 REP68  IWQIFEMNGYDPAYAGSVFLGWAQKKFGKRNTVWLYGPATTGKTNIAEAIAHTVPFYGCVNWTNENFPFNDCVDK
AAV6 REP68  IYRILELNGYEPAYAGSVFLGMAQKRFGKRNTIWLFGPATTGKTNIAEAIAHAVPFYGCVNWTNENFPFNDCVDK
AAV7 REP68  IYRILELNGYDPAYAGSVFLGWAQKKFGKRNTIWLFGPATTGKTNIAEAIAHAVPFYGCVNWTNENFPFNDCVDK
AAV8 REP68  IYRILALNGYDPAYAGSVFLGWAQKKFGKRNTIWLFGPATTGKTNIAEAIAHAVPFYGCVNWTNENFPFNDCVDK
```

FIG. 31 (cont.)

```
                 380       390       400       410       420       430       440
AAV1 REP68   MVIWWEEGKMTAKVVESAKAILGGSKVRVDQKCKSSAQIDPTPVIVTSNTNMCAVIDGNSTTFEHQQPLQDRMFK
AAV2 REP68   MVIWWEEGKMTAKVVESAKAILGGSKVRVDQKCKSSAQIDPTPVIVTSNTNMCAVIDGNSTTFEHQQPLQDRMFK
AAV3A REP68  MVIWWEEGKMTAKVVESAKAILGGSKVRVDQKCKSSAQIEPTPVIVTSNTNMCAVIDGNSTTFEHQPLQDRMFE
AAV3B REP68  MVIWWEEGKMTAKVVESAKAILGGSKVRVDQKCKSSAQIEPTPVIVTSNTNMCAVIDGNSTTFEHQQPLQDRMFK
AAV4 REP68   MVIWWEEGKMTAKVVESAKAILGGSKVRVDQKCKSSAQIDPTPVIVTSNTNMCAVIDGNSTTFEHQQPLQDRMFK
AAV5 REP68   MLIWWEEGKMTNKVVESAKAILGGSKVRVDQKCKSSVQIDSTPVIVTSNTNMCVVVDGNSTTFEHQQPLQDRMFK
AAV6 REP68   MVIWWEEGKMTAKVVESAKAILGGSKVRVDQKCKSSAQIDPTPVIVTSNTNMCAVIDGNSTTFEHQQPLEDRMFK
AAV7 REP68   MVIWWEEGKMTAKVVESAKAILGGSKVRVDQKCKSSAQIDPTPVIVTSNTNMCAVIDGNSTTFEHQQPLQDRMFK
AAV8 REP68   MVIWWEEGKMTAKVVESAKAILGGSKVRVDQKCKSSAQIDPTPVIVTSNTNMCAVIDGNSTTFEHQQPLQDRMFK 450       460       470       480       490       500       510
AAV1 REP68   FELTRRLEHDFGKVTKQEVKEFFRWAQDHVTEVAHEFYVR-------KGGAN---KRPAPDDADKSEP----
AAV2 REP68   FELTRRLDHDFGKVTKQEVKDFFRWAKDHVVEVEHEFYVK-------KGGAK---KRPAPSDADISEP----
AAV3A REP68  FELTRRLDHDFGKVTKQEVKDFFRWASDHVTDVAHEFYVR-------KGGAK---KRPASNDADVSEP----
AAV3B REP68  FELTRRLDHDFGKVTKQEVKDFFRWASDHVTDVAHEFYVR-------KGGAK---KRPASNDADVSEP----
AAV4 REP68   FELTRRLEHDFGKVTKQEVKDFFRWASDHVTEVTHEFYVR-------KGGAR---KRPAPNDADISEP----
AAV5 REP68   FELTRRLPPDFGKITKQEVKDFFAWAKVNQVPVTHEFKVPRELAGTKGAEKSLKRPLGDVTNTSYKSLEK---
AAV6 REP68   FELTRRLEHDFGKVTKQEVKEFFRWAQDHVTEVAHEFYVR-------KGGAN---KRPAPDDADKSEP----
AAV7 REP68   FELTRRLEHDFGKVTKQEVKDFFRWASDHVTEVAHEFYVR-------KGGAS---KRPAPDDADISEP----
AAV8 REP68   FELTRRLEHDFGKVTKQEVKDFFRWASDHVTEVAHEFYVR-------KGGAS---KRPAPDDADKSEP----
```

FIG. 31 (cont.)

```
                    520       530       540       555
AAV1 REP68  -KRACPSVADPSTSDAEGAPVDFADLARGQPL----   (SEQ ID NO:104)
AAV2 REP68  -KRVRESVAQPSTSDAE-ASINYADLARGHSL----   (SEQ ID NO:105)
AAV3A REP68 -KRECTSLAQPTTSDAE-APADYADLARGQPF----   (SEQ ID NO:106)
AAV3B REP68 -KRQCTSLAQPTTSDAE-APADYADLARGQPF----   (SEQ ID NO:107)
AAV4 REP68  -KRACPSVAQPSTSDAE-APVDYADLARGQPL----   (SEQ ID NO:108)
AAV5 REP68  RARLSFVPETPRSSDVTVDPAPLRPLNWNSLVGRSW   (SEQ ID NO:109)
AAV6 REP68  -KRACPSVADPSTSDAEGAPVDFADLARGQPL----   (SEQ ID NO:110)
AAV7 REP68  -KRACPSVADPSTSDAEGAPVDFADLARGQPL----   (SEQ ID NO:111)
AAV8 REP68  -KRACPSVADPSTSDAEGAPVDFADLARGQPL----   (SEQ ID NO:112)
```

FIG. 31 (cont.)

```
              1         10        20        30        40        50        60        70
AAV1 REP78   MPGFYEIVIKVPSDLDEHLPGISDSFVSWVAEKEWELPPDSDMDLNLIEQAPLTVAEKLQRDFLVQWRRVSKAP
AAV2 REP78   MPGFYEIVLKVPSDLDEHLPGISDSFVNWVAEKEWELPPDSDMDLNLIEQAPLTVAEKLQRDFLTEWRRVSKAP
AAV3A REP78  MPGFYEIVLKVPSDLDEHLPGISNSFVNWVAEKEWDVPPDSDMDPNLIEQAPLTVAEKLQREFLVEWRRVSKAP
AAV3B REP78  MPGFYEIVLKVPSDLDERLPGISNSFVNWVAEKEWELPPDSDMDPNLIEQAPLTVAEKLQREFLVEWRRVSKAP
AAV4 REP78   MPGFYEIVLKVPSDLDEHLPGISDSFVSWVAEKEWELPPDSDMDLNLIEQAPLTVAEKLQREFLVEWRRVSKAP
AAV5 REP78   MATFYEIVLKVPSDLDEHLPGISDSFVDWVTGQIWELPPESDLNLTLVEQPQLTVADRIRRVFLYEWNKFSKQ-
AAV6 REP78   MPGFYEIVIKVPSDLDEHLPGISDSFVSWVAEKEWELPPDSDMDLNLIEQAPLTVAEKLQRDFLVQWRRVSKAP
AAV7 REP78   MPGFYEIVIKVPSDLDEHLPGISDSFVNWVAEKEWELPPDSDMDLNLIEQAPLTVAEKLQRDFLVQWRRVSKAP
AAV8 REP78   MPGFYEIVIKVPSDLDEHLPGISDSFVNWVAEKEWELPPDSDMDRNLIEQAPLTVAEKLQRDFLVQWRRVSKAP
CONSENSUS    MPGFYEIVIKVPSDLDEHLPGISDSFVNWVAEKEWELPPDSDMDLNLIEQAPLTVAEKLQRDFLVEWRRVSKAP
```

FIG. 32

```
            230        240        250        260        270        280        290
AAV1 REP78   RYMELVGWLVDRGITSEKQWIQEDQASYISFNAASNSRSQIKAALDNAGKIMALTKSAPDYLVGPAPPADIKTNR
AAV2 REP78   RYMELVGWLVDKGITSEKQWIQEDQASYISFNAASNSRSQIKAALDNAGKIMSLTKTAPDYLVGQQPVEDISSNR
AAV3A REP78  RYMELVGWLVDRGITSEKQWIQEDQASYISFNAASNSRSQIKAALDNAGKIMSLTKTAPDYLVGSNPPEDITKNR
AAV3B REP78  RYMELVGWLVDRGITSEKQWIQEDQASYISFNAASNSRSQIKAALDNAGKIMSLTKTAPDYLVGSNPPEDITKNR
AAV4 REP78   RYMELVGWLVDRGITSEKQWIQEDQASYISFNAASNSRSQIKAALDNATKIMSLTKSAVDYLVGSSVPEDISKNR
AAV5 REP78   KYMALVNWLVEHGITSEKQWIQENQESYLSFNSTGNSRSQIKAALDNAGKIMALTKSAPDYLVGPAPPADIKTNR
AAV6 REP78   RYMELVGWLVDRGITSEKQWIQEDQASYISFNAASNSRSQIKAALDNAGKIMALTKSAPDYLVGPAPPADIKTNR
AAV7 REP78   RYMELVGWLVDRGITSEKQWIQEDQASYISFNAASNSRSQIKAALDNAGKIMSLTKSAPDYLVGPSLPADIKTNR
AAV8 REP78   RYMELVGWLVDRGITSEKQWIQEDQASYISFNAASNSRSQIKAALDNAGKIMSLTKSAPDYLVGPSLPADITQNR
CONSENSUS                                                                    SPPEDISTNR 300        310        320        330        340        350        360        370
AAV1 REP78   IYRILELNGYEPAYAGSVFLGWAQKRFGKRNTIWLFGPATTGKTNIAEAIAHAVPFYGCVNWTNENFPFNDCVDK
AAV2 REP78   IYKILELNGYDPQYAASVFLGWATKKFGKRNTIWLFGPATTGKTNIAEAIAHTVPFYGCVNWTNENFPFNDCVDK
AAV3A REP78  IYQILELNGYDPQYAASVFLGWAQKKFGKRNTIWLFGPATTGKTNIAEAIAHAVPFYGCVNWTNENFPFNDCVDK
AAV3B REP78  IYQILELNGYDPQYAASVFLGWAQKKFGKRNTIWLFGPATTGKTNIAEAIAHAVPFYGCVNWTNENFPFNDCVDK
AAV4 REP78   IYRILEMNGYDPQYAASVFLGWAQKRFGKRNTIWLFGPATTGKTNIAEAIAHAVPFYGCVNWTNENFPFNDCVDK
AAV5 REP78   IWQIFEMNGYDPAYAGSILYGWCQRSFNKRNTVWLYGPATTGKTNIAEAIAHTVPFYGCVNWTNENFPFNDCVDK
AAV6 REP78   IYRILELNGYDPAYAGSVFLGWAQKRFGKRNTIWLFGPATTGKTNIAEAIAHAVPFYGCVNWTNENFPFNDCVDK
AAV7 REP78   IYRILELNGYDPAYAGSVFLGWAQKRFGKRNTIWLFGPATTGKTNIAEAIAHAVPFYGCVNWTNENFPFNDCVDK
AAV8 REP78   IYRILALNGYDPAYAGSVFLGWAQKKFGKRNTIWLFGPATTGKTNIAEAIAHAVPFYGCVNWTNENFPFNDCVDK
CONSENSUS
```

FIG. 32 (cont.)

|              | 380        390        400        410        420        430        440 |
|--------------|---------------------------------------------------------------------------|
| AAV1 REP78   | MVIWWEEGKMTAKVVESAKAILGGSKVRVDQKCKSSAQIDPTPVIVTSNTNMCAVIDGNSTTFEHQQPLQDRMFK |
| AAV2 REP78   | MVIWWEEGKMTAKVVESAKAILGGSKVRVDQKCKSSAQIDPTPVIVTSNTNMCAVIDGNSTTFEHQQPLQDRMFK |
| AAV3A REP78  | MVIWWEEGKMTAKVVESAKAILGGSKVRVDQKCKSSAQIDPTPVIVTSNTNMCAVIDGNSTTFEHQQPLQDRMFE |
| AAV3B REP78  | MVIWWEEGKMTAKVVESAKAILGGSKVRVDQKCKSSAQIEPTPVIVTSNTNMCAVIDGNSTTFEHQQPLQDRMFK |
| AAV4 REP78   | MVIWWEEGKMTAKVVESAKAILGGSKVRVDQKCKSSAQIDPTPVIVTSNTNMCAVIDGNSTTFEHQQPLEDRMFK |
| AAV5 REP78   | MLIWWEEGKMTNKVVESAKAILGGSKVRVDQKCKSSVQIDSTPVIVTSNTNMCVVVDGNSTTFEHQQPLQDRMFK |
| AAV6 REP78   | MVIWWEEGKMTAKVVESAKAILGGSKVRVDQKCKSSAQIDPTPVIVTSNTNMCAVIDGNSTTFEHQQPLQDRMFK |
| AAV7 REP78   | MVIWWEEGKMTAKVVESAKAILGGSKVRVDQKCKSSAQIDPTPVIVTSNTNMCAVIDGNSTTFEHQQPLQDRMFK |
| AAV8 REP78   | MVIWWEEGKMTAKVVESAKAILGGSKVRVDQKCKSSAQIDPTPVIVTSNTNMCAVIDGNSTTFEHQQPLQDRMFK |
| CONSENSUS    |                                                                           |

|              | 450        460        470        480        490        500        510        520 |
|--------------|----------------------------------------------------------------------------------------|
| AAV1 REP78   | FELTRRLEHDFGKVTKQEVKEFFRWAQDHVTEVAHEFYVR--------KGGAN--KRPAPDDADKSEP---KRA--- |
| AAV2 REP78   | FELTRRLDHDFGKVTKQEVKDFFRWAKDHVVEVEHEFYVR--------KGGAK--KRPAPSDADISEP---KRV--- |
| AAV3A REP78  | FELTRRLDHDFGKVTKQEVKDFFRWASDHVTDVAHEFYVR--------KGGAK--KRPASNDADVSEP---KRE--- |
| AAV3B REP78  | FELTKRLPPDFGKITKQEVKDFFRWASDHVTDVAHEFYVR--------KGGAK--KRPASNDADVSEP---KRQ=== |
| AAV4 REP78   | FELTKRLPPDFGKITKQEVKDFFAWAKVNQVPVTHEFKVPTHEFYVR-KGGAR--KRPAPNDADISEP---KRA--- |
| AAV5 REP78   | FELTRRLEHDFGKVTKQEVKDFFRWASDHVTEVAHEFYVRPRELAGTKGAEKSLKRPLGDVTNTSYKSLEKRARLS |
| AAV6 REP78   | FELTRRLEHDFGKVTKQEVKEFFRWAQDHVTEVAHEFYVR--------KGGAN--KRPAPDDADKSEP---KRA--- |
| AAV7 REP78   | FELTRRLEHDFGKVTKQEVKEFFRWASDHVTEVAHEFYVR--------KGGAS--KRPAPDDADISEP---KRA--- |
| AAV8 REP78   | FELTRRLEHDFGKVTKQEVKDFFRWASDHVTEVAHEFYVR--------KGGAS--KRPAPDDADKSEP---KRA--- |
| CONSENSUS    |                                                               KGGAK  KRPAPDDADISEP    KRA |

FIG. 32 (cont.)

```
                    530        540        550        560        570        580        590
AAV1 REP78     ----CPSVADPSTSDAEGAPVDFADRYQNKCSRHAGMLQMLFPCKTCERMNQNFNICFTHGTRDCSECFPGVSES
AAV2 REP78     ----RESVAQPSTSDAE-ASINYADRYQNKCSRHVGMNLMLFPCRQCERMNQNSNICFTHGQKDCLECFPVS-ES
AAV3A REP78    ----CTSLAQPTTSDAE-APADYADRYQNKCSRHVGMNLMLFPCKTCERMNQISNVCFTHGQRDCGECFPGMSES
AAV3B REP78    ----CTSLAQPTTSDAE-APADYADRYQNKCSRHVGMNLMLFPCKTCERMNQISNVCFTHGQRDCGECFPGMSES
AAV4 REP78     ----CPSVAQPSTSDAE-APVDYADRYQNKCSRHVGMNLMLFPCRQCERMNQNVDICFTHGVMDCAECFPVS-ES
AAV5 REP78     FVPETPRSSDVTVDPAPLRPLNWNSRYDCKCDYHAQFDNISNKCDECEYLNRGKNGCICHNVTHCQICHGIPPWE
AAV6 REP78     ----CPSVADPSTSDAEGAPVDFADRYQNKCSRHAGMLQMLFPCKTCERMNQNFNICFTHGTRDCSECFPGVSES
AAV7 REP78     ----CPSVADPSTSDAEGAPVDFADRYQNKCSRHAGMLQMLFPCKTCERMNQNFNICFTHGVRDCLECFPGVSES
AAV8 REP78     ----CPSVADPSTSDAEGAPVDFADRYQNKCSRHAGMLQMLFPCKTCERMNQNFNICFTHGVRDCSECFPGVSES
CONSENSUS          CPSVADPSTSDAE APVDFADRYQNKCSRHAGM QMLFPCKTCERMNQN NICFTHG RDC ECFPGVSES 600        610        620        630     646
AAV1 REP78     Q--PVVRKRTYRKLCAIHHLLGRAPEIACSACDLVNVDLDDCVSEQ-         (SEQ ID NO:113)
AAV2 REP78     QPVSVVKK-AYQKLCYIHHIMGKVPD-ACTACDLVNVDLDDCIFEQ-         (SEQ ID NO:114)
AAV3A REP78    QPVSVVKKTYQKLCPIHHILGRAPEIACSACDLANVDLDDCVSEQ-          (SEQ ID NO:115)
AAV3B REP78    QPVSVVKKTYQKLCPIHHILGRAPEIACSACDLANVDLDDCVSEQ-          (SEQ ID NO:116)
AAV4 REP78     QPVSVVRKRTYQKLCPIHHIMGRAPEVACSACELANVDLDDCDMEQ-         (SEQ ID NO:117)
AAV5 REP78     K---------------E---NLSD---FGDEFDDANKEQ-               (SEQ ID NO:118)
AAV6 REP78     Q--PVVRKRTYRKLCAIHHLLGRAPEIACSACDLVNVDLDDCVSEQ-         (SEQ ID NO:119)
AAV7 REP78     Q--PVVRKRTYRKLCAIHHLLGRAPEIACSACDLVNVDLDDCVSEQ-         (SEQ ID NO:120)
AAV8 REP78     Q--PVVRKRTYRKLCAIHHLLGRAPEIACSACDLVNVDLDDCVSEQ-         (SEQ ID NO:121)
CONSENSUS      Q   VVRKRTY KLC IHHILGRAPEIACSACDLVNVDLDDCVSEQ          (SEQ ID NO:122)
```

FIG. 32 (cont.)

```
SNAKE ITR
  1 CGCCCCACCC CTAGTGATCG CGGCGCGTCT CTCTTGGGGC CTGACGGGCCG AAGGCCGTCA TTCGCTCGAGC GCTGCCGAGC AGGCCCAAG
 91 AGAGAGCGCG CGCGATCACT AGGGGTGGGG CG
```

SNAKE REPCAP2 PLASMID (PSNREPCAP2)
TCGCGCGTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCTGGCTTAACTATGCGGC
ATCAGAGCAGATTGTACTGAGAGTGCACCATATGCGGTGTGAAATACCGCACAGATGCGTAAGGAGAAAATACCGCA
TCAGGAAATTGTAAACGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGGAAGCGAAGAGCGCCCGCGCTTAATGCGCCGCTACAGGGCGCGTC
GCGCTGGCAAGTGTAGCGGTCACGCTGCGCGTAACCACCACACCCGCCGCGCTTAATGCGCCGCTACAGGGCGCGTC
GCGCCATTCGCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGTAAAACGACG
GCCAGTGAATTGTAATACGACTCACTATAGGGCGAATTCGAGCTCGCAGCGGACATGTCTGGACATGTCTTTGAGCA
AGTCCATATAAGGAGTTCCGCCGGATATGCAAATGAGCAATCGCGCAAAGCATTTTGGGTAGTCACCATGAATAAAA
AGGACAGCAAGAAAGATGACGCCCCATAATTTTAATAGGAATTTTAACCATGCGGTTTTACGAGGTTGTGTTTCGTT
TGCCAAGAGACAATAACAACTTGTTGGATGAAGATAGATATCAGCCAGAGTTGAAAGAAGAAGATGACTGGCCTGAG
GAATATTTAACCAGTGAAGATGCCAGCTTTATCGGACTAGCGTATGCTGTGCTAAGTGAAATTCGGAGATTCTTTGG
AAAGGAACTACAATGGTTTGCCCAGGTTGAATGTGTGTCCTACTGCTGGTTACCACATGCATGTTTTGTTGAACCATC
CTAAGCTGAGTAACCAGACTTATGGAAGAAAGGTCAATGAACTGGCTTGCCGTATAGTCGATACCTTTGGCCTAATT
AATCCAGAAGAAGTCATCAGTACCCATTATGTTAAAAGCAACTATGGACATAAAAAGGTGAGAGTCATTCACCTAGA
GTCTTATTTGAAGAACTACTTTTTTCAGAAAGACTTTAGCTCCTCCAATTATACCGAGGAAGGAGACTATAAAAGAG
AGGAAGAAGTCGTGCTGTGGGCATTTACGAATATCGTCGCTTGGAAGCCATTCGTGCGGAATCTCATCAAGAGATCG
GAGCTAGCGACTGTTCCTAAGCAACCAGAGAATCCGGCGGGAGACGGACCGGCACCTCGAGTGACTGCAGGAACCCG
CCATTTTATGGAAACCATCGACTGGTTGGTGAAACATGGAATTACTACAGAACGAGAATTCTGCCACGCCAACCGCC
CTTTGTACCTGTCTATGCTGGCTTCTACTTCGGGTGCTGGGCAGATTAAAAGAGCGCTGGACCAGGCGAAACACATG
ATGACCAGCACCATGTCAGCAGAGGATTACCTGACAACAGAAGAGGATGTGATCGAACCACCTACTGAAAATAGAAT
CTACAAGATTATGAAACTGAATCGCTATGATCCAGCATAGCAGCTGCTCTCTTCTACGGCTTGGACCTGACAAGAACT
TTGGCAAGAGAAACACCATCTGGCTGTATGGTCCAGCTACTACCGGCAAAACCATCATCGCTCAAGCTATTGCACAT
GCTGTTAAACTGTTTGCTGGTGTTAATTGGACTAATGAAAACTTTCCCTTCTGTAACTGTCCAGGGAAACTGCTTAT
CTGGTGGAGGAGGGCAAGATGACAAACAAAATGGTGGAGACGGCTAAATGTATACTGGGGGATCTGCTGTACCTG
TAGACATCAAAGGCAAACCCGCTGAAATGTGTCCTCAAACACCCTGTATTATTACTAGCAATACTAACATGTGTCAA
GTATATGATGGTAATAGTTCTAGCTTTGAGCACCAAGAACCCTAGAGGAACGCATGTTTATGTTCAGACTTAATAC
TAAACTGCCATCGACCTTTGGCAAGATCACAGAAGAGGAAGTCAAACAGTTTATTACCTGGGGGAGGAGCTTAAAGG
TTCAAGTTCCACATCAGTTCAGAGTGCCTACCACAGGAGAGTATAAAAGGCCAGCCCCCGAGGCGAAAGCTCATTCT
TCGGATGAGCCGCAAAAGAGAAGGTCGCGCGTATTGATGACTCTCTAACCAGGTATGTTAACAATATTGATGAGTC
AGCTACCAGTAGAGAAATGTTTCTAGAGATTGCTAATACTAATCAATGTATGTTGCATCATTGCTTTCTTGTACCG
AATGTTATCCTGAATTGCTTGATGACATGGACAAGGAACAATAAACTTACTGATAACAGATATGGCTGCCGATGGTT
ATCTTCCAGATTGGCTCGAGGACACTCTCTCTGAAGGAATAAGACAGTGGTGGAAGCTCAAACCTGGCCCACCACCA
CCAAAGCCCGCAGAGCGGCATAAGGACGACAGCAGGGGTCTTGTGCTTCCTGGGTACAAGTACCTCGGACCCCTTCAA
CGGACTCGACAAGGGAGAGCCGGTCAACGAGGCAGAGCCGCGGCCCTCGAGCACGACAAAGCCTACGACCGGCAGC
TCGACAGCGGAGACAAACCCGTACCTCAAGTACAACCACGCCGACGCGGAGTTTCAGGAGCGCCTTAAAGAAGATACG
TCTTTTGGGGGCAACCTCGGACGAGCAGTCTTCCAGGCGAAAAAGAGGGTTCTTGAACCTCTGGGCCTGGTTGAGGA
ACCTGTTAAGACGGCTCCGGGAAAAAAGAGGCCGGTAGAGCACTCTCCTGTGGAGCCAGACTCCTCCTCGGGAACCG
GAAAGGCGGCCAGCCTGCAGAAAAAAGATTGAATTTTGGTCAGACTGGAGACGCAGACTCAGTACCTGACCCC
CAGCCTCTCGGACAGCCACCAGCAGCCCCTCTGGTCTGGGAACTAATACGATGGCTACAGGCAGTGGCGCACCAAT
GGCAGACAATAACGAGGGCGCCGACGGAGTGGGTAATTCCTCGGGAAATTGGCATTGCGATTCCACATGGATGGGCG
ACAGAGTCATCACCACCAGCACCCGAACCTGGGCCCTGCCCACCTACAACAACCACCTCTACAAACAAATTTCCAGC
CAATCAGGAGCCTCGAACGACAATCACTACTTTGGCTACAGCACCCCTTGGGGGTATTTTGACTTCAACAGATTCCA
CTGCCACTTTTCACCACGTGACTGGAAAGACTCATCAACAACAACTGGGGATTCCGACCCAAGAGACTCAACTTCA
AGCTCTTTAACATTCAAGTCAAAGAGGTCACGCAGAATAGACGGTACGACGATTGCCAATAACCTTACCAGCACG
GTTCAGGTGTTTACTGACTCGGAGTACCAGCTCCCGTACGTCCTCGGCTCGGCACATCAAGGATGCCTCCCGCCGTT
CCCAGCAGACGTCTTCATGGTGCCACAGTATGGATACCTCACCCTGAACAACGGGAGTCAGGCAGTAGGACGCTCTT
CATTTTACTGCCTGGAGTACTTTCCTTCTCAGATGCTGCGTACCGGAAACAACTTTACCTTCAGCTACACTTTTGAG
GACGTTCCTTTCCACAGCAGCTACGCTCACAGCCAGAGTCTGGACCGTCTCATGAATCCTCTCATCGACCAGTACCT
GTATTACTTGAGCAGAACAAACACTCCAAGTGGAACCACCACGCAGTCAAGGCTTCAGTTTTCTCAGGCCGGAGCGA
GTGACATTCGGGACCAGTCTAGGAACTGGCTTCCTGGACCCTGTTACCGCCAGCAGCGAGTATCAAAGACATCTGCG
GATAACAACAACAGTGAATACTCGTGGACTGGAGCTACCAAGTACCACCTCAATGGCAGAGACTCTCTGGTGAATCC
GGGCCCGGCCATGGCAAGCCACAAGGACGATGAAGAAAAGTTTTTTCCTCAGAGCGGGGTTCTCATCTTTGGGAAGC
AAGGCTCAGAGAAAACAAATGTGGACATTGAAAAGGTCATGATTACAGACGAAGAGGAAATCAGGACAACCAATCCC
GTGGCTACGGAGCAGTATGGTTCTGTATCTACCAACCTCCAGAGAGGCAACAGACAAGCAGCTACCGCAGATGTCAA
CACACAAGGCGTTCTTCCAGGCATGGTCTGGCAGGACAGAGATGTGTACCTTCAGGGGCCCATCTGGGCAAAGATTC
CACACACGGACGGACATTTTCACCCCTCTCCCCTCATGGGTGGATTCGGACTTAAACACCCTCCTCCACAGATTCTC

*FIG. 35*

```
ATCAAGAACACCCCGGTACCTGCGAATCCTTCGACCACCTTCAGTGCGGCAAAGTTTGCTTCCTTCATCACACAGTA
CTCCACGGGACAGGTCAGCGTGGAGATCGAGTGGGAGCTGCAGAAGGAAAACAGCAAACGCTGGAATCCCGAAATTC
AGTACACTTCCAACTACAACAAGTCTGTTAATGTGGACTTTACTGTGGACACTAATGGCGTGTATTCAGAGCCTCGC
CCCATTGGCACCAGATACCTGACTCGTAATCTGTAATTGCTTGTTAATCAATAAACCGTTTAATTCGTTTCAGTTGA
ACTTTGGTGTCGCGGCCGCTCGATAAGCTTTTGTTCCCTTTAGTGAGGGTTAATTCCGAGCTTGGCGTAATCATGGT
CATAGCTGTTTCCTGTGTGAAATTGTTATCCGCTCACAATTCCACACAACATACGAGCCGGAAGCATAAAGTGTAAA
GCCTGGGGTGCCTAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGC
GTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCGTC
```

FIG. 35 (cont.)

SEQUENCE LISTING

<160> NUMBER OF SEQ ID NOS: 155

<210> SEQ ID NO 1
<211> LENGTH: 4718
<212> TYPE: DNA
<213> ORGANISM: Adeno-associated virus 1

<400> SEQUENCE: 1

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcatagggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg ggcttctacg agatcgtgat     360
caaggtgccg agcgacctgg acgagcacct gccgggcatt tctgactcgt ttgtgagctg     420
ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660 gagtcagatt agggacaagc tggtgcagac catctaccgc gggatcgagc cgaccctgcc     720
caactggttc gcggtgacca agacgcgtaa tggcgccgga gggggaaca aggtggtgga     780 cgagtgctac atccccaact acctcctgcc caagactcag cccgagctgc agtgggcgtg     840
gactaacatg gaggagtata taagcgcctg tttgaacctg gccgagcgca aacggctcgt     900
ggcgcagcac ctgacccacg tcagccagac ccaggagcag aacaaggaga atctgaaccc     960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaatc cgcgcccgac tacctggtag gccccgctcc    1200
gcccgcggac attaaaacca accgcatcta ccgcatcctg gagctgaacg gctacgaacc    1260
tgcctacgcc ggctccgtct ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acgcccaagg tcgtggagtc    1500
cgccaaggcc attctcggcg gcagcaaggt gcgcgtggac caaaagtgca gtcgtccgc    1560 ccagatcgac cccaccccgg tgatcgtcac ctccaacacc aacatgtgcg ccgtgattga    1620
cgggaacagc accaccttcg agcaccagca gccgttgcag gaccggatgt tcaaatttga    1680
```

```
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg cccccgatga cgcggataaa agcgagccca agcgggcctg    1860
cccctcagtc gcggatccat cgacgtcaga gcgggaagga gctccggtgg actttgccga    1920
caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400
acaaggggga gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt ttggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc acaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct gctgtgggac    2820 ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag cacccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
cttctcagat gctgagaacg ggcaacaact ttaccttcag ctacacctt gaggaagtgc    3480 cttttccacag cagctacgcg cacagccaga gcctggaccg gctgatgaat cctctcatcg    3540
accaatacct gtattacctg aacagaactc aaaatcagtc cggaagtgcc caaacaagg    3600 acttgctgtt tagccgtggg tctccagctg gcatgtctgt tcagcccaaa aactggctac    3660
ctggaccctg ttatcggcag cagcgcgttt ctaaaacaaa acagacaac aacaacagca    3720 attttacctg gactggtgct tcaaaatata acctcaatgg gcgtgaatcc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta ccctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
```

```
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                            4718

<210> SEQ ID NO 2
<211> LENGTH: 4679
<212> TYPE: DNA
<213> ORGANISM: Adeno-associated virus 2

<400> SEQUENCE: 2
ttggccactc cctctctgcg cgctcgctcg ctcactgagg ccgggcgacc aaaggtcgcc      60
cgacgcccgg gctttgcccg gcggcctcca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacga gcatctgccc ggcatttctg acagctttgt gaactgggtg gccgagaagg     420
aatgggagtt gccgccagat tctgacatgg atctgaatct gattgagcag gcaccccctga    480 ccgtggccga aagctgcagc gcgactttc tgacggaatg gcgccgtgtg agtaaggccc       540
cggaggccct tttctttgtg caatttgaga agggagagag ctacttccac atgcacgtgc     600
tcgtggaaac caccgggggtg aaatccatgt ttttggacg tttcctgagt cagattcgcg       660
aaaaactgat tcagagaatt taccgcggga tcgagccgac tttgccaaac tggttcgcgg     720
tcacaaagac cagaaatggc gccggaggcg ggaacaaggt ggtggatgag tgctacatcc     780
ccaattactt gctccccaaa acccagcctg agctccagtg ggcgtggact aatatggaac     840
agtatttaag cgcctgtttg aatctcacgg agcgtaaacg gttggtggcg cagcatctga     900
cgcacgtgtc gcagacgcag gagcagaaca agagaatca gaatcccaat tctgatgcgc      960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa attttggaac taaacggtta cgatcccca tatgcggctt     1260 ccgtctttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact ttccccttca cgactgtgtc gacaagatgg    1440
```

```
tgatctggtg ggaggagggg aagatgaccg ccaaggtcgt ggagtcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa     1740 aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcgaga cggcataagg acgacagcag gggtcttgtg    2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt ttcaggagcg ccttaaagaa    2520
gatacgtctt tgggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag     2760 cctctcggac agccaccagc agccccctct ggtctgggaa ctaatacgat ggctacaggc    2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtattttga cttcaacaga    3060
ttccactgcc acttttcacc acgtgactgg caaagactca tcaacaacaa ctgggggattc    3120 cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420 aacaactta ccttcagcta cacttttgag gacgttcctt tccacagcag ctacgctcac     3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg accctgttta ccgccagcag    3660
cgagtatcaa agacatctgc ggataacaac aacagtgaat actcgtggac tggagctacc    3720
aagtaccacc tcaatggcag agactctctg gtgaatccgg gccggccat ggcaagccac     3780 aaggacgatg aagaaaagtt ttttcctcag agcgggggttc tcatctttgg gaagcaaggc    3840
```

```
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acaccctcc tccacagatt    4140 ctcatcaaga cacccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgcccatt    4380 ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679

<210> SEQ ID NO 3
<211> LENGTH: 4726
<212> TYPE: DNA
<213> ORGANISM: Adeno-associated virus 3A

<400> SEQUENCE: 3
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaactcca tcactagagg tatggcagtg acgtaacgcg aagcgcgcga agcgagacca     180
cgcctaccag ctgcgtcagc agtcaggtga ccctttttgcg acagtttgcg acaccacgtg     240
gccgctgagg gtatatattc tcgagtgagc gaaccaggag ctccattttg accgcgaaat     300
ttgaacgagc agcagccatg ccgggggttct acgagattgt cctgaaggtc ccagtgacc      360 tggacgagcg cctgccgggc atttctaact cgtttgttaa ctgggtggcc gagaaggaat     420
gggacgtgcc gccggattct gacatggatc cgaatctgat tgagcaggca cccctgaccg     480
tggccgaaaa gctttcagcgc gagttcctgg tggagtggcg ccgcgtgagt aaggcccggg     540
aggccctctt ttttgtccag ttcgaaaagg gggagaccta cttccacctg acgtgctga     600 ttgagaccat cggggtcaaa tccatggtgg tcggccgcta cgtgagccag attaaagaga     660
agctggtgac ccgcatctac cgcggggtcg agccgcagct tccgaactgg ttcgcggtga     720
ccaaaacgcg aaatggcgcc gggggcggga caaggtggt ggacgactgc tacatccccca     780 actacctgct ccccaagacc cagcccgagc tccagtgggc gtggactaac atggaccagt     840
atttaagcgc ctgtttgaat ctcgcggagc gtaaacggct ggtggcgcag catctgacgc     900
acgtgtcgca gacgcaggag cagaacaaag agaatcagaa ccccaattct gacgcgccgg     960
tcatcaggtc aaaaacctca gccaggtaca tggagctggt cggtggctg gtggaccgcg    1020 ggatcacgtc agaaaagcaa tggattcagg aggaccagg ctcgtacatc tccttcaacg    1080
ccgcctccaa ctcgcggtcc cagatcaagg ccgcgctgga caatgcctcc aagatcatga    1140
gcctgacaaa acggctccg gactacctgg tgggcagcaa cccgccggag gacattacca    1200
aaaatcggat ctaccaaatc ctggagctga acggtacga tccgcagtac gcggcctccg    1260
```

```
tcttcctggg ctgggcgcaa agaagttcg ggaagaggaa caccatctgg ctctttgggc      1320
cggccacgac gggtaaaacc aacatcgcgg aagccatcgc ccacgccgtg cccttctacg      1380
gctgcgtaaa ctggaccaat gagaactttc ccttcaacga ttgcgtcgac aagatggtga      1440
tctggtggga ggagggcaag atgacggcca aggtcgtgga gagcgccaag gccattctgg      1500
gcggaagcaa ggtgcgcgtg gaccaaaagt gcaagtcatc ggcccagatc gaacccactc      1560
ccgtgatcgt cacctccaac accaacatgt gcgccgtgat tgacgggaac agcaccacct      1620
tcgagcatca gcagccgctg caggaccgga tgtttgaatt tgaacttacc cgccgtttgg      1680
accatgactt tgggaaggtc accaaacagg aagtaaagga cttttccgg tgggcttccg      1740
atcacgtgac tgacgtggct catgagttct acgtcagaaa gggtggagct aagaaacgcc      1800
ccgcctccaa tgacgcggat gtaagcgagc caaaacggga gtgcacgtca cttgcgcagc      1860
cgacaacgtc agacgcggaa gcaccggcgg actacgcgga caggtaccaa aacaaatgtt      1920
ctcgtcacgt gggcatgaat ctgatgcttt ttccctgtaa acatgcgag agaatgaatc      1980
aaatttccaa tgtctgtttt acgcatggtc aaagagactg tggggaatgc ttccctggaa      2040
tgtcagaatc tcaacccgtt tctgtcgtca aaagaagac ttatcagaaa ctgtgtccaa      2100
ttcatcatat cctgggaagg gcaccgaga ttgcctgttc ggcctgcgat ttggccaatg      2160
tggacttgga tgactgtgtt tctgagcaat aaatgactta aaccaggtat ggctgctgac      2220
ggttatcttc cagattggct cgaggacaac ctttctgaag gcattcgtga gtggtgggct      2280
ctgaaacctg gagtccctca acccaaagcg aaccaacaac accaggacaa ccgtcggggt      2340
cttgtgcttc cgggttacaa atacctcgga cccggtaacg gactcgacaa aggagagccg      2400
gtcaacgagg cggacgcggc agccctcgaa cacgacaaag cttacgacca gcagctcaag      2460
gccggtgaca acccgtacct caagtacaac cacgccgacg ccgagtttca ggagcgtctt      2520
caagaagata cgtctttgg gggcaacctt ggcagagcag tcttccaggc caaaaagagg      2580
atccttgagc ctcttggtct ggttgaggaa gcagctaaaa cggctcctgg aaagaagggg      2640
gctgtagatc agtctcctca ggaaccggac tcatcatctg gtgttggcaa atcgggcaaa      2700
cagcctgcca gaaaaagact aaatttcggt cagactggag actcagagtc agtcccagac      2760
cctcaacctc tcggagaacc accagcagcc cccacaagtt tgggatctaa tacaatggct      2820
tcaggcggtg gcgcaccaat ggcagacaat aacgagggtg ccgatggagt gggtaattcc      2880
tcaggaaatt ggcattgcga ttcccaatgg ctgggcgaca gagtcatcac caccagcacc      2940
agaacctggg ccctgcccac ttacaacaac catctctaca agcaaatctc cagccaatca      3000
ggagcttcaa acgacaacca ctactttggc tacagcaccc cttgggggta ttttgacttt      3060
aacagattcc actgccactt ctcaccacgt gactggcagc gactcattaa caacaactgg      3120
ggattccggc ccaagaaact cagcttcaag ctcttcaaca tccaagttag aggggtcacg      3180
cagaacgatg gcacgacgac tattgccaat aaccttacca gcacggttca agtgtttacg      3240
gactcggagt atcagctccc gtacgtgctc gggtcggcgc accaaggctg tctcccgccg      3300
tttccagcgg acgtcttcat ggtccctcag tatggatacc tcaccctgaa caacggaagt      3360
caagcggtgg gacgctcatc cttttactgc ctggagtact tcccttcgca gatgctaagg      3420
actggaaata acttccaatt cagctatacc ttcgaggatg tacctttca cagcagctac      3480
gctcacagcc agagtttgga tcgcttgatg aatcctctta ttgatcagta tctgtactac      3540
ctgaacagaa cgcaaggaac aaccctctgga acaaccaacc aatcacgct gcttttagc      3600
caggctgggc ctcagtctat gtctttgcag gccagaaatt ggctacctgg gccctgctac      3660
```

```
cggcaacaga gactttcaaa gactgctaac gacaacaaca acagtaactt tccttggaca   3720
gcggccagca aatatcatct caatggccgc gactcgctgg tgaatccagg accagctatg   3780
gccagtcaca aggacgatga agaaaaattt ttccctatgc acggcaatct aatatttggc   3840
aaagaaggga caacggcaag taacgcagaa ttagataatg taatgattac ggatgaagaa   3900
gagattcgta ccaccaatcc tgtggcaaca gagcagtatg gaactgtggc aaataacttg   3960
cagagctcaa atacagctcc cacgactgga actgtcaatc atcagggggc cttacctggc   4020
atggtgtggc aagatcgtga cgtgtacctt caaggaccta tctgggcaaa gattcctcac   4080
acggatggac actttcatcc ttctcctctg atgggaggct ttggactgaa acatccgcct   4140
cctcaaatca tgatcaaaaa tactccggta ccggcaaatc ctccgacgac tttcagcccg   4200
gccaagtttg cttcatttat cactcagtac tccactggac aggtcagcgt ggaaattgag   4260
tgggagctac agaaagaaaa cagcaaacgt tggaatccag agattcagta cacttccaac   4320
tacaacaagt ctgttaatgt ggactttact gtagacacta atggtgttta tagtgaacct   4380
cgccctattg aacccggtat ctcacacgaa acttgtgaa tcctggttaa tcaataaacc   4440
gtttaattcg tttcagttga actttggctc ttgtgcactt ctttatcttt atcttgtttc   4500
catggctact gcgtagataa gcagcggcct gcggcgcttg cgcttcgcgg tttacaactg   4560
ctggttaata tttaactctc gccataccte tagtgatgga gttggccact ccctctatgc   4620
gcactcgctc gctcggtggg gcctggcgac caaaggtcgc cagacggacg tgctttgcac   4680
gtccggcccc accgagcgag cgagtgcgca tagagggagt ggccaa         4726
```

<210> SEQ ID NO 4
<211> LENGTH: 4722
<212> TYPE: DNA
<213> ORGANISM: Adeno-associated virus 3B

<400> SEQUENCE: 4

```
tggccactcc ctctatgcgc actcgctcgc tcggtggggc ctggcgacca aaggtcgcca     60
gacggacgtg ctttgcacgt ccggccccac cgagcgagcg agtgcgcata gagggagtgg    120
ccaactccat cactagaggt atggcagtga cgtaacgcga agcgcgcgaa gcgagaccac    180
gcctaccagc tcgtcagca gtcaggtgac ccttttgcga cagtttgcga caccacgtgg    240
ccgctgaggg tatatattct cgagtgagcg aaccaggagc tccattttga ccgcgaaatt    300
tgaacgagca gcagccatgc cggggttcta cgagattgtc ctgaaggtcc gagtgacct    360
ggacgagcac ctgccgggca tttctaactc gtttgttaac tgggtggccg agaaggaatg    420
ggagctgccg ccggattctg acatggatcc gaatctgatt gagcaggcac ccctgaccgt    480
ggccgaaaag cttcagcgcg agttcctggt ggagtggcgc cgcgtgagta aggccccgga    540
ggccctcttt tttgtccagt tcgaaaaggg ggagacctac ttccacctgc acgtgctgat    600
tgagaccatc ggggtcaaat ccatggtggt cggccgctac gtgagccaga ttaaagagaa    660
gctggtgacc cgcatctacc gcggggtcga gccgcagctt ccgaactggt tcgcggtgac    720
caaaacgcga aatggcgccg ggggcgggaa caaggtggtg gacgactgct acatccccaa    780
ctacctgctc cccaagaccc agcccgagct ccagtgggcg tggactaaca tggaccagta    840
tttaagcgcc tgtttgaatc tcgcggagcg taaacggctg gtggcgcagc atctgacgca    900
cgtgtcgcag acgcaggagc agaacaaaga gaatcagaac cccaattctg acgcgccggt    960
catcaggtca aaaacctcag ccaggtacat ggagctggtc gggtggctgg tggaccgcgg   1020
```

-continued

```
gatcacgtca gaaaagcaat ggattcagga ggaccaggcc tcgtacatct ccttcaacgc   1080
cgcctccaac tcgcggtccc agatcaaggc cgcgctggac aatgcctcca agatcatgag   1140
cctgacaaag acggctccgg actacctggt gggcagcaac ccgccggagg acattaccaa   1200
aaatcggatc taccaaatcc tggagctgaa cgggtacgat ccgcagtacg cggcctccgt   1260
cttcctgggc tgggcgcaaa agaagttcgg gaagaggaac accatctggc tctttgggcc   1320
ggccacgacg ggtaaaacca acatcgcgga agccatcgcc cacgccgtgc ccttctacgg   1380
ctgcgtaaac tggaccaatg agaactttcc cttcaacgat tgcgtcgaca agatggtgat   1440
ctggtgggag gagggcaaga tgacggccaa ggtcgtggag agcgccaagg ccattctggg   1500
cggaagcaag gtgcgcgtgg accaaaagtg caagtcatcg gcccagatcg aacccactcc   1560
cgtgatcgtc acctccaaca ccaacatgtg cgccgtgatt gacgggaaca gcaccacctt   1620
cgagcatcag cagccgctgc aggaccggat gtttaaattt gaacttaccc gccgtttgga   1680
ccatgacttt gggaaggtca ccaaacagga agtaaaggac tttttccggt gggcttccga   1740
tcacgtgact gacgtggctc atgagttcta cgtcagaaag ggtggagcta agaaacgccc   1800
cgcctccaat gacgcggatg taagcgagcc aaaacggcag tgcacgtcac ttgcgcagcc   1860
gacaacgtca gacgcggaag caccggcgga ctacgcggac aggtaccaaa acaaatgttc   1920
tcgtcacgtg ggcatgaatc tgatgctttt tccctgtaaa acatgcgaga gaatgaatca   1980
aatttccaat gtctgtttta cgcatggtca aagagactgt ggggaatgct tccctggaat   2040
gtcagaatct caacccgttt ctgtcgtcaa aaagaagact tatcagaaac tgtgtccaat   2100
tcatcatatc ctgggaaggg cacccgagat tgcctgttcg gcctgcgatt tggccaatgt   2160
ggacttggat gactgtgttt ctgagcaata aatgacttaa accaggtatg gctgctgacg   2220
gttatcttcc agattggctc gaggacaacc tttctgaagg cattcgtgag tggtgggctc   2280
tgaaacctgg agtccctcaa cccaaagcga accaacaaca ccaggacaac cgtcggggtc   2340
ttgtgcttcc gggttacaaa tacctcggac ccggtaacgg actcgacaaa ggagagccgg   2400
tcaacgaggc ggacgcggca gccctcgaac acgacaaagc ttacgaccag cagctcaagg   2460
ccggtgacaa cccgtacctc aagtacaacc acgccgacgc cgagtttcag gagcgtcttc   2520
aagaagatac gtcttttggg ggcaaccttg gcagagcagt cttccaggcc aaaaagagga   2580
tccttgagcc tcttggtctg gttgaggaag cagctaaaac ggctcctgga aagaagaggc   2640
ctgtagatca gtctcctcag gaaccggact catcatctgg tgttggcaaa tcgggcaaac   2700
agcctgccag aaaaagacta aatttcggtc agactggcga ctcagagtca gtcccagacc   2760
ctcaacctct cggagaacca ccagcagccc ccacaagttt gggatctaat acaatggctt   2820
caggcggtgg cgcaccaatg gcagacaata acgagggtgc cgatggagtg ggtaattcct   2880
caggaaattg gcattgcgat tcccaatggc tgggcgacag agtcatcacc accagcacca   2940
gaacctgggc cctgcccact tacaacaacc atctctacaa gcaaatctcc agccaatcag   3000
gagcttcaaa cgacaaccac tactttggct acagcacccc ttgggggtat tttgacttta   3060
acagattcca ctgccacttc tcaccacgtg actggcagcg actcattaac aacaactggg   3120
gattccggcc caagaaactc agcttcaagc tcttcaacat ccaagttaaa gaggtcacgc   3180
agaacgatgg cacgacgact attgccaata accttaccag cacggttcaa gtgtttacgg   3240
actcggagta tcagctcccg tacgtgctcg ggtcggcgca ccaaggctgt ctcccgccgt   3300
ttccagcgga cgtcttcatg gtccctcagt atggatacct caccctgaac aacggaagtc   3360
aagcggtggg acgctcatcc ttttactgcc tggagtactt cccttcgcag atgctaagga   3420
```

-continued

```
ctggaaataa cttccaattc agctatacct tcgaggatgt accttttcac agcagctacg    3480
ctcacagcca gagtttggat cgcttgatga atcctcttat tgatcagtat ctgtactacc    3540
tgaacagaac gcaaggaaca acctctggaa caaccaacca atcacggctg cttttagcc    3600
aggctgggcc tcagtctatg tctttgcagg ccagaaattg gctacctggg ccctgctacc    3660
ggcaacagag actttcaaag actgctaacg acaacaacaa cagtaacttt ccttggacag    3720
cggccagcaa atatcatctc aatggccgcg actcgctggt gaatccagga ccagctatgg    3780
ccagtcacaa ggacgatgaa gaaaaatttt tccctatgca cggcaatcta atatttggca    3840
aagaagggac aacggcaagt aacgcagaat tagataatgt aatgattacg gatgaagaag    3900
agattcgtac caccaatcct gtggcaacag agcagtatgg aactgtggca ataacttgc    3960
agagctcaaa tacagctccc acgactagaa ctgtcaatga tcaggggggcc ttacctggca    4020
tggtgtggca agatcgtgac gtgtaccttc aaggacctat ctgggcaaag attcctcaca    4080
cggatggaca ctttcatcct tctcctctga tgggaggctt tggactgaaa catccgcctc    4140
ctcaaatcat gatcaaaaat actccggtac cggcaaatcc tccgacgact ttcagcccgg    4200
ccaagtttgc ttcatttatc actcagtact ccactggaca ggtcagcgtg gaaattgagt    4260
gggagctaca gaaagaaaac agcaaacgtt ggaatccaga gattcagtac acttccaact    4320
acaacaagtc tgttaatgtg gacttactg tagacactaa tggtgtttat agtgaacctc    4380
gccctattgg aacccggtat ctcacacgaa acttgtaatc ctggttaatc aataaaccgt    4440
ttaattcgtt tcagttgaac tttggctctt gtgcacttct tatcttatct tgtttccatg    4500
gctactgcgt agataagcag cggcctgcgg cgcttgcgct tcgcggttta caactgctgg    4560
ttaatattta actctcgcca tacctctagt gatggagttg gccactccct ctatgcgcac    4620
tcgctcgctc ggtggggccg gacgtgcaaa gcacgtccgt ctggcgacct ttggtcgcca    4680
ggccccaccg agcgagcgag tgcgcataga gggagtggcc aa    4722
```

<210> SEQ ID NO 5
<211> LENGTH: 4767
<212> TYPE: DNA
<213> ORGANISM: Adeno-associated virus 4

<400> SEQUENCE: 5

```
ttggccactc cctctatgcg cgctcgctca ctcactcggc cctggagacc aaaggtctcc     60
agactgccgg cctctggccg gcagggccga gtgagtgagc gagcgcgcat agagggagtg    120
gccaactcca tcatctaggt ttgcccactg acgtcaatgt gacgtcctag ggttagggag    180
gtccctgtat tagcagtcac gtgagtgtcg tatttcgcgg agcgtagcgg agcgcatacc    240
aagctgccac gtcacagcca cgtggtccgt ttgcgacagt ttgcgacacc atgtggtcag    300
gagggtatat aaccgcgagt gagccagcga ggagctccat tttgcccgcg aatttgaac    360
gagcagcagc catgccgggg ttctacgaga tcgtgctgaa ggtgcccagc gacctggacg    420
agcacctgcc cggcatttct gactcttttg tgagctgggt ggccgagaag gaatgggagc    480
tgccgccgga ttctgacatg gacttgaatc tgattgagca ggcaccctg accgtggccg    540
aaaagctgca acgcgagttc ctggtcgagt ggcgccgcgt gagtaaggcc ccggaggccc    600
tcttctttgt ccagttcgag aagggggaca gctacttcca cctgcacatc ctggtggaga    660
ccgtgggcgt caaatccatg gtggtgggcc gctacgtgag ccagattaaa gagaagctgg    720
tgacccgcat ctaccgcggg gtcgagccgc agcttccgaa ctggttcgcg gtgaccaaga    780
```

-continued

```
cgcgtaatgg cgccggaggc gggaacaagg tggtggacga ctgctacatc cccaactacc    840
tgctccccaa gacccagccc gagctccagt gggcgtggac taacatggac cagtatataa    900
gcgcctgttt gaatctcgcg gagcgtaaac ggctggtggc gcagcatctg acgcacgtgt    960
cgcagacgca ggagcagaac aaggaaaacc agaaccccaa ttctgacgcg ccggtcatca   1020
ggtcaaaaac ctccgccagg tacatggagc tggtcgggtg gctggtggac cgcgggatca   1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
caaagacggc tccggactac ctggtgggcc agaacccgcc ggaggacatt ccagcaacc    1260 gcatctaccg aatcctcgag atgaacgggt acgatccgca gtacgcggcc tccgtcttcc   1320
tgggctgggc gcaaaagaag ttcgggaaga ggaacaccat ctggctcttt ggccggcca    1380 cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca agactttttt ccgtgggcg tcagatcacg    1800 tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg ctttttccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340 gccctaaac ccaaggcaaa tcaacaacat caggacaacg ctcggggtct tgtgcttccg    2400
ggttacaaat acctcggacc cggcaacgga ctcgacaagg gggaacccgt caacgcagcg   2460
gacgcggcag ccctcgagca cgacaaggcc tacgaccagc agctcaaggc cggtgacaac   2520
ccctacctca gtacaaccca cgccgacgcg gagttccagc agcggcttca gggcgacaca   2580
tcgtttgggg gcaacctcgg cagagcagtc ttccaggcca aaaagagggt tcttgaacct   2640
cttggtctgg ttgagcaagc gggtgagacg gctcctggaa agaagagacc gttgattgaa   2700
tccccccagc agcccgactc ctccacgggg atcggcaaaa aaggcaagca gccggctaaa   2760
aagaagctcg ttttcgaaga cgaaactgga gcaggcgacg gacccctga gggatcaact    2820 tccggagcca tgtctgatga cagtgagatg cgtgcagcag ctggcggagc tgcagtcgag   2880 ggcgacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctct acaagcgact cggagagagc ctgcagtcca acacctacaa cggattctcc   3060
accccctggg gatactttga cttcaaccgc ttccactgcc acttctcacc acgtgactgg   3120
cagcgactca tcaacaacaa ctgggggcatg cgacccaaag ccatgcgggt caaaatcttc   3180
```

```
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca caactttga aattacgtac    3480 agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac tccaatggc cacggctgga    3840 cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg gtgaccagag caacagcaac    4020
ctgccgaccg tggacagact gacagccttg ggagccgtgc tggaatggt ctggcaaaac    4080 agagacattt actaccaggg tcccatttgg gccaagattc ctcataccga tggacacttt    4140
cacccctcac cgctgattgg tgggtttggg ctgaaacacc cgcctcctca aattttatc    4200 aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                        4767

<210> SEQ ID NO 6
<211> LENGTH: 4642
<212> TYPE: DNA
<213> ORGANISM: Adeno-associated virus 5

<400> SEQUENCE: 6
ctctcccccc tgtcgcgttc gctcgctcgc tggctcgttt ggggggggtgg cagctcaaag      60 agctgccaga cgacggccct ctggccgtcg ccccccaaa cgagccagcg agcgagcgaa     120
cgcgacaggg gggagagtgc cacactctca agcaagggg ttttgtaagc agtgatgtca     180
taatgatgta atgcttattg tcacgcgata gttaatgatt aacagtcatg tgatgtgttt     240
tatccaatag gaagaaagcg cgcgtatgag ttctcgcgag acttccgggg tataaaagac     300
cgagtgaacg agcccgccgc cattctttgc tctggactgc tagaggaccc tcgctgccat     360
ggctaccttc tatgaagtca ttgttcgcgt cccatttgac gtggaggaac atctgcctgg     420
aatttctgac agctttgtgg actgggtaac tggtcaaatt tgggagctgc ctccagagtc     480
```

```
agatttaaat ttgactctgg ttgaacagcc tcagttgacg gtggctgata gaattcgccg    540
cgtgttcctg tacgagtgga acaaattttc caagcaggag tccaaattct ttgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
caataaggtg gtggattctg gtatattcc cgcctacctg ctgccgaagg tccaaccgga    840
gcttcagtgg gcgtggacaa acctggacga gtataaattg gccgccctga atctggagga    900
gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aaacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca acatcgcgga   1380
ggccatcgcc cacactgtgc cttttacgg ctgcgtgaac tggaccaatg aaaactttcc   1440
ctttaatgac tgtgtggaca aaatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt tgaacaccag cagccgctgg aggaccgcat   1680
gttcaaattt gaactgacta gcggctcccc gccagatttt ggcaagatta ctaagcagga   1740
agtcaaggac tttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagattttgg   2160
ggattttgac gatgccaata agaacagta aataaagcga gtagtcatgt cttttgttga   2220
tcaccctcca gattggttgg aagaagttgg tgaaggtctt cgcgagtttt tgggccttga   2280
agcgggccca ccgaaaccaa acccaatca gcagcatcaa gatcaagccc gtggtcttgt   2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460
agacaacccc tacctcaagt acaaccacgc ggacgccgag tttcaggaga agctcgccga   2520
cgacacatcc ttcggggaa acctcggaaa ggcagtcttt caggccaaga aaagggttct   2580 cgaaccttt ggcctggttg aagagggtgc taagacggcc cctaccggaa agcggataga   2640
cgaccacttt ccaaaaagaa agaaggctcg gaccgaagag gactccaagc cttccacctc   2700
gtcagacgcc gaagctggac ccagcggatc ccagcagctg caaatcccag cccaaccagc   2760
ctcaagtttg ggagctgata caatgtctgc ggggaggtggc ggcccattgg gcgacaataa   2820
ccaaggtgcc gatggagtgg gcaatgcctc gggagattgg cattgcgatt ccacgtggat   2880
```

```
ggggacaga gtcgtcacca agtccacccg aacctgggtg ctgcccagct acaacaacca    2940
ccagtaccga gagatcaaaa gcggctccgt cgacggaagc aacgccaacg cctactttgg    3000
atacagcacc ccctgggggt actttgactt taaccgcttc cacagccact ggagccccg     3060 agactggcaa agactcatca acaactactg gggcttcaga ccccggtccc tcagagtcaa    3120
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtctttta cgctgccgca    3300 gtacggttac gcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg agatacgcc aacacctaca aaaactggtt     3600
cccgggcccc atgggccgaa cccagggctg gaacctgggc tccggggtca ccgcgccag     3660 tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa cccgggcacc accgcacgt acctcgaggg    3840 caacatgctc atcaccagcg agagcgagac gcagccggtg aaccgcgtgg cgtacaacgt    3900
cggcgggcag atggccacca caaccgagc tccaccact gccccgcga ccggcacgta      3960 caacctccag gaaatcgtgc ccggcagcgt gtggatggag agggacgtgt acctccaagg    4020
acccatctgg gccaagatcc cagagacggg ggcgcacttt caccctctc cggccatggg    4080 cggattcgga ctcaaacacc caccgcccat gatgctcatc aagaacacgc ctgtgcccgg    4140
aaatatcacc agcttctcgg acgtgccgt cagcagcttc atcacccagt acagcaccgg    4200
gcaggtcacc gtggagatgg agtgggagct caagaaggaa aactccaaga ggtggaaccc    4260
agagatccag tacacaaaca actacaacga ccccagtttt gtggactttg ccccggacag    4320
caccggggaa tacagaacca ccagacctat cggaacccga taccttaccc gacccctta    4380 acccattcat gtcgcatacc ctcaataaac cgtgtattcg tgtcagtaaa atactgcctc    4440
ttgtggtcat tcaatgaata acagcttaca acatctacaa aacctccttg cttgagagtg    4500
tggcactctc cccctgtcg cgttcgctcg ctcgctggct cgtttggggg ggtggcagct    4560
caaagagctg ccagacgacg gccctctggc cgtcgccccc ccaaacgagc cagcgagcga    4620
gcgaacgcga cagggggag ag                                             4642

<210> SEQ ID NO 7
<211> LENGTH: 4683
<212> TYPE: DNA
<213> ORGANISM: Adeno-associated virus 6

<400> SEQUENCE: 7
ttggccactc cctctctgcg cgctcgctcg ctcactgagg ccgggcgacc aaaggtcgcc      60
cgacgcccgg gctttgcccg gcggcctca gtgagcgagc gagcgcgcag agaggagtg       120 gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga    300
```

```
ggtttgaacg cgcagcgcca tgccggggtt ttacgagatt gtgattaagg tccccagcga    360
ccttgacgag catctgcccg gcatttctga cagctttgtg aactgggtgg ccgagaagga    420
atgggagttg ccgccagatt ctgacatgga tctgaatctg attgagcagg cacccctgac    480
cgtggccgag aagctgcagc gcgacttcct ggtccagtgg cgccgcgtga gtaaggcccc    540
ggaggccctc ttctttgttc agttcgagaa gggcgagtcc tacttccacc tccatattct    600
ggtggagacc acgggggtca atccatggt gctgggccgc ttcctgagtc agattaggga    660
caagctggtg cagaccatct accgcgggat cgagccgacc ctgcccaact ggttcgcggt    720
gaccaagacg cgtaatggcg ccggagggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg gtcgggtggc tggtggaccg   1020
gggcatcacc tccgagaagc agtggatcca ggaggaccag gcctcgtaca tctccttcaa   1080
cgccgcctcc aactcgcggt cccagatcaa ggccgctctg gacaatgccg gcaagatcat   1140
ggcgctgacc aaatccgcgc ccgactacct ggtaggcccc gctccgcccg ccgacattaa   1200
aaccaaccgc atttaccgca tcctggagct gaacggctac gaccctgcct acgccggctc   1260
cgtctttctc ggctgggccc agaaaaggtt cggaaaacgc aacaccatct ggctgtttgg   1320
gccggccacc acgggcaaga ccaacatcgc ggaagccatc gcccacgccg tgcccttcta   1380
cggctgcgtc aactggacca atgagaactt cccttcaac gattgcgtcg acaagatggt   1440
gatctggtgg gaggagggca agatgacggc caaggtcgtg gagtccgcca aggccattct   1500
cggcggcagc aaggtgcgcg tggaccaaaa gtgcaagtcg tccgcccaga tcgatcccac   1560
ccccgtgatc gtcacctcca acaccaacat gtgcgccgtg attgacggga acagcaccac   1620
cttcgagcac cagcagccgt tgcaggaccg gatgttcaaa tttgaactca cccgccgtct   1680
ggagcatgac tttggcaagg tgacaaagca ggaagtcaaa gagttcttcc gctgggcgca   1740
ggatcacgtg accgaggtgg cgcatgagtt ctacgtcaga aagggtggag ccaacaagag   1800
acccgccccc gatgacgcgg ataaaagcga gcccaagcgg gcctgcccct cagtcgcgga   1860
tccatcgacg tcagacgcgg aaggagctcc ggtggacttt gccgacaggt accaaaacaa   1920
atgttctcgt cacgcgggca tgcttcagat gctgtttccc tgcaaaacat gcgagagaat   1980
gaatcagaat ttcaacattt gcttcacgca cgggaccaga gactgttcag aatgtttccc   2040
cggcgtgtca gaatctcaac cggtcgtcag aaagaggacg tatcggaaac tctgtgccat   2100
tcatcatctg ctgggcggg ctcccgagat tgcttgctcg gcctgcgatc tggtcaacgt   2160
ggatctggat gactgtgttt ctgagcaata aatgacttaa accaggtatg gctgccgatg   2220
gttatcttcc agattggctc gaggacaacc tctctgaggg cattgcgag tggtgggact   2280 tgaaacctgg agccccgaaa cccaaagcca accagcaaaa gcaggacgac ggccgggtc    2340 tggtgcttcc tggctacaag tacctcggac ccttcaacgg actcgacaag ggggagcccg   2400
tcaacgcggc ggatgcagcg gccctcgagc acgacaaggc ctacgaccag cagctcaaag   2460
cgggtgacaa tccgtacctg cggtataacc acgccgacgc cgagtttcag gagcgtctgc   2520
aagaagatac gtcttttggg ggcaacctcg gcgagcagt cttccaggcc aagaagaggg   2580
ttctcgaacc ttttggtctg gttgaggaag gtgctaagac ggctcctgga aagaaacgtc   2640
cggtagagca gtcgccacaa gagccagact cctcctcggg cattggcaag acaggccagc   2700
```

```
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata cgaaggcgc cgacggagtg gtaatgcct     2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000
cgggggccag caacgacaac cactacttcg gctacagcac ccctgggggg tattttgatt    3060
tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tcctttttact gcctggaata tttcccatcg cagatgctga    3420
gaacgggcaa taactttacc ttcagctaca ccttcgagga cgtgccttc cacagcagct    3480
acgcgcacag ccagagcctg gaccggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg atttttggaa    3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
tggtgtggca agacagagac gtatacctgc agggtcctat ttgggccaaa attcctcaca    4080
cggatggaca ctttcacccg tctcctctca tgggcggctt tggacttaag caccccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggactttat actgagcctc    4380
gccccattgg caccgttac ctcacccgtc cctgtaatt gtgtgttaat caataaaccg    4440
gttaattcgt gtcagttgaa ctttggtctc atgtcgttat tatcttatct ggtcaccata    4500
gcaaccggtt acacattaac tgcttagttg cgcttcgcga ataccctag tgatggagtt    4560
gccccactcc tctatgcgcg ctcgctcgct cggtggggcc ggcagagcag agctctgccg    4620
tctgcggacc tttggtccgc aggccccacc gagcgagcga gcgcgcatag agggagtggg    4680
caa                                                                 4683
```

<210> SEQ ID NO 8
<211> LENGTH: 4721
<212> TYPE: DNA
<213> ORGANISM: Adeno-associated virus 7

<400> SEQUENCE: 8

```
ttggccactc cctctatgcg cgctcgctcg ctcggtgggg cctgcggacc aaaggtccgc    60
```

| | |
|---|---|
| agacggcaga gctctgctct gccggccccca ccgagcgagc gagcgcgcat agagggagtg | 120 |
| gccaactcca tcactagggg taccgcgaag cgcctcccac gctgccgcgt cagcgctgac | 180 |
| gtaaatcacg tcataggggga gtggtcctgt attagctgtc acgtgagtgc ttttgcgaca | 240 |
| ttttgcgaca ccacgtggcc atttgaggta tatatggccg agtgagcgag caggatctcc | 300 |
| attttgaccg cgaaatttga acgagcagca gccatgccgg gtttctacga gatcgtgatc | 360 |
| aaggtgccga cgacctggac gagcacctg ccgggcattt ctgactcgtt tgtgaactgg | 420 |
| gtggccgaga aggaatggga gctgccccg gattctgaca tggatctgaa tctgatcgag | 480 |
| caggcacccc tgaccgtggc cgagaagctg cagcgcgact tcctggtcca atggcgccgc | 540 |
| gtgagtaagg ccccggaggc cctgttcttt gttcagttcg agaagggcga gagctacttc | 600 |
| caccttcacg ttctggtgga gaccacgggg gtcaagtcca tggtgctagg ccgcttcctg | 660 |
| agtcagattc gggagaagct ggtccagacc atctaccgcg gggtcgagcc cacgctgccc | 720 |
| aactggttcg cggtgaccaa gacgcgtaat ggcgccggcg gggggaacaa ggtggtggac | 780 |
| gagtgctaca tccccaacta cctcctgccc aagacccagc ccgagctgca gtgggcgtgg | 840 |
| actaacatgg aggagtatat aagcgcgtgt ttgaacctgg ccgaacgcaa acggctcgtg | 900 |
| gcgcagcacc tgacccacgt cagccagacg caggagcaga acaaggagaa tctgaacccc | 960 |
| aattctgacg cgcccgtgat caggtcaaaa acctccgcgc gctacatgga gctggtcggg | 1020 |
| tggctggtgg accggggcat cacctccgag aagcagtgga tccaggagga ccaggcctcg | 1080 |
| tacatctcct tcaacgccgc ctccaactcg cggtcccaga tcaaggccgc gctggacaat | 1140 |
| gccggcaaga tcatgcgct gaccaaatcc gcgcccgact acctggtggg gccctcgctg | 1200 |
| cccgcggaca ttaaaaccaa ccgcatctac cgcatcctgg agctgaacgg gtacgatcct | 1260 |
| gcctacgccg gctccgtctt tctcggctgg gcccagaaaa agttcgggaa cgcaacaccc | 1320 |
| atctggctgt ttgggcccgc caccaccggc aagaccaaca ttgcggaagc catcgcccac | 1380 |
| gccgtgccct tctacggctg cgtcaactgg accaatgaga ctttcccctt caacgattgc | 1440 |
| gtcgacaaga tggtgatctg gtgggaggag ggcaagatga cggccaaggt cgtggagtcc | 1500 |
| gccaaggcca ttctcggcgg cagcaaggtg cgcgtggacc aaaagtgcaa gtcgtccgcc | 1560 |
| cagatcgacc ccaccccccgt gatcgtcacc tccaacacca acatgtgcgc cgtgattgac | 1620 |
| gggaacagca ccaccttcga gcaccagcag ccgttgcagg accggatgtt caaatttgaa | 1680 |
| ctcacccgcc gtctggagca cgactttggc aaggtgacga agcaggaagt caaagagttc | 1740 |
| ttccgctggg ccagtgatca cgtgaccgag gtggcgcatg agttctacgt cagaaagggc | 1800 |
| ggagccagca aaagacccgc ccccgatgac gcggatataa gcgagcccaa gcgggcctgc | 1860 |
| ccctcagtcg cggatccatc gacgtcagac gcggaaggag ctccggtgga ctttgccgac | 1920 |
| aggtaccaaa acaaatgttc tcgtcacgcg ggcatgattc agatgctgtt tccctgcaaa | 1980 |
| acgtgcgaga gaatgaatca gaatttcaac atttgcttca cacacggggt cagagactgt | 2040 |
| ttagagtgtt tccccggcgt gtcagaatct caaccggtcg tcagaaaaaa gacgtatcgg | 2100 |
| aaactctgcg cgattcatca tctgctgggg cgggcgcccg agattgcttg ctcggcctgc | 2160 |
| gacctggtca acgtggacct ggacgactgc gtttctgagc aataaatgac ttaaaccagg | 2220 |
| tatggctgcc gatggttatc ttccagattg gctcgaggac aacctctctg agggcattcg | 2280 |
| cgagtggtgg gacctgaaac ctggagcccc gaaacccaaa gccaaccagc aaaagcagga | 2340 |
| caacggccgg ggtctggtgc ttcctggcta caagtacctc ggaccttca acggactcga | 2400 |
| caaggggggag cccgtcaacg cggcggacgc agcggcccctc gagcacgaca aggcctacga | 2460 |

```
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cgggttctcg aacctctcgg tctggttgag gaaggcgcta agacggctcc    2640
tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgaccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060
ctgggggtat tttgactta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420 ccccctctcag atgctgagaa cgggcaacaa ctttgagttc agctacagct cgaggacgt    3480 gcctttccac agcagctacg cacacagcca gagcctggac cggctgatga atcccctcat    3540
cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgctttt tcccatccag    3840
cggagtcctg attttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccgggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga cccggagat    4320 tcagtacacc tccaactttg aaaagcagac tggtgtggac tttgccgttg acagccaggg    4380
tgtttactct gagcctcgcc ctattggcac tcgttacctc acccgtaatc tgtaattgca    4440
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a                       4721
```

<210> SEQ ID NO 9

<211> LENGTH: 4393
<212> TYPE: DNA
<213> ORGANISM: Adeno-associated virus 8

<400> SEQUENCE: 9

```
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180
gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc cgcgtgagta aggccccgga ggccctcttc tttgttcagt cgagaaggg      480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca gactcagcc     720
cgagctgcag tgggcgtgga ctaacatgga ggagtatata agcgcgtgct gaacctggc     780
cgagcgcaaa cggctcgtgg cgcagcacct gacccacgtc agccagacgc aggagcagaa     840
caaggagaat ctgaacccca attctgacgc gcccgtgatc aggtcaaaaa cctccgcgcg     900
ctatatggag ctggtcgggt ggctggtgga ccggggcatc acctccgaga gcagtggat      960
ccaggaggac caggcctcgt acatctcctt caacgccgcc tccaactcgc ggtcccagat    1020
caaggccgcg ctgacaatg ccggcaagat catggcgctg accaaatccg cgcccgacta    1080
cctggtgggg ccctcgctgc ccgcggacat tacccagaac cgcatctacc gcatcctcgc    1140
tctcaacggc tacgaccctg cctacgccgg ctccgtcttt ctcggctggg ctcagaaaaa    1200
gttcgggaaa cgcaacacca tctggctgtt tggacccgcc accaccggca gaccaacat    1260
tgcggaagcc atcgcccacg ccgtgccctt ctacggctgc gtcaactgga ccaatgagaa    1320
ctttcccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc cacccccgtg atcgtcacct ccaacaccaa    1500
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa agaccccgcc ccgatgacg cggataaaag    1740
cgagcccaag cggcctgcc cctcagtcgc ggatccatcg acgtcagacg cggaaggagc    1800
tccggtggac tttgccgaca ggtaccaaaa caatgttct cgtcacgcgg gcatgcttca    1860
gatgctgttt ccctgcaaaa cgtgcgagag aatgaatcag aatttcaaca tttgcttcac    1920
acacgggtc agagactgct cagagtgttt ccccggcgtg tcagaatctc aaccggtcgt    1980
cagaaagagg acgtatcgga aactctgtgc gattcatcat ctgctggggc gggctcccga    2040
gattgcttgc tcggcctgcg atctggtcaa cgtggacctg gatgactgtg tttctgagca    2100
ataaaatgact taaaccaggt atggctgccg atggttatct tccagattgg ctcgaggaca    2160
acctctctga gggcattcgc gagtggtggg cgctgaaacc tggagccccg aagcccaaag    2220
```

```
ccaaccagca aaagcaggac gacggccggg gtctggtgct tcctggctac aagtacctcg   2280
gacccttcaa cggactcgac aaggggagc ccgtcaacgc ggcggacgca gcggccctcg    2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg ggacatcggg aggagccacc aacgacaaca   2940
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg acgtgttca    3240
tgattcccca gtacggctac ctaacactca acaacggtag tcaggccgtg ggacgctcct   3300
ccttctactg cctggaatac tttccttcgc agatgctgag aaccggcaac aacttccagt   3360
ttacttacac cttcgaggac gtgcctttcc acagcagcta cgcccacagc cagagcttgg   3420
accggctgat gaatcctctg attgaccagt acctgtacta cttgtctcgg actcaaacaa   3480
caggaggcac ggcaaatacg cagactctgg gcttcagcca aggtgggcct aatacaatgg   3540
ccaatcaggc aaagaactgg ctgccaggac cctgttaccg ccaacaacgc gtctcaacga   3600
caaccgggca aaacaacaat agcaactttg cctggactgc tgggaccaaa taccatctga   3660
atggaagaaa ttcattggct aatcctggca tcgctatggc aacacacaaa gacgacgagg   3720
agcgtttttt tcccagtaac gggatcctga tttttggcaa acaaaatgct gccagagaca   3780
atgcggatta cagcgatgtc atgctcacca gcgaggaaga aatcaaaacc actaaccctg   3840
tggctacaga ggaatacggt atcgtggcag ataacttgca gcagcaaaac acggctcctc   3900
aaattggaac tgtcaacagc caggggggcct acccggtat ggtctggcag aaccgggacg   3960
tgtacctgca gggtcccatc tgggccaaga ttcctcacac ggacggcaac ttccacccgt   4020
ctccgctgat gggcggcttt ggcctgaaac atcctccgcc tcagatcctg atcaagaaca   4080
cgcctgtacc tgcggatcct ccgaccacct tcaaccagtc aaagctgaac tctttcatca   4140
cgcaatacag caccggacag gtcagcgtgg aaattgaatg ggagctgcag aaggaaaaca   4200
gcaagcgctg gaaccccgag atccagtaca cctccaacta ctacaaatct acaagtgtgg   4260
actttgctgt taatacagaa ggcgtgtact ctgaaccccg ccccattggc acccgttacc   4320
tcacccgtaa tctgtaattg cctgttaatc aataaaccgg ttgattcgtt tcagttgaac   4380
tttggtctct gcg                                                      4393
```

<210> SEQ ID NO 10
<211> LENGTH: 4385
<212> TYPE: DNA

<213> ORGANISM: Adeno-associated virus 9

<400> SEQUENCE: 10

| | | | | | |
|---|---|---|---|---|---|
| cagagaggga | gtggccaact | ccatcactag | gggtaatcgc | gaagcgcctc | ccacgctgcc | 60 |
| gcgtcagcgc | tgacgtagat | tacgtcatag | gggagtggtc | ctgtattagc | tgtcacgtga | 120 |
| gtgcttttgc | gacattttgc | gacaccacat | ggccatttga | ggtatatatg | gccgagtgag | 180 |
| cgagcaggat | ctccattttg | accgcgaaat | ttgaacgagc | agcagccatg | ccgggcttct | 240 |
| acgagattgt | gatcaaggtg | ccgagcgacc | tggacgagca | cctgccgggc | atttctgact | 300 |
| cttttgtgaa | ctgggtggcc | gagaaggaat | gggagctgcc | cccggattct | gacatggatc | 360 |
| ggaatctgat | cgagcaggca | cccctgaccg | tggccgagaa | gctgcagcgc | gacttcctgg | 420 |
| tccaatggcg | ccgcgtgagt | aaggccccgg | aggccctctt | ctttgttcag | ttcgagaagg | 480 |
| gcgagagcta | ctttcacctg | cacgttctgg | tcgagaccac | ggggtcaag | tccatggtgc | 540 |
| taggccgctt | cctgagtcag | attcgggaga | agctggtcca | gaccatctac | cgcgggatcg | 600 |
| agccgaccct | gcccaactgg | ttcgcggtga | ccaagacgcg | taatggcgcc | ggcggggga | 660 |
| acaaggtggt | ggacgagtgc | tacatcccca | actacctcct | gcccaagact | cagcccgagc | 720 |
| tgcagtgggc | gtggactaac | atggaggagt | atataagcgc | gtgcttgaac | ctggccgagc | 780 |
| gcaaacggct | cgtggcgcag | cacctgaccc | acgtcagcca | gacgcaggag | cagaacaagg | 840 |
| agaatctgaa | ccccaattct | gacgcgcccg | tgatcaggtc | aaaaacctcc | gcgcgctaca | 900 |
| tggagctggt | cgggtggctg | gtggaccggg | gcatcacctc | cgagaagcag | tggatccagg | 960 |
| aggaccaggc | ctcgtacatc | tccttcaacg | ccgcctccaa | ctcgcggtcc | cagatcaagg | 1020 |
| ccgcgctgga | caatgccggc | aagatcatgg | cgctgaccaa | atccgcgccc | gactacctgg | 1080 |
| taggcccttc | acttccggtg | gacattacgc | agaaccgcat | ctaccgcatc | ctgcagctca | 1140 |
| acggctacga | ccctgcctac | gccggctccg | tctttctcgg | ctgggcacaa | agaagttcg | 1200 |
| ggaaacgcaa | caccatctgg | ctgtttgggc | cggccaccac | gggaaagacc | aacatcgcag | 1260 |
| aagccattgc | ccacgccgtg | cccttctacg | gctgcgtcaa | ctggaccaat | gagaactttc | 1320 |
| ccttcaacga | ttgcgtcgac | aagatggtga | tctggtggga | ggagggcaag | atgacggcca | 1380 |
| aggtcgtgga | gtccgccaag | gccattctcg | gcggcagcaa | ggtgcgcgtg | gaccaaaagt | 1440 |
| gcaagtcgtc | cgcccagatc | gaccccactc | ccgtgatcgt | cacctccaac | accaacatgt | 1500 |
| gcgccgtgat | tgacgggaac | agcaccacct | tcgagcacca | gcagcctctc | caggaccgga | 1560 |
| tgtttaagtt | cgaactcacc | cgccgtctgg | agcacgactt | tggcaaggtg | acaaagcagg | 1620 |
| aagtcaaaga | gttcttccgc | tgggccagtg | atcacgtgac | cgaggtggcg | catgagtttt | 1680 |
| acgtcagaaa | gggcggagcc | agcaaaagac | ccgcccccga | tgacgcggat | aaaagcgagc | 1740 |
| ccaagcgggc | ctgcccctca | gtcgcggatc | catcgacgtc | agacgcggaa | ggagctccgg | 1800 |
| tggactttgc | cgacaggtac | caaaacaaat | gttctcgtca | cgcggcatg | cttcagatgc | 1860 |
| tgcttccctg | caaaacgtgc | gagagaatga | atcagaattt | caacatttgc | ttcacacacg | 1920 |
| gggtcagaga | ctgctcagag | tgtttccccg | gcgtgtcaga | atctcaaccg | gtcgtcagaa | 1980 |
| agaggacgta | tcggaaactc | tgtgcgattc | atcatctgct | ggggcgggct | cccgagattg | 2040 |
| cttgctcggc | ctgcgatctg | gtcaacgtgg | acctggatga | ctgtgtttct | gagcaataaa | 2100 |
| tgacttaaac | caggtatggc | tgccgatggt | tatcttccag | attggctcga | ggacaacctc | 2160 |
| tctgagggca | ttcgcgagtg | gtgggcgctg | aaacctggag | cccgaagcc | caaagccaac | 2220 |
| cagcaaaagc | aggacgacgg | ccggggtctg | gtgcttcctg | gctacaagta | cctcggaccc | 2280 |

```
ttcaacggac tcgacaaggg ggagcccgtc aacgcggcgg acgcagcggc cctcgagcac    2340
ggcaaggcct acgaccagca gctgcaggcg ggtgacaatc cgtacctgcg gtataaccac    2400
gccgacgccg agtttcagga gcgtctgcaa gaagatacgt cttttggggg caacctcggg    2460
cgagcagtct tccaggccaa gaagcgggtt ctcgaacctc tcggtctggt tgaggaaggc    2520
gctaagacgg ctcctggaaa gaagagaccg gtagagccat caccccagcg ttctccagac    2580
tcctctacgg gcatcggcaa gaaaggccaa cagcccgcca gaaaaagact caattttggt    2640
cagactggcg actcagagtc agttccagac cctcaacctc tcggagaacc tccagcagcg    2700
ccctctggtg tgggacctaa tacaatggct gcaggcggtg gcgcaccaat ggcagacaat    2760
aacgaaggcg ccgacggagt gggtaattcc tcgggaaatt ggcattgcga ttccacatgg    2820
ctgggggaca gagtcatcac caccagcacc cgaacctggg cattgcccac ctacaacaac    2880
cacctctaca gcaaatctc caatggaaca tcgggaggaa gcaccaacga caacacctac    2940
tttggctaca gcacccctg ggggtatttt gacttcaaca gattccactg ccacttctca    3000
ccacgtgact ggcagcgact catcaacaac aactgggga tccggccaaa gagactcaac    3060
ttcaagctgt tcaacatcca ggtcaaggag gttacgacga acgaaggcac caagaccatc    3120
gccaataacc ttaccagcac cgtccaggtc tttacggact cggagtacca gctaccgtac    3180
gtcctaggct ctgcccacca aggatgcctg ccaccgtttc ctgcagacgt cttcatggtt    3240
cctcagtacg gctacctgac gctcaacaat ggaagtcaag cgttaggacg ttcttctttc    3300
tactgtctgg aatacttccc ttctcagatg ctgagaaccg gcaacaactt tcagttcagc    3360
tacactttcg aggacgtgcc tttccacagc agctacgcac acagccagag tctagatcga    3420
ctgatgaacc ccctcatcga ccagtaccta tactacctgg tcagaacaca gaactggga    3480
actggggaa ctcaaacttt ggcattcagc caagcaggcc ctagctcaat ggccaatcag    3540
gctagaaact gggtacccgg gccttgctac cgtcagcagc gcgtctccac aaccaccaac    3600
caaaataaca acagcaactt tgcgtggacg ggagctgcta aattcaagct gaacgggaga    3660
gactcgctaa tgaatcctgg cgtggctatg gcatcgcaca agacgacga ggaccgcttc    3720
tttccatcaa gtggcgttct catatttggc aagcaaggag ccgggaacga tggagtcgac    3780
tacagccagg tgctgattac agatgaggaa gaaattaaag ccaccaaccc tgtagccaca    3840
gaggaataca gagcagtggc catcaacaac caggccgcta acacgcaggc gcaaactgga    3900
cttgtgcata accagggagt tattcctggt atggtctggc agaaccggga cgtgtacctg    3960
cagggcccta tttgggctaa aatacctcac acagatggca actttcaccc gtctcctctg    4020
atgggtggat ttggactgaa acacccacct ccacagattc taattaaaaa tacaccagtg    4080
ccggcagatc ctcctcttac cttcaatcaa gccaagctga actctttcat cacgcagtac    4140
agcacgggac aagtcagcgt ggaaatcgag tgggagctgc agaaagaaaa cagcaagcgc    4200
tggaatccag agatccagta cacttcaaac tactacaaat ctacaaatgt ggactttgct    4260
gtcaatacca aaggtgttta ctctgagcct cgccccattg gtactcgtta cctcacccgt    4320
aatttgtaat tgcctgttaa tcaataaacc ggttaattcg tttcagttga actttggtct    4380
ctgcg                                                                 4385
```

<210> SEQ ID NO 11  
<211> LENGTH: 4087  
<212> TYPE: DNA  
<213> ORGANISM: Adeno-associated virus 11

<400> SEQUENCE: 11

```
atgccgggct tctacgagat cgtgatcaag gtgccgagcg acctggacga gcacctgccg      60
ggcatttctg actcgtttgt gaactgggtg gccgagaagg aatgggagct gccccggat     120
tctgacatgg atcggaatct gatcgagcag gcacccctga ccgtggccga gaagctgcag    180
cgcgacttcc tggtccactg gcgccgcgtg agtaaggccc cggaggccct cttcttgtt    240
cagttcgaga agggcgagtc ctacttccac ctccacgttc tcgtcgagac cacggggtc    300
aagtccatgg tcctgggccg cttcctgagt cagatcagag acaggctggt gcagaccatc   360
taccgcgggg tcgagcccac gctgcccaac tggttcgcgg tgaccaagac gcgaaatggc   420
gccggcgggg ggaacaaggt ggtggacgag tgctacatcc ccaactacct cctgcccaag   480
acccagcccg agctgcagtg ggcgtggact aacatggagg agtatataag cgcgtgtcta   540
aacctcgcgg agcgtaaacg gctcgtggcg cagcacctga cccacgtcag ccagacgcag   600
gagcagaaca aggagaatct gaacccgaat tctgacgcgc ccgtgatcag gtcaaaaacc   660
tccgcgcgct acatggagct ggtcggtgg ctggtggacc ggggcatcac ctccgagaag   720
cagtggatcc aggaggacca ggcctcgtac atctccttca cgccgcctc caactcgcgg   780
tcccagatca aggccgcgct ggacaatgcc ggaaagatca tggcgctgac caaatccgcg   840
cccgactacc tggtaggccc gtccttaccc gcggacatta aggccaaccg catctaccgc   900
atcctggagc tcaacggcta cgaccccgcc tacgccggct ccgtcttcct gggctgggcg   960
cagaaaaagt tcggtaaacg caacaccatc tggctgtttg gcccgccac caccggcaag   1020
accaacatcg cggaagccat agcccacgcc gtgcccttct acggctgcgt gaactggacc   1080
aatgagaact tccccttcaa cgattgcgtc gacaagatgg tgatctggtg ggaggagggc   1140
aagatgaccg ccaaggtcgt ggagtccgcc aaggccattc tgggcggaag caaggtgcgc   1200
gtggaccaaa agtgcaagtc ctcggcccag atcgacccca cgcccgtgat cgtcacctcc   1260
aacaccaaca tgtgcgccgt gatcgacggg aacagcacca ccttcgagca ccagcagccg   1320
ctgcaggacc gcatgttcaa gttcgagctc acccgccgtc tggagcacga cttttggcaag  1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagcg agcccaagcg ggcctgcccc tcagttccgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg gcgcgtcaga atctcaaccc   1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataaa tgacttaaac caggtatggc tgctgacggt tatcttccag attggctcga   1920
ggacaacctc tctgagggca ttcgcgagtg gtgggacctg aaacctggag ccccgaagcc   1980
caaggccaac cagcagaagc aggacgacgg ccggggtctg gtgcttcctg gctacaagta   2040
cctcggaccc ttcaacggac tcgacaaggg ggagcccgtc aacgcggcgg acgcagcggc   2100
cctcgagcac gacaaggcct acgaccagca gctcaaagcg ggtgacaatc cgtacctgcg   2160
gtataaccac gccgacgccg agtttcagga gcgtctgcaa aagatacgt cttttggggg   2220
caacctcggg cgagcagtct tccaggccaa gaagaggta ctcgaacctc tgggcctggt   2280
tgaagaaggt gctaaaacgg ctcctggaaa gaagagaccg ttagagtcac cacaagagcc   2340
```

| | |
|---|---|
| cgactcctcc tcgggcatcg gcaaaaaagg caaacaacca gccagaaaga ggctcaactt | 2400 |
| tgaagaggac actggagccg gagacggacc ccctgaagga tcagatacca gcgccatgtc | 2460 |
| ttcagacatt gaaatgcgtg cagcaccggg cggaaatgct gtcgatgcgg acaaggttc | 2520 |
| cgatggagtg ggtaatgcct cgggtgattg gcattgcgat tccacctggt ctgagggcaa | 2580 |
| ggtcacaaca acctcgacca gaacctgggt cttgcccacc tacaacaacc acttgtacct | 2640 |
| gcgtctcgga acaacatcaa gcagcaacac ctacaacgga ttctccaccc cctggggata | 2700 |
| ttttgacttc aacagattcc actgtcactt ctcaccacgt gactggcaaa gactcatcaa | 2760 |
| caacaactgg ggactacgac caaaagccat gcgcgttaaa atcttcaata tccaagttaa | 2820 |
| ggaggtcaca acgtcgaacg gcgagactac ggtcgctaat aaccttacca gcacggttca | 2880 |
| gatatttgcg gactcgtcgt atgagctccc gtacgtgatg gacgctggac aagaggggag | 2940 |
| cctgcctcct ttccccaatg acgtgttcat ggtgcctcaa tatggctact gtggcatcgt | 3000 |
| gactggcgag aatcagaacc aaacggacag aaacgctttc tactgcctgg agtattttcc | 3060 |
| ttcgcaaatg ttgagaactg gcaacaactt tgaaatggct acaactttg agaaggtgcc | 3120 |
| gttccactca atgtatgctc acagccagag cctggacaga ctgatgaatc ccctcctgga | 3180 |
| ccagtacctg tggcacttac agtcgactac ctctggagag actctgaatc aaggcaatgc | 3240 |
| agcaaccaca tttggaaaaa tcaggagtgg agactttgcc ttttacagaa agaactggct | 3300 |
| gcctgggcct tgtgttaaac agcagagatt ctcaaaaact gccagtcaaa attacaagat | 3360 |
| tcctgccagc gggggcaacg ctctgttaaa gtatgacacc cactataccct aaacaaccg | 3420 |
| ctggagcaac atcgcgcccg gacctccaat ggccacagcc ggaccttcgg atggggactt | 3480 |
| cagtaacgcc cagcttatat tccctggacc atctgttacc ggaaatacaa caacttcagc | 3540 |
| caacaatctg ttgtttacat cagaagaaga aattgctgcc accaacccaa gagacacgga | 3600 |
| catgtttggc cagattgctg acaataatca gaatgctaca actgctccca taccggcaa | 3660 |
| cgtgactgct atgggagtgc tgcctggcat ggtgtggcaa aacagagaca tttactacca | 3720 |
| agggccaatt tgggccaaga tcccacacgc ggacggacat tttcatcctt caccgctgat | 3780 |
| tggtgggttt ggactgaaac acccgcctcc ccagatattc atcaagaaca ctcccgtacc | 3840 |
| tgccaatcct gcgacaacct tcactgcagc cagagtggac tctttcatca cacaatacag | 3900 |
| caccggccag gtcgctgttc agattgaatg ggaaattgaa aaggaacgct ccaaacgctg | 3960 |
| gaatcctgaa gtgcagttta cttcaaacta tgggaaccag tcttctatgt tgtgggctcc | 4020 |
| tgatacaact gggaagtata cagagccgcg ggttattggc tctcgttatt tgactaatca | 4080 |
| tttgtaa | 4087 |

<210> SEQ ID NO 12
<211> LENGTH: 4180
<212> TYPE: DNA
<213> ORGANISM: Adeno-associated virus 13

<400> SEQUENCE: 12

| | |
|---|---|
| ccgcgagtga gcgaaccagg agctccattt tgcccgcgaa ttttgaacga gcagcagcca | 60 |
| tgccgggatt ctacgagatt gtcctgaagg tgcccagcga cctggacgag cacctgcctg | 120 |
| gcatttctga ctcttttgta aactgggtgg cggagaagga atgggagctg ccgccggatt | 180 |
| ctgacatgga tctgaatctg attgagcagg caccctaac cgtggccgaa aagctgcaac | 240 |
| gcgaattcct ggtcgagtgg cgccgcgtga gtaaggcccc ggaggccctc ttctttgttc | 300 |

```
agttcgagaa gggggacagc tacttccacc tacacattct ggtggagacc gtgggcgtga      360
aatccatggt ggtgggccgc tacgtgagcc agattaaaga gaagctggtg acccgcatct      420
accgcgggt cgagccgcag cttccgaact ggttcgcggt gaccaagacg cgtaatggcg       480
ccggaggcgg gaacaaggtg gtggacgact gctacatccc caactacctg ctccccaaga      540
cccagcccga gctccagtgg gcgtggacta atatggacca gtatttaagc gcctgtttga      600
atctcgcgga gcgtaaacgg ctggtggcgc agcatctgac gcacgtgtcg cagacgcagg      660
agcagaacaa agagaaccag aatcccaatt ctgacgcgcc ggtgatcaga tcaaaaacct      720
ccgcgaggta catggagctg gtcgggtggc tggtggaccg cgggatcacg tcagaaaagc      780
aatggatcca ggaggaccag gcctcttaca tctccttcaa cgccgcctcc aactcgcggt      840
cacaaatcaa ggccgcactg gacaatgcct ccaaatttat gagcctgaca aaaacggctc      900
cggactacct ggtgggaaac aacccgccgg aggacattac cagcaaccgg atctacaaaa      960
tcctcgagat gaacgggtac gatccgcagt acgcggcctc cgtcttcctg ggctgggcgc     1020
aaaagaagtt cgggaagagg aacaccatct ggctctttgg gccggccacg acgggtaaaa     1080
ccaacatcgc tgaagctatc gcccacgccg tgcccttta cggctgcgtg aactggacca      1140
atgagaactt tccgttcaac gattgcgtcg acaagatggt gatctggtgg gaggagggca     1200
agatgacggc caaggtcgtg gagtccgcca aggccattct gggcggaagc aaggtgcgcg     1260
tggaccaaaa gtgcaagtca tcggcccaga tcgacccaac tcccgtcatc gtcacctcca     1320
acaccaacat gtgcgcggtc atcgacggaa attccaccac cttcgagcac caacaaccac     1380
tccaagaccg gatgttcaag ttcgagctca ccaagcgcct ggagcacgac tttggcaagg     1440
tcaccaagca ggaagtcaag gactttttcc ggtgggcgtc agatcacgtg actgaggtgt     1500
ctcacgagtt ttacgtcaga aagggtggag ctagaaagag gccgcccccc aatgacgcag     1560
atataagtga gcccaagcgg gcctgtccgt cagttgcgca gccatcgacg tcagacgcgg     1620
aagctccggt ggactacgcg gacaggtacc aaaacaaatg ttctcgtcac gtgggcatga     1680
atctgatgct ttttccctgc cggcaatgcg agagaatgaa tcagaatgtg acatttgct      1740
tcacgcacgg ggtcatggac tgtgccgagt gcttccccgt gtcagaatct caacccgtgt     1800
ctgtcgtcag aaagcggaca tatcagaaac tgtgtccgat tcatcacatc atggggaggg     1860
cgcccgaggt ggcttgttcg gcctgcgatc tggccaatgt ggactggat gactgtgaca      1920
tggagcaata aatgactcaa accagatatg actgacggtt accttccaga ttggctagag     1980
gacaacctct ctgaaggcgt tcgagagtgg tgggcgctgc aacctggagc ccctaaaccc     2040
aaggcaaatc aacaacatca ggacaacgct cggggtcttg tgcttccggg ttacaaatac     2100
ctcggacccg gcaacggact tgacaagggg gaacccgtca acgcagcgga cgcggcagcc     2160
ctcgaacacg acaaggccta cgaccagcag ctcaaggccg gtgacaaccc ctacctcaag     2220
tacaaccacg ccgacgccga gtttcaggag cgtcttcaag aagatacgtc ttttgggggc     2280
aacctcggac gagcagtctt ccaggccaaa aagaggatcc ttgagcctct gggtctggtt     2340
gaggaagcgg ctaagacggc tcctggaaaa aagagacctg tagagcaatc tccagcagaa     2400
ccggactcct cttcgggcat cggcaaatca ggccagcagc ccgctagaaa aagactgaat     2460
tttggtcaga ctggcgacac agagtcagtc ccagaccctc aaccactcgg acaacctccc     2520
gcagccccct ctggtgtggg atctactaca atggcttcag gcggtggcgc accaatggca     2580
gacaataacg agggtgccga tggagtgggt aattcctcag gaaattggca ttgcgattcc     2640
caatggctgg gcgacagagt catcaccacc agcacccgca cctgggccct gcccacctac     2700
```

| | | | |
|---|---|---|---|
| aacaatcacc | tctacaagca aatctccagc caatcaggag ccaccaacga | caaccactac | 2760 |
| tttggctaca | gcaccccctg ggggtatttt gacttcaaca | gattccactg ccactttca | 2820 |
| ccacgtgact | ggcaaagact catcaacaac aactggggat | tccgacccaa gagactcaac | 2880 |
| ttcaagctct | ttaacattca agtcaaagag gtcacgcaga | atgacggtac gacgacgatt | 2940 |
| gccaataacc | ttaccagcac ggttcaggtg tttactgact | ccgagtacca gctcccgtac | 3000 |
| gtcctcggct | cggcgcatca gggatgcctc ccgccgttcc | cagcagacgt cttcatggtc | 3060 |
| ccacagtatg | gataccctcac cctgaacaac gggagtcagg | cggtaggacg ctcttccttt | 3120 |
| tactgcctgg | agtactttcc ttctcagatg ctgcgtactg | gaaacaactt tcagtttagc | 3180 |
| tacactttg | aagacgtgcc tttccacagc agctacgctc | acagccaaag tctggaccgt | 3240 |
| ctcatgaatc | ctctgatcga ccagtacctg tactatctga | acaggacaca aacagccagt | 3300 |
| ggaactcagc | agtctcggct actgtttagc caagctggac | ccaccagtat gtctcttcaa | 3360 |
| gctaaaaact | ggctgcctgg accttgctac agacagcagc | gtctgtcaaa gcaggcaaac | 3420 |
| gacaacaaca | acagcaactt tccctggact ggtgccacca | aatatcatct gaatggccgg | 3480 |
| gactcattgg | tgaacccggg ccctgctatg gccagtcaca | aggatgacaa agaaaagttt | 3540 |
| ttccccatgc | atggaaccct gatatttggt aaagaaggaa | caaatgccaa caacgcggat | 3600 |
| ttggaaaatg | tcatgattac agatgaagaa gaaatccgca | ccaccaatcc cgtggctacg | 3660 |
| gagcagtacg | ggactgtgtc aaataatttg caaaactcaa | acgctggtcc aactactgga | 3720 |
| actgtcaatc | accaaggagc gttacctggt atggtgtggc | aggatcgaga cgtgtacctg | 3780 |
| cagggaccca | tttgggccaa gattcctcac accgatggac | actttcatcc ttctccactg | 3840 |
| atgggaggtt | ttgggctcaa acacccgcct cctcagatca | tgatcaaaaa cactcccgtt | 3900 |
| ccagccaatc | ctcccacaaa ctttagtgcg gcaaagtttg | cttccttcat cacacagtac | 3960 |
| tccacggggc | aggtcagcgt ggagatcgag tgggagctgc | agaaggagaa cagcaaacgc | 4020 |
| tggaatcccg | aaattcagta cacttccaac tacaacaaat | ctgttaatgt ggactttact | 4080 |
| gtggacacta | atggtgtgta ttcagagcct cgccccattg | caccagata cctgactcgt | 4140 |
| aatctgtaat | tgcttgttaa tcaataaacc ggttaattcg | | 4180 |

<210> SEQ ID NO 13
<211> LENGTH: 5594
<212> TYPE: DNA
<213> ORGANISM: Human parvovirus B19

<400> SEQUENCE: 13

| | | | |
|---|---|---|---|
| ccaaatcaga | tgccgccggt cgccgccggt aggcgggact | tccggtacaa gatggcggac | 60 |
| aattacgtca | tttcctgtga cgtcatttcc tgtgacgtca | cttccggtgg gcgggacttc | 120 |
| cggaattagg | gttggctctg gccagcttcg cttgggggttg | ccttgacact aagacaagcg | 180 |
| gcgcgccgct | tgtcttagtg gcacgtcaac cccaagcgct | ggcccagagc caaccctaat | 240 |
| tccggaagtc | ccgcccaccg gaagtgacgt cacaggaaat | gacgtcacag gaaatgacgt | 300 |
| aattgtccgc | catcttgtac cggaagtccc gcctaccggc | ggcgaccggc ggcatctgat | 360 |
| ttggtgtctt | cttttaaatt ttagcgggct ttttccccgc | cttatgcaaa tgggcagcca | 420 |
| ttttaagtgt | ttcactataa ttttattggt cagttttgta | acggttaaaa tgggcggagc | 480 |
| gtaggcgggg | actacagtat atatagcacg gcactgccgc | agctctttct ttctgggctg | 540 |
| cttttttcctg | gactttcttg ctgttttttg tgagctaact | aacaggtatt tatactactt | 600 |

```
gttaacatac taacatggag ctatttagag gggtgcttca agtttcttct aatgttctgg    660
actgtgctaa cgataactgg tggtgctctt tactggattt agacacttct gactgggaac    720
cactaactca tactaacaga ctaatggcaa tatacttaag cagtgtggct tctaagcttg    780
actttaccgg ggggccacta gcggggtgct tgtactttt tcaagtagaa tgtaacaaat    840
ttgaagaagg ctatcatatt catgtggtta ttgggggcc agggttaaac cccagaaacc    900
tcacagtgtg tgtagagggg ttatttaata atgtacttta tcaccttgta actgaaaatg    960
taaagctaaa atttttgcca ggaatgacta caaaaggcaa atactttaga gatggagagc   1020
agtttataga aaactattta atgaaaaaaa tacctttaaa tgttgtatgg tgtgttacta   1080
atattgatgg atatatagat acctgtattt ctgctacttt tagaagggga gcttgccatg   1140
ccaagaaacc ccgcattacc acagccataa atgacactag tagtgatgct ggggagtcta   1200
gcggcacagg ggcagaggtt gtgccaatta atgggaaggg aactaaggct agcataaagt   1260
ttcaaactat ggtaaactgg ttgtgtgaaa acagagtgtt tacagaggat aagtggaaac   1320
tagttgactt taaccagtac actttactaa gcagtagtca cagtggaagt tttcaaattc   1380
aaagtgcact aaaactagca atttataaag caactaattt agtgcctaca agcacatttc   1440
tattgcatac agactttgag caggttatgt gtattaaaga caataaaatt gttaaattgt   1500
tactttgtca aaactatgac cccctattag tggggcagca tgtgttaaag tggattgata   1560
aaaaatgtgg caagaaaaat acactgtggt tttatgggcc gccaagtaca ggaaaaacaa   1620
acttggcaat ggccattgct aaaagtgttc cagtatatgg catggttaac tggaataatg   1680
aaaactttcc atttaatgat gtagcaggga aaagcttggt ggtctgggat gaaggtatta   1740
ttaagtctac aattgtagaa gctgcaaaag ccatttagg cgggcaaccc accagggtag   1800
atcaaaaaat gcgtggaagt gtagctgtgc ctggagtacc tgtggttata accagcaatg   1860
gtgacattac ttttgttgta agcgggaaca ctacaacaac tgtacatgct aaagccttaa   1920
aagagcgaat ggtaaagtta aactttactg taagatgcag ccctgacatg gggttactaa   1980
cagaggctga tgtacaacag tggcttacat ggtgtaatgc acaaagctgg gaccactatg   2040
aaaactgggc aataaactac acttttgatt cccctggaat taatgcagat gccctccacc   2100
cagacctcca aaccaccccca attgtcacag acaccagtat cagcagcagt ggtggtgaaa   2160
gctctgaaga actcagtgaa agcagctttt ttaacctcat caccccaggc gcctggaaca   2220
ctgaaacccc gcgctctagt acgcccatcc ccgggaccag ttcaggagaa tcatttgtcg   2280
gaagctcagt ttcctccgaa gttgtagctg catcgtggga agaagccttc tacacacctt   2340
tggcagacca gtttcgtgaa ctgttagttg gggttgatta tgtgtgggac ggtgtaaggg   2400
gtttacctgt gtgttgtgtg caacatatta acaatagtgg gggaggcttg gactttgtc    2460
cccattgcat taatgtaggg gcttggtata atggatggaa atttcgagaa tttaccccag   2520
atttggtgcg gtgtagctgc catgtgggag cttctaatcc cttttctgtg ctaacctgca   2580
aaaaatgtgc ttacctgtct ggattgcaaa gctttgtaga ttatgagtaa agaaagtggc   2640
aaatggtggg aaagtgatga taaatttgct aaagctgtgt atcagcaatt tgtggaattt   2700
tatgaaaagg ttactggaac agacttagag cttattcaaa tattaaaaga tcactataat   2760
atttctttag ataatcccct agaaaaccca tcctctctgt ttgacttagt tgctcgtatt   2820
aaaaataacc ttaaaaactc tccagactta tatagtcatc attttcaaag tcatggacag   2880
ttatctgacc acccccatgc cttatcatcc agtagcagtc atgcagaacc tagaggagaa   2940
aatgcagtat tatctagtga agacttacac aagcctgggc aagttagcgt acaactaccc   3000
```

```
ggtactaact atgttgggcc tggcaatgag ctacaagctg ggcccccgca aagtgctgtt    3060
gacagtgctg caaggattca tgactttagg tatagccaac tggctaagtt gggaataaat    3120
ccatatactc attggactgt agcagatgaa gagcttttaa aaatataaa  aaatgaaact    3180 gggtttcaag cacaagtagt aaaagactac tttactttaa aaggtgcagc tgcccctgtg    3240
gcccattttc aaggaagttt gccggaagtt cccgcttaca acgcctcaga aaaataccca    3300
agcatgactt cagttaattc tgcagaagcc agcactggtg caggaggggg tggcagtaat    3360
cctgtcaaaa gcatgtggag tgagggggcc acttttagtg ccaactctgt aacttgtaca    3420
ttttccagac agttttttaat tccttatgac ccagagcacc attataaggt gttttctccc    3480
gcagcaagca gctgccacaa tgccagtgga aaggaggcaa aggtttgcac aattagtccc    3540
ataatgggat actcaacccc atggagatat ttagatttta atgctttaaa tttatttttt    3600
tcacctttag agtttcagca cttaattgaa aattatggaa gtatagctcc tgatgcttta    3660
actgtaacca tatcagaaat tgctgttaag gatgttacag acaaaactgg aggggggta     3720 caggttactg acagcactac agggcgccta tccatgttag tagaccatga atacaagtac    3780
ccatatgtgt taggacaagg tcaggatact ttagccccag aacttcctat ttgggtatac    3840 tttcccccte aatatgctta cttaacagta ggagatgtta acacacaagg aatctctgga    3900
gacagcaaaa aattagcaag tgaagaatca gcattttatg ttttggaaca cagttctttt    3960
cagcttttag gtacaggagg tacagcaact atgtcttata agtttcctcc agtgccccca    4020
gaaaatttag agggctgcag tcaacacttt tatgaaatgt acaatccctt atacggatcc    4080
cgcttagggg ttcctgacac attaggaggt gacccaaaat ttagatcttt aacacatgaa    4140
gaccatgcaa ttcagcccca aaacttcatg ccagggccac tagtaaactc agtgtctaca    4200
aaggagggag acagctctaa tactggagct ggaaaagcct aacaggcct  tagcacaggc    4260 acctctcaaa acactagaat atccttacgc cctgggccag tgtcacagcc ataccaccac    4320
tgggacacag ataaatatgt tccaggaata aatgccattt ctcatggtca gaccactat     4380 ggtaacgctg aagacaaaga gtatcagcaa ggagtgggta gatttccaaa tgaaaaagaa    4440
cagctaaaac agttacaggg tttaaacatg cacacctatt tccccaataa aggaacccag    4500
caatatacag atcaaattga gcgcccccta atggtgggtt ctgtatggaa cagaagagcc    4560
cttcactatg aaagccagct gtggagtaaa attccaaatt tagatgacag ttttaaaact    4620
cagtttgcag ccttaggagg atggggtttg catcagccac ctcctcaaat atttttaaaa    4680
atattaccac aaagtgggcc aattggaggt attaaatcaa tgggaattac taccttagtt    4740
cagtatgccg tgggaattat gacagtaact atgacattta aattggggcc ccgtaaagct    4800
acgggacggt ggaatcctca acctggagta tatccccgc  acgcagcagg tcatttacca    4860
tatgtactat atgaccccac agctacagat gcaaacaac  accacaggca tggatacgaa    4920
aagcctgaag aattgtggac agccaaaagc cgtgtgcacc cattgtaaac actcccacc     4980 gtgccctcag ccaggatgcg taactaaacg cccaccagta ccacccagac tgtacctgcc    5040
ccctcctgta cctataagac agcctaacac aaaagatata gacaatgtag aatttaagta    5100
cttaaccaga tatgaacaac atgttattag aatgttaaga ttgtgtaata tgtatcaaaa    5160
tttagaaaaa taaacatttg ttgtggttaa aaaattatgt tgttgcgctt taaaaattta    5220
aaagaagaca ccaaatcaga tgccgccggt cgccgccggt aggcgggact tccggtacaa    5280
gatggcggac aattacgtca tttcctgtga cgtcatttcc tgtgacgtca cttccggtgg    5340
```

```
gcgggacttc cggaattagg gttggctctg ggccagcgct tggggttgac gtgccactaa      5400
gacaagcggc gcgccgcttg tcttagtgtc aaggcaaccc caagcaagct ggcccagagc      5460
caaccctaat tccggaagtc ccgcccaccg gaagtgacgt cacaggaaat gacgtcacag      5520
gaaatgacgt aattgtccgc catcttgtac cggaagtccc gcctaccggc ggcgaccggc      5580
ggcatctgat ttgg                                                       5594

<210> SEQ ID NO 14
<211> LENGTH: 5149
<212> TYPE: DNA
<213> ORGANISM: Minute virus of mice

<400> SEQUENCE: 14 attttagaa ctgaccaacc atgttcacgt aagtgacgtg atgacgcgcg ctgcgcgcgc        60
gccttcggac gtcacacgtc acttacgttt cacatggttg gtcagttcta aaaatgataa      120
gcggttcagg gagtttaaac caaggcgcga aaaggaagtg ggcgtggttt aaagtatata      180
agcaactact gaagtcagtt acttatcttt tctttcattc tgtgagtcga gacgcacaga      240
aagagagtaa ccaactaacc atggctggaa atgcttactc tgatgaagtt ttgggagcaa      300
ccaactggtt aaaggaaaaa agtaaccagg aagtgttctc atttgttttt aaaaatgaaa      360
atgttcaact gaatgaaaaa gatatcggat ggaatagtta caaaaaagag ctgcaggagg      420
acgagctgaa atctttacaa cgaggagcgg aaactacttg gaccaaagc gaggacatgg       480 aatgggaaac cacagtggat gaaatgacca aaagcaagt attcatttt gattctttgg         540 ttaaaaatg tttatttgaa gtgcttaaca caaagaatat atttcctggt gatgttaatt       600
ggtttgtgca acatgaatgg ggaaaagacc aaggctggca ctgccatgta ctaattggag      660
gaaaggactt tagtcaagct caagggaaat ggtggagaag gcaactaaat gtttactgga     720
gcagatggtt ggtaacagcc tgtaatgtgc aactaacacc agctgaaaga attaaactaa      780
gagaaatagc agaagacaat gagtgggtta ctctacttac ttataagcat aagcaaacca      840
aaaaagacta taccaagtgt gttctttttg gaaacatgat tgcttactat tttttaacta      900 aaagaaaat aagcactagt ccaccaagag acggaggcta ttttcttagc agtgactctg       960
gctggaaaac taactttta aaagaaggcg agcgccatct agtgagcaaa ctatacactg     1020
atgacatgcg gccagaaacg gttgaaacca cagtaaccac tgcgcaggaa actaagcgcg     1080
gcagaattca aactaaaaaa gaagtttcta ttaaaactac acttaaagag ctggtgcata     1140
aaagagtaac ctcaccagag gactggatga tgatgcagcc agacagttac attgaaatga     1200
tggctcaacc aggtggagaa aacctgctga aaaatacgct agagatttgt acactaactc     1260
tagccagaac caaaacagca tttgacttaa ttttagaaaa agctgaaacc agcaaactaa     1320
ccaacttttc actgcctgac acaagaacct gcagaatttt tgcttttcat ggctggaact     1380
atgttaaagt ttgccatgct atttgctgtg ttttaaacag acaaggaggc aaaagaaata     1440 ctgtttatt tcatggacca gccagcacag gcaaatctat tattgcacaa gccatagcac     1500
aagcagttgg caatgttggt tgctataatg cagccaatgt aaactttcca tttaatgact     1560
gtaccaacaa gaacttgatt tgggtagaag aagctggtaa ctttgacag caagtaaacc      1620 agtttaaagc catttgctct ggtcaaacta ttcgcattga tcaaaagga aaaggcagca     1680 aacagattga accaacacca gtcatcatga ccacaaatga aacattaca gtggtcagaa      1740 taggctgcga agaagaccga gaacacactc aaccaatcag agacagaatg cttaacattc      1800
atctaacaca taccttgcct ggtgactttg gtttggttga caaaatgaa tggcccatga     1860
```

```
tttgtgcttg gttggtaaag aatggttacc aatctaccat ggcaagctac tgtgctaaat    1920
ggggcaaagt tcctgattgg tcagaaaact gggcggagcc aaaggtgcca actcctataa    1980
atttactagg ttcggcacgc tcaccattca cgacaccgaa aagtacgcct ctcagccaga    2040
actatgcact aactccactt gcatcggatc tcgaggacct ggctttagag ccttggagca    2100
caccaaatac tcctgttgcg ggcactgcag aaacccagaa cactggggaa gctggttcca    2160
aagcctgcca agatggtcaa ctgagcccaa cttggtcaga gatcgaggag gatttgagag    2220
cgtgcttcgg tgcggaaccg ttgaagaaag acttcagcga gccgctgaac ttggactaag    2280
gtacgatggc gcctccagct aaaagagcta aagaggtaa gggtttaagg gatggttggt    2340
tggtggggta ttaatgttta attacctgtt ttacaggcct gaaatcactt ggttttaggt    2400
tgggtgcctc ctggctacaa gtacctggga ccagggaaca gccttgacca aggagaacca    2460
accaatccat ctgacgccgc tgccaaagag cacgacgagg cctatgatca atacatcaaa    2520
tctggaaaaa atccttacct gtacttctct gctgctgatc aacgctttat tgaccaaacc    2580
aaggacgcca aagactgggg aggcaaggtt ggtcactact ttttagaac caagcgcgct    2640
tttgcaccta agcttgctac tgactctgaa cctggaactt ctggtgtaag cagagctggt    2700
aaacgcacta gaccacctgc ttacattttt attaaccaag ccagagctaa aaaaaaactt    2760
acttcttctg ctgcacagca aagcagtcaa accatgagtg atggcaccag ccaacctgac    2820
agcggaaacg ctgtccactc agctgcaaga gttaacgag cagctgacgg ccctggaggc    2880
tctgggggtg ggggctctgg cggggtggg gttggtgttt ctactgggtc ttatgataat    2940
caaacgcatt atagattctt gggtgacggc tgggtagaaa ttactgcact agcaactaga    3000
ctagtacatt taaacatgcc taaatcagaa aactattgca gaatcagagt tcacaataca    3060
acagacacat cagtcaaagg caacatggca aaagatgatg ctcatgagca aatttggaca    3120
ccatggagct tggtggatgc taatgcttgg ggagtttggc tccagccaag tgactggcaa    3180
tacatttgca acaccatgag ccagcttaac ttggtatcac ttgatcaaga atattcaat    3240
gtagtgctga aaactgttac agagcaagac ttaggaggtc aagctataaa aatatacaac    3300
aatgacctta cagcttgcat gatggttgca gtagactcaa caacattttt gccatacaca    3360
cctgcagcaa actcaatgga aacacttggt ttctacccct ggaaaccaac catagcatca    3420
ccatacaggt actattttg cgttgacaga gatctttcag tgacctacga aaatcaagaa    3480
ggcacagttg aacataatgt gatgggaaca ccaaaaggaa tgaattctca atttttacc    3540
attgagaaca cacaacaaat cacattgctc agaacagggg acgaatttgc cacaggtact    3600
tactactttg acacaaattc agttaaactc acacacacgt ggcaaaccaa ccgtcaactt    3660
ggacagcctc cactgctgtc aacctttcct gaagctgaca ctgatgcagg tacacttact    3720
gctcaaggga gcagacatgg aacaacacaa atgggggtta actgggtgag tgaagcaatc    3780
agaaccagac ctgctcaagt aggattttgt caaccacaca tgactttga agccagcaga    3840
gctggaccat ttgctgcccc aaaagttcca gcagatatta ctcaaggagt agacaaagaa    3900
gccaatggca gtgttagata cagttatggc aaacagcatg gtgaaaattg ggcttcacat    3960
ggaccagcac cagagcgcta cacatgggat gaaacaagct tggttcagg tagagacacc    4020
aaagatggtt ttattcaatc agcaccacta gttgttccac caccactaaa tggcattctt    4080
acaaatgcaa accctattgg gactaaaaat gacattcatt tttcaaatgt ttttaacagc    4140
tatggtccac taactgcatt ttcacaccca agtcctgtat accctcaagg acaaatatgg    4200
```

```
gacaaagaac tagatcttga acacaaacct agacttcaca taactgctcc atttgtttgt   4260
aaaaacaatg cacctggaca aatgttggtt agattaggac caaacctaac tgaccaatat   4320
gatccaaacg gagccacact ttctagaatt gttacatacg gtacattttt ctggaaagga   4380
aaactaacca tgagagcaaa acttagagct aacaccactt ggaacccagt gtaccaagta   4440
agtgctgaag acaatggcaa ctcatacatg agtgtaacta aatggttacc aactgctact   4500
ggaaacatgc agtctgtgcc gcttataaca agacctgttg ctagaaatac ttactaacta   4560
accatgcttt ttctttctgt acttcatata ttattaagac taataaagat acaacataga   4620
aatataatat tacgtataga tttaagaaat agaataatat ggtacttagt aactgttaaa   4680
aataatagaa cctttggaat aacaagatag ttagttggtt aatgttagat agaataagaa   4740
gatcatgtat aatgaataaa agggtggaag ggtggttggt aggttaatgt tagatagaat   4800
aagaagatca tgtataatga ataaagggt ggaagggtgg ttggtaggta ttcccttaga   4860
cttgatgtta aggaccaaaa aaataataaa actttttaa aactcaacca agactactgt   4920
ctattcagtg aaccaactga accattagta ttactatgtt tttagggtgg gagggtggga   4980
gatacatgtg ttcgctatga gcgaactggt actggttggt tgctctgctc aaccaaccag   5040
accggcaaag ccggtctggt tggttgagcg caaccaacca gtaccagttc gctcatagcg   5100
aacacatgta tctcccaccc tcccacccta aaaacatagt aatactaat                5149
```

<210> SEQ ID NO 15
<211> LENGTH: 5106
<212> TYPE: DNA
<213> ORGANISM: Goose parvovirus

<400> SEQUENCE: 15

```
ctcattggag ggttcgttcg ttcgaaccag ccaatcaggg gaggggggaag tgacgcaagt     60
tccggtcaca tgcttccggt gacgcacatc cggtgacgta gttccggtca cgtgcttcct    120
gtcacgtgtt tccggtcacg tgacttccgg tcatgtgact tccggtgacg tgtttccggc    180
tgttaggttg accacgcgca tgccgcgcgg tcagcccaat agttaagccg gaaacacgtc    240
accggaagtc acatgaccgg aagtcacgtg accggaaaca cgtgacagga agcacgtgac    300
cggaactacg tcaccggatg tgcgtcaccg gaagcatgtg accggaactt gcgtcacttc    360
ccctcccct gattggctgg ttcgaacgaa cgaaccctcc aatgagactc aaggacaaga    420
ggatattttg cgcgccagga agtgacgtgc aatgccaccc tatataagcc aggaaacttc    480
cggtttagtt cattcgttac tctgctctca gagagaacgg acctcaggtc ggagagatgg    540
cactttctag gcctcttcag atttcttctg ataaattcta tgaagttatt attagattat    600
catcggatat tgatcaagat gtccccggtc tgtctcttaa cttttgtagaa tggctttcta    660
ccggagtttg ggagcccacg ggcatctgga acatggagca tgtgaatcta ccgatggtga    720
ccttggcaga aagatcaag aacatttca tacaaagatg gaatcagttc aaccaggacg    780
aaacggactt cttctttcaa ctggaagaag gcagtgagta cattcatctt cattgctgta    840
ttgcccaggg caatgtacgg tcttttgttc tcgggagata tatgtctcag ataaaagact    900
ctatcataag agatgtatat gaagggaaac aaatcaagat ccccgattgg tttgctatta    960
ctaaaaccaa gaggggagga cagaataaga ccgtgactgc agcatacata ctgcattacc   1020
ttattcctaa aaagcaacct gaactgcaat gggcctttac caatatgcct ttattcactg   1080
ctgctgctct ttgtctgcaa aagcggcaag aattgctgga tgcatttcaa gaaagtgatt   1140
tggctgcccc tttacctgat cctcaagcat caactgtggc accgcttatt ccaacagag   1200
```

```
cggcaaagaa ctatagcaac cttgttgatt ggctcattga aatgggdata acatctgaga   1260
agcaatggct cactgagaac cgagagagct acagaagctt tcaagcaact tcttcaaata   1320
atagacaagt gaaagctgca ctggaaaatg cccgtgctga atgttattg acaaagactg   1380 caactgatta cctgatagga aaagaccctg tcctggatat aactaagaat agggtctatc   1440
aaattctgaa aatgaataac tacaaccctc aatacatagg aagtatcctg tgcggctggg   1500
tgaagagaga gttcaacaaa agaaacgcca tatggctcta cggacctgcc accaccggga   1560
agaccaacat tgcagaagct attgcccatg ctgtacccct ctatggctgt gttaactgga   1620
ctaatgagaa cttttccttttt aatgattgtg ttgataaaat gctgatttgg tgggaggagg   1680
gaaaaatgac taataaggtt gttgaatctg caaaagcaat tttgggaggg tctgctgtcc   1740
gggtagacca gaaatgtaaa ggatctgttt gtattgaacc tactcctgta attattacta   1800
gtaatactga tatgtgtatg attgttgatg gcaactctac tacaatggaa catagaatac   1860
cattagagga gcgtatgttt caaattgtcc tatcacataa attggagcct tcttttggaa   1920
aaatttctaa aaaagaagtc agagaatttt tcaaatgggc caatgacaat ctagttcctg   1980
ttgtgtctga gttcaaagtc cgaactaatg aacaaaccaa cttgccagag cccgttcctg   2040
aacgagcgaa cgagccggag gagcctccta agatctgggc tcctcctact agggaggagt   2100
tagaagagct tttaagagcc agcccagaat tgttctcatc agtcgctcca attcctgtga   2160
ctcctcagaa ctcccctgag cctaagagaa gcaggaacaa ttaccaggta cgctgcgctt   2220
tgcatactta tgacaattct atggatgtat ttgaatgtat ggaatgtgag aaagcaaact   2280
ttcctgaatt tcaacctctg ggagaaaatt attgtgatga acatgggtgg tatgattgtg   2340
ctatatgtaa agagttgaaa atgaacttgc agaaaattga gcatgtgttt gagcttgatg   2400
atgctgaaaa tgaacaataa agatgactca aagcagatat gtctactttt ttagattctt   2460
ttgaagagtg gtatgagact gcagccgcct cgtggcggaa tctgaaagct ggagcccctc   2520
agccaaaacc aaaccagcag tctcagtctg tgtctccaga cagagaaccc gaacgaaaag   2580
ataataatcg gggctttgta cttcctggct ataagtatct tgggcctggt aacggcctgg   2640
ataaaggccc acctgtcaat aaggcggaca gcgtcgcgct tgaacacgac aaggcctatg   2700
accagcagct taaagcggga gacaaccat atataaaatt caatcacgct gaccaggact   2760
ttatagatag cctccaagac gaccagtcat tcggaggtaa tcttggaaag gctgtatttc   2820
aggccaaaaa acgtatctta gagccatttg gcctagtaga agatcctgtc aacacggcac   2880
ctgcaaaaaa aaatacaggg aagcttactg accattaccc ggtagttaag aagcctaaac   2940
ttaccgagga agtcagtgcg ggaggtggta gcagtgccgt acaagacgga ggagccaccg   3000
cggagggcac cgaacctgtg gcagcatctg aaatggcaga gggaggaggc ggagctatgg   3060
gcgactcttc aggggtgcc gatggagtgg gtaatgcctc gggaaattgg cattgcgatt   3120
cccaatggat gggaaacaca gtcatcacaa agaccaccag aacctgggtc ctgccaagct   3180
acaacaacca catctacaaa gcaattacca gcggaacctc tcaagatgca aatgtccagt   3240
atgcaggata cagtaccccc tgggggtact ttgatttcaa ccgcttccac tgccacttct   3300
cccctagaga ctggcagaga cttatcaaca accattgggg aatcagaccc aagtctctta   3360
aattcaagat cttcaatgtc caagtcaaag aagtcacaac gcaggatcag acaaagacca   3420
ttgcaaacaa tctcacctca acaattcaag tcttacgga tgatgagcat caactcccgt   3480
atgtcctggg ctcggctacg gaaggcacca tgccgccgtt cccgtcggat gtctatgccc   3540
```

```
tgccgcagta cgggtactgc acaatgcaca ccaaccagaa tggagcacgg ttcaatgacc      3600
gtagtgcatt ctactgctta gagtacttcc ctagtcagat gctaagaaca ggcaacaact      3660
ttgagttcac atttgacttt gaagaagttc ctttccatag catgttcgct cattcacagg      3720
acttagacag gctgatgaac cccctagtgg atcaatacct ctggaatttc aatgaggtag      3780
acagcagcag aaatgctcaa tttaaaaagg ctgtgaaagg ggcttatggc accatgggcc      3840
gcaattggct gccaggacct aaattcctgg atcaaagagt tagggcctac acaggaggaa      3900
cagacaacta tgcaaactgg aacatctgga gtaatgggaa caaggtgaat ttgaaagaca      3960
gacagtatct cctacaaccc ggacctgtgt cagctactta cacagaaggg gaggcttcca      4020
gccttccagc tcaaaatatt ttagggatag ctaaagatcc atacagatca ggcagcacta      4080
cagcaggaat aagtgacatt atggtcacgg aagaacaaga agtagcacct acaaatggag      4140
tagggtggaa accatatggt aggactgtaa cgaatgaaca aaacactact acagctccta      4200
caagttcaga tctggatgtt cttggagctt taccaggaat ggtttggcag aacagggata      4260
tatatctgca gggacctatt ggggcaaaaa taccgaagac tgatggtaaa ttccatcctt      4320
ctccgaatct cggaggattt ggcctgcaca atccaccacc gcaggtgttc atcaagaata      4380
caccagtgcc tgcagaccct ccagtagaat acgtgcacca aagtggaat tcctacataa      4440 cccagtactc tacgggccag tgtacagtag agatggtgtg ggagctgaga aaagagaatt      4500
caaagagatg gaacccagaa atccagttca ccagtaattt cagtaacaga caagcataa      4560 tgtttgcacc taatgaaact ggtggatatg tagaagatag attgattgga accagatatc      4620
taactcaaaa tctgtaaatt ctgtgtaaaa attcaaataa agcacttcct ggcgcgcaaa      4680
atatcctctt gtccttgagt ctcattggag ggttcgttcg ttcgaaccag ccaatcaggg      4740 gaggggaag tgacgcaagt tccggtcaca tgcttccggt gacgcacatc cggtgacgta      4800
gttccggtca cgtgcttcct gtcacgtgtt tccggtcacg tgacttccgg tcatgtgact      4860
tccggtgacg tgtttccggc ttaactattg ggctgaccgc gcgcatgcgc gtggtcaacc      4920
taacagccgg aaacacgtca ccggaagtca catgaccgga agtcacgtga ccggaaacac      4980
gtgacaggaa gcacgtgacc ggaactacgt caccggatgt gcgtcaccgg aagcatgtga      5040
ccggaacttg cgtcacttcc ccctcccctg attggctggt tcgaacgaac gaaccctcca      5100
atgaga                                                               5106
```

<210> SEQ ID NO 16
<211> LENGTH: 4432
<212> TYPE: DNA
<213> ORGANISM: Snake parvovirus 1

<400> SEQUENCE: 16

```
cgccccaccc ctagtgatcg cgcgcgctct ctcttggggc ctgacggccg aaggccgtca       60
gctgccgagc ttcgctcggc aggccccaag agagagcgcg cgcgatcact aggggtgggg      120
cgagtgccct gctcaacggg ttttttggtg ggcggagcaa tgacgtcagc ggacatgtct      180
ggacatgtct ttgagcaagt ccatataagg agttccgccg gatatgcaaa tgagcaatcg      240
cgcaaagcat tttgggtagt caccatgaat aaaaaggaca gcaagaaaga tgacgcccca      300 taatttaat aggaatttta accatggcgt tttacgaggt tgtgtttcgt ttgccaagag      360
acaataacaa cttgttggat gaagatagat atcagccaga gttgaaagaa gaagatgact      420
ggcctgagga atatttaacc agtgaagatg ccagctttat cggactagcg tatgctgtgc      480
taagtgaaat tcggagattc tttggaaagg aactacaatg gtttgcccag gttgaatggt      540
```

```
gtcctactgc tggttaccac atgcatgttt tgttgaacca tcctaagctg agtaaccaga    600
cttatggaag aaaggtcaat gaactggctt gccgtatagt cgatacctt tggcctaatta    660 atccagaaga agtcatcagt acccattatg ttaaaagcaa ctatggacat aaaaaggtga    720
gagtcattca cctagagtct tatttgaaga actactttt cagaaagact ttagctcctc    780
ccaattatac cgaggaagga gactataaaa gagaggaaga agtcgtgctg tgggcattta    840
cgaatatcgt cgcttggaag ccattcgtgc ggaatctcat caagagatcg gagctagcga    900
ctgttcctaa gcaaccagag aatccggcgg gagacggacc ggcacctcga gtgactgcag    960
gaacccgcca ttttatggaa accatcgact ggttggtgaa acatggaatt actacagaac   1020
gagaattctg ccacgccaac cgcccttttgt acctgtctat gctggcttct acttcgggtg   1080
ctgggcagat taaagagcg ctggaccagg cgaaacacat gatgaccagc accatgtcag   1140
cagaggatta cctgacaaca aagaggatg tgatcgaacc acctactgaa aatagaatct   1200
acaagattat gaaactgaat cgctatgatc cagaactagc agctgctctc ttctacggct   1260
ggacctgcaa gaactttggc aagagaaaca ccatctggct gtatggtcca gctactaccg   1320
gcaaaaccat catcgctcaa gctattgcac atgctgttaa actgtttgct ggtgttaatt   1380
ggactaatga aaactttccc ttctgtaact gtccagggaa actgcttatc tggtgggagg   1440
agggcaagat gacaaacaaa atggtggaga cggctaaatg tatactgggg ggatctgctg   1500
tacctgtaga catcaaaggc aaacccgctg aaatgtgtcc tcaaacaccc tgtattatta   1560
ctagcaatac taacatgtgt caagtatatg atggtaatag ttctagcttt gagcaccaag   1620 aaccccctaga ggaacgcatg tttatgttca gacttaatac taaactgcca tcgacctttg   1680
gcaagatcac agaagaggaa gtcaaacagt ttattacctg ggggaggagc ttaaaggttc   1740
aagttccaca tcagttcaga gtgcctacca caggagagta taaaaggcca gcccccgagg   1800
cgaaagctca ttcttcggat gagccgccaa aagagaaggt cgcgcgtatt gatgactctc   1860
taaccaggta tgttaacaat attgatgagt cagctaccag tagagaaatg tttctagaga   1920
ttgctaatac taatcaatgt atgttgcatc attgcttttc ttgtaccgaa tgttatcctg   1980
aattgcttga tgacatggac aaggaacaat aaacttactg ataacagata tggatttttct  2040 cgatgatttc tttgcagata aatataaaga gactgttaac gaactcggta accggtcaa   2100 tcctaaacct gtaaaacaca ttagcgaagc tcactcgcaa cctggcagca ggaggggctt   2160
tgtggtgcct gggtatcggt atcttgggcc tggtaatagc ttggaccgtg aaagcccgt   2220 taacaaagca gacgaggctg ctaaaaagca cgatcaagaa tacgatcaac agcttaaagc   2280
gggagacaat ccctacataa aatataatca cgcggacgaa cagttccaga aagacctaca   2340
aggtgatacc agtctagccg gcaacgcggc taacgctcta tttcaaggca aaaagactct   2400
actagcgccc cttggcctag tagagacccc tgtcggcaaa acgtctgaaa agcacaaatt   2460
agacgaatac tatcctaaag ctaaaaaggc caaacaaggc ttgcagatac cagctccacc   2520
taaaggcgga gaagaagaag ctacatcgtc acaatctgga gggagcccag caggttccga   2580
tactagcggc acatctgtca tggctacagg aggaggcggt ccgatggcag acgataacca   2640
gggcgccgag ggagtgggta attcctcagg tgattggcat tgcgatacca agtggatggg   2700
agaccacgtc attacaaagt caaccagaac ttgggtgctc cccacttacg ggaatcatct   2760
ctacgggcct atcaactttg acggcaccac aggttcgggt gctaatgcag cctatgcagg   2820
atacaagact ccctgggggt actttgactt caatcgattc cattgccact tctcccccg   2880
```

```
agactggcaa agactcatca acaaccacac aggcatcagg ccgaaaggac tcaaaatcaa    2940
agtctttaac gtccaagtca aagaagttac aacacaagat tcaacgaaaa caattgccaa    3000
caatctcacc agcaccgtac agatctttgc ggacgagaac tacgacttac catatgtatt    3060
aggcagtgct acacaaggca catttcctcc atttcccaat gatgtattta tgttaccaca    3120
atatgcttat tgtacacttc aaggaaattc ggggaaattt gtagatagaa gtgcctttta    3180
ttgtttagaa tattttcctt cacaaatgct gagaacagga acaattttg agttccagtt     3240 taaatttgaa gaagttccct ttcattctgg atgggcacag agtcaaagcc tagacagatt    3300
gatgaatccg ttgcttgatc aatatctgat aggagactat ggaacagatg catcaggaaa    3360
ccttatttat cacagagctg gtccaaatga tttgaatgaa ttctacaaga attgggcacc    3420
tgcaccctat gaatgtatcc agaatattaa cagcagtgat aataccaaga atgctaattc    3480
tataaatggt tcaaattcta ccaacaaatg gggactacaa ggaagacaag catgggatgc    3540
tccaggattt gttcaagcta gtacctatga aggtgcagca gcaggacaat ctcttcttaa    3600
tggcgtactt actttcgata aaagttcagc tactacttca tctccagctg ctactgcagt    3660
aaacagaaca attgaagacg aaatacaggg taccaataat tttggtaatg ctagaaataa    3720
cattgttgct atcaatcaac aaacgaaagg aacaaatcca acaacaggta gtacatctca    3780
atttgagaca atgccaggta tggtgtggtc taatagagac atttacttac aggggcctat    3840
ttgggctaaa attccaaata cagatggaca ttttcatcct tctcccagaa tgggtggttt    3900
tggattaaaa catcctccgc ctatgattct gatcaaaaat acaccagttc ctgctgatcc    3960
tccaactacc ttcaatccaa tgccacagac tagtttcatt actgaataca gtacaggaca    4020
agtaactgtt gaaatgttgt gggaggtaca gaaagaatcc tccaaaagat ggaatccaga    4080
agtacagttt acttccaatt ttggaacttc agatccagct gttgatggaa taccgtttgg    4140
aattaataat ttgggtactt atgttgaatc tagacctatt ggaactcgtt atatttctaa    4200
acacttgtaa ataataaaaa ttgtcaaatt tgcactaaga attgttgtca cgtggttgtt    4260
tacatgcttg ctaaaacacg cccaccaaaa aacccgttga gcagggcact cgccccaccc    4320
ctagtgatcg cgcgcgctct ctcttggggc ctgccgagcg aagctcggca gctgacggcc    4380
ttcggccgtc aggccccaag agagagcgcg cgcgatcact aggggtgggg cg            4432
```

<210> SEQ ID NO 17
<211> LENGTH: 165
<212> TYPE: DNA
<213> ORGANISM: Artificial
<220> FEATURE:
<223> OTHER INFORMATION: Chimeric ITR sequence

<400> SEQUENCE: 17

```
aggaacccct agtgatggag ttggccactc cctctctgcg cgctcgctcg ctcactgagg     60
gcgggcgacc aaaggtcgcc cgagcccggc cctttgggcc gggcccctca gtgagcgagc    120
gagcgcgcag agagggagtg gccaactcca tcactagggg ttcct                    165
```

<210> SEQ ID NO 18
<211> LENGTH: 198
<212> TYPE: DNA
<213> ORGANISM: Artificial
<220> FEATURE:
<223> OTHER INFORMATION: Chimeric ITR sequence

<400> SEQUENCE: 18

```
tacaaaacct ccttgcttga gagtgtggca ctctcccccc tgtcgcgttc gctcgctcgc     60
```

```
tggctcgttt ggggggggcga cggcccaaag ggccgtcgtc tggcagctct ttgagctgcc      120 accccccaa cgagccagc gagcgagcga acgcgacagg ggggagagtg ccacactctc         180
aagcaaggag gttttgta                                                     198

<210> SEQ ID NO 19
<211> LENGTH: 189
<212> TYPE: DNA
<213> ORGANISM: Artificial
<220> FEATURE:
<223> OTHER INFORMATION: Chimeric ITR sequence

<400> SEQUENCE: 19
aggaacccct agtgatggag ttggccactc cctccccct gtcgcgttcg cgcgctcgct        60
cgctcactga gggcgggcga ccaaaggtcg cccgagcccg gccctttggg ccgggccct        120 cagtgagcga gcgagcgcgc gaacgcgaca gggggagggg agtggccaac tccatcacta      180
ggggttcct                                                               189

<210> SEQ ID NO 20
<211> LENGTH: 190
<212> TYPE: DNA
<213> ORGANISM: Artificial
<220> FEATURE:
<223> OTHER INFORMATION: Chimeric ITR sequence

<400> SEQUENCE: 20
tacaaaacct ccttgcttga gagtgtggca ctctccccc tgtcgcgttc gcgcgctcgc        60
tcgctcactg agggcgggcg accaaaggtc gcccgagccc ggccctttgg gccgggcccc      120
tcagtgagcg agcgagcgcg cgaacgcgac aggggggaga gtgccacact ctcaagcaag      180
gaggttttgt                                                              190

<210> SEQ ID NO 21
<211> LENGTH: 196
<212> TYPE: DNA
<213> ORGANISM: Artificial
<220> FEATURE:
<223> OTHER INFORMATION: Chimeric ITR sequence

<400> SEQUENCE: 21
aggaacccct agtgatggag ttggccactc cctccccct gtcgcgttcg ctcgctcgct        60
ggctcgtttg gggggcgac ggcccaaagg gccgtcgtct ggcagctctt tgagctgcca      120 ccccccaaa cgagccagcg agcgagcgaa cgcgacaggg ggagggagt ggccaactcc        180 atcactaggg gttcct                                                       196

<210> SEQ ID NO 22
<211> LENGTH: 170
<212> TYPE: DNA
<213> ORGANISM: Artificial
<220> FEATURE:
<223> OTHER INFORMATION: Chimeric ITR sequence

<400> SEQUENCE: 22
tacaaaacct ccttgcttga gagtgtggca ctctctctgc gcgctcgctc gctcactgag       60
ggcgggcgac caaaggtcgc ccgacgcccg gccctttggg ccgggcggcc ctcagtgagc      120
gagcgagcgc gcagagagag tgccacactc tcaagcaagg aggttttgta                  170

<210> SEQ ID NO 23
```

```
<211> LENGTH: 164
<212> TYPE: DNA
<213> ORGANISM: Artificial
<220> FEATURE:
<223> OTHER INFORMATION: Chimeric ITR sequence

<400> SEQUENCE: 23
aggaacccct agtgatggag tggccctccc tctctgcgcg ctcgctcgct cactgagggc     60
gggcgaccaa aggtcgcccg acgcccggcc ctttgggccg gcggccctc agtgagcgag    120 cgagcgcgca gagagggagg gccactccat cactaggggt tcct                    164

<210> SEQ ID NO 24
<211> LENGTH: 202
<212> TYPE: DNA
<213> ORGANISM: Artificial
<220> FEATURE:
<223> OTHER INFORMATION: Chimeric ITR sequence

<400> SEQUENCE: 24
tacaaaacct ccttgcttga gagtgttgga cactctcccc cctgtcgcgt tcgctcgctc     60
gctggctcgt ttggggggc gacggcccaa agggccgtcg tctggcagct ctttgagctg    120 ccacccccc aaacgagcca gcgagcgagc gaacgcgaca gggggagag tgtccaacac     180 tctcaagcaa ggaggttttg ta                                            202

<210> SEQ ID NO 25
<211> LENGTH: 161
<212> TYPE: DNA
<213> ORGANISM: Artificial
<220> FEATURE:
<223> OTHER INFORMATION: Chimeric ITR sequence

<400> SEQUENCE: 25
aggaacccct agtatggagt tggccactcc attctgcgcg ctcgctcgct cactgagggc     60
gggcgaccaa aggtcgcccg agcccggcc tttgggccgg gccctcagt gagcgagcga    120 gcgcgcagaa tggagtggcc aactccatac tagggttcc t                        161

<210> SEQ ID NO 26
<211> LENGTH: 202
<212> TYPE: DNA
<213> ORGANISM: Artificial
<220> FEATURE:
<223> OTHER INFORMATION: Chimeric ITR sequence

<400> SEQUENCE: 26
tacaaaacct ccttgcttgg agagtgtggc actctcccc cctgtcgcgt tcgctcgctc     60
gctggctcgt ttggggggc gacggcccaa agggccgtcg tctggcagct ctttgagctg    120 ccacccccc aaacgagcca gcgagcgagc gaacgcgaca gggggagag tgccacact     180 ctccaagcaa ggaggttttg ta                                            202

<210> SEQ ID NO 27
<211> LENGTH: 155
<212> TYPE: DNA
<213> ORGANISM: Artificial
<220> FEATURE:
<223> OTHER INFORMATION: Chimeric ITR sequence

<400> SEQUENCE: 27
aggaacccct agtgctggag ttggccactc ccgcgcgctc gctcgctcac tgagggcggg     60
cgaccaaagg tcgcccgagc ccggcccttt gggccgggcc cctcagtgag cgagcgagcg    120
```
cgcgggagtg gccaactcca gcactagggg ttcct       155

<210> SEQ ID NO 28
<211> LENGTH: 153
<212> TYPE: DNA
<213> ORGANISM: Artificial
<220> FEATURE:
<223> OTHER INFORMATION: Chimeric ITR sequence

<400> SEQUENCE: 28
aggaacccct agtggagttg ccactcctc tgcgcgctcg ctcgctcact gagggcgggc       60
gaccaaaggt cgcccgagcc cggccctttg ggcgggccc ctcagtgagc gagcgagcgc      120
gcagaggagt ggccaactcc actagggggtt cct       153

<210> SEQ ID NO 29
<211> LENGTH: 182
<212> TYPE: DNA
<213> ORGANISM: Artificial
<220> FEATURE:
<223> OTHER INFORMATION: Chimeric ITR sequence

<400> SEQUENCE: 29
aggaacccct agtgatggag ttggccactc cctccacgcg ttctgcgcgc tcgctcgctc       60
actgagggcg ggcgaccaaa ggtcgcccga cgcccggccc tttgggcgg gcggccctca      120 gtgagcgagc gagcgcgcag aacgcgtgga gggagtggcc aactccatca ctaggggttc      180
ct       182

<210> SEQ ID NO 30
<211> LENGTH: 161
<212> TYPE: DNA
<213> ORGANISM: Artificial
<220> FEATURE:
<223> OTHER INFORMATION: Chimeric ITR sequence

<400> SEQUENCE: 30
aggaacccct agtggatgga gttggccact ccctcctctg cgcgctcgct cgctcactga       60
gggcgggcga ccaaaggtcg cccgagcccg gccctttggg ccgggcccct cagtgagcga      120
gcgagcgcgc agaggagtgg ccaactccac tagggggttcc t       161

<210> SEQ ID NO 31
<211> LENGTH: 182
<212> TYPE: DNA
<213> ORGANISM: Artificial
<220> FEATURE:
<223> OTHER INFORMATION: Chimeric ITR sequence

<400> SEQUENCE: 31
aggaacccct agtgatggag ttggccactc cctccacgcg ttctgcgcgc tcgctcgctc       60
actgagggcg ggcgaccaaa ggtcgcccga cgcccggccc tttgggcgg gcggccctca      120 gtgagcgagc gagcgcgcag aacgcgtgga gggagtggcc aactccatca ctaggggttc      180
ct       182

<210> SEQ ID NO 32
<211> LENGTH: 177
<212> TYPE: DNA
<213> ORGANISM: Artificial
<220> FEATURE:
<223> OTHER INFORMATION: Chimeric ITR sequence

```
<400> SEQUENCE: 32
aggaacccct agtcgtgatg gagttggcca ctccctcacg tctgcgcgct cgctcgctca      60
ctgagggcgg gcgaccaaag gtcgcccgag cccggccctt tgggccgggc ccctcagtga     120
gcgagcgagc gcgcagacgt gagggagtgg ccaactccat cacgactagg ggttcct       177

<210> SEQ ID NO 33
<211> LENGTH: 177
<212> TYPE: DNA
<213> ORGANISM: Artificial
<220> FEATURE:
<223> OTHER INFORMATION: Chimeric ITR sequence

<400> SEQUENCE: 33
aggaacccct agtgatggag ttggccactc cctcccccct gtcgcgttcg cgcgctcgct      60
cgctcactga gggcgggcga ccaaaggtcg cccgagcccg gccctttggg ccgggcccct     120
cagtgagcga gcgagcgcgc agagagggag tggccaactc catcactagg ggttcct       177

<210> SEQ ID NO 34
<211> LENGTH: 173
<212> TYPE: DNA
<213> ORGANISM: Artificial
<220> FEATURE:
<223> OTHER INFORMATION: Chimeric ITR sequence

<400> SEQUENCE: 34
tacaaaacct ccttgcttga gagtgtggca ctcttctgct cgctcgctgg ctcgtttggg      60
ggggcgacgg cccaaagggc cgtcgtctgg cagctctttg agctgccacc cccccaaacg     120
agccagcgag cgagcagaga gagtgccaca ctctcaagca aggagttttt gta           173

<210> SEQ ID NO 35
<211> LENGTH: 194
<212> TYPE: DNA
<213> ORGANISM: Artificial
<220> FEATURE:
<223> OTHER INFORMATION: Chimeric ITR sequence

<400> SEQUENCE: 35
tacaaaacct ccttgcttag agtgtggcac tctcccctg tcgcgttcgc tcgctcgctg       60
gctcgtttgg gggggcgacg gcccaaaggg ccgtcgtctg gcagctcttt gagctgccac     120 cccccaaac gagccagcga gcgagcgaac gcgacagggg gagagtgcca cactctaagc     180
aaggaggttt tgta                                                      194

<210> SEQ ID NO 36
<211> LENGTH: 206
<212> TYPE: DNA
<213> ORGANISM: Artificial
<220> FEATURE:
<223> OTHER INFORMATION: Chimeric ITR sequence

<400> SEQUENCE: 36
tacaaaacct ccttgcttga gagagtgtgg cactctctcc ccctgtcgc gttcgctcgc       60 tcgctggctc gtttgggggg gcgacggccc aaagggccgt cgtctggcag ctctttgagc     120
tgccaccccc ccaaacgagc cagcgagcga gcgaacgcga caggggggag agagtgccac     180
actctctcaa gcaaggaggt tttgta                                         206

<210> SEQ ID NO 37
<211> LENGTH: 210
```

<212> TYPE: DNA
<213> ORGANISM: Artificial
<220> FEATURE:
<223> OTHER INFORMATION: Chimeric ITR sequence

<400> SEQUENCE: 37

| | | |
|---|---|---|
| tacaaaacct ccttgcttga gagtgtggca ctctacgcgt cccccctgtc gcgttcgctc | 60 |
| gctcgctggc tcgtttgggg gggcgacggc caaagggcc gtcgtctggc agctctttga | 120 |
| gctgccaccc cccaaacga gccagcgagc gagcgaacgc gacagggggc gcgtggagag | 180 |
| tgccacactc tcaagcaagg aggttttgta | 210 |

<210> SEQ ID NO 38
<211> LENGTH: 227
<212> TYPE: DNA
<213> ORGANISM: Artificial
<220> FEATURE:
<223> OTHER INFORMATION: Chimeric ITR sequence

<400> SEQUENCE: 38

| | | |
|---|---|---|
| tacaaaacct ccttgcttga gagtgtggca ctctcacgcg tagatctaga cccctgtcg | 60 |
| cgttcgctcg ctcgctggct cgtttggggg ggcgacggcc caaagggccg tcgtctggca | 120 |
| gctctttgag ctgccacccc cccaaacgag ccagcgagcg agcgaacgcg acaggggggtc | 180 |
| tagatctacg gtgagagtgc cacactctca agcaaggagg ttttgta | 227 |

<210> SEQ ID NO 39
<211> LENGTH: 198
<212> TYPE: DNA
<213> ORGANISM: Artificial
<220> FEATURE:
<223> OTHER INFORMATION: Chimeric ITR sequence

<400> SEQUENCE: 39

| | | |
|---|---|---|
| tacaaaacct ccttgcttga gagtgtggca ctctccccgc tcgctcgctc gctcgctcgc | 60 |
| tggctcgttt gggggggcga cggcccaaag ggccgtcgtc tggcagctct ttgagctgcc | 120 |
| accccccaa acgagccagc gagcgagcga gcgagcgagc ggggagagtg ccacactctc | 180 |
| aagcaaggag gttttgta | 198 |

<210> SEQ ID NO 40
<211> LENGTH: 198
<212> TYPE: DNA
<213> ORGANISM: Artificial
<220> FEATURE:
<223> OTHER INFORMATION: Chimeric ITR sequence

<400> SEQUENCE: 40

| | | |
|---|---|---|
| tacaaaacct ccttgcttga gagtgtggca ctctccccag ctaagatgca gctcgctcgc | 60 |
| tggctcgttt gggggggcga cggcccaaag ggccgtcgtc tggcagctct ttgagctgcc | 120 |
| accccccaa acgagccagc gagcgagctg catcttagct ggggagagtg ccacactctc | 180 |
| aagcaaggag gttttgta | 198 |

<210> SEQ ID NO 41
<211> LENGTH: 181
<212> TYPE: DNA
<213> ORGANISM: Artificial
<220> FEATURE:
<223> OTHER INFORMATION: Chimeric ITR sequence

<400> SEQUENCE: 41

```
aggaacccct agtgatggag ttggccactc cctctctgct cgctcgcgcg ctcgctcgct    60
cactgagggc gggcgaccaa aggtcgcccg agcccggccc tttgggccgg gcccctcagt   120
gagcgagcga gcgcgcgagc gagcagagag ggagtggcca actccatcac taggggttcc   180
t                                                                   181

<210> SEQ ID NO 42
<211> LENGTH: 198
<212> TYPE: DNA
<213> ORGANISM: Artificial
<220> FEATURE:
<223> OTHER INFORMATION: Chimeric ITR sequence

<400> SEQUENCE: 42
tacaaaacct ccttgcttga gagtgtggca ctctccccccc tgtcgcgttc gctcagctaa    60
gatgcagttt ggggggggcga cggcccaaag ggccgtcgtc tggcagctct ttgagctgcc   120
acccccccaa actgcatctt agctgagcga acgcgacagg ggggagagtg ccacactctc   180
aagcaaggag gttttgta                                                 198

<210> SEQ ID NO 43
<211> LENGTH: 180
<212> TYPE: DNA
<213> ORGANISM: Artificial
<220> FEATURE:
<223> OTHER INFORMATION: Chimeric ITR sequence

<400> SEQUENCE: 43
aggaacccct agtgatggag ttggccactc cctctctgct cgctcgcgcg ctcaagatgc    60
actgagggcg ggcgaccaaa ggtcgcccga gcccggccct ttgggccggg cccctcagtt   120
gcatcttgag cgcgcgagcg agcagagagg gagtggccaa ctccatcact agggggttcct   180

<210> SEQ ID NO 44
<211> LENGTH: 197
<212> TYPE: DNA
<213> ORGANISM: Artificial
<220> FEATURE:
<223> OTHER INFORMATION: Chimeric ITR sequence

<400> SEQUENCE: 44
tacaaaacct ccttgcttga gagtgtggca ctctccccccc tgtcgcgttc gctcgctcgc    60
tggctcgttt ggggggggcgg gcgaccaaag gtcgcccgag cccggccctt tgggccgggc   120
cccccccaaa cgagccagcg agcgagcgaa cgcgacaggg gggagagtgc cacactctca   180
agcaaggagg ttttgta                                                  197

<210> SEQ ID NO 45
<211> LENGTH: 135
<212> TYPE: DNA
<213> ORGANISM: Artificial
<220> FEATURE:
<223> OTHER INFORMATION: Chimeric ITR sequence

<400> SEQUENCE: 45
aggaacccct agtgatggag ttggccactc cctctctgcg cgctcgctcg ctcactgagg    60
cggccctttg ggccgcctca gtgagcgagc gagcgcgcag agagggagtg gccaactcca   120
tcactagggg ttcct                                                    135

<210> SEQ ID NO 46
<211> LENGTH: 153
```

```
<212> TYPE: DNA
<213> ORGANISM: Artificial
<220> FEATURE:
<223> OTHER INFORMATION: Chimeric ITR sequence

<400> SEQUENCE: 46
aggaacccct agtgatggag ttggggtctg cgcgcgctcg ctcgctcact gagggcgggc    60
gaccaaaggt cgcccgagcc cggccctttg gccgggccc ctcagtgagc gagcgagcgc   120
gcgcagaccc caactccatc actaggggtt cct                                153

<210> SEQ ID NO 47
<211> LENGTH: 164
<212> TYPE: DNA
<213> ORGANISM: Artificial
<220> FEATURE:
<223> OTHER INFORMATION: Chimeric ITR sequence

<400> SEQUENCE: 47
aggaacccct agtgatggag ttgggactcc ctctctgcgc gctcgctcgc tcactgaggg    60
cgggcgacca aggtcgccc gagcccggcc ctttgggccg ggcccctcag tgagcgagcg   120
agcgcgcaga gagggagtcc ccaactccat cactagggg tcct                    164

<210> SEQ ID NO 48
<211> LENGTH: 159
<212> TYPE: DNA
<213> ORGANISM: Artificial
<220> FEATURE:
<223> OTHER INFORMATION: Chimeric ITR sequence

<400> SEQUENCE: 48
aggaacccct agtgatggag ttggggttaa ctctgcgcgc tcgctcgctc actgagggcg    60
ggcgaccaaa ggtcgcccga gcccggccct ttgggccggg cccctcagtg agcgagcgag   120
cgcgcagagt taaccccaac tccatcacta ggggttcct                          159

<210> SEQ ID NO 49
<211> LENGTH: 157
<212> TYPE: DNA
<213> ORGANISM: Artificial
<220> FEATURE:
<223> OTHER INFORMATION: Chimeric ITR sequence

<400> SEQUENCE: 49
aggaacccct agtgatggag ttggtccctc tctgcgcgct cgctcgctca ctgagggcgg    60
gcgaccaaag gtcgcccgag cccggccctt tgggccgggc ccctcagtga gcgagcgagc   120
gcgcagagag ggaccaactc catcactagg ggttcct                            157

<210> SEQ ID NO 50
<211> LENGTH: 165
<212> TYPE: DNA
<213> ORGANISM: Artificial
<220> FEATURE:
<223> OTHER INFORMATION: Chimeric ITR sequence

<400> SEQUENCE: 50
aggaacccct agtgatggag ttggggttaa cccctctgcg cgctcgctcg ctcactgagg    60
gcgggcgacc aaaggtcgcc cgagcccggc cctttgggcc gggcccctca gtgagcgagc   120
gagcgcgcag aggggttaac cccaactcca tcactagggg ttcct                   165

<210> SEQ ID NO 51
```

```
<211> LENGTH: 172
<212> TYPE: DNA
<213> ORGANISM: Artificial
<220> FEATURE:
<223> OTHER INFORMATION: Chimeric ITR sequence

<400> SEQUENCE: 51
aggaacccct agtgatggag ttggccactc cctcttcgct cgctcgctgg ctcgtttggg      60
ggggcgacgg cccaaagggc cgtcgtctgg cagctctttg agctgccacc ccccaaacg     120 agccagcgag cgagcgaaga gggagtggcc aactccatca ctaggggttc ct            172

<210> SEQ ID NO 52
<211> LENGTH: 181
<212> TYPE: DNA
<213> ORGANISM: Artificial
<220> FEATURE:
<223> OTHER INFORMATION: Chimeric ITR sequence

<400> SEQUENCE: 52
aggaacccct agtgatggag ttggggttaa ccccactccc tctctgcgcg ctcgctcgct      60
cactgagggc gggcgaccaa aggtcgcccg agccggcccc tttgggccgg cccctcagt     120 gagcgagcga gcgcgcagag agggagtggg gttaaccccca actccatcac tagggggttcc    180 t                                                                      181

<210> SEQ ID NO 53
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 53

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
```

```
            195                 200                 205
Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
610                 615                 620
```

<210> SEQ ID NO 54
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 54

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Glu Ser Tyr Phe His Met His Val Leu Val Glu Thr
                85                  90                  95

Thr Gly Val Lys Ser Met Val Leu Gly Arg Phe Leu Ser Gln Ile Arg
                100                 105                 110

Glu Lys Leu Ile Gln Arg Ile Tyr Arg Gly Ile Glu Pro Thr Leu Pro
            115                 120                 125

Asn Trp Phe Ala Val Thr Lys Thr Arg Asn Gly Ala Gly Gly Gly Asn
        130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
                180                 185                 190

Thr His Val Ser Gln Thr Gln Glu Gln Asn Lys Glu Asn Gln Asn Pro
            195                 200                 205

Asn Ser Asp Ala Pro Val Ile Arg Ser Lys Thr Ser Ala Arg Tyr Met
        210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
                260                 265                 270

Met Ser Leu Thr Lys Thr Ala Pro Asp Tyr Leu Val Gly Gln Gln Pro
            275                 280                 285

Val Glu Asp Ile Ser Ser Asn Arg Ile Tyr Lys Ile Leu Glu Leu Asn
        290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365
```

Val Asp Lys Met Val Ile Trp Trp Glu Glu Gly Lys Met Thr Ala Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
            405                 410                 415

Val Thr Ser Asn Thr Asn Met Cys Ala Val Ile Asp Gly Asn Ser Thr
        420                 425                 430

Thr Phe Glu His Gln Gln Pro Leu Gln Asp Arg Met Phe Lys Phe Glu
    435                 440                 445

Leu Thr Arg Arg Leu Asp His Asp Phe Gly Lys Val Thr Lys Gln Glu
    450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
            485                 490                 495

Ser Asp Ala Asp Ile Ser Glu Pro Lys Arg Val Arg Glu Ser Val Ala
        500                 505                 510

Gln Pro Ser Thr Ser Asp Ala Glu Ala Ser Ile Asn Tyr Ala Asp Arg
    515                 520                 525

Tyr Gln Asn Lys Cys Ser Arg His Val Gly Met Asn Leu Met Leu Phe
530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
            565                 570                 575

Gln Pro Val Ser Val Lys Lys Ala Tyr Gln Lys Leu Cys Tyr Ile
        580                 585                 590

His His Ile Met Gly Lys Val Pro Asp Ala Cys Thr Ala Cys Asp Leu
    595                 600                 605

Val Asn Val Asp Leu Asp Asp Cys Ile Phe Glu Gln
    610                 615                 620

<210> SEQ ID NO 55
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 55

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

```
Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
    130                 135                 140

Lys Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
                180                 185                 190

Thr His Val Ser Gln Thr Gln Glu Gln Asn Lys Glu Asn Gln Asn Pro
                195                 200                 205

Asn Ser Asp Ala Pro Val Ile Arg Ser Lys Thr Ser Ala Arg Tyr Met
210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
                260                 265                 270

Met Ser Leu Thr Lys Thr Ala Pro Asp Tyr Leu Val Gly Gln Gln Pro
        275                 280                 285

Val Glu Asp Ile Ser Ser Asn Arg Ile Tyr Lys Ile Leu Glu Leu Asn
        290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
        340                 345                 350

Tyr Gly Cys Val Asn Trp Thr Asn Glu Asn Phe Pro Phe Asn Asp Cys
        355                 360                 365

Val Asp Lys Met Val Ile Trp Trp Glu Glu Gly Lys Met Thr Ala Lys
        370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
                420                 425                 430

Thr Phe Glu His Gln Gln Pro Leu Gln Asp Arg Met Phe Lys Phe Glu
        435                 440                 445

Leu Thr Arg Arg Leu Asp His Asp Phe Gly Lys Val Thr Lys Gln Glu
        450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
                485                 490                 495

Ser Asp Ala Asp Ile Ser Glu Pro Lys Arg Val Arg Glu Ser Val Ala
                500                 505                 510

Gln Pro Ser Thr Ser Asp Ala Glu Ala Ser Ile Asn Tyr Ala Asp Arg
        515                 520                 525
```

```
Tyr Gln Asn Lys Cys Ser Arg His Val Gly Met Asn Leu Met Leu Phe
        530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Lys Lys Ala Tyr Gln Lys Leu Cys Tyr Ile
                580                 585                 590

His His Ile Met Gly Lys Val Pro Asp Ala Cys Thr Ala Cys Asp Leu
            595                 600                 605

Val Asn Val Asp Leu Asp Asp Cys Ile Phe Glu Gln
610                 615                 620

<210> SEQ ID NO 56
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 56

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Thr Leu Pro
        115                 120                 125

Asn Trp Phe Ala Val Thr Lys Thr Arg Asn Gly Ala Gly Gly Gly Asn
130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
            260                 265                 270
```

```
Met Ser Leu Thr Lys Thr Ala Pro Asp Tyr Leu Val Gly Gln Gln Pro
            275                 280                 285

Val Glu Asp Ile Ser Ser Asn Arg Ile Tyr Lys Ile Leu Glu Leu Asn
290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
                355                 360                 365

Val Asp Lys Met Val Ile Trp Trp Glu Glu Gly Lys Met Thr Ala Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
            420                 425                 430

Thr Phe Glu His Gln Gln Pro Leu Gln Asp Arg Met Phe Lys Phe Glu
            435                 440                 445

Leu Thr Arg Arg Leu Asp His Asp Phe Gly Lys Val Thr Lys Gln Glu
        450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
                485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
            515                 520                 525

Tyr Gln Asn Lys Cys Ser Arg His Val Gly Met Asn Leu Met Leu Phe
530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Lys Lys Ala Tyr Gln Lys Leu Cys Tyr Ile
            580                 585                 590

His His Ile Met Gly Lys Val Pro Asp Ala Cys Thr Ala Cys Asp Leu
            595                 600                 605

Val Asn Val Asp Leu Asp Asp Cys Ile Phe Glu Gln
610                 615                 620

<210> SEQ ID NO 57
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 57

Met Ala Thr Phe Tyr Glu Val Ile Val Arg Val Pro Phe Asp Val Glu
1               5                   10                  15
```

-continued

Glu His Leu Pro Gly Ile Ser Asp Ser Phe Val Asp Trp Thr Gly
            20                  25                  30

Gln Ile Trp Glu Leu Pro Pro Glu Ser Asp Leu Asn Leu Thr Leu Val
    35                  40                      45

Glu Gln Pro Gln Leu Thr Val Ala Asp Arg Ile Arg Arg Val Phe Leu
50                      55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Asn Lys Val
            130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
            195                 200                 205

Asp Ala Pro Val Ile Arg Ser Lys Thr Ser Ala Arg Tyr Met Glu Leu
210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Gln Pro Val Glu
            275                 280                 285

Asp Ile Ser Ser Asn Arg Ile Tyr Lys Ile Leu Glu Leu Asn Gly Tyr
290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
            355                 360                 365

Lys Met Val Ile Trp Trp Glu Glu Gly Lys Met Thr Ala Lys Val Val
            370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
                405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr

```
                435                 440                 445
Arg Arg Leu Asp His Asp Phe Gly Lys Val Thr Lys Gln Glu Val Lys
450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
                500                 505                 510

Ser Thr Ser Asp Ala Glu Ala Ser Ile Asn Tyr Ala Asp Arg Tyr Gln
                515                 520                 525

Asn Lys Cys Ser Arg His Val Gly Met Asn Leu Met Leu Phe Pro Cys
530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
                580                 585                 590

Ile Met Gly Lys Val Pro Asp Ala Cys Thr Ala Cys Asp Leu Val Asn
                595                 600                 605

Val Asp Leu Asp Asp Cys Ile Phe Glu Gln
610                 615

<210> SEQ ID NO 58
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 58

Met Ala Thr Phe Tyr Glu Val Ile Val Arg Val Pro Phe Asp Val Glu
1               5                  10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Phe Gln Gly Ile Glu Pro Gln Ile Asn
            115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
```

```
                180             185             190
Val Ser Gln Thr Gln Glu Gln Asn Lys Glu Asn Gln Asn Pro Asn Ser
            195                 200                 205
Asp Ala Pro Val Ile Arg Ser Lys Thr Ala Arg Tyr Met Glu Leu Val
            210                 215                 220
Gly Trp Leu Val Asp Lys Gly Ile Thr Ser Glu Lys Gln Trp Ile Gln
225                 230                 235                 240
Glu Asp Gln Ala Ser Tyr Ile Ser Phe Asn Ala Ala Ser Asn Ser Arg
                245                 250                 255
Ser Gln Ile Lys Ala Ala Leu Asp Asn Ala Gly Lys Ile Met Ser Leu
                260                 265                 270
Thr Lys Thr Ala Pro Asp Tyr Leu Val Gly Gln Gln Pro Val Glu Asp
                275                 280                 285
Ile Ser Ser Asn Arg Ile Tyr Lys Ile Leu Glu Leu Asn Gly Tyr Asp
                290                 295                 300
Pro Gln Tyr Ala Ala Ser Val Phe Leu Gly Trp Ala Thr Lys Lys Phe
305                 310                 315                 320
Gly Lys Arg Asn Thr Ile Trp Leu Phe Gly Pro Ala Thr Thr Gly Lys
                325                 330                 335
Thr Asn Ile Ala Glu Ala Ile Ala His Thr Val Pro Phe Tyr Gly Cys
                340                 345                 350
Val Asn Trp Thr Asn Glu Asn Phe Pro Phe Asn Asp Cys Val Asp Lys
                355                 360                 365
Met Val Ile Trp Trp Glu Glu Gly Lys Met Thr Ala Lys Val Val Glu
                370                 375                 380
Ser Ala Lys Ala Ile Leu Gly Gly Ser Lys Val Arg Val Asp Gln Lys
385                 390                 395                 400
Cys Lys Ser Ser Ala Gln Ile Asp Pro Thr Pro Val Ile Val Thr Ser
                405                 410                 415
Asn Thr Asn Met Cys Ala Val Ile Asp Gly Asn Ser Thr Thr Phe Glu
                420                 425                 430
His Gln Gln Pro Leu Gln Asp Arg Met Phe Lys Phe Glu Leu Thr Arg
                435                 440                 445
Arg Leu Asp His Asp Phe Gly Lys Val Thr Lys Gln Glu Val Lys Asp
                450                 455                 460
Phe Phe Arg Trp Ala Lys Asp His Val Val Glu Val Glu His Glu Phe
465                 470                 475                 480
Tyr Val Lys Lys Gly Gly Ala Lys Lys Arg Pro Ala Pro Ser Asp Ala
                485                 490                 495
Asp Ile Ser Glu Pro Lys Arg Val Arg Glu Ser Val Ala Gln Pro Ser
                500                 505                 510
Thr Ser Asp Ala Glu Ala Ser Ile Asn Tyr Ala Asp Arg Tyr Gln Asn
                515                 520                 525
Lys Cys Ser Arg His Val Gly Met Asn Leu Met Leu Phe Pro Cys Arg
                530                 535                 540
Gln Cys Glu Arg Met Asn Gln Asn Ser Asn Ile Cys Phe Thr His Gly
545                 550                 555                 560
Gln Lys Asp Cys Leu Glu Cys Phe Pro Val Ser Glu Ser Gln Pro Val
                565                 570                 575
Ser Val Val Lys Lys Ala Tyr Gln Lys Leu Cys Tyr Ile His His Ile
                580                 585                 590
Met Gly Lys Val Pro Asp Ala Cys Thr Ala Cys Asp Leu Val Asn Val
                595                 600                 605
```

```
Asp Leu Asp Asp Cys Ile Phe Glu Gln
    610             615
```

<210> SEQ ID NO 59
<211> LENGTH: 616
<212> TYPE: PRT
<213> ORGANISM: Artificial
<220> FEATURE:
<223> OTHER INFORMATION: Chimeric Rep protein sequence

<400> SEQUENCE: 59

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Asp
        195                 200                 205

Ala Pro Val Ile Arg Ser Lys Thr Ala Arg Tyr Met Glu Leu Val Gly
    210                 215                 220

Trp Leu Val Asp Lys Gly Ile Thr Ser Glu Lys Gln Trp Ile Gln Glu
225                 230                 235                 240

Asp Gln Ala Ser Tyr Ile Ser Phe Asn Ala Ala Ser Asn Ser Arg Ser
                245                 250                 255

Gln Ile Lys Ala Ala Leu Asp Asn Ala Gly Lys Ile Met Ser Leu Thr
            260                 265                 270

Lys Thr Ala Pro Asp Tyr Leu Val Gly Gln Gln Pro Val Glu Asp Ile
        275                 280                 285

Ser Ser Asn Arg Ile Tyr Lys Ile Leu Glu Leu Asn Gly Tyr Asp Pro
    290                 295                 300

Gln Tyr Ala Ala Ser Val Phe Leu Gly Trp Ala Thr Lys Lys Phe Gly
305                 310                 315                 320

Lys Arg Asn Thr Ile Trp Leu Phe Gly Pro Ala Thr Thr Gly Lys Thr
                325                 330                 335

Asn Ile Ala Glu Ala Ile Ala His Thr Val Pro Phe Tyr Gly Cys Val
            340                 345                 350
```

```
Asn Trp Thr Asn Glu Asn Phe Pro Phe Asn Asp Cys Val Asp Lys Met
            355                 360                 365
Val Ile Trp Trp Glu Glu Gly Lys Met Thr Ala Lys Val Val Glu Ser
370                 375                 380
Ala Lys Ala Ile Leu Gly Gly Ser Lys Val Arg Val Asp Gln Lys Cys
385                 390                 395                 400
Lys Ser Ser Ala Gln Ile Asp Pro Thr Pro Val Ile Val Thr Ser Asn
            405                 410                 415
Thr Asn Met Cys Ala Val Ile Asp Gly Asn Ser Thr Thr Phe Glu His
            420                 425                 430
Gln Gln Pro Leu Gln Asp Arg Met Phe Lys Phe Glu Leu Thr Arg Arg
            435                 440                 445
Leu Asp His Asp Phe Gly Lys Val Thr Lys Gln Glu Val Lys Asp Phe
            450                 455                 460
Phe Arg Trp Ala Lys Asp His Val Val Glu Val Glu His Glu Phe Tyr
465                 470                 475                 480
Val Lys Lys Gly Gly Ala Lys Lys Arg Pro Ala Pro Ser Asp Ala Asp
                485                 490                 495
Ile Ser Glu Pro Lys Arg Val Arg Glu Ser Val Ala Gln Pro Ser Thr
            500                 505                 510
Ser Asp Ala Glu Ala Ser Ile Asn Tyr Ala Asp Arg Tyr Gln Asn Lys
            515                 520                 525
Cys Ser Arg His Val Gly Met Asn Leu Met Leu Phe Pro Cys Arg Gln
            530                 535                 540
Cys Glu Arg Met Asn Gln Asn Ser Asn Ile Cys Phe Thr His Gly Gln
545                 550                 555                 560
Lys Asp Cys Leu Glu Cys Phe Pro Val Ser Glu Ser Gln Pro Val Ser
                565                 570                 575
Val Val Lys Lys Ala Tyr Gln Lys Leu Cys Tyr Ile His His Ile Met
            580                 585                 590
Gly Lys Val Pro Asp Ala Cys Thr Ala Cys Asp Leu Val Asn Val Asp
            595                 600                 605
Leu Asp Asp Cys Ile Phe Glu Gln
            610                 615

<210> SEQ ID NO 60
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 60

Met Ala Thr Phe Tyr Glu Val Ile Val Arg Val Pro Phe Asp Val Glu
1               5                   10                  15
Glu His Leu Pro Gly Ile Ser Asp Ser Phe Val Asp Trp Val Thr Gly
            20                  25                  30
Gln Ile Trp Glu Leu Pro Pro Glu Ser Asp Leu Asn Leu Thr Leu Val
            35                  40                  45
Glu Gln Pro Gln Leu Thr Val Ala Asp Arg Ile Arg Arg Val Phe Leu
            50                  55                  60
Tyr Glu Trp Asn Lys Phe Ser Lys Gln Glu Ser Lys Phe Phe Val Gln
65                  70                  75                  80
Phe Glu Lys Gly Ser Glu Tyr Phe His Leu His Thr Leu Val Glu Thr
                85                  90                  95
```

```
Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
            165                 170                 175

Leu Asn Leu Glu Glu Arg Lys Arg Arg Lys Arg Leu Val Ala Gln His
            180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510
```

```
Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
595                 600                 605

Leu Val Asn Val Asp Leu Asp Asp Cys Ile Phe Glu Gln
610                 615                 620

<210> SEQ ID NO 61
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 61

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Glu Gln Asn Lys Glu Asn Gln Asn Pro Asn Ser
        195                 200                 205

Asp Ala Pro Val Ile Arg Ser Lys Ser Ala Arg Tyr Met Glu Leu Val
210                 215                 220

Gly Trp Leu Val Asp Lys Gly Ile Thr Ser Glu Lys Gln Trp Ile Gln
225                 230                 235                 240

Glu Asp Gln Ala Ser Tyr Ile Ser Phe Asn Ala Ala Ser Asn Ser Arg
                245                 250                 255
```

```
Ser Gln Ile Lys Ala Ala Leu Asp Asn Ala Gly Lys Ile Met Ser Leu
            260                 265                 270

Thr Lys Thr Ala Pro Asp Tyr Leu Val Gly Gln Pro Val Glu Asp
        275                 280                 285

Ile Ser Ser Asn Arg Ile Tyr Lys Ile Leu Glu Leu Asn Gly Tyr Asp
            290                 295                 300

Pro Gln Tyr Ala Ala Ser Val Phe Leu Gly Trp Ala Thr Lys Lys Phe
305                 310                 315                 320

Gly Lys Arg Asn Thr Ile Trp Leu Phe Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Val Ile Trp Trp Glu Glu Gly Lys Met Thr Ala Lys Val Val Glu
            370                 375                 380

Ser Ala Lys Ala Ile Leu Gly Gly Ser Lys Val Arg Val Asp Gln Lys
385                 390                 395                 400

Cys Lys Ser Ser Ala Gln Ile Asp Pro Thr Pro Val Ile Val Thr Ser
                405                 410                 415

Asn Thr Asn Met Cys Ala Val Ile Asp Gly Asn Ser Thr Thr Phe Glu
            420                 425                 430

His Gln Gln Pro Leu Gln Asp Arg Met Phe Lys Phe Glu Leu Thr Arg
            435                 440                 445

Arg Leu Asp His Asp Phe Gly Lys Val Thr Lys Gln Glu Val Lys Asp
        450                 455                 460

Phe Phe Arg Trp Ala Lys Asp His Val Val Glu Val Glu His Glu Phe
465                 470                 475                 480

Tyr Val Lys Lys Gly Gly Ala Lys Lys Arg Pro Ala Pro Ser Asp Ala
                485                 490                 495

Asp Ile Ser Glu Pro Lys Arg Val Arg Glu Ser Val Ala Gln Pro Ser
            500                 505                 510

Thr Ser Asp Ala Glu Ala Ser Ile Asn Tyr Ala Asp Arg Tyr Gln Asn
        515                 520                 525

Lys Cys Ser Arg His Val Gly Met Asn Leu Met Leu Phe Pro Cys Arg
530                 535                 540

Gln Cys Glu Arg Met Asn Gln Asn Ser Asn Ile Cys Phe Thr His Gly
545                 550                 555                 560

Gln Lys Asp Cys Leu Glu Cys Phe Pro Val Ser Glu Ser Gln Pro Val
                565                 570                 575

Ser Val Val Lys Lys Ala Tyr Gln Lys Leu Cys Tyr Ile His His Ile
            580                 585                 590

Met Gly Lys Val Pro Asp Ala Cys Thr Ala Cys Asp Leu Val Asn Val
        595                 600                 605

Asp Leu Asp Asp Cys Ile Phe Glu Gln
610                 615

<210> SEQ ID NO 62
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 62
```

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Asp Phe Leu
50                  55                  60

Thr Glu Trp Arg Arg Val Ser Lys Gln Glu Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
    195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
    275                 280                 285

Ile Ser Lys Asn Arg Ile Trp Gln Ile Phe Glu Met Asn Gly Tyr Asp
    290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
    355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Val Asp Gly Asn Ser Thr Thr Phe Glu
```

```
                   420                 425                 430
His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
        450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
        595                 600                 605

Glu Gln
    610

<210> SEQ ID NO 63
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 63

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Ser Glu Tyr Phe His Leu His Thr Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Phe Gln Gly Ile Glu Pro Gln Ile
        115                 120                 125

Asn Asp Trp Val Ala Ile Thr Lys Val Lys Gly Gly Ala Asn Lys
            130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
```

```
                165                 170                 175
Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
    210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Leu Ile Trp Trp Glu Glu Gly Lys Met Thr Asn Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Val Asp Gly Asn Ser Thr Thr Phe
            420                 425                 430

Glu His Gln Gln Pro Leu Glu Asp Arg Met Phe Lys Phe Glu Leu Thr
        435                 440                 445

Lys Arg Leu Pro Pro Asp Phe Gly Lys Ile Thr Lys Gln Glu Val Lys
    450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
        515                 520                 525

Asp Val Thr Val Asp Pro Ala Pro Leu Arg Pro Leu Asn Trp Asn Ser
    530                 535                 540

Arg Tyr Asp Cys Lys Cys Asp Tyr His Ala Gln Phe Asn Ile Ser
545                 550                 555                 560

Asn Lys Cys Asp Glu Cys Glu Tyr Leu Asn Arg Gly Lys Asn Gly Cys
                565                 570                 575

Ile Cys His Asn Val Thr His Cys Gln Ile Cys His Gly Ile Pro Pro
            580                 585                 590
```

Trp Glu Lys Glu Asn Leu Ser Asp Phe Gly Asp Phe Asp Ala Asn
        595                 600                 605
Lys Glu Gln
    610

<210> SEQ ID NO 64
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 64

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
    210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

-continued

Lys Thr Asn Ile Ala Glu Ala Ile Ala His Thr Val Pro Phe Tyr Gly
                340                 345                 350

Cys Val Asn Trp Thr Asn Glu Asn Phe Pro Phe Asn Asp Cys Val Asp
            355                 360                 365

Lys Met Leu Ile Trp Trp Glu Glu Gly Lys Met Thr Asn Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Val Asp Gly Asn Ser Thr Thr Phe
            420                 425                 430

Glu His Gln Gln Pro Leu Glu Asp Arg Met Phe Lys Phe Glu Leu Thr
    435                 440                 445

Lys Arg Leu Pro Pro Asp Phe Gly Lys Ile Thr Lys Gln Glu Val Lys
450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
    515                 520                 525

Asp Val Thr Val Asp Pro Ala Pro Leu Arg Pro Leu Asn Trp Asn Ser
530                 535                 540

Arg Tyr Asp Cys Lys Cys Asp Tyr His Ala Gln Phe Asp Asn Ile Ser
545                 550                 555                 560

Asn Lys Cys Asp Glu Cys Glu Tyr Leu Asn Arg Gly Lys Asn Gly Cys
                565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Ala Asn
    595                 600                 605

Lys Glu Gln
    610

<210> SEQ ID NO 65
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 65

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                    85                  90                  95

Thr Thr Gly Val Lys Ser Met Val Leu Gly Arg Phe Leu Ser Gln Ile
                100                 105                 110

Arg Glu Lys Leu Val Lys Val Val Phe Gln Gly Ile Glu Pro Gln Ile
                115                 120                 125

Asn Asp Trp Val Ala Ile Thr Lys Val Lys Lys Gly Gly Ala Asn Lys
            130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
                180                 185                 190

Glu Ser Ser Gln Arg Ser Gln Glu Ala Ala Ser Gln Arg Glu Phe Ser
            195                 200                 205

Ala Asp Pro Val Ile Lys Ser Lys Thr Ser Gln Lys Tyr Met Ala Leu
            210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
                260                 265                 270

Leu Thr Lys Ser Ala Val Asp Tyr Leu Val Gly Ser Ser Val Pro Glu
                275                 280                 285

Asp Ile Ser Lys Asn Arg Ile Trp Gln Ile Phe Glu Met Asn Gly Tyr
            290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
                340                 345                 350

Cys Val Asn Trp Thr Asn Glu Asn Phe Pro Phe Asn Asp Cys Val Asp
                355                 360                 365

Lys Met Leu Ile Trp Trp Glu Glu Gly Lys Met Thr Asn Lys Val Val
                370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Asp Gly Asn Ser Thr Thr Phe
                420                 425                 430

Glu His Gln Gln Pro Leu Glu Asp Arg Met Phe Lys Phe Glu Leu Thr
                435                 440                 445

Lys Arg Leu Pro Pro Asp Phe Gly Lys Ile Thr Lys Gln Glu Val Lys
                450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

```
Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
            515                 520                 525

Asp Val Thr Val Asp Pro Ala Pro Leu Arg Pro Leu Asn Trp Asn Ser
            530                 535                 540

Arg Tyr Asp Cys Lys Cys Asp Tyr His Ala Gln Phe Asp Asn Ile Ser
545                 550                 555                 560

Asn Lys Cys Asp Glu Cys Glu Tyr Leu Asn Arg Gly Lys Asn Gly Cys
            565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Ala Asn
            595                 600                 605

Lys Glu Gln
    610

<210> SEQ ID NO 66
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 66

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
            50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
            85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Gln Ile
            115                 120                 125

Asn Asp Trp Val Ala Ile Thr Lys Val Lys Lys Gly Gly Ala Asn Lys
            130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
            165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
            195                 200                 205

Ala Asp Pro Val Ile Lys Ser Lys Thr Ser Gln Lys Tyr Met Ala Leu
            210                 215                 220

Val Asn Trp Leu Val Glu His Gly Ile Thr Ser Glu Lys Gln Trp Ile
225                 230                 235                 240
```

```
Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Leu Ile Trp Trp Glu Glu Gly Lys Met Thr Asn Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Val Asp Gly Asn Ser Thr Thr Phe
            420                 425                 430

Glu His Gln Gln Pro Leu Glu Asp Arg Met Phe Lys Phe Glu Leu Thr
        435                 440                 445

Lys Arg Leu Pro Pro Asp Phe Gly Lys Ile Thr Lys Gln Glu Val Lys
    450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
        515                 520                 525

Asp Val Thr Val Asp Pro Ala Pro Leu Arg Pro Leu Asn Trp Asn Ser
    530                 535                 540

Arg Tyr Asp Cys Lys Cys Asp Tyr His Ala Gln Phe Asp Asn Ile Ser
545                 550                 555                 560

Asn Lys Cys Asp Glu Cys Glu Tyr Leu Asn Arg Gly Lys Asn Gly Cys
                565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Asp Ala Asn
        595                 600                 605

Lys Glu Gln
    610

<210> SEQ ID NO 67
<211> LENGTH: 613
<212> TYPE: PRT
<213> ORGANISM: Artificial
<220> FEATURE:
<223> OTHER INFORMATION: Chimeric Rep protein sequence
```

<400> SEQUENCE: 67

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65              70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Ala
        130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Leu Val Ala Gln Phe
            180                 185                 190

Leu Ala Glu Ser Ser Gln Arg Ser Gln Glu Ala Ala Ser Gln Arg Glu
        195                 200                 205

Phe Ser Ala Asp Pro Val Ile Lys Ser Lys Thr Ser Gln Lys Tyr Met
210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
        275                 280                 285

Pro Glu Asp Ile Ser Lys Asn Arg Ile Trp Gln Ile Phe Glu Met Asn
    290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Leu Ile Trp Trp Glu Glu Gly Lys Met Thr Asn Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
```

```
                405                 410                 415
Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
            435                 440                 445

Leu Thr Lys Arg Leu Pro Pro Asp Phe Gly Lys Ile Thr Lys Gln Glu
            450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
            515                 520                 525

Ser Ser Asp Val Thr Val Asp Pro Ala Pro Leu Arg Pro Leu Asn Trp
530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
                565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
            595                 600                 605

Ala Asn Lys Glu Gln
            610

<210> SEQ ID NO 68
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 68

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Ser Gly Tyr Ile Pro Ala Tyr Leu Leu Pro Lys
```

```
                145                 150                 155                 160
        Val Gln Pro Glu Leu Gln Trp Ala Trp Thr Asn Leu Asp Tyr Lys
                        165                 170                 175

Leu Ala Ala Leu Asn Leu Glu Glu Arg Lys Arg Leu Val Ala Gln Phe
                            180                 185                 190

Leu Ala Glu Ser Ser Gln Arg Ser Gln Glu Ala Ala Ser Gln Arg Glu
                        195                 200                 205

Phe Ser Ala Asp Pro Val Ile Lys Ser Lys Thr Ser Gln Lys Tyr Met
            210                 215                 220

Ala Leu Val Asn Trp Leu Val Glu His Gly Ile Thr Ser Glu Lys Gln
        225                 230                 235                 240

Trp Ile Gln Glu Asn Gln Glu Ser Tyr Leu Ser Phe Asn Ser Thr Gly
                        245                 250                 255

Asn Ser Arg Ser Gln Ile Lys Ala Ala Leu Asp Asn Ala Thr Lys Ile
                        260                 265                 270

Met Ser Leu Thr Lys Ser Ala Val Asp Tyr Leu Val Gly Ser Ser Val
                        275                 280                 285

Pro Glu Asp Ile Ser Lys Asn Arg Ile Trp Gln Ile Phe Glu Met Asn
                        290                 295                 300

Gly Tyr Asp Pro Ala Tyr Ala Gly Ser Ile Leu Tyr Gly Trp Cys Gln
        305                 310                 315                 320

Arg Ser Phe Asn Lys Arg Asn Thr Val Trp Leu Tyr Gly Pro Ala Thr
                        325                 330                 335

Thr Gly Lys Thr Asn Ile Ala Glu Ala Ile Ala His Thr Val Pro Phe
                        340                 345                 350

Tyr Gly Cys Val Asn Trp Thr Asn Glu Asn Phe Pro Phe Asn Asp Cys
                        355                 360                 365

Val Asp Lys Met Leu Ile Trp Trp Glu Glu Gly Lys Met Thr Asn Lys
                        370                 375                 380

Val Val Glu Ser Ala Lys Ala Ile Leu Gly Gly Ser Lys Val Arg Val
        385                 390                 395                 400

Asp Gln Lys Cys Lys Ser Ser Val Gln Ile Asp Ser Thr Pro Val Ile
                        405                 410                 415

Val Thr Ser Asn Thr Asn Met Cys Val Val Asp Gly Asn Ser Thr
                        420                 425                 430

Thr Phe Glu His Gln Gln Pro Leu Glu Asp Arg Met Phe Lys Phe Glu
                        435                 440                 445

Leu Thr Lys Arg Leu Pro Pro Asp Phe Gly Lys Ile Thr Lys Gln Glu
                        450                 455                 460

Val Lys Asp Phe Phe Ala Trp Ala Lys Val Asn Gln Val Pro Val Thr
        465                 470                 475                 480

His Glu Phe Lys Val Pro Arg Glu Leu Ala Gly Thr Lys Gly Ala Glu
                        485                 490                 495

Lys Ser Leu Lys Arg Pro Leu Gly Asp Val Thr Asn Thr Ser Tyr Lys
                        500                 505                 510

Ser Leu Glu Lys Arg Ala Arg Leu Ser Phe Val Pro Glu Thr Pro Arg
                        515                 520                 525

Ser Ser Asp Val Thr Val Asp Pro Ala Pro Leu Arg Pro Leu Asn Trp
                        530                 535                 540

Asn Ser Arg Tyr Asp Cys Lys Cys Asp Tyr His Ala Gln Phe Asp Asn
        545                 550                 555                 560

Ile Ser Asn Lys Cys Asp Glu Cys Glu Tyr Leu Asn Arg Gly Lys Asn
                        565                 570                 575
```

-continued

```
Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
        595                 600                 605

Ala Asn Lys Glu Gln
        610

<210> SEQ ID NO 69
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 69

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Leu Val Ala Gln Phe
            180                 185                 190

Leu Ala Glu Ser Ser Gln Arg Ser Gln Glu Ala Ala Ser Gln Arg Glu
        195                 200                 205

Phe Ser Ala Asp Pro Val Ile Lys Ser Lys Thr Ser Gln Lys Tyr Met
    210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
        275                 280                 285

Pro Glu Asp Ile Ser Lys Asn Arg Ile Trp Gln Ile Phe Glu Met Asn
    290                 295                 300

Gly Tyr Asp Pro Ala Tyr Ala Gly Ser Ile Leu Tyr Gly Trp Cys Gln
305                 310                 315                 320
```

```
Arg Ser Phe Asn Lys Arg Asn Thr Val Trp Leu Tyr Gly Pro Ala Thr
            325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
            355                 360                 365

Val Asp Lys Met Leu Ile Trp Trp Glu Glu Gly Lys Met Thr Asn Lys
            370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
            405                 410                 415

Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
            435                 440                 445

Leu Thr Lys Arg Leu Pro Pro Asp Phe Gly Lys Ile Thr Lys Gln Glu
            450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
            485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
            515                 520                 525

Ser Ser Asp Val Thr Val Asp Pro Ala Pro Leu Arg Pro Leu Asn Trp
530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
            565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
            595                 600                 605

Ala Asn Lys Glu Gln
            610

<210> SEQ ID NO 70
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 70

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
50                  55                  60
```

```
Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
            165                 170                 175

Ser Ala Cys Leu Asn Leu Thr Glu Arg Lys Arg Leu Val Ala Gln Phe
            180                 185                 190

Leu Ala Glu Ser Ser Gln Arg Ser Gln Glu Ala Ala Ser Gln Arg Glu
            195                 200                 205

Phe Ser Ala Asp Pro Val Ile Lys Ser Lys Thr Ser Gln Lys Tyr Met
            210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
            245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
            275                 280                 285

Pro Glu Asp Ile Ser Lys Asn Arg Ile Trp Gln Ile Phe Glu Met Asn
290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
            325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
            355                 360                 365

Val Asp Lys Met Leu Ile Trp Trp Glu Glu Gly Lys Met Thr Asn Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
            405                 410                 415

Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
            435                 440                 445

Leu Thr Lys Arg Leu Pro Pro Asp Phe Gly Lys Ile Thr Lys Gln Glu
            450                 455                 460

Val Lys Asp Phe Phe Ala Trp Ala Lys Val Asn Gln Val Pro Val Thr
465                 470                 475                 480
```

```
His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
        515                 520                 525

Ser Ser Asp Val Thr Val Asp Pro Ala Pro Leu Arg Pro Leu Asn Trp
    530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
                565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
        595                 600                 605

Ala Asn Lys Glu Gln
    610

<210> SEQ ID NO 71
<211> LENGTH: 614
<212> TYPE: PRT
<213> ORGANISM: Artificial
<220> FEATURE:
<223> OTHER INFORMATION: Chimeric Rep protein sequence

<400> SEQUENCE: 71

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Lys Ser Lys Thr Ser Gln Lys Tyr
    210                 215                 220
```

Met Ala Leu Val Asn Trp Leu Val Glu His Gly Ile Thr Ser Glu Lys
225                 230                 235                 240

Gln Trp Ile Gln Glu Asn Gln Glu Ser Tyr Leu Ser Phe Asn Ser Thr
                245                 250                 255

Gly Asn Ser Arg Ser Gln Ile Lys Ala Ala Leu Asp Asn Ala Thr Lys
            260                 265                 270

Ile Met Ser Leu Thr Lys Ser Ala Val Asp Tyr Leu Val Gly Ser Ser
        275                 280                 285

Val Pro Glu Asp Ile Ser Lys Asn Arg Ile Trp Gln Ile Phe Glu Met
    290                 295                 300

Asn Gly Tyr Asp Pro Ala Tyr Ala Gly Ser Ile Leu Tyr Gly Trp Cys
305                 310                 315                 320

Gln Arg Ser Phe Asn Lys Arg Asn Thr Val Trp Leu Tyr Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Leu Ile Trp Trp Glu Glu Gly Lys Met Thr Asn
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Val Gln Ile Asp Ser Thr Pro Val
                405                 410                 415

Ile Val Thr Ser Asn Thr Asn Met Cys Val Val Asp Gly Asn Ser
            420                 425                 430

Thr Thr Phe Glu His Gln Gln Pro Leu Glu Asp Arg Met Phe Lys Phe
        435                 440                 445

Glu Leu Thr Lys Arg Leu Pro Pro Asp Phe Gly Lys Ile Thr Lys Gln
    450                 455                 460

Glu Val Lys Asp Phe Phe Ala Trp Ala Lys Val Asn Gln Val Pro Val
465                 470                 475                 480

Thr His Glu Phe Lys Val Pro Arg Glu Leu Ala Gly Thr Lys Gly Ala
                485                 490                 495

Glu Lys Ser Leu Lys Arg Pro Leu Gly Asp Val Thr Asn Thr Ser Tyr
            500                 505                 510

Lys Ser Leu Glu Lys Arg Ala Arg Leu Ser Phe Val Pro Glu Thr Pro
        515                 520                 525

Arg Ser Ser Asp Val Thr Val Asp Pro Ala Pro Leu Arg Pro Leu Asn
530                 535                 540

Trp Asn Ser Arg Tyr Asp Cys Lys Cys Asp Tyr His Ala Gln Phe Asp
545                 550                 555                 560

Asn Ile Ser Asn Lys Cys Asp Glu Cys Glu Tyr Leu Asn Arg Gly Lys
                565                 570                 575

Asn Gly Cys Ile Cys His Asn Val Thr His Cys Gln Ile Cys His Gly
            580                 585                 590

Ile Pro Pro Trp Glu Lys Glu Asn Leu Ser Asp Phe Gly Asp Phe Asp
        595                 600                 605

Asp Ala Asn Lys Glu Gln
    610

<210> SEQ ID NO 72
<211> LENGTH: 612
<212> TYPE: PRT

<213> ORGANISM: Artificial
<220> FEATURE:
<223> OTHER INFORMATION: Chimeric Rep protein sequence

<400> SEQUENCE: 72

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Ser Asp Leu Asn Leu Thr Leu Val
            35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Glu Lys Leu Ile Gln Arg Ile Tyr Arg Gly Ile Glu Pro Thr Leu Pro
            115                 120                 125

Asn Trp Phe Ala Val Thr Lys Thr Arg Asn Gly Ala Gly Gly Gly Asn
    130                 135                 140

Lys Val Val Asp Ser Gly Tyr Ile Pro Ala Tyr Leu Leu Pro Lys Val
145                 150                 155                 160

Gln Pro Glu Leu Gln Trp Ala Trp Thr Asn Leu Asp Glu Tyr Lys Leu
                165                 170                 175

Ala Ala Leu Asn Leu Glu Glu Arg Lys Arg Leu Val Ala Gln Phe Leu
                180                 185                 190

Ala Glu Ser Ser Gln Arg Ser Gln Glu Ala Ala Ser Gln Arg Glu Phe
            195                 200                 205

Ser Ala Asp Pro Val Ile Lys Ser Lys Thr Ser Gln Lys Tyr Met Ala
    210                 215                 220

Leu Val Asn Trp Leu Val Glu His Gly Ile Thr Ser Glu Lys Gln Trp
225                 230                 235                 240

Ile Gln Glu Asn Gln Glu Ser Tyr Leu Ser Phe Asn Ser Thr Gly Asn
                245                 250                 255

Ser Arg Ser Gln Ile Lys Ala Ala Leu Asp Asn Ala Thr Lys Ile Met
                260                 265                 270

Ser Leu Thr Lys Ser Ala Val Asp Tyr Leu Val Gly Ser Ser Val Pro
            275                 280                 285

Glu Asp Ile Ser Lys Asn Arg Ile Trp Gln Ile Phe Glu Met Asn Gly
    290                 295                 300

Tyr Asp Pro Ala Tyr Ala Gly Ser Ile Leu Tyr Gly Trp Cys Gln Arg
305                 310                 315                 320

Ser Phe Asn Lys Arg Asn Thr Val Trp Leu Tyr Gly Pro Ala Thr Thr
                325                 330                 335

Gly Lys Thr Asn Ile Ala Glu Ala Ile Ala His Thr Val Pro Phe Tyr
                340                 345                 350

Gly Cys Val Asn Trp Thr Asn Glu Asn Phe Pro Phe Asn Asp Cys Val
            355                 360                 365

Asp Lys Met Leu Ile Trp Trp Glu Glu Gly Lys Met Thr Asn Lys Val
    370                 375                 380

Val Glu Ser Ala Lys Ala Ile Leu Gly Gly Ser Lys Val Arg Val Asp
```

```
                385                 390                 395                 400
Gln Lys Cys Lys Ser Ser Val Gln Ile Asp Ser Thr Pro Val Ile Val
                405                 410                 415

Thr Ser Asn Thr Asn Met Cys Val Val Val Asp Gly Asn Ser Thr Thr
            420                 425                 430

Phe Glu His Gln Gln Pro Leu Glu Asp Arg Met Phe Lys Phe Glu Leu
            435                 440                 445

Thr Lys Arg Leu Pro Pro Asp Phe Gly Lys Ile Thr Lys Gln Glu Val
        450                 455                 460

Lys Asp Phe Phe Ala Trp Ala Lys Val Asn Gln Val Pro Val Thr His
465                 470                 475                 480

Glu Phe Lys Val Pro Arg Glu Leu Ala Gly Thr Lys Gly Ala Glu Lys
                485                 490                 495

Ser Leu Lys Arg Pro Leu Gly Asp Val Thr Asn Thr Ser Tyr Lys Ser
            500                 505                 510

Leu Glu Lys Arg Ala Arg Leu Ser Phe Val Pro Glu Thr Pro Arg Ser
        515                 520                 525

Ser Asp Val Thr Val Asp Pro Ala Pro Leu Arg Pro Leu Asn Trp Asn
    530                 535                 540

Ser Arg Tyr Asp Cys Lys Cys Asp Tyr His Ala Gln Phe Asp Asn Ile
545                 550                 555                 560

Ser Asn Lys Cys Asp Glu Cys Glu Tyr Leu Asn Arg Gly Lys Asn Gly
                565                 570                 575

Cys Ile Cys His Asn Val Thr His Cys Gln Ile Cys His Gly Ile Pro
            580                 585                 590

Pro Trp Glu Lys Glu Asn Leu Ser Asp Phe Gly Asp Phe Asp Asp Ala
        595                 600                 605

Asn Lys Glu Gln
    610

<210> SEQ ID NO 73
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 73

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
```

```
            130                 135                 140
Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln Phe Leu Ala Glu
                180                 185                 190

Ser Ser Gln Arg Ser Gln Glu Ala Ala Ser Gln Arg Glu Phe Ser Ala
                195                 200                 205

Asp Pro Val Ile Lys Ser Lys Thr Ser Gln Lys Tyr Met Ala Leu Val
                210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
                260                 265                 270

Thr Lys Ser Ala Val Asp Tyr Leu Val Gly Ser Ser Val Pro Glu Asp
                275                 280                 285

Ile Ser Lys Asn Arg Ile Trp Gln Ile Phe Glu Met Asn Gly Tyr Asp
                290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
                340                 345                 350

Val Asn Trp Thr Asn Glu Asn Phe Pro Phe Asn Asp Cys Val Asp Lys
                355                 360                 365

Met Leu Ile Trp Trp Glu Glu Gly Lys Met Thr Asn Lys Val Val Glu
370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
                420                 425                 430

His Gln Gln Pro Leu Glu Asp Arg Met Phe Lys Phe Glu Leu Thr Lys
                435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
                500                 505                 510

Lys Arg Ala Arg Leu Ser Phe Val Pro Glu Thr Pro Arg Ser Ser Asp
                515                 520                 525

Val Thr Val Asp Pro Ala Pro Leu Arg Pro Leu Asn Trp Asn Ser Arg
                530                 535                 540

Tyr Asp Cys Lys Cys Asp Tyr His Ala Gln Phe Asp Asn Ile Ser Asn
545                 550                 555                 560
```

```
Lys Cys Asp Glu Cys Glu Tyr Leu Asn Arg Gly Lys Asn Gly Cys Ile
            565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
            595                 600                 605

Glu Gln
    610

<210> SEQ ID NO 74
<211> LENGTH: 612
<212> TYPE: PRT
<213> ORGANISM: Artificial
<220> FEATURE:
<223> OTHER INFORMATION: Chimeric Rep protein sequence

<400> SEQUENCE: 74

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln Phe Leu
            180                 185                 190

Ala Glu Ser Ser Gln Arg Ser Gln Glu Ala Ala Ser Gln Arg Glu Phe
        195                 200                 205

Ser Ala Asp Pro Val Ile Lys Ser Lys Thr Ser Gln Lys Tyr Met Ala
    210                 215                 220

Leu Val Asn Trp Leu Val Glu His Gly Ile Thr Ser Glu Lys Gln Trp
225                 230                 235                 240

Ile Gln Glu Asn Gln Glu Ser Tyr Leu Ser Phe Asn Ser Thr Gly Asn
                245                 250                 255

Ser Arg Ser Gln Ile Lys Ala Ala Leu Asp Asn Ala Thr Lys Ile Met
            260                 265                 270

Ser Leu Thr Lys Ser Ala Val Asp Tyr Leu Val Gly Ser Ser Val Pro
        275                 280                 285

Glu Asp Ile Ser Lys Asn Arg Ile Trp Gln Ile Phe Glu Met Asn Gly
    290                 295                 300
```

Tyr Asp Pro Ala Tyr Ala Gly Ser Ile Leu Tyr Gly Trp Cys Gln Arg
305                 310                 315                 320

Ser Phe Asn Lys Arg Asn Thr Val Trp Leu Tyr Gly Pro Ala Thr Thr
            325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
            355                 360                 365

Asp Lys Met Leu Ile Trp Trp Glu Gly Lys Met Thr Asn Lys Val
            370                 375                 380

Val Glu Ser Ala Lys Ala Ile Leu Gly Gly Ser Lys Val Arg Val Asp
385                 390                 395                 400

Gln Lys Cys Lys Ser Ser Val Gln Ile Asp Ser Thr Pro Val Ile Val
            405                 410                 415

Thr Ser Asn Thr Asn Met Cys Val Val Val Asp Gly Asn Ser Thr Thr
            420                 425                 430

Phe Glu His Gln Gln Pro Leu Glu Asp Arg Met Phe Lys Phe Glu Leu
            435                 440                 445

Thr Lys Arg Leu Pro Pro Asp Phe Gly Lys Ile Thr Lys Gln Glu Val
            450                 455                 460

Lys Asp Phe Phe Ala Trp Ala Lys Val Asn Gln Val Pro Val Thr His
465                 470                 475                 480

Glu Phe Lys Val Pro Arg Glu Leu Ala Gly Thr Lys Gly Ala Glu Lys
            485                 490                 495

Ser Leu Lys Arg Pro Leu Gly Asp Val Thr Asn Thr Ser Tyr Lys Ser
            500                 505                 510

Leu Glu Lys Arg Ala Arg Leu Ser Phe Val Pro Glu Thr Pro Arg Ser
            515                 520                 525

Ser Asp Val Thr Val Asp Pro Ala Pro Leu Arg Pro Leu Asn Trp Asn
530                 535                 540

Ser Arg Tyr Asp Cys Lys Cys Asp Tyr His Ala Gln Phe Asp Asn Ile
545                 550                 555                 560

Ser Asn Lys Cys Asp Glu Cys Glu Tyr Leu Asn Arg Gly Lys Asn Gly
            565                 570                 575

Cys Ile Cys His Asn Val Thr His Cys Gln Ile Cys His Gly Ile Pro
            580                 585                 590

Pro Trp Glu Lys Glu Asn Leu Ser Asp Phe Gly Asp Phe Asp Asp Ala
            595                 600                 605

Asn Lys Glu Gln
    610

<210> SEQ ID NO 75
<211> LENGTH: 619
<212> TYPE: PRT
<213> ORGANISM: Artificial
<220> FEATURE:
<223> OTHER INFORMATION: Chimeric Rep protein sequence

<400> SEQUENCE: 75

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

```
Glu Gln Ala Pro Leu Thr Val Ala Glu Lys Leu Gln Arg Asp Phe Leu
     50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Ser Gly Ile Ser Ser Met Val Leu Gly Arg Tyr Val Ser Gln Ile
                100                 105                 110

Arg Ala Gln Leu Val Lys Val Phe Gln Gly Ile Glu Pro Gln Ile
                115                 120                 125

Asn Asp Trp Val Ala Ile Thr Lys Val Lys Gly Gly Ala Asn Lys
    130                 135                 140

Val Val Asp Glu Cys Tyr Ile Pro Asn Tyr Leu Leu Pro Lys Thr Gln
145                 150                 155                 160

Pro Glu Leu Gln Trp Ala Trp Thr Asn Met Glu Gln Tyr Leu Ser Ala
                165                 170                 175

Cys Leu Asn Leu Thr Glu Arg Lys Arg Leu Val Ala Gln His Leu Thr
                180                 185                 190

His Val Ser Gln Thr Gln Glu Gln Asn Lys Glu Asn Gln Asn Pro Asn
    195                 200                 205

Ser Asp Ala Pro Val Ile Arg Ser Lys Thr Ser Ala Arg Tyr Met Glu
    210                 215                 220

Leu Val Gly Trp Leu Val Asp Lys Gly Ile Thr Ser Glu Lys Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
        260                 265                 270

Ser Leu Thr Lys Thr Ala Pro Asp Tyr Leu Val Gly Gln Gln Pro Val
        275                 280                 285

Glu Asp Ile Ser Ser Asn Arg Ile Tyr Lys Ile Leu Glu Leu Asn Gly
    290                 295                 300

Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
                340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
                420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460
```

```
Lys Asp Phe Phe Arg Trp Ala Lys Asp His Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro
    530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
            580                 585                 590

His Ile Met Gly Lys Val Pro Asp Ala Cys Thr Ala Cys Asp Leu Val
        595                 600                 605

Asn Val Asp Leu Asp Asp Cys Ile Phe Glu Gln
    610                 615

<210> SEQ ID NO 76
<211> LENGTH: 624
<212> TYPE: PRT
<213> ORGANISM: Artificial
<220> FEATURE:
<223> OTHER INFORMATION: Chimeric Rep protein sequence

<400> SEQUENCE: 76

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Leu Val Ala Glu Phe Val
            180                 185                 190

Ala Gln His Leu Thr His Val Ser Gln Thr Gln Glu Gln Asn Lys Glu
        195                 200                 205
```

-continued

Asn Gln Asn Pro Asn Ser Asp Ala Pro Val Ile Arg Ser Lys Thr Ser
210             215             220

Ala Arg Tyr Met Glu Leu Val Gly Trp Leu Val Asp Lys Gly Ile Thr
225             230             235             240

Ser Glu Lys Gln Trp Ile Gln Glu Asp Gln Ala Ser Tyr Ile Ser Phe
                245             250             255

Asn Ala Ala Ser Asn Ser Arg Ser Gln Ile Lys Ala Ala Leu Asp Asn
            260             265             270

Ala Gly Lys Ile Met Ser Leu Thr Lys Thr Ala Pro Asp Tyr Leu Val
        275             280             285

Gly Gln Gln Pro Val Glu Asp Ile Ser Ser Asn Arg Ile Tyr Lys Ile
    290             295             300

Leu Glu Leu Asn Gly Tyr Asp Pro Gln Tyr Ala Ala Ser Val Phe Leu
305             310             315             320

Gly Trp Ala Thr Lys Lys Phe Gly Lys Arg Asn Thr Ile Trp Leu Phe
                325             330             335

Gly Pro Ala Thr Thr Gly Lys Thr Asn Ile Ala Glu Ala Ile Ala His
            340             345             350

Thr Val Pro Phe Tyr Gly Cys Val Asn Trp Thr Asn Glu Asn Phe Pro
        355             360             365

Phe Asn Asp Cys Val Asp Lys Met Val Ile Trp Trp Glu Glu Gly Lys
370             375             380

Met Thr Ala Lys Val Val Glu Ser Ala Lys Ala Ile Leu Gly Gly Ser
385             390             395             400

Lys Val Arg Val Asp Gln Lys Cys Lys Ser Ser Ala Gln Ile Asp Pro
                405             410             415

Thr Pro Val Ile Val Thr Ser Asn Thr Asn Met Cys Ala Val Ile Asp
            420             425             430

Gly Asn Ser Thr Thr Phe Glu His Gln Gln Pro Leu Gln Asp Arg Met
        435             440             445

Phe Lys Phe Glu Leu Thr Arg Arg Leu Asp His Asp Phe Gly Lys Val
    450             455             460

Thr Lys Gln Glu Val Lys Asp Phe Phe Arg Trp Ala Lys Asp His Val
465             470             475             480

Val Glu Val Glu His Glu Phe Tyr Val Lys Lys Gly Gly Ala Lys Lys
                485             490             495

Arg Pro Ala Pro Ser Asp Ala Asp Ile Ser Glu Pro Lys Arg Val Arg
            500             505             510

Glu Ser Val Ala Gln Pro Ser Thr Ser Asp Ala Glu Ala Ser Ile Asn
        515             520             525

Tyr Ala Asp Arg Tyr Gln Asn Lys Cys Ser Arg His Val Gly Met Asn
    530             535             540

Leu Met Leu Phe Pro Cys Arg Gln Cys Glu Arg Met Asn Gln Asn Ser
545             550             555             560

Asn Ile Cys Phe Thr His Gly Gln Lys Asp Cys Leu Glu Cys Phe Pro
                565             570             575

Val Ser Glu Ser Gln Pro Val Ser Val Val Lys Ala Tyr Gln Lys
            580             585             590

Leu Cys Tyr Ile His His Ile Met Gly Lys Val Pro Asp Ala Cys Thr
        595             600             605

Ala Cys Asp Leu Val Asn Val Asp Leu Asp Asp Cys Ile Phe Glu Gln
    610             615             620

```
<210> SEQ ID NO 77
<211> LENGTH: 622
<212> TYPE: PRT
<213> ORGANISM: Artificial
<220> FEATURE:
<223> OTHER INFORMATION: Chimeric Rep protein sequence

<400> SEQUENCE: 77

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Arg Lys Arg Leu Val Ala Gln
            180                 185                 190

His Leu Thr His Val Ser Gln Thr Gln Glu Gln Asn Lys Glu Asn Gln
        195                 200                 205

Asn Pro Asn Ser Asp Ala Pro Val Ile Arg Ser Lys Thr Ser Ala Arg
    210                 215                 220

Tyr Met Glu Leu Val Gly Trp Leu Val Asp Lys Gly Ile Thr Ser Glu
225                 230                 235                 240

Lys Gln Trp Ile Gln Glu Asp Gln Ala Ser Tyr Ile Ser Phe Asn Ala
                245                 250                 255

Ala Ser Asn Ser Arg Ser Gln Ile Lys Ala Ala Leu Asp Asn Ala Gly
            260                 265                 270

Lys Ile Met Ser Leu Thr Lys Thr Ala Pro Asp Tyr Leu Val Gly Gln
        275                 280                 285

Gln Pro Val Glu Asp Ile Ser Ser Asn Arg Ile Tyr Lys Ile Leu Glu
    290                 295                 300

Leu Asn Gly Tyr Asp Pro Gln Tyr Ala Ala Ser Val Phe Leu Gly Trp
305                 310                 315                 320

Ala Thr Lys Lys Phe Gly Lys Arg Asn Thr Ile Trp Leu Phe Gly Pro
                325                 330                 335

Ala Thr Thr Gly Lys Thr Asn Ile Ala Glu Ala Ile Ala His Thr Val
            340                 345                 350

Pro Phe Tyr Gly Cys Val Asn Trp Thr Asn Glu Asn Phe Pro Phe Asn
        355                 360                 365

Asp Cys Val Asp Lys Met Val Ile Trp Trp Glu Glu Gly Lys Met Thr
```

```
                370             375                 380
Ala Lys Val Val Glu Ser Ala Lys Ala Ile Leu Gly Gly Ser Lys Val
385                 390                 395                 400

Arg Val Asp Gln Lys Cys Lys Ser Ser Ala Gln Ile Asp Pro Thr Pro
                405                 410                 415

Val Ile Val Thr Ser Asn Thr Asn Met Cys Ala Val Ile Asp Gly Asn
            420                 425                 430

Ser Thr Thr Phe Glu His Gln Gln Pro Leu Gln Asp Arg Met Phe Lys
        435                 440                 445

Phe Glu Leu Thr Arg Arg Leu Asp His Asp Phe Gly Lys Val Thr Lys
    450                 455                 460

Gln Glu Val Lys Asp Phe Phe Arg Trp Ala Lys Asp His Val Val Glu
465                 470                 475                 480

Val Glu His Glu Phe Tyr Val Lys Lys Gly Gly Ala Lys Lys Arg Pro
                485                 490                 495

Ala Pro Ser Asp Ala Asp Ile Ser Glu Pro Lys Arg Val Arg Glu Ser
            500                 505                 510

Val Ala Gln Pro Ser Thr Ser Asp Ala Glu Ala Ser Ile Asn Tyr Ala
        515                 520                 525

Asp Arg Tyr Gln Asn Lys Cys Ser Arg His Val Gly Met Asn Leu Met
    530                 535                 540

Leu Phe Pro Cys Arg Gln Cys Glu Arg Met Asn Gln Asn Ser Asn Ile
545                 550                 555                 560

Cys Phe Thr His Gly Gln Lys Asp Cys Leu Glu Cys Phe Pro Val Ser
                565                 570                 575

Glu Ser Gln Pro Val Ser Val Val Lys Lys Ala Tyr Gln Lys Leu Cys
            580                 585                 590

Tyr Ile His His Ile Met Gly Lys Val Pro Asp Ala Cys Thr Ala Cys
        595                 600                 605

Asp Leu Val Asn Val Asp Leu Asp Asp Cys Ile Phe Glu Gln
    610                 615                 620

<210> SEQ ID NO 78
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 78
atggctacct tctatgaagt cattgttcgc gtcccatttg acgtggagga acatctgcct    60
ggaatttctg acagctttgt ggactgggta actggtcaaa tttgggagct gcctccagag   120
tcagatttaa atttgactct ggttgaacag cctcagttga cggtggctga tagaattcgc   180
cgcgtgttcc tgtacgagtg gaacaaattt ccaagcagg agtccaaatt ctttgtgcag   240
tttgaaaagg gatctgaata ttttcatctg cacacgcttg tggagacctc cggcatctct   300
tccatggtcc tcggccgcta cgtgagtcag attcgcgccc agctggtgaa agtggtcttc   360
cagggaattg aacccagat caacgactgg gtcgccatca ccaaggtaaa gaagggcgga   420
gccaataagg tggtggatga gtgctacatc cccaattact tgctccccaa acccagcct   480 gagctccagt gggcgtggac taatatggaa cagtatttaa gcgcctgttt gaatctcacg   540
gagcgtaaac ggttggtggc gcagcatctg acgcacgtgt cgcagacgca ggagcagaac   600
aaagagaatc agaatcccaa ttctgatgcg ccggtgatca gatcaaaaac ttcagccagg   660
```

```
tacatggagc tggtcgggtg gctcgtggac aagggggatta cctcggagaa gcagtggatc    720
caggaggacc aggcctcata catctccttc aatgcggcct ccaactcgcg gtcccaaatc    780
aaggctgcct tggacaatgc gggaaagatt atgagcctga ctaaaaccgc ccccgactac    840
ctggtgggcc agcagcccgt ggaggacatt tccagcaatc ggatttataa aattttggaa    900
ctaaacgggt acgatcccca atatgcggct tccgtctttc tgggatgggc cacgaaaaag    960
ttcggcaaga ggaacaccat ctggctgttt gggcctgcaa ctaccgggaa gaccaacatc   1020
gcggaggcca tagcccacac tgtgcccttc tacgggtgcg taaactggac caatgagaac   1080
tttcccttca cgactgtgt cgacaagatg gtgatctggt gggaggaggg gaagatgacc    1140
gccaaggtcg tggagtcggc caaagccatt ctcggaggaa gcaaggtgcg cgtggaccag   1200
aaatgcaagt cctcggccca gatagacccg actcccgtga tcgtcacctc caacaccaac   1260
atgtgcgccg tgattgacgg gaactcaacg accttcgaac accagcagcc gttgcaagac   1320
cggatgttca aatttgaact cacccgccgt ctggatcatg actttgggaa ggtcaccaag   1380
caggaagtca agacttttt ccggtgggca aaggatcacg tggttgaggt ggagcatgaa   1440
ttctacgtca aaaagggtgg agccaagaaa agacccgccc ccagtgacgc agatataagt   1500
gagcccaaac gggtgcgcga gtcagttgcg cagccatcga cgtcagacgc ggaagcttcg   1560
atcaactacg cagacaggta ccaaaacaaa tgttctcgtc acgtgggcat gaatctgatg   1620
ctgtttccct gcagacaatg cgagagatg aatcagaatt caaatatctg cttcactcac   1680
ggacagaaag actgtttaga gtgctttccc gtgtcagaat ctcaacccgt ttctgtcgtc   1740
aaaaaggcgt atcagaaact gtgctacatt catcatatca tgggaaaggt gccagacgct   1800
tgcactgcct gcgatctggt caatgtggat ttggatgact gcatctttga acaataa     1857
```

<210> SEQ ID NO 79
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 79

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
        115                 120                 125

Asp Trp Val Ala Ile Thr Lys Val Lys Gly Gly Ala Asn Lys Val
        130                 135                 140

Val Asp Glu Cys Tyr Ile Pro Asn Tyr Leu Leu Pro Lys Thr Gln Pro
145                 150                 155                 160
```

```
Glu Leu Gln Trp Ala Trp Thr Asn Met Glu Gln Tyr Leu Ser Ala Cys
                165                 170                 175
Leu Asn Leu Thr Glu Arg Lys Arg Leu Val Ala Gln His Leu Thr His
            180                 185                 190
Val Ser Gln Thr Gln Glu Gln Asn Lys Glu Asn Gln Asn Pro Asn Ser
        195                 200                 205
Asp Ala Pro Val Ile Arg Ser Lys Thr Ser Ala Arg Tyr Met Glu Leu
    210                 215                 220
Val Gly Trp Leu Val Asp Lys Gly Ile Thr Ser Glu Lys Gln Trp Ile
225                 230                 235                 240
Gln Glu Asp Gln Ala Ser Tyr Ile Ser Phe Asn Ala Ala Ser Asn Ser
                245                 250                 255
Arg Ser Gln Ile Lys Ala Ala Leu Asp Asn Ala Gly Lys Ile Met Ser
            260                 265                 270
Leu Thr Lys Thr Ala Pro Asp Tyr Leu Val Gly Gln Gln Pro Val Glu
        275                 280                 285
Asp Ile Ser Ser Asn Arg Ile Tyr Lys Ile Leu Glu Leu Asn Gly Tyr
    290                 295                 300
Asp Pro Gln Tyr Ala Ala Ser Val Phe Leu Gly Trp Ala Thr Lys Lys
305                 310                 315                 320
Phe Gly Lys Arg Asn Thr Ile Trp Leu Phe Gly Pro Ala Thr Thr Gly
                325                 330                 335
Lys Thr Asn Ile Ala Glu Ala Ile Ala His Thr Val Pro Phe Tyr Gly
            340                 345                 350
Cys Val Asn Trp Thr Asn Glu Asn Phe Pro Phe Asn Asp Cys Val Asp
        355                 360                 365
Lys Met Val Ile Trp Trp Glu Glu Gly Lys Met Thr Ala Lys Val Val
    370                 375                 380
Glu Ser Ala Lys Ala Ile Leu Gly Gly Ser Lys Val Arg Val Asp Gln
385                 390                 395                 400
Lys Cys Lys Ser Ser Ala Gln Ile Asp Pro Thr Pro Val Ile Val Thr
                405                 410                 415
Ser Asn Thr Asn Met Cys Ala Val Ile Asp Gly Asn Ser Thr Thr Phe
            420                 425                 430
Glu His Gln Gln Pro Leu Gln Asp Arg Met Phe Lys Phe Glu Leu Thr
        435                 440                 445
Arg Arg Leu Asp His Asp Phe Gly Lys Val Thr Lys Gln Glu Val Lys
    450                 455                 460
Asp Phe Phe Arg Trp Ala Lys Asp His Val Val Glu Val Glu His Glu
465                 470                 475                 480
Phe Tyr Val Lys Lys Gly Gly Ala Lys Lys Arg Pro Ala Pro Ser Asp
                485                 490                 495
Ala Asp Ile Ser Glu Pro Lys Arg Val Arg Glu Ser Val Ala Gln Pro
            500                 505                 510
Ser Thr Ser Asp Ala Glu Ala Ser Ile Asn Tyr Ala Asp Arg Tyr Gln
        515                 520                 525
Asn Lys Cys Ser Arg His Val Gly Met Asn Leu Met Leu Phe Pro Cys
    530                 535                 540
Arg Gln Cys Glu Arg Met Asn Gln Asn Ser Asn Ile Cys Phe Thr His
545                 550                 555                 560
Gly Gln Lys Asp Cys Leu Glu Cys Phe Pro Val Ser Glu Ser Gln Pro
                565                 570                 575
```

| Val | Ser | Val | Val | Lys | Lys | Ala | Tyr | Gln | Lys | Leu | Cys | Tyr | Ile | His | His |
|---|---|---|---|---|---|---|---|---|---|---|---|---|---|---|---|
| | | | 580 | | | | 585 | | | | | 590 | | | |

| Ile | Met | Gly | Lys | Val | Pro | Asp | Ala | Cys | Thr | Ala | Cys | Asp | Leu | Val | Asn |
|---|---|---|---|---|---|---|---|---|---|---|---|---|---|---|---|
| | 595 | | | | 600 | | | | | 605 | | | | | |

| Val | Asp | Leu | Asp | Asp | Cys | Ile | Phe | Glu | Gln |
|---|---|---|---|---|---|---|---|---|---|
| 610 | | | | 615 | | | | | |

<210> SEQ ID NO 80
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 80

| atggctacct | tctatgaagt | cattgttcgc | gtcccatttg | acgtggagga | acatctgcct | 60 |
| ggaatttctg | acagctttgt | ggactgggta | actggtcaaa | tttgggagct | gcctccagag | 120 |
| tcagatttaa | atttgactct | ggttgaacag | cctcagttga | cggtggctga | tagaattcgc | 180 |
| cgcgtgttcc | tgtacgagtg | aacaaattt | ccaagcagg | agtccaaatt | ctttgtgcag | 240 |
| tttgaaaagg | gatctgaata | ttttcatctg | cacacgcttg | tggagacctc | cggcatctct | 300 |
| tccatggtcc | tcggccgcta | cgtgagtcag | attcgcgccc | agctggtgaa | agtggtcttc | 360 |
| cagggaattg | aaccccagat | caacgactgg | gtcgccatca | ccaaggtaaa | gagggcgga | 420 |
| gccaataagg | tggtggattc | ttgctacatc | cccaattact | tgctccccaa | acccagcct | 480 |
| gagctccagt | gggcgtggac | taatatgaaa | cagtatttaa | cgcctgtttt | gaatctcacg | 540 |
| gagcgtaaac | ggttggtggc | gcagcatctg | acgcacgtgt | cgcagacgca | ggagcagaac | 600 |
| aaagagaatc | agaatcccaa | ttctgatgcg | ccggtgatca | gatcaaaaac | ttcagccagg | 660 |
| tacatggagc | tggtcgggtg | gctcgtggac | aagggattac | cctcggagaa | gcagtggatc | 720 |
| caggaggacc | aggcctcata | catctccttc | aatgcggcct | ccaactcgcg | gtcccaaatc | 780 |
| aaggctgcct | tggacaatgc | gggaaagatt | atgagcctga | ctaaaaccgc | cccgactac | 840 |
| ctggtgggcc | agcagcccgt | ggaggacatt | tccagcaatc | ggatttataa | aattttggaa | 900 |
| ctaaacgggt | acgatcccca | atatgcggct | tccgtctttc | tgggatgggc | cacgaaaaag | 960 |
| ttcggcaaga | gaacaccat | ctggctgttt | gggcctgcaa | ctaccgggaa | gaccaacatc | 1020 |
| gcggaggcca | tagcccacac | tgtgcccttc | tacgggtgcg | taaactggac | caatgagaac | 1080 |
| tttcccttca | acgactgtgt | cgacaagatg | gtgatctggt | gggaggaggg | gaagatgacc | 1140 |
| gccaaggtcg | tggagtcggc | caaagccatt | ctcggaggaa | gcaaggtgcg | cgtggaccag | 1200 |
| aaatgcaagt | cctcggccca | gatagacccg | actcccgtga | tcgtcacctc | caacaccaac | 1260 |
| atgtgcgccg | tgattgacgg | gaactcaacg | accttcgaac | accagcagcc | gttgcaagac | 1320 |
| cggatgttca | aatttgaact | cacccgccgt | ctggatcatg | actttgggaa | ggtcaccaag | 1380 |
| caggaagtca | agacttttt | ccggtgggca | aaggatcacg | tggttgaggt | ggagcatgaa | 1440 |
| ttctacgtca | aaaagggtgg | agccaagaaa | agacccgccc | ccagtgacgc | agatataagt | 1500 |
| gagcccaaac | gggtgcgcga | gtcagttgcg | cagccatcga | cgtcagacgc | ggaagcttcg | 1560 |
| atcaactacg | cagacaggta | ccaaaacaaa | tgttctcgtc | acgtgggcat | gaatctgatg | 1620 |
| ctgtttccct | gcagacaatg | cgagagaatg | aatcagaatt | caaatatctg | cttcactcac | 1680 |
| ggacagaaag | actgtttaga | gtgctttccc | gtgtcagaat | ctcaacccgt | ttctgtcgtc | 1740 |
| aaaaaggcgt | atcagaaact | gtgctacatt | catcatatca | tgggaaaggt | gccagacgct | 1800 | tgcactgcct gcgatctggt caatgtggat ttggatgact gcatctttga acaataa 1857

<210> SEQ ID NO 81
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 81

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
    210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Gln Pro Val Glu
        275                 280                 285

Asp Ile Ser Ser Asn Arg Ile Tyr Lys Ile Leu Glu Leu Asn Gly Tyr
    290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp

```
                355                 360                 365
Lys Met Val Ile Trp Trp Glu Glu Gly Lys Met Thr Ala Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
                405                 410                 415

Ser Asn Thr Asn Met Cys Ala Val Ile Asp Gly Asn Ser Thr Thr Phe
                420                 425                 430

Glu His Gln Gln Pro Leu Gln Asp Arg Met Phe Lys Phe Glu Leu Thr
            435                 440                 445

Arg Arg Leu Asp His Asp Phe Gly Lys Val Thr Lys Gln Glu Val Lys
        450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
        595                 600                 605

Val Asp Leu Asp Asp Cys Ile Phe Glu Gln
    610                 615

<210> SEQ ID NO 82
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 82
atggctacct tctatgaagt cattgttcgc gtcccatttg acgtggagga acatctgcct       60
ggaatttctg acagctttgt ggactgggta actggtcaaa tttgggagct gcctccagag      120
tcagatttaa atttgactct ggttgaacag cctcagttga cggtggctga tagaattcgc      180
cgcgtgttcc tgtacgagtg gaacaaattt tccaagcagg agtccaaatt ctttgtgcag      240
tttgaaaagg gatctgaata ttttcatctg cacacgcttg tggagacctc cggcatctct      300
tccatggtcc tcggccgcta cgtgagtcag attcgcgccc agctggtgaa agtggtcttc      360
cagggaattg aaccccagat caacgactgg gtcgccatca ccaaggtaaa gaagggcgga      420
gccaataagg tggtggattc tgggtatatt cccaattact tgctccccaa aacccagcct      480
gagctccagt gggcgtggac taatatggaa cagtatttaa gcgcctgttt gaatctcacg      540
gagcgtaaac ggttggtggc gcagcatctg acgcacgtgt cgcagacgca ggagcagaac      600
```

```
aaagagaatc agaatcccaa ttctgatgcg ccggtgatca gatcaaaaac ttcagccagg   660
tacatggagc tggtcgggtg gctcgtggac aaggggatta cctcggagaa gcagtggatc   720
caggaggacc aggcctcata catctccttc aatgcggcct ccaactcgcg gtcccaaatc   780
aaggctgcct tggacaatgc gggaaagatt atgagcctga ctaaaaccgc ccccgactac   840
ctggtgggcc agcagcccgt ggaggacatt ccagcaatc ggatttataa aattttggaa    900
ctaaacgggt acgatcccca atatgcggct ccgtctttc tgggatgggc cacgaaaaag    960
ttcggcaaga ggaacaccat ctggctgttt gggcctgcaa ctaccgggaa gaccaacatc   1020
gcggaggcca tagcccacac tgtgcccttc tacgggtgcg taaactggac caatgagaac   1080
tttcccttca cgactgtgt cgacaagatg gtgatctggt gggaggaggg gaagatgacc    1140
gccaaggtcg tggagtcggc caaagccatt ctcggaggaa gcaaggtgcg cgtgaccag    1200
aaatgcaagt cctcggccca gatagacccg actcccgtga tcgtcacctc caacaccaac   1260
atgtgcgccg tgattgacgg gaactcaacg accttcgaac accagcagcc gttgcaagac   1320
cggatgttca aatttgaact cacccgccgt ctggatcatg actttgggaa ggtcaccaag   1380
caggaagtca aagactttt ccggtgggca aaggatcacg tggttgaggt ggagcatgaa    1440
ttctacgtca aaaagggtgg agccaagaaa agacccgccc ccagtgacgc agatataagt   1500
gagcccaaac gggtgcgcga gtcagttgcg cagccatcga cgtcagacgc ggaagcttcg   1560
atcaactacg cagacaggta ccaaaacaaa tgttctcgtc acgtgggcat gaatctgatg   1620
ctgtttccct gcagacaatg cgagagaatg aatcagaatt caaatatctg cttcactcac   1680
ggacagaaag actgtttaga gtgctttccc gtgtcagaat ctcaacccgt ttctgtcgtc   1740
aaaaaggcgt atcagaaact gtgctacatt catcatatca tgggaaaggt gccagacgct   1800
tgcactgcct gcgatctggt caatgtggat ttggatgact gcatctttga acaataa     1857
```

<210> SEQ ID NO 83
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 83

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

-continued

Val Asp Ser Gly Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
    210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Pro Val Glu
        275                 280                 285

Asp Ile Ser Ser Asn Arg Ile Tyr Lys Ile Leu Glu Leu Asn Gly Tyr
    290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Val Ile Trp Trp Glu Glu Gly Lys Met Thr Ala Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
                405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr
        435                 440                 445

Arg Arg Leu Asp His Asp Phe Gly Lys Val Thr Lys Gln Glu Val Lys
    450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

```
Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
            595                 600                 605

Val Asp Leu Asp Asp Cys Ile Phe Glu Gln
    610                 615

<210> SEQ ID NO 84
<211> LENGTH: 312
<212> TYPE: PRT
<213> ORGANISM: Adeno-associated virus 1

<400> SEQUENCE: 84

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
290                 295                 300

Asp Leu Ala Arg Gly Gln Pro Leu
305                 310
```

<210> SEQ ID NO 85
<211> LENGTH: 312
<212> TYPE: PRT
<213> ORGANISM: Adeno-associated virus 2

<400> SEQUENCE: 85

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Leu Ala Arg Gly His Ser Leu
305                 310

<210> SEQ ID NO 86
<211> LENGTH: 311
<212> TYPE: PRT
<213> ORGANISM: Adeno-associated virus 3A

<400> SEQUENCE: 86

Met Glu Leu Val Gly Trp Leu Val Asp Arg Gly Ile Thr Ser Glu Lys
1               5                   10                  15

```
Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
 50                  55                  60

Pro Pro Glu Asp Ile Thr Lys Asn Arg Ile Tyr Gln Ile Leu Glu Leu
 65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Glu Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Glu Cys Thr Ser Leu
        275                 280                 285

Ala Gln Pro Thr Thr Ser Asp Ala Glu Ala Pro Ala Asp Tyr Ala Asp
290                 295                 300

Leu Ala Arg Gly Gln Pro Phe
305                 310

<210> SEQ ID NO 87
<211> LENGTH: 311
<212> TYPE: PRT
<213> ORGANISM: Adeno-associated virus 3B

<400> SEQUENCE: 87

Met Glu Leu Val Gly Trp Leu Val Asp Arg Gly Ile Thr Ser Glu Lys
 1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
 50                  55                  60

Pro Pro Glu Asp Ile Thr Lys Asn Arg Ile Tyr Gln Ile Leu Glu Leu
```

```
            65                  70                  75                  80
Asn Gly Tyr Asp Pro Gln Tyr Ala Ala Ser Val Phe Leu Gly Trp Ala
                85                  90                  95
Gln Lys Lys Phe Gly Lys Arg Asn Thr Ile Trp Leu Phe Gly Pro Ala
                100                 105                 110
Thr Thr Gly Lys Thr Asn Ile Ala Glu Ala Ile Ala His Ala Val Pro
                115                 120                 125
Phe Tyr Gly Cys Val Asn Trp Thr Asn Glu Asn Phe Pro Phe Asn Asp
                130                 135                 140
Cys Val Asp Lys Met Val Ile Trp Trp Glu Glu Gly Lys Met Thr Ala
145                 150                 155                 160
Lys Val Val Glu Ser Ala Lys Ala Ile Leu Gly Gly Ser Lys Val Arg
                165                 170                 175
Val Asp Gln Lys Cys Lys Ser Ser Ala Gln Ile Glu Pro Thr Pro Val
                180                 185                 190
Ile Val Thr Ser Asn Thr Asn Met Cys Ala Val Ile Asp Gly Asn Ser
                195                 200                 205
Thr Thr Phe Glu His Gln Gln Pro Leu Gln Asp Arg Met Phe Lys Phe
                210                 215                 220
Glu Leu Thr Arg Arg Leu Asp His Asp Phe Gly Lys Val Thr Lys Gln
225                 230                 235                 240
Glu Val Lys Asp Phe Phe Arg Trp Ala Ser Asp His Val Thr Asp Val
                245                 250                 255
Ala His Glu Phe Tyr Val Arg Lys Gly Gly Ala Lys Lys Arg Pro Ala
                260                 265                 270
Ser Asn Asp Ala Asp Val Ser Glu Pro Lys Arg Gln Cys Thr Ser Leu
                275                 280                 285
Ala Gln Pro Thr Thr Ser Asp Ala Glu Ala Pro Ala Asp Tyr Ala Asp
                290                 295                 300
Leu Ala Arg Gly Gln Pro Phe
305                 310

<210> SEQ ID NO 88
<211> LENGTH: 311
<212> TYPE: PRT
<213> ORGANISM: Adeno-associated virus 4

<400> SEQUENCE: 88

Met Glu Leu Val Gly Trp Leu Val Asp Arg Gly Ile Thr Ser Glu Lys
1               5                   10                  15
Gln Trp Ile Gln Glu Asp Gln Ala Ser Tyr Ile Ser Phe Asn Ala Ala
                20                  25                  30
Ser Asn Ser Arg Ser Gln Ile Lys Ala Ala Leu Asp Asn Ala Ser Lys
                35                  40                  45
Ile Met Ser Leu Thr Lys Thr Ala Pro Asp Tyr Leu Val Gly Gln Asn
                50                  55                  60
Pro Pro Glu Asp Ile Ser Ser Asn Arg Ile Tyr Arg Ile Leu Glu Met
65                  70                  75                  80
Asn Gly Tyr Asp Pro Gln Tyr Ala Ala Ser Val Phe Leu Gly Trp Ala
                85                  90                  95
Gln Lys Lys Phe Gly Lys Arg Asn Thr Ile Trp Leu Phe Gly Pro Ala
                100                 105                 110
Thr Thr Gly Lys Thr Asn Ile Ala Glu Ala Ile Ala His Ala Val Pro
                115                 120                 125
```

```
Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
                180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
                245                 250                 255

Thr His Glu Phe Tyr Val Arg Lys Gly Gly Ala Arg Lys Arg Pro Ala
                260                 265                 270

Pro Asn Asp Ala Asp Ile Ser Glu Pro Lys Arg Ala Cys Pro Ser Val
                275                 280                 285

Ala Gln Pro Ser Thr Ser Asp Ala Glu Ala Pro Val Asp Tyr Ala Asp
                290                 295                 300

Leu Ala Arg Gly Gln Pro Leu
305                 310

<210> SEQ ID NO 89
<211> LENGTH: 329
<212> TYPE: PRT
<213> ORGANISM: Adeno-associated virus 5

<400> SEQUENCE: 89

Met Ala Leu Val Asn Trp Leu Val Glu His Gly Ile Thr Ser Glu Lys
1               5                   10                  15

Gln Trp Ile Gln Glu Asn Gln Glu Ser Tyr Leu Ser Phe Asn Ser Thr
                20                  25                  30

Gly Asn Ser Arg Ser Gln Ile Lys Ala Ala Leu Asp Asn Ala Thr Lys
            35                  40                  45

Ile Met Ser Leu Thr Lys Ser Ala Val Asp Tyr Leu Val Gly Ser Ser
        50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
                100                 105                 110

Thr Thr Gly Lys Thr Asn Ile Ala Glu Ala Ile Ala His Thr Val Pro
            115                 120                 125

Phe Tyr Gly Cys Val Asn Trp Thr Asn Glu Asn Phe Pro Phe Asn Asp
    130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
                180                 185                 190
```

```
Ile Val Thr Ser Asn Thr Asn Met Cys Val Val Asp Gly Asn Ser
            195                 200                 205
Thr Thr Phe Glu His Gln Gln Pro Leu Glu Asp Arg Met Phe Lys Phe
        210                 215                 220
Glu Leu Thr Lys Arg Leu Pro Pro Asp Phe Gly Lys Ile Thr Lys Gln
225                 230                 235                 240
Glu Val Lys Asp Phe Phe Ala Trp Ala Lys Val Asn Gln Val Pro Val
                245                 250                 255
Thr His Glu Phe Lys Val Pro Arg Glu Leu Ala Gly Thr Lys Gly Ala
            260                 265                 270
Glu Lys Ser Leu Lys Arg Pro Leu Gly Asp Val Thr Asn Thr Ser Tyr
            275                 280                 285
Lys Ser Leu Glu Lys Arg Ala Arg Leu Ser Phe Val Pro Glu Thr Pro
            290                 295                 300
Arg Ser Ser Asp Val Thr Val Asp Pro Ala Pro Leu Arg Pro Leu Asn
305                 310                 315                 320
Trp Asn Ser Leu Val Gly Pro Ser Trp
                325

<210> SEQ ID NO 90
<211> LENGTH: 312
<212> TYPE: PRT
<213> ORGANISM: Adeno-associated virus 6

<400> SEQUENCE: 90

Met Glu Leu Val Gly Trp Leu Val Asp Arg Gly Ile Thr Ser Glu Lys
1               5                   10                  15
Gln Trp Ile Gln Glu Asp Gln Ala Ser Tyr Ile Ser Phe Asn Ala Ala
            20                  25                  30
Ser Asn Ser Arg Ser Gln Ile Lys Ala Ala Leu Asp Asn Ala Gly Lys
        35                  40                  45
Ile Met Ala Leu Thr Lys Ser Ala Pro Asp Tyr Leu Val Gly Pro Ala
    50                  55                  60
Pro Pro Ala Asp Ile Lys Thr Asn Arg Ile Tyr Arg Ile Leu Glu Leu
65                  70                  75                  80
Asn Gly Tyr Asp Pro Ala Tyr Ala Gly Ser Val Phe Leu Gly Trp Ala
                85                  90                  95
Gln Lys Arg Phe Gly Lys Arg Asn Thr Ile Trp Leu Phe Gly Pro Ala
            100                 105                 110
Thr Thr Gly Lys Thr Asn Ile Ala Glu Ala Ile Ala His Ala Val Pro
        115                 120                 125
Phe Tyr Gly Cys Val Asn Trp Thr Asn Glu Asn Phe Pro Phe Asn Asp
    130                 135                 140
Cys Val Asp Lys Met Val Ile Trp Trp Glu Glu Gly Lys Met Thr Ala
145                 150                 155                 160
Lys Val Val Glu Ser Ala Lys Ala Ile Leu Gly Gly Ser Lys Val Arg
                165                 170                 175
Val Asp Gln Lys Cys Lys Ser Ser Ala Gln Ile Asp Pro Thr Pro Val
            180                 185                 190
Ile Val Thr Ser Asn Thr Asn Met Cys Ala Val Ile Asp Gly Asn Ser
        195                 200                 205
Thr Thr Phe Glu His Gln Gln Pro Leu Gln Asp Arg Met Phe Lys Phe
    210                 215                 220
Glu Leu Thr Arg Arg Leu Glu His Asp Phe Gly Lys Val Thr Lys Gln
```

```
              225                 230                 235                 240
Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
                260                 265                 270

Pro Asp Asp Ala Asp Lys Ser Glu Pro Lys Arg Ala Cys Pro Ser Val
                275                 280                 285

Ala Asp Pro Ser Thr Ser Asp Ala Glu Gly Ala Pro Val Asp Phe Ala
                290                 295                 300

Asp Leu Ala Arg Gly Gln Pro Leu
305                 310

<210> SEQ ID NO 91
<211> LENGTH: 312
<212> TYPE: PRT
<213> ORGANISM: Adeno-associated virus 7

<400> SEQUENCE: 91

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
            35                  40                  45

Ile Met Ala Leu Thr Lys Ser Ala Pro Asp Tyr Leu Val Gly Pro Ser
    50                  55                  60

Leu Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
    115                 120                 125

Phe Tyr Gly Cys Val Asn Trp Thr Asn Glu Asn Phe Pro Phe Asn Asp
            130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
    195                 200                 205

Thr Thr Phe Glu His Gln Gln Pro Leu Gln Asp Arg Met Phe Lys Phe
            210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
                260                 265                 270

Pro Asp Asp Ala Asp Ile Ser Glu Pro Lys Arg Ala Cys Pro Ser Val
                275                 280                 285
```

Ala Asp Pro Ser Thr Ser Asp Ala Glu Gly Ala Pro Val Asp Phe Ala
            290                 295                 300

Asp Leu Ala Arg Gly Gln Pro Leu
305                 310

<210> SEQ ID NO 92
<211> LENGTH: 312
<212> TYPE: PRT
<213> ORGANISM: Adeno-associated virus 8

<400> SEQUENCE: 92

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Leu Ala Arg Gly Gln Pro Leu
305                 310

<210> SEQ ID NO 93
<211> LENGTH: 311
<212> TYPE: PRT
<213> ORGANISM: Artificial

<220> FEATURE:
<223> OTHER INFORMATION: AAV Rep40 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (290)..(290)
<223> OTHER INFORMATION: Xaa can be Asp, Gln or Thr

<400> SEQUENCE: 93

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Xaa Ser
    50                  55                  60

Pro Pro Glu Asp Ile Ser Thr Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Lys Lys Arg Pro Ala
            260                 265                 270

Pro Asp Asp Ala Asp Lys Ser Glu Pro Lys Arg Ala Cys Pro Ser Val
        275                 280                 285

Ala Xaa Pro Ser Thr Ser Asp Ala Glu Ala Pro Val Asp Phe Ala Asp
    290                 295                 300

Leu Ala Arg Gly Gln Pro Leu
305                 310
```

<210> SEQ ID NO 94
<211> LENGTH: 399
<212> TYPE: PRT
<213> ORGANISM: Adeno-associated virus 1

```
<400> SEQUENCE: 94

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Thr Arg Asp Cys Ser Glu Cys Phe Pro Gly Val
            340                 345                 350

Ser Glu Ser Gln Pro Val Val Arg Lys Arg Thr Tyr Arg Lys Leu Cys
        355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 95
```

```
<211> LENGTH: 397
<212> TYPE: PRT
<213> ORGANISM: Adeno-associated virus 2

<400> SEQUENCE: 95
```

| | | | | | | | | | | | | | | |
|---|---|---|---|---|---|---|---|---|---|---|---|---|---|---|
| Met | Glu | Leu | Val | Gly | Trp | Leu | Val | Asp | Lys | Gly | Ile | Thr | Ser | Glu | Lys |
| 1 | | | | 5 | | | | | 10 | | | | | 15 | |

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
 50                  55                  60

Pro Val Glu Asp Ile Ser Ser Asn Arg Ile Tyr Lys Ile Leu Glu Leu
 65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
370                 375                 380

Leu Val Asn Val Asp Leu Asp Asp Cys Ile Phe Glu Gln 385                 390                 395

<210> SEQ ID NO 96
<211> LENGTH: 400
<212> TYPE: PRT
<213> ORGANISM: Adeno-associated virus 3A

<400> SEQUENCE: 96

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Glu Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Glu Cys Thr Ser Leu
        275                 280                 285

Ala Gln Pro Thr Thr Ser Asp Ala Glu Ala Pro Ala Asp Tyr Ala Asp
    290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
            340                 345                 350

Glu Ser Gln Pro Val Ser Val Val Lys Lys Thr Tyr Gln Lys Leu
        355                 360                 365
```

Cys Pro Ile His His Ile Leu Gly Arg Ala Pro Glu Ile Ala Cys Ser
370                 375                 380

Ala Cys Asp Leu Ala Asn Val Asp Leu Asp Asp Cys Val Ser Glu Gln
385                 390                 395                 400

<210> SEQ ID NO 97
<211> LENGTH: 400
<212> TYPE: PRT
<213> ORGANISM: Adeno-associated virus 3B

<400> SEQUENCE: 97

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Gln Cys Thr Ser Leu
        275                 280                 285

Ala Gln Pro Thr Thr Ser Asp Ala Glu Ala Pro Ala Asp Tyr Ala Asp
290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
            340                 345                 350

Glu Ser Gln Pro Val Ser Val Lys Lys Thr Tyr Gln Lys Leu
            355                 360                 365

Cys Pro Ile His His Ile Leu Gly Arg Ala Pro Glu Ile Ala Cys Ser
    370                 375                 380

Ala Cys Asp Leu Ala Asn Val Asp Leu Asp Asp Cys Val Ser Glu Gln
385                 390                 395                 400

<210> SEQ ID NO 98
<211> LENGTH: 399
<212> TYPE: PRT
<213> ORGANISM: Adeno-associated virus 4

<400> SEQUENCE: 98

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
                245                 250                 255

Thr His Glu Phe Tyr Val Arg Lys Gly Gly Ala Arg Lys Arg Pro Ala
            260                 265                 270

Pro Asn Asp Ala Asp Ile Ser Glu Pro Lys Arg Ala Cys Pro Ser Val
        275                 280                 285

Ala Gln Pro Ser Thr Ser Asp Ala Glu Ala Pro Val Asp Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Val Asp Ile Cys

```
                    325                 330                 335
Phe Thr His Gly Val Met Asp Cys Ala Glu Cys Phe Pro Val Ser Glu
            340                 345                 350

Ser Gln Pro Val Ser Val Val Arg Lys Arg Thr Tyr Gln Lys Leu Cys
            355                 360                 365

Pro Ile His His Ile Met Gly Arg Ala Pro Glu Val Ala Cys Ser Ala
            370                 375                 380

Cys Glu Leu Ala Asn Val Asp Leu Asp Asp Cys Asp Met Glu Gln
385                 390                 395

<210> SEQ ID NO 99
<211> LENGTH: 390
<212> TYPE: PRT
<213> ORGANISM: Adeno-associated virus 5

<400> SEQUENCE: 99

Met Ala Leu Val Asn Trp Leu Val Glu His Gly Ile Thr Ser Glu Lys
1               5                   10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Thr Lys
        35                  40                  45

Ile Met Ser Leu Thr Lys Ser Ala Val Asp Tyr Leu Val Gly Ser Ser
    50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Asp Gly Asn Ser
        195                 200                 205

Thr Thr Phe Glu His Gln Gln Pro Leu Glu Asp Arg Met Phe Lys Phe
    210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
    290                 295                 300
```

Arg Ser Ser Asp Val Thr Val Asp Pro Ala Pro Leu Arg Pro Leu Asn
305                 310                 315                 320

Trp Asn Ser Arg Tyr Asp Cys Lys Cys Asp Tyr His Ala Gln Phe Asp
            325                 330                 335

Asn Ile Ser Asn Lys Cys Asp Glu Cys Glu Tyr Leu Asn Arg Gly Lys
        340                 345                 350

Asn Gly Cys Ile Cys His Asn Val Thr His Cys Gln Ile Cys His Gly
        355                 360                 365

Ile Pro Pro Trp Glu Lys Glu Asn Leu Ser Asp Phe Gly Asp Phe Asp
370                 375                 380

Asp Ala Asn Lys Glu Gln
385                 390

<210> SEQ ID NO 100
<211> LENGTH: 399
<212> TYPE: PRT
<213> ORGANISM: Adeno-associated virus 6

<400> SEQUENCE: 100

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
50                  55                  60

Pro Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

```
Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Thr Arg Asp Cys Ser Glu Cys Phe Pro Gly Val
                340                 345                 350

Ser Glu Ser Gln Pro Val Val Arg Lys Arg Thr Tyr Arg Lys Leu Cys
                355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 101
<211> LENGTH: 399
<212> TYPE: PRT
<213> ORGANISM: Adeno-associated virus 7

<400> SEQUENCE: 101

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
```

-continued

```
                260                 265                 270
Pro Asp Asp Ala Asp Ile Ser Glu Pro Lys Arg Ala Cys Pro Ser Val
            275                 280                 285

Ala Asp Pro Ser Thr Ser Asp Ala Glu Gly Ala Pro Val Asp Phe Ala
        290                 295                 300

Asp Arg Tyr Gln Asn Lys Cys Ser Arg His Ala Gly Met Ile Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Leu Glu Cys Phe Pro Gly Val
            340                 345                 350

Ser Glu Ser Gln Pro Val Val Arg Lys Lys Thr Tyr Arg Lys Leu Cys
        355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 102
<211> LENGTH: 399
<212> TYPE: PRT
<213> ORGANISM: Adeno-associated virus 8

<400> SEQUENCE: 102

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240
```

```
Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Ser Glu Cys Phe Pro Gly Val
            340                 345                 350

Ser Glu Ser Gln Pro Val Val Arg Lys Arg Thr Tyr Arg Lys Leu Cys
        355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 103
<211> LENGTH: 398
<212> TYPE: PRT
<213> ORGANISM: Artificial
<220> FEATURE:
<223> OTHER INFORMATION: AAV Rep52 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (317)..(317)
<223> OTHER INFORMATION: Xaa can be Asn, Asp, Ile or Leu
<220> FEATURE:
<221> NAME/KEY: MISC_FEATURE
<222> LOCATION: (333)..(333)
<223> OTHER INFORMATION: Xaa can be Lys, Phe, Ser or Val
<220> FEATURE:
<221> NAME/KEY: MISC_FEATURE
<222> LOCATION: (341)..(341)
<223> OTHER INFORMATION: Xaa can be Gln, Thr or Val
<220> FEATURE:
<221> NAME/KEY: MISC_FEATURE
<222> LOCATION: (345)..(345)
<223> OTHER INFORMATION: Xaa can be Ala, Gln, Gly, Leu or Ser
<220> FEATURE:
<221> NAME/KEY: MISC_FEATURE
<222> LOCATION: (356)..(356)
<223> OTHER INFORMATION: Xaa can be Pro or Ser
<220> FEATURE:
<221> NAME/KEY: MISC_FEATURE
<222> LOCATION: (364)..(364)
<223> OTHER INFORMATION: Xaa can be Gln or Arg
<220> FEATURE:
<221> NAME/KEY: MISC_FEATURE
<222> LOCATION: (368)..(368)
<223> OTHER INFORMATION: Xaa can be Ala, Pro or Tyr

<400> SEQUENCE: 103

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
```

```
            35                  40                  45
Ile Met Ala Leu Thr Lys Ser Ala Pro Asp Tyr Leu Val Gly Xaa Ser
 50                  55                  60

Pro Pro Glu Asp Ile Ser Thr Asn Arg Ile Tyr Arg Ile Leu Ala Leu
 65                  70                  75                  80

Asn Gly Tyr Asp Pro Ala Tyr Ala Gly Ser Val Phe Leu Gly Trp Ala
                 85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Lys Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Ala Pro Val Asp Phe Ala Asp
290                 295                 300

Arg Tyr Gln Asn Lys Cys Ser Arg His Ala Gly Met Xaa Gln Met Leu
305                 310                 315                 320

Phe Pro Cys Lys Thr Cys Glu Arg Met Asn Gln Asn Xaa Asn Ile Cys
                325                 330                 335

Phe Thr His Gly Xaa Arg Asp Cys Xaa Glu Cys Phe Pro Gly Val Ser
            340                 345                 350

Glu Ser Gln Xaa Val Val Arg Lys Arg Thr Tyr Xaa Lys Leu Cys Xaa
        355                 360                 365

Ile His His Leu Leu Gly Arg Ala Pro Glu Ile Ala Cys Ser Ala Cys
370                 375                 380

Asp Leu Val Asn Val Asp Leu Asp Asp Cys Val Ser Glu Gln
385                 390                 395

<210> SEQ ID NO 104
<211> LENGTH: 536
<212> TYPE: PRT
<213> ORGANISM: Adeno-associated virus 1

<400> SEQUENCE: 104

Met Pro Gly Phe Tyr Glu Ile Val Ile Lys Val Pro Ser Asp Leu Asp
 1               5                  10                  15
```

-continued

```
Glu His Leu Pro Gly Ile Ser Asp Ser Phe Val Ser Trp Val Ala Glu
             20                  25                  30
Lys Glu Trp Glu Leu Pro Pro Asp Ser Asp Met Asp Leu Asn Leu Ile
         35                  40                  45
Glu Gln Ala Pro Leu Thr Val Ala Glu Lys Leu Gln Arg Asp Phe Leu
     50                  55                  60
Val Gln Trp Arg Arg Val Ser Lys Ala Pro Glu Ala Leu Phe Phe Val
 65                  70                  75                  80
Gln Phe Glu Lys Gly Glu Ser Tyr Phe His Leu His Ile Leu Val Glu
                 85                  90                  95
Thr Thr Gly Val Lys Ser Met Val Leu Gly Arg Phe Leu Ser Gln Ile
            100                 105                 110
Arg Asp Lys Leu Val Gln Thr Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Glu Tyr Ile
                165                 170                 175
Ser Ala Cys Leu Asn Leu Ala Glu Arg Lys Arg Leu Val Ala Gln His
            180                 185                 190
Leu Thr His Val Ser Gln Thr Gln Glu Gln Asn Lys Glu Asn Leu Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ala Leu Thr Lys Ser Ala Pro Asp Tyr Leu Val Gly Pro Ala
        275                 280                 285
Pro Pro Ala Asp Ile Lys Thr Asn Arg Ile Tyr Arg Ile Leu Glu Leu
    290                 295                 300
Asn Gly Tyr Glu Pro Ala Tyr Ala Gly Ser Val Phe Leu Gly Trp Ala
305                 310                 315                 320
Gln Lys Arg Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
```

-continued

```
                435                 440                 445
Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
                500                 505                 510

Ala Asp Pro Ser Thr Ser Asp Ala Glu Gly Ala Pro Val Asp Phe Ala
                515                 520                 525

Asp Leu Ala Arg Gly Gln Pro Leu
530                 535

<210> SEQ ID NO 105
<211> LENGTH: 536
<212> TYPE: PRT
<213> ORGANISM: Adeno-associated virus 2

<400> SEQUENCE: 105

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270
```

Ile Met Ser Leu Thr Lys Thr Ala Pro Asp Tyr Leu Val Gly Gln Gln
              275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
              325                 330                 335

Thr Thr Gly Lys Thr Asn Ile Ala Glu Ala Ile Ala His Thr Val Pro
              340                 345                 350

Phe Tyr Gly Cys Val Asn Trp Thr Asn Glu Asn Phe Pro Phe Asn Asp
              355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
              405                 410                 415

Ile Val Thr Ser Asn Thr Asn Met Cys Ala Val Ile Asp Gly Asn Ser
              420                 425                 430

Thr Thr Phe Glu His Gln Gln Pro Leu Gln Asp Arg Met Phe Lys Phe
              435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
              485                 490                 495

Pro Ser Asp Ala Asp Ile Ser Glu Pro Lys Arg Val Arg Glu Ser Val
              500                 505                 510

Ala Gln Pro Ser Thr Ser Asp Ala Glu Ala Ser Ile Asn Tyr Ala Asp
              515                 520                 525

Arg Leu Ala Arg Gly His Ser Leu
530                 535

<210> SEQ ID NO 106
<211> LENGTH: 535
<212> TYPE: PRT
<213> ORGANISM: Adeno-associated virus 3A

<400> SEQUENCE: 106

Met Pro Gly Phe Tyr Glu Ile Val Leu Lys Val Pro Ser Asp Leu Asp
1                 5                   10                  15

Glu Arg Leu Pro Gly Ile Ser Asn Ser Phe Val Asn Trp Val Ala Glu
              20                  25                  30

Lys Glu Trp Asp Val Pro Pro Asp Ser Asp Met Asp Pro Asn Leu Ile
              35                  40                  45

Glu Gln Ala Pro Leu Thr Val Ala Glu Lys Leu Gln Arg Glu Phe Leu
50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
              85                  90                  95

Thr Ile Gly Val Lys Ser Met Val Val Gly Arg Tyr Val Ser Gln Ile
              100                 105                 110

```
Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Glu Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
            500                 505                 510

Ala Gln Pro Thr Thr Ser Asp Ala Glu Ala Pro Ala Asp Tyr Ala Asp
        515                 520                 525
```

-continued

```
Leu Ala Arg Gly Gln Pro Phe
    530                 535

<210> SEQ ID NO 107
<211> LENGTH: 535
<212> TYPE: PRT
<213> ORGANISM: Adeno-associated virus 3B

<400> SEQUENCE: 107

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
            20                  25                  30

Lys Glu Trp Glu Leu Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365
```

```
Cys Val Asp Lys Met Val Ile Trp Trp Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
                500                 505                 510

Ala Gln Pro Thr Thr Ser Asp Ala Glu Ala Pro Ala Asp Tyr Ala Asp
            515                 520                 525

Leu Ala Arg Gly Gln Pro Phe
    530                 535

<210> SEQ ID NO 108
<211> LENGTH: 535
<212> TYPE: PRT
<213> ORGANISM: Adeno-associated virus 4

<400> SEQUENCE: 108

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
```

```
                195                 200                 205
Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Gln Asn
        275                 280                 285

Pro Pro Glu Asp Ile Ser Ser Asn Arg Ile Tyr Arg Ile Leu Glu Met
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Lys Arg Leu Glu His Asp Phe Gly Lys Val Thr Lys Gln
450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
        515                 520                 525

Leu Ala Arg Gly Gln Pro Leu
530                 535

<210> SEQ ID NO 109
<211> LENGTH: 549
<212> TYPE: PRT
<213> ORGANISM: Adeno-associated virus 5

<400> SEQUENCE: 109

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30
```

-continued

```
Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
 50                  55                  60

Tyr Glu Trp Asn Lys Phe Ser Lys Gln Glu Ser Lys Phe Phe Val Gln
 65                  70                  75                  80

Phe Glu Lys Gly Ser Glu Tyr Phe His Leu His Thr Leu Val Glu Thr
                 85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
                115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
                180                 185                 190

Ser Ser Gln Arg Ser Gln Glu Ala Ala Ser Gln Arg Glu Phe Ser Ala
                195                 200                 205

Asp Pro Val Ile Lys Ser Lys Thr Ser Gln Lys Tyr Met Ala Leu Val
                210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
                260                 265                 270

Thr Lys Ser Ala Val Asp Tyr Leu Val Gly Ser Ser Val Pro Glu Asp
                275                 280                 285

Ile Ser Lys Asn Arg Ile Trp Gln Ile Phe Glu Met Asn Gly Tyr Asp
290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
                340                 345                 350

Val Asn Trp Thr Asn Glu Asn Phe Pro Phe Asn Asp Cys Val Asp Lys
                355                 360                 365

Met Leu Ile Trp Trp Glu Glu Gly Lys Met Thr Asn Lys Val Val Glu
370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
                420                 425                 430

His Gln Gln Pro Leu Glu Asp Arg Met Phe Lys Phe Glu Leu Thr Lys
                435                 440                 445

Arg Leu Pro Pro Asp Phe Gly Lys Ile Thr Lys Gln Glu Val Lys Asp
```

```
                    450                 455                 460
Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                    485                 490                 495

Lys Arg Pro Leu Gly Asp Val Thr Asn Thr Ser Tyr Lys Ser Leu Glu
                500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Leu
        530                 535                 540

Val Gly Pro Ser Trp
545

<210> SEQ ID NO 110
<211> LENGTH: 536
<212> TYPE: PRT
<213> ORGANISM: Adeno-associated virus 6

<400> SEQUENCE: 110

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270
```

```
Ile Met Ala Leu Thr Lys Ser Ala Pro Asp Tyr Leu Val Gly Pro Ala
            275                 280                 285

Pro Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Leu Ala Arg Gly Gln Pro Leu
            530                 535

<210> SEQ ID NO 111
<211> LENGTH: 536
<212> TYPE: PRT
<213> ORGANISM: Adeno-associated virus 7

<400> SEQUENCE: 111

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110
```

```
Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525
```

```
Asp Leu Ala Arg Gly Gln Pro Leu
    530                 535

<210> SEQ ID NO 112
<211> LENGTH: 538
<212> TYPE: PRT
<213> ORGANISM: Adeno-associated virus 8

<400> SEQUENCE: 112

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Gly Pro Asp His Leu Pro Ala Gly Ser Ser Pro Thr
        115                 120                 125

Leu Pro Asn Trp Phe Ala Val Thr Lys Asp Ala Val Met Ala Pro Ala
    130                 135                 140

Gly Gly Asn Lys Val Val Asp Glu Cys Tyr Ile Pro Asn Tyr Leu Leu
145                 150                 155                 160

Pro Lys Thr Gln Pro Glu Leu Gln Trp Ala Trp Thr Asn Met Glu Glu
                165                 170                 175

Tyr Ile Ser Ala Cys Leu Asn Leu Ala Glu Arg Lys Arg Leu Val Ala
            180                 185                 190

Gln His Leu Thr His Val Ser Gln Thr Gln Glu Gln Asn Lys Glu Asn
        195                 200                 205

Leu Asn Pro Asn Ser Asp Ala Pro Val Ile Arg Ser Lys Thr Ser Ala
    210                 215                 220

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
                245                 250                 255

Ala Ala Ser Asn Ser Arg Ser Gln Ile Lys Ala Ala Leu Asp Asn Ala
            260                 265                 270

Gly Lys Ile Met Ala Leu Thr Lys Ser Ala Pro Asp Tyr Leu Val Gly
        275                 280                 285

Pro Ser Leu Pro Ala Asp Ile Thr Gln Asn Arg Ile Tyr Arg Ile Leu
    290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
                325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
        355                 360                 365
```

Asn Asp Cys Val Asp Lys Met Val Ile Trp Trp Glu Glu Gly Lys Met
370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
            405                 410                 415

Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
            435                 440                 445

Lys Phe Glu Leu Thr Arg Arg Leu Glu His Asp Phe Gly Lys Val Thr
450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
            485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Gly Ala Pro Val Asp
            515                 520                 525

Phe Ala Asp Leu Ala Arg Gly Gln Pro Leu
530                 535

<210> SEQ ID NO 113
<211> LENGTH: 623
<212> TYPE: PRT
<213> ORGANISM: Adeno-associated virus 1

<400> SEQUENCE: 113

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn

```
            195                 200                 205
Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ala
                275                 280                 285

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
                500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
    530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
                580                 585                 590

Ala Ile His His Leu Leu Gly Arg Ala Pro Glu Ile Ala Cys Ser Ala
                595                 600                 605

Cys Asp Leu Val Asn Val Asp Leu Asp Asp Cys Val Ser Glu Gln
                610                 615                 620
```

<210> SEQ ID NO 114
<211> LENGTH: 621
<212> TYPE: PRT
<213> ORGANISM: Adeno-associated virus 2

<400> SEQUENCE: 114

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
```

370                 375                 380
Lys Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
                610                 615                 620

<210> SEQ ID NO 115
<211> LENGTH: 624
<212> TYPE: PRT
<213> ORGANISM: Adeno-associated virus 3A

<400> SEQUENCE: 115

Met Pro Gly Phe Tyr Glu Ile Val Leu Lys Val Pro Ser Asp Leu Asp
1               5                   10                  15

Glu Arg Leu Pro Gly Ile Ser Asn Ser Phe Val Asn Trp Val Ala Glu
                20                  25                  30

Lys Glu Trp Asp Val Pro Pro Asp Ser Asp Met Asp Pro Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

-continued

```
Pro Asn Trp Phe Ala Val Thr Lys Thr Arg Asn Gly Ala Gly Gly
130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Asn Lys Glu Asn Gln Asn
                195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Ser Asn
275                 280                 285

Pro Pro Glu Asp Ile Thr Lys Asn Arg Ile Tyr Gln Ile Leu Glu Leu
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Glu Phe
                435                 440                 445

Glu Leu Thr Arg Arg Leu Asp His Asp Phe Gly Lys Val Thr Lys Gln
450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
                500                 505                 510

Ala Gln Pro Thr Thr Ser Asp Ala Glu Ala Pro Ala Asp Tyr Ala Asp
                515                 520                 525

Arg Tyr Gln Asn Lys Cys Ser Arg His Val Gly Met Asn Leu Met Leu
530                 535                 540

Phe Pro Cys Lys Thr Cys Glu Arg Met Asn Gln Ile Ser Asn Val Cys
```

```
                  545                  550                   555                  560
           Phe Thr His Gly Gln Arg Asp Cys Gly Glu Cys Phe Pro Gly Met Ser
                           565                   570                  575

Glu Ser Gln Pro Val Ser Val Val Lys Lys Thr Tyr Gln Lys Leu
                       580                    585                  590

Cys Pro Ile His His Ile Leu Gly Arg Ala Pro Glu Ile Ala Cys Ser
                       595                    600                  605

Ala Cys Asp Leu Ala Asn Val Asp Leu Asp Asp Cys Val Ser Glu Gln
                       610                    615                  620

<210> SEQ ID NO 116
<211> LENGTH: 624
<212> TYPE: PRT
<213> ORGANISM: Adeno-associated virus 3B

<400> SEQUENCE: 116

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
                20                  25                  30

Lys Glu Trp Glu Leu Pro Pro Asp Ser Asp Met Asp Pro Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
        130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Ser Asn
            275                 280                 285

Pro Pro Glu Asp Ile Thr Lys Asn Arg Ile Tyr Gln Ile Leu Glu Leu
        290                 295                 300
```

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
            485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
            515                 520                 525

Arg Tyr Gln Asn Lys Cys Ser Arg His Val Gly Met Asn Leu Met Leu
530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
            565                 570                 575

Glu Ser Gln Pro Val Ser Val Val Lys Lys Lys Thr Tyr Gln Lys Leu
            580                 585                 590

Cys Pro Ile His His Ile Leu Gly Arg Ala Pro Glu Ile Ala Cys Ser
            595                 600                 605

Ala Cys Asp Leu Ala Asn Val Asp Leu Asp Asp Cys Val Ser Glu Gln
610                 615                 620

<210> SEQ ID NO 117
<211> LENGTH: 623
<212> TYPE: PRT
<213> ORGANISM: Adeno-associated virus 4

<400> SEQUENCE: 117

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Glu Phe Leu
    50                  55                  60

```
Val Glu Trp Arg Arg Val Ser Lys Ala Pro Glu Ala Leu Phe Phe Val
 65                  70                  75                  80

Gln Phe Glu Lys Gly Asp Ser Tyr Phe His Leu His Ile Leu Val Glu
                 85                  90                  95

Thr Val Gly Val Lys Ser Met Val Gly Arg Tyr Val Ser Gln Ile
            100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
            130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Gln Asn
            275                 280                 285

Pro Pro Glu Asp Ile Ser Ser Asn Arg Ile Tyr Arg Ile Leu Glu Met
            290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Lys Arg Leu Glu His Asp Phe Gly Lys Val Thr Lys Gln
            450                 455                 460

Glu Val Lys Asp Phe Phe Arg Trp Ala Ser Asp His Val Thr Glu Val
465                 470                 475                 480
```

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
                565                 570                 575

Ser Gln Pro Val Ser Val Val Arg Lys Arg Thr Tyr Gln Lys Leu Cys
            580                 585                 590

Pro Ile His His Ile Met Gly Arg Ala Pro Glu Val Ala Cys Ser Ala
            595                 600                 605

Cys Glu Leu Ala Asn Val Asp Leu Asp Asp Cys Asp Met Glu Gln
            610                 615                 620

<210> SEQ ID NO 118
<211> LENGTH: 610
<212> TYPE: PRT
<213> ORGANISM: Adeno-associated virus 5

<400> SEQUENCE: 118

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Ala Asn Lys Val
        130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
            195                 200                 205

Asp Pro Val Ile Lys Ser Lys Thr Ser Gln Lys Tyr Met Ala Leu Val
        210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
            245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
            290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
            370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
            405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
            450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
            485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
            530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
            565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
            595                 600                 605

Glu Gln
610

<210> SEQ ID NO 119
<211> LENGTH: 623
<212> TYPE: PRT
<213> ORGANISM: Adeno-associated virus 6

<400> SEQUENCE: 119

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415
```

```
Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Arg Tyr Gln Asn Lys Cys Ser Arg His Ala Gly Met Leu Gln Met
530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
            595                 600                 605

Cys Asp Leu Val Asn Val Asp Leu Asp Asp Cys Val Ser Glu Gln
            610                 615                 620

<210> SEQ ID NO 120
<211> LENGTH: 623
<212> TYPE: PRT
<213> ORGANISM: Adeno-associated virus 7

<400> SEQUENCE: 120

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
```

```
                165                 170                 175
Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
    530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590
```

```
Ala Ile His His Leu Leu Gly Arg Ala Pro Glu Ile Ala Cys Ser Ala
            595                 600                 605

Cys Asp Leu Val Asn Val Leu Asp Asp Cys Val Ser Glu Gln
610                 615                 620
```

<210> SEQ ID NO 121
<211> LENGTH: 625
<212> TYPE: PRT
<213> ORGANISM: Adeno-associated virus 8

<400> SEQUENCE: 121

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Gly Pro Asp His Leu Pro Ala Gly Ser Ser Pro Thr
        115                 120                 125

Leu Pro Asn Trp Phe Ala Val Thr Lys Asp Ala Val Met Ala Pro Ala
    130                 135                 140

Gly Gly Asn Lys Val Val Asp Glu Cys Tyr Ile Pro Asn Tyr Leu Leu
145                 150                 155                 160

Pro Lys Thr Gln Pro Glu Leu Gln Trp Ala Trp Thr Asn Met Glu Glu
                165                 170                 175

Tyr Ile Ser Ala Cys Leu Asn Leu Ala Glu Arg Lys Arg Leu Val Ala
            180                 185                 190

Gln His Leu Thr His Val Ser Gln Thr Gln Glu Gln Asn Lys Glu Asn
        195                 200                 205

Leu Asn Pro Asn Ser Asp Ala Pro Val Ile Arg Ser Lys Thr Ser Ala
    210                 215                 220

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
                245                 250                 255

Ala Ala Ser Asn Ser Arg Ser Gln Ile Lys Ala Ala Leu Asp Asn Ala
            260                 265                 270

Gly Lys Ile Met Ala Leu Thr Lys Ser Ala Pro Asp Tyr Leu Val Gly
        275                 280                 285

Pro Ser Leu Pro Ala Asp Ile Thr Gln Asn Arg Ile Tyr Arg Ile Leu
    290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
                325                 330                 335

Pro Ala Thr Thr Gly Lys Thr Asn Ile Ala Glu Ala Ile Ala His Ala
```

```
                340             345             350
    Val Pro Phe Tyr Gly Cys Val Asn Trp Thr Asn Glu Asn Phe Pro Phe
                355                 360                 365

Asn Asp Cys Val Asp Lys Met Val Ile Trp Trp Glu Gly Lys Met
        370                 375                 380

Thr Ala Lys Val Val Glu Ser Ala Lys Ala Ile Leu Gly Gly Ser Lys
    385                 390                 395                 400

Val Arg Val Asp Gln Lys Cys Lys Ser Ser Ala Gln Ile Asp Pro Thr
                    405                 410                 415

Pro Val Ile Val Thr Ser Asn Thr Asn Met Cys Ala Val Ile Asp Gly
                420                 425                 430

Asn Ser Thr Thr Phe Glu His Gln Gln Pro Leu Gln Asp Arg Met Phe
            435                 440                 445

Lys Phe Glu Leu Thr Arg Arg Leu Glu His Asp Phe Gly Lys Val Thr
                450                 455                 460

Lys Gln Glu Val Lys Glu Phe Phe Arg Trp Ala Ser Asp His Val Thr
    465                 470                 475                 480

Glu Val Ala His Glu Phe Tyr Val Arg Lys Gly Gly Ala Ser Lys Arg
                    485                 490                 495

Pro Ala Pro Asp Asp Ala Asp Lys Ser Glu Pro Lys Arg Ala Cys Pro
                500                 505                 510

Ser Val Ala Asp Pro Ser Thr Ser Asp Ala Glu Gly Ala Pro Val Asp
            515                 520                 525

Phe Ala Asp Arg Tyr Gln Asn Lys Cys Ser Arg His Ala Gly Met Leu
        530                 535                 540

Gln Met Leu Phe Pro Cys Lys Thr Cys Glu Arg Met Asn Gln Asn Phe
    545                 550                 555                 560

Asn Ile Cys Phe Thr His Gly Val Arg Asp Cys Ser Glu Cys Phe Pro
                    565                 570                 575

Gly Val Ser Glu Ser Gln Pro Val Val Arg Lys Arg Thr Tyr Arg Lys
                580                 585                 590

Leu Cys Ala Ile His His Leu Leu Gly Arg Ala Pro Glu Ile Ala Cys
            595                 600                 605

Ser Ala Cys Asp Leu Val Asn Val Asp Leu Asp Asp Cys Val Ser Glu
        610                 615                 620

Gln
    625

<210> SEQ ID NO 122
<211> LENGTH: 622
<212> TYPE: PRT
<213> ORGANISM: Artificial
<220> FEATURE:
<223> OTHER INFORMATION: AAV Rep78 consensus sequence
<220> FEATURE:
<221> NAME/KEY: MISC_FEATURE
<222> LOCATION: (118)..(118)
<223> OTHER INFORMATION: Xaa can be Gln, Lys, Pro or Thr
<220> FEATURE:
<221> NAME/KEY: MISC_FEATURE
<222> LOCATION: (119)..(119)
<223> OTHER INFORMATION: Xaa can be Arg, Asp, Thr or Val
<220> FEATURE:
<221> NAME/KEY: MISC_FEATURE
<222> LOCATION: (287)..(287)
<223> OTHER INFORMATION: Xaa can be Gln, Pro or Ser
<220> FEATURE:
<221> NAME/KEY: MISC_FEATURE
<222> LOCATION: (541)..(541)
<223> OTHER INFORMATION: Xaa can be Asn, Asp, Ile and Leu
```

```
<220> FEATURE:
<221> NAME/KEY: MISC_FEATURE
<222> LOCATION: (557)..(557)
<223> OTHER INFORMATION: Xaa can be Lys, Phe, Ser or Val
<220> FEATURE:
<221> NAME/KEY: MISC_FEATURE
<222> LOCATION: (565)..(565)
<223> OTHER INFORMATION: Xaa can be Gln, Thr or Val
<220> FEATURE:
<221> NAME/KEY: MISC_FEATURE
<222> LOCATION: (569)..(569)
<223> OTHER INFORMATION: Xaa can be Ala, Gln, Gly, Leu or Ser
<220> FEATURE:
<221> NAME/KEY: MISC_FEATURE
<222> LOCATION: (580)..(580)
<223> OTHER INFORMATION: Xaa can be Pro or Ser
<220> FEATURE:
<221> NAME/KEY: MISC_FEATURE
<222> LOCATION: (588)..(588)
<223> OTHER INFORMATION: Xaa can be Arg or Gln
<220> FEATURE:
<221> NAME/KEY: MISC_FEATURE
<222> LOCATION: (592)..(592)
<223> OTHER INFORMATION: Xaa can be Ala, Pro or Tyr

<400> SEQUENCE: 122

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Xaa Xaa Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Xaa Ser
```

```
            275                 280                 285
Pro Pro Glu Asp Ile Ser Thr Asn Arg Ile Tyr Arg Ile Leu Ala Leu
290                 295                 300
Asn Gly Tyr Asp Pro Ala Tyr Ala Gly Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
                355                 360                 365
Cys Val Asp Lys Met Val Ile Trp Trp Glu Glu Gly Lys Met Thr Ala
                370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
                435                 440                 445
Glu Leu Thr Arg Arg Leu Glu His Asp Phe Gly Lys Val Thr Lys Gln
450                 455                 460
Glu Val Lys Glu Phe Phe Arg Trp Ala Ser Asp His Val Thr Glu Val
465                 470                 475                 480
Ala His Glu Phe Tyr Val Arg Lys Gly Gly Ala Lys Lys Arg Pro Ala
                485                 490                 495
Pro Asp Asp Ala Asp Lys Ser Glu Pro Lys Arg Ala Cys Pro Ser Val
                500                 505                 510
Ala Asp Pro Ser Thr Ser Asp Ala Glu Ala Pro Val Asp Phe Ala Asp
                515                 520                 525
Arg Tyr Gln Asn Lys Cys Ser Arg His Ala Gly Met Xaa Gln Met Leu
                530                 535                 540
Phe Pro Cys Lys Thr Cys Glu Arg Met Asn Gln Asn Xaa Asn Ile Cys
545                 550                 555                 560
Phe Thr His Gly Xaa Arg Asp Cys Xaa Glu Cys Phe Pro Gly Val Ser
                565                 570                 575
Glu Ser Gln Xaa Val Val Arg Lys Arg Thr Tyr Xaa Lys Leu Cys Xaa
                580                 585                 590
Ile His His Leu Leu Gly Arg Ala Pro Glu Ile Ala Cys Ser Ala Cys
                595                 600                 605
Asp Leu Val Asn Val Asp Leu Asp Cys Val Ser Glu Gln
                610                 615                 620

<210> SEQ ID NO 123
<211> LENGTH: 122
<212> TYPE: DNA
<213> ORGANISM: Snake parvovirus

<400> SEQUENCE: 123
cgccccaccc ctagtgatcg cgcgcgctct ctcttggggc ctgacggccg aaggccgtca    60
gctgccgagc ttcgctcggc aggccccaag agagagcgcg cgcgatcact aggggtgggg   120
cg                                                                  122
```

<210> SEQ ID NO 124
<211> LENGTH: 6107
<212> TYPE: DNA
<213> ORGANISM: Artificial
<220> FEATURE:
<223> OTHER INFORMATION: Snake ITR eGFP vector sequence

<400> SEQUENCE: 124

| | | | | | |
|---|---|---|---|---|---|
| gtggcacttt | tcggggaaat | gtgcgcggaa | cccctatttg | tttattttc | taaatacatt | 60 |
| caaatatgta | tccgctcatg | agacaataac | cctgataaat | gcttcaataa | tattgaaaaa | 120 |
| ggaagagtat | gagtattcaa | catttccgtg | tcgcccttat | tcccttttt | gcggcatttt | 180 |
| gccttcctgt | ttttgctcac | ccagaaacgc | tggtgaaagt | aaaagatgct | gaagatcagt | 240 |
| tgggtgcacg | agtgggttac | atcgaactgg | atctcaacag | cggtaagatc | cttgagagtt | 300 |
| ttcgccccga | agaacgtttt | ccaatgatga | gcacttttaa | agttctgcta | tgtggcgcgg | 360 |
| tattatcccg | tattgacgcc | gggcaagagc | aactcggtcg | ccgcatacac | tattctcaga | 420 |
| atgacttggt | tgagtactca | ccagtcacag | aaaagcatct | tacggatggc | atgacagtaa | 480 |
| gagaattatg | cagtgctgcc | ataaccatga | gtgataacac | tgcggccaac | ttacttctga | 540 |
| caacgatcgg | aggaccgaag | gagctaaccg | cttttttgca | caacatgggg | gatcatgtaa | 600 |
| ctcgccttga | tcgttgggaa | ccggagctga | atgaagccat | accaaacgac | gagcgtgaca | 660 |
| ccacgatgcc | tgtagcaatg | gcaacaacgt | tgcgcaaact | attaactggc | gaactactta | 720 |
| ctctagcttc | ccggcaacaa | ttaatagact | ggatggaggc | ggataaagtt | gcaggaccac | 780 |
| ttctgcgctc | ggcccttccg | gctggctggt | ttattgctga | taaatctgga | gccggtgagc | 840 |
| gtgggtctcg | cggtatcatt | gcagcactgg | ggccagatgg | taagccctcc | cgtatcgtag | 900 |
| ttatctacac | gacggggagt | caggcaacta | tggatgaacg | aaatagacag | atcgctgaga | 960 |
| taggtgcctc | actgattaag | cattggtaac | tgtcagacca | agtttactca | tatatacttt | 1020 |
| agattgattt | aaaacttcat | ttttaattta | aaaggatcta | ggtgaagatc | cttttttgata | 1080 |
| atctcatgac | caaaatccct | taacgtgagt | tttcgttcca | ctgagcgtca | gaccccgtag | 1140 |
| aaaagatcaa | aggatcttct | tgagatcctt | tttttctgcg | cgtaatctgc | tgcttgcaaa | 1200 |
| caaaaaaacc | accgctacca | gcggtggttt | gtttgccgga | tcaagagcta | ccaactcttt | 1260 |
| ttccgaaggt | aactggcttc | agcagagcgc | agataccaaa | tactgtcctt | ctagtgtagc | 1320 |
| cgtagttagg | ccaccacttc | aagaactctg | tagcaccgcc | tacatacctc | gctctgctaa | 1380 |
| tcctgttacc | agtggctgct | gccagtggcg | ataagtcgtg | tcttaccggg | ttggactcaa | 1440 |
| gacgatagtt | accggataag | gcgcagcggt | cgggctgaac | ggggggttcg | tgcacacagc | 1500 |
| ccagcttgga | gcgaacgacc | tacaccgaac | tgagatacct | acagcgtgag | ctatgagaaa | 1560 |
| gcgccacgct | tcccgaaggg | agaaaggcgg | acaggtatcc | ggtaagcggc | agggtcggaa | 1620 |
| caggagagcg | cacgagggag | cttccagggg | gaaacgcctg | gtatctttat | agtcctgtcg | 1680 |
| ggtttcgcca | cctctgactt | gagcgtcgat | ttttgtgatg | ctcgtcaggg | gggcggagcc | 1740 |
| tatggaaaaa | cgccagcaac | gcggcctttt | tacggttcct | ggccttttgc | tggccttttg | 1800 |
| ctcacatgtt | ctttcctgcg | ttatcccctg | attctgtgga | taaccgtatt | accgcctttg | 1860 |
| agtgagctga | taccgctcgc | cgcagccgaa | cgaccgagcg | cagcgagtca | gtgagcgagg | 1920 |
| aagcggaaga | gcgcccaata | cgcaaaccgc | ctctccccgc | gcgttggccg | attcattaat | 1980 |
| gcagctggca | cgacaggttt | cccgactgga | aagcgggcag | tgagcgcaac | gcaattaatg | 2040 |
| tgagttagct | cactcattag | gcaccccagg | ctttacactt | tatgcttccg | gctcgtatgt | 2100 |

```
tgtgtggaat tgtgagcgga taacaatttc acacaggaaa cagctatgac catgattacg    2160
ccaagcgcgc aattaaccct cactaaaggg aacaaaagct gggtaccggg ccccccctcg    2220
aggtcgacgg tatcgataag cttgatcgcc caccccctag tgatcgcgcg cgctctctct    2280
tggggcctga cggccgaagg ccgtcagctg ccgagcttcg ctcggcaggc cccaagagag    2340
agcgcgcgcg atcactaggg gtggggcgag tgccctgctc aacgggtttt ttggtgggcg    2400
gagcaatgac gtcagcggac atgtctggac atgtctttga gcaagtccat ataaggagtt    2460
ccgccggata tgcaaatgag caatcgcgca aagcattttg ggtagtcacc atgaataaaa    2520
aggacagcaa gaaagatgac gccccataat tttaatagga attttaacca tgttcttttcc   2580 tgcgttatcc cctgattctg tggataaccg tattaccgcc tttgagtgag ctgataccgc    2640
tcgccgcagc cgaacgaccg agcgcagcga gtcagtgagc gaggaagcgg aagagcgccc    2700
aatacgcaaa ccgcctctcc ccgcgcgttg gccgattcat taatgcagct ggcacgacag    2760
gtttcccgac tggaaagcgg gcagtgagcg caacgcaatt aatgtgagtt agctcactca    2820
ttaggcaccc caggctttac actttatgct tccggctcgt atgttgtgtg gaattgtgag    2880
cggataacaa tttcacacag gaaacagcta tgaccatgat tacgaattgt tgttgttaac    2940
ttgtttattg cagcttataa tggttacaaa taaagcaata gcatcacaaa tttcacaaat    3000
aaagcatttt tttcactgca ttctagttgt ggtttgtcca aactcatcaa tgtatcttat    3060
catgtctgga tccccgcggc cgctttactt gtacagctcg tccatgccga gagtgatccc    3120
ggcggcggtc acgaactcca gcaggaccat gtgatcgcgc ttctcgttgg ggtcttttgct  3180 cagggcggac tgggtgctca ggtagtggtt gtcgggcagc agcacggggc cgtcgccgat    3240
gggggtgttc tgctggtagt ggtcggcgag ctgcacgctg ccgtcctcga tgttgtggcg    3300
gatcttgaag ttcaccttga tgccgttctt ctgcttgtcg gccatgatat agacgttgtg    3360
gctgttgtag ttgtactcca gcttgtgccc caggatgttg ccgtcctcct tgaagtcgat    3420
gcccttcagc tcgatgcggt tcaccagggt gtcgccctcg aacttcacct cggcgcgggt    3480
cttgtagttg ccgtcgtcct tgaagaagat ggtgcgctcc tggacgtagc cttcgggcat    3540
ggcggacttg aagaagtcgt gctgcttcat gtggtcgggg tagcggctga agcactgcac    3600
gccgtaggtc agggtggtca cgagggtggg ccagggcacg ggcagcttgc cggtggtgca    3660
gatgaacttc agggtcagct tgccgtaggt ggcatcgccc tcgccctcgc cggacacgct    3720
gaacttgtgg ccgtttacgt cgccgtccag ctcgaccagg atgggcacca ccccggtgaa    3780
cagctcctcg cccttgctca ccatggtggc gaccggtgga tcccgggccg cgggtacaat    3840
tccgcagctt ttagagcaga agtaacactt ccgtacaggc ctagaagtaa aggcaacatc    3900
cactgaggag cagttctttg atttgcacca ccaccggatc cgggacctga aataaaagac    3960
aaaaagacta aacttaccag ttaactttct ggttttttcag ttcctcgagt accggatcct  4020
ctagagtccg gaggctggat cggtcccggt gtcttctatg gaggtcaaaa cagcgtggat    4080
ggcgtctcca ggcgatctga cggttcacta aacgagctct gcttatatag acctcccacc    4140
gtacacgcct accgcccatt tgcgtcaatg gggcggagtt gttacgacat tttggaaagt    4200
cccgttgatt ttggtgccaa acaaactcc cattgacgtc aatggggtgg agacttggaa    4260
atccccgtga gtcaaaccgc tatccacgcc cattgatgta ctgccaaaac cgcatcacca    4320
tggtaatagc gatgactaat acgtagatgt actgccaagt aggaaagtcc cataaggtca    4380
tgtactgggc ataatgccag gcgggccatt taccgtcatt gacgtcaata gggggcgtac    4440
```

```
ttggcatatg atacacttga tgtactgcca agtgggcagt ttaccgtaaa tactccaccc    4500
attgacgtca atgggaaagtc cctattggcg ttactattga cgtcaatggg cgggggtcgt   4560
```



```
ttggcatatg atacacttga tgtactgcca agtgggcagt ttaccgtaaa tactccaccc    4500
attgacgtca atgaaagtc  cctattggcg ttactattga cgtcaatggg cgggggtcgt    4560
tgggcggtca gccaggcggg ccatttaccg taagttatgt aacgggtacc cggggatcct    4620
ctagagtcga cctgcagtaa acagaacaat tgaagacgaa atacagggta ccaataattt    4680
tggtaatgct agaaataaca ttgttgctat caatcaacaa acgaaaggaa caaatccaac    4740
aacaggtagt acatctcaat ttgagacaat gccaggtatg gtgtggtcta atagagacat    4800
ttacttacag gggcctattt gggctaaaat tccaaataca gatggacatt ttcatccttc    4860
tcccagaatg ggtggttttg gattaaaaca tcctccgcct atgattctga tcaaaaatac    4920
accagttcct gctgatcctc aactaccttt caatccaatg ccacagacta gtttcattac    4980
tgaatacagt acaggacaag taactgttga aatgttgtgg gaggtacaga aagaatcctc    5040
caaaagatgg aatccagaag tacagtttac ttccaatttt ggaacttcag atccagctgt    5100
tgatggaata ccgtttggaa ttaataattt gggtacttat gttgaatcta gacctattgg    5160
aactcgttat atttctaaac acttgtaaat aataaaaatt gtcaaatttg cactaagaat    5220
tgttgtcacg tggttgttta catgcttgct aaaacacgcc caccaaaaaa cccgttgagc    5280
agggcactcg ccccaccccct agtgatcgcg cgcgctctct cttggggcct gccgagcgaa    5340
gctcggcagc tgacggcctt cggccgtcag gccccaagag agagcgcgcg cgatcactag    5400
gggtggggcg gggggatcca ctagttctag agcggccgcc accgcggtgg agctccaatt    5460
cgccctatag tgagtcgtat tacgcgcgct cactggccgt cgttttacaa cgtcgtgact    5520
gggaaaaccc tggcgttacc caacttaatc gccttgcagc acatccccct ttcgccagct    5580
ggcgtaatag cgaagaggcc cgcaccgatc gcccttccca acagttgcgc agcctgaatg    5640
gcgaatggga cgcgccctgt agcggcgcat taagcgcggc gggtgtggtg gttacgcgca    5700
gcgtgaccgc tacacttgcc agcgccctag cgcccgctcc tttcgctttc ttcccttcct    5760
ttctcgccac gttcgccggc tttccccgtc aagctctaaa tcgggggctc cctttagggt    5820
tccgatttag tgctttacgg cacctcgacc ccaaaaaact tgattagggt gatggttcac    5880
gtagtgggcc atcgccctga tagacggttt ttcgcccttt gacgttggag tccacgttct    5940
ttaatagtgg actcttgttc caaactggaa caacactcaa ccctatctcg gtctattctt    6000
ttgatttata agggattttg ccgatttcgg cctattggtt aaaaaatgag ctgatttaac    6060
aaaaatttaa cgcgaatttt aacaaaatat taacgcttac aatttag               6107

<210> SEQ ID NO 125
<211> LENGTH: 7302
<212> TYPE: DNA
<213> ORGANISM: Artificial
<220> FEATURE:
<223> OTHER INFORMATION: pSnRepCap2 plasmid sequence

<400> SEQUENCE: 125
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggaaat     240
tgtaaacgtt aatattttgt taaaattcgc gttaaatttt tgttaaatca gctcattttt     300
taaccaatag gccgaaatcg gcaaaatccc ttataaatca aagaataga ccgagatagg      360 gttgagtgtt gttccagttt ggaacaagag tccactatta agaacgtgg actccaacgt      420
```

```
caaagggcga aaaaccgtct atcagggcga tggcccacta cgtgaaccat caccctaatc    480
aagttttttg gggtcgaggt gccgtaaagc actaaatcgg aaccctaaag ggagcccccg    540
atttagagct tgacggggaa agccggcgaa cgtggcgagg aaggaaggga agaaagcgaa    600
aggagcgggc gctagggcgc tggcaagtgt agcggtcacg ctgcgcgtaa ccaccacacc    660
cgccgcgctt aatgcgccgc tacagggcgc gtcgcgccat tcgccattca ggctgcgcaa    720
ctgttgggaa gggcgatcgg tgcgggcctc ttcgctatta cgccagctgg cgaaagggg    780 atgtgctgca aggcgattaa gttgggtaac gccagggttt cccagtcac gacgttgtaa     840 aacgacggcc agtgaattgt aatacgactc actatagggc gaattcgagc tcgcagcgga    900
catgtctgga catgtctttg agcaagtcca tataaggagt ccgccggat atgcaaatga      960 gcaatcgcgc aaagcatttt gggtagtcac catgaataaa aaggacagca agaaagatga    1020
cgccccataa ttttaatagg aattttaacc atggcgtttt acgaggttgt gtttcgtttg    1080
ccaagagaca ataacaactt gttggatgaa gatagatatc agccagagtt gaaagaagaa    1140
gatgactggc ctgaggaata tttaaccagt gaagatgcca gctttatcgg actagcgtat    1200
gctgtgctaa gtgaaattcg gagattcttt ggaaaggaac tacaatggtt tgcccaggtt    1260
gaatggtgtc ctactgctgg ttaccacatg catgttttgt tgaaccatcc taagctgagt    1320
aaccagactt atgaagaaa ggtcaatgaa ctggcttgcc gtatagtcga tacctttggc      1380
ctaattaatc cagaagaagt catcagtacc cattatgtta aaagcaacta tggacataaa    1440
aaggtgagag tcattcacct agagtcttat ttgaagaact acttttcag aaagacttta      1500 gctcctccca attataccga ggaaggagac tataaaagag aggaagaagt cgtgctgtgg    1560
gcatttacga atatcgtcgc ttggaagcca ttcgtgcgga atctcatcaa gagatcggag    1620
ctagcgactg ttcctaagca accagagaat ccggcggag acggaccggc acctcgagtg     1680
actgcaggaa cccgccattt tatggaaacc atcgactggt tggtgaaaca tggaattact    1740
acagaacgag aattctgcca cgccaaccgc cctttgtacc tgtctatgct ggcttctact    1800
tcgggtgctg gcagattaa aagagcgctg accaggcga acacatgat gaccagcacc        1860 atgtcagcag aggattacct gacaacagaa gaggatgtga tcgaaccacc tactgaaaat    1920
agaatctaca agattatgaa actgaatcgc tatgatccag aactagcagc tgctctcttc    1980
tacggctgga cctgcaagaa ctttggcaag agaaacacca tctggctgta tggtccagct    2040
actaccggca aaaccatcat cgctcaagct attgcacatg ctgttaaact gtttgctggt    2100
gttaattgga ctaatgaaaa cttttccttc tgtaactgtc cagggaaact gcttatctgg    2160
tgggaggagg gcaagatgac aaacaaaatg gtggagacgg ctaaatgtat actgggggga    2220
tctgctgtac ctgtagacat caaaggcaaa cccgctgaaa tgtgtcctca acaccctgt      2280 attattacta gcaatactaa catgtgtcaa gtatatgatg gtaatagttc tagctttgag    2340
caccaagaac ccctagagga acgcatgttt atgttcagac ttaatactaa actgccatcg    2400
acctttggca agatcacaga agaggaagtc aaacagttta ttacctgggg gaggagctta    2460
aaggttcaag ttccacatca gttcagagtg cctaccacag gagagtataa aaggccagcc    2520
cccgaggcga aagctcattc ttcggatgag ccgccaaaag agaaggtcgc gcgtattgat    2580
gactctctaa ccaggtatgt taacaatatt gatgagtcag ctaccagtag agaaatgttt    2640
ctagagattg ctaatactaa tcaatgtatg ttgcatcatt gcttttcttg taccgaatgt    2700
tatcctgaat tgcttgatga catggacaag gaacaataaa cttactgata acagatatgg    2760
```

-continued

```
ctgccgatgg ttatcttcca gattggctcg aggacactct ctctgaagga ataagacagt   2820
ggtggaagct caaacctggc ccaccaccac caaagcccgc agagcggcat aaggacgaca   2880
gcaggggtct tgtgcttcct gggtacaagt acctcggacc cttcaacgga ctcgacaagg   2940
gagagccggt caacgaggca gacgccgcgg ccctcgagca cgacaaagcc tacgaccggc   3000
agctcgacag cggagacaac ccgtacctca agtacaacca cgccgacgcg gagtttcagg   3060
agcgccttaa agaagatacg tcttttgggg gcaacctcgg acgagcagtc ttccaggcga   3120
aaaagagggt tcttgaacct ctgggcctgg ttgaggaacc tgttaagacg gctccgggaa   3180
aaaagaggcc ggtagagcac tctcctgtgg agccagactc ctcctcggga accggaaagg   3240
cgggccagca gcctgcaaga aaaagattga attttggtca gactggagac gcagactcag   3300
tacctgaccc ccagcctctc ggacagccac cagcagcccc ctctggtctg ggaactaata   3360
cgatggctac aggcagtggc gcaccaatgg cagacaataa cgagggcgcc gacggagtgg   3420
gtaattcctc gggaaattgg cattgcgatt ccacatggat gggcgacaga gtcatcacca   3480
ccagcacccg aacctgggcc ctgcccacct acaacaacca cctctacaaa caaatttcca   3540
gccaatcagg agcctcgaac gacaatcact actttggcta cagcacccct tgggggtatt   3600
ttgacttcaa cagattccac tgccactttt caccacgtga ctggcaaaga ctcatcaaca   3660
acaactgggg attccgaccc aagagactca acttcaagct ctttaacatt caagtcaaag   3720
aggtcacgca gaatgacggt acgacgacga ttgccaataa ccttaccagc acggttcagg   3780
tgtttactga ctcggagtac cagctcccgt acgtcctcgg ctcggcgcat caaggatgcc   3840
tcccgccgtt cccagcagac gtcttcatgg tgccacagta tggatacctc accctgaaca   3900
acgggagtca ggcagtagga cgctcttcat tttactgcct ggagtacttt ccttctcaga   3960
tgctgcgtac cggaaacaac tttaccttca gctacacttt tgaggacgtt cctttccaca   4020
gcagctacgc tcacagccag agtctggacc gtctcatgaa tcctctcatc gaccagtacc   4080
tgtattactt gagcagaaca aacactccaa gtggaaccac cacgcagtca aggcttcagt   4140
tttctcaggc cggagcgagt gacattcggg accagtctag gaactggctt cctggaccct   4200
gttaccgcca gcagcgagta tcaaagacat ctgcggataa caacaacagt gaatactcgt   4260
ggactggagc taccaagtac cacctcaatg gcagagactc tctggtgaat ccgggcccgg   4320
ccatggcaag ccacaaggac gatgaagaaa agtttttttcc tcagagcggg gttctcatct   4380
ttgggaagca aggctcagag aaaacaaatg tggacattga aaaggtcatg attacagacg   4440
aagaggaaat caggacaacc aatcccgtgg ctacggagca gtatggttct gtatctacca   4500
acctccagag aggcaacaga caagcagcta ccgcagatgt caacacacaa ggcgttcttc   4560
caggcatggt ctggcaggac agagatgtgt accttcaggg gcccatctgg gcaaagattc   4620
cacacacgga cggacatttt cacccctctc ccctcatggg tggattcgga cttaaacacc   4680
ctcctccaca gattctcatc aagaacaccc cggtacctgc gaatccttcg accaccttca   4740
gtgcggcaaa gtttgcttcc ttcatcacac agtactccac gggacaggtc agcgtggaga   4800
tcgagtggga gctgcagaag gaaaacagca aacgctggaa tcccgaaatt cagtacactt   4860
ccaactacaa caagtctgtt aatgtggact ttactgtgga cactaatggc gtgtattcag   4920
agcctcgccc cattggcacc agatacctga ctcgtaatct gtaattgctt gttaatcaat   4980
aaaccgttta attcgtttca gttgaacttt ggtgtcgcgg ccgctcgata agcttttgtt   5040
ccctttagtg agggttaatt ccgagcttgg cgtaatcatg gtcatagctg tttcctgtgt   5100
gaaattgtta tccgctcaca attccacaca acatacgagc cggaagcata aagtgtaaag   5160
```

```
cctggggtgc ctaatgagtg agctaactca cattaattgc gttgcgctca ctgcccgctt   5220
tccagtcggg aaacctgtcg tgccagctgc attaatgaat cggccaacgc gcggggagag   5280
gcggtttgcg tattgggcgc tcttccgctt cctcgctcac tgactcgctg cgctcggtcg   5340
ttcggctgcg cgagcggta tcagctcact caaaggcggt aatacggtta ccacagaat    5400 caggggataa cgcaggaaag aacatgtgag caaaaggcca gcaaaaggcc aggaaccgta   5460
aaaaggccgc gttgctggcg ttttccata ggctccgccc cctgacgag catcacaaaa    5520 atcgacgctc aagtcagagg tggcgaaacc cgacaggact ataaagatac caggcgtttc   5580
cccctggaag ctccctcgtg cgctctcctg ttccgaccct gccgcttacc ggatacctgt   5640
ccgcctttct cccttcggga agcgtggcgc tttctcatag ctcacgctgt aggtatctca   5700
gttcggtgta ggtcgttcgc tccaagctgg gctgtgtgca cgaaccccc gttcagcccg   5760 accgctgcgc cttatccggt aactatcgtc ttgagtccaa cccggtaaga cacgacttat   5820
cgccactggc agcagccact ggtaacagga ttagcagagc gaggtatgta ggcggtgcta   5880
cagagttctt gaagtggtgg cctaactacg gctacactag aaggacagta tttggtatct   5940
gcgctctgct gaagccagtt accttcggaa aaagagttgg tagctcttga tccggcaaac   6000
aaaccaccgc tggtagcggt ggttttttg tttgcaagca gcagattacg cgcagaaaaa    6060
aaggatctca agaagatcct ttgatctttt ctacggggtc tgacgctcag tggaacgaaa   6120
actcacgtta agggattttg gtcatgagat tatcaaaaag gatcttcacc tagatccttt   6180
taaattaaaa atgaagtttt aaatcaatct aaagtatata tgagtaaact ggtctgaca    6240 gttaccaatg cttaatcagt gaggcaccta tctcagcgat ctgtctattt cgttcatcca   6300
tagttgcctg actccccgtc gtgtagataa ctacgatacg ggagggctta ccatctggcc   6360
ccagtgctgc aatgataccg cgagacccac gctcaccggc tccagattta tcagcaataa   6420
accagccagc cggaagggcc gagcgcagaa gtggtcctgc aactttatcc gcctccatcc   6480
agtctattaa ttgttgccgg gaagctagag taagtagttc gccagttaat agtttgcgca   6540
acgttgttgc cattgctaca ggcatcgtgg tgtcacgctc gtcgtttggt atggcttcat   6600
tcagctccgg ttcccaacga tcaaggcgag ttacatgatc ccccatgttg tgcaaaaaag   6660
cggttagctc cttcggtcct ccgatcgttg tcagaagtaa gttggccgca gtgttatcac   6720
tcatggttat ggcagcactg cataattctc ttactgtcat gccatccgta agatgctttt   6780
ctgtgactgg tgagtactca accaagtcat tctgagaata gtgtatgcgg cgaccgagtt   6840
gctcttgccc ggcgtcaata cgggataata ccgcgccaca tagcagaact ttaaaagtgc   6900
tcatcattgg aaaacgttct cggggcgaa aactctcaag gatcttaccg ctgttgagat    6960
ccagttcgat gtaacccact cgtgcaccca actgatcttc agcatctttt actttcacca   7020
gcgtttctgg gtgagcaaaa acaggaaggc aaaatgccgc aaaaaaggga ataagggcga   7080
cacgaaaatg ttgaatactc atactcttcc ttttcaata ttattgaagc atttatcagg    7140
gttattgtct catgagcgga tacatatttg aatgtattta gaaaaataaa caaataggg    7200 ttccgcgcac atttccccga aaagtgccac ctgacgtcta agaaaccatt attatcatga   7260
cattaaccta taaaaatagg cgtatcacga ggccctttcg tc                      7302
```

<210> SEQ ID NO 126
<211> LENGTH: 30
<212> TYPE: DNA
<213> ORGANISM: Artificial
<220> FEATURE:

<223> OTHER INFORMATION: PCR primer

<400> SEQUENCE: 126
cgaaaagtgc cacctgacgt ctaagaaacc                                    30

<210> SEQ ID NO 127
<211> LENGTH: 35
<212> TYPE: DNA
<213> ORGANISM: Artificial
<220> FEATURE:
<223> OTHER INFORMATION: PCR primer

<400> SEQUENCE: 127
tcgaattcga cggccagtga attgtaatac gactc                              35

<210> SEQ ID NO 128
<211> LENGTH: 37
<212> TYPE: DNA
<213> ORGANISM: Artificial
<220> FEATURE:
<223> OTHER INFORMATION: PCR primer

<400> SEQUENCE: 128
ccatgattac gccaagctcg gaattaaccg catgcga                            37

<210> SEQ ID NO 129
<211> LENGTH: 23
<212> TYPE: DNA
<213> ORGANISM: Artificial
<220> FEATURE:
<223> OTHER INFORMATION: PCR primer

<400> SEQUENCE: 129
ccatggccgg gcccggattc acc                                           23

<210> SEQ ID NO 130
<211> LENGTH: 69
<212> TYPE: DNA
<213> ORGANISM: Artificial
<220> FEATURE:
<223> OTHER INFORMATION: PCR primer

<400> SEQUENCE: 130
ttcaccccgg tggtttccac gagcacgtgc atgtggaagt agctctctcc cttttcaaac   60
tgcacaaag                                                           69

<210> SEQ ID NO 131
<211> LENGTH: 45
<212> TYPE: DNA
<213> ORGANISM: Artificial
<220> FEATURE:
<223> OTHER INFORMATION: PCR primer

<400> SEQUENCE: 131
cctcggccgc tacgtgagtc agattcgcga aaaactgatt cagag                   45

<210> SEQ ID NO 132
<211> LENGTH: 48
<212> TYPE: DNA
<213> ORGANISM: Artificial
<220> FEATURE:
<223> OTHER INFORMATION: PCR primer

<400> SEQUENCE: 132
gtggtcttcc agggaattga acccactttg ccaaactggt tcgcggtc                48

<210> SEQ ID NO 133
<211> LENGTH: 55
<212> TYPE: DNA
<213> ORGANISM: Artificial
<220> FEATURE:
<223> OTHER INFORMATION: PCR primer

<400> SEQUENCE: 133
ctgggtcgcc atcaccaagg taaagaaggg aggcgggaac aaggtggtgg atgag    55

<210> SEQ ID NO 134
<211> LENGTH: 50
<212> TYPE: DNA
<213> ORGANISM: Artificial
<220> FEATURE:
<223> OTHER INFORMATION: PCR primer

<400> SEQUENCE: 134
gcggagccaa taaggtggtg gatgagtgct acatccccaa ttacttgctc    50

<210> SEQ ID NO 135
<211> LENGTH: 35
<212> TYPE: DNA
<213> ORGANISM: Artificial
<220> FEATURE:
<223> OTHER INFORMATION: PCR primer

<400> SEQUENCE: 135
actggagctc aggttggacc ttcggcagca ggtag    35

<210> SEQ ID NO 136
<211> LENGTH: 57
<212> TYPE: DNA
<213> ORGANISM: Artificial
<220> FEATURE:
<223> OTHER INFORMATION: PCR primer

<400> SEQUENCE: 136
cgtggacaaa cctggacgag tataaattgg cctgtttgaa tctcacggag cgtaaac    57

<210> SEQ ID NO 137
<211> LENGTH: 48
<212> TYPE: DNA
<213> ORGANISM: Artificial
<220> FEATURE:
<223> OTHER INFORMATION: PCR primer

<400> SEQUENCE: 137
ctgaatctgg aggagcgcaa acggttggtg gcgcagcatc tgacgcac    48

<210> SEQ ID NO 138
<211> LENGTH: 36
<212> TYPE: DNA
<213> ORGANISM: Artificial
<220> FEATURE:
<223> OTHER INFORMATION: PCR primer

<400> SEQUENCE: 138
gatcaccggc gcatccgaga actcacgctg cgaagc    36

<210> SEQ ID NO 139
<211> LENGTH: 47
<212> TYPE: DNA
<213> ORGANISM: Artificial
<220> FEATURE:

<223> OTHER INFORMATION: PCR primer

<400> SEQUENCE: 139
taaggccccg gaggcccttt tctttgtgca gtttgaaaag ggatctg        47

<210> SEQ ID NO 140
<211> LENGTH: 50
<212> TYPE: DNA
<213> ORGANISM: Artificial
<220> FEATURE:
<223> OTHER INFORMATION: PCR primer

<400> SEQUENCE: 140
ccacatgcac gtgctcgtgg aaacctccgg catctcttcc atggtcctcg        50

<210> SEQ ID NO 141
<211> LENGTH: 38
<212> TYPE: DNA
<213> ORGANISM: Artificial
<220> FEATURE:
<223> OTHER INFORMATION: PCR primer

<400> SEQUENCE: 141
tcagattcgc gaaaaactgg tgaaagtggt cttccagg        38

<210> SEQ ID NO 142
<211> LENGTH: 47
<212> TYPE: DNA
<213> ORGANISM: Artificial
<220> FEATURE:
<223> OTHER INFORMATION: PCR primer

<400> SEQUENCE: 142
gaatttaccg cgggatcgag ccgcagatca acgactgggt cgccatc        47

<210> SEQ ID NO 143
<211> LENGTH: 54
<212> TYPE: DNA
<213> ORGANISM: Artificial
<220> FEATURE:
<223> OTHER INFORMATION: PCR primer

<400> SEQUENCE: 143
ggtcacaaag accagaaatg gcgccggcgg agccaataag gtggtggatt ctgg        54

<210> SEQ ID NO 144
<211> LENGTH: 48
<212> TYPE: DNA
<213> ORGANISM: Artificial
<220> FEATURE:
<223> OTHER INFORMATION: PCR primer

<400> SEQUENCE: 144
gaggcgggaa caaggtggtg gattctgggt atattcccgc ctacctgc        48

<210> SEQ ID NO 145
<211> LENGTH: 34
<212> TYPE: DNA
<213> ORGANISM: Artificial
<220> FEATURE:
<223> OTHER INFORMATION: PCR primer

<400> SEQUENCE: 145
ccagcctgag ctccagtggg cgtggacaaa cctg        34

```
<210> SEQ ID NO 146
<211> LENGTH: 48
<212> TYPE: DNA
<213> ORGANISM: Artificial
<220> FEATURE:
<223> OTHER INFORMATION: PCR primer

<400> SEQUENCE: 146
gtttgaatct cacggagcgt aaacggctcg tcgcgcagtt tctggcag                    48

<210> SEQ ID NO 147
<211> LENGTH: 42
<212> TYPE: DNA
<213> ORGANISM: Artificial
<220> FEATURE:
<223> OTHER INFORMATION: PCR primer

<400> SEQUENCE: 147
atgcgccggt gatcaaaagc aagacttccc agaaatacat gg                         42

<210> SEQ ID NO 148
<211> LENGTH: 29
<212> TYPE: DNA
<213> ORGANISM: Artificial
<220> FEATURE:
<223> OTHER INFORMATION: PCR primer

<400> SEQUENCE: 148
attataggta ccaggaaccc ctagtgatg                                        29

<210> SEQ ID NO 149
<211> LENGTH: 22
<212> TYPE: DNA
<213> ORGANISM: Artificial
<220> FEATURE:
<223> OTHER INFORMATION: PCR primer

<400> SEQUENCE: 149
taatagggcc caaagggccg gg                                               22

<210> SEQ ID NO 150
<211> LENGTH: 22
<212> TYPE: DNA
<213> ORGANISM: Artificial
<220> FEATURE:
<223> OTHER INFORMATION: PCR primer

<400> SEQUENCE: 150
ttaataggcc ctttgggccg gg                                               22

<210> SEQ ID NO 151
<211> LENGTH: 32
<212> TYPE: DNA
<213> ORGANISM: Artificial
<220> FEATURE:
<223> OTHER INFORMATION: PCR primer

<400> SEQUENCE: 151
tataataagc ttaggaaccc ctagtgatgg ag                                    32

<210> SEQ ID NO 152
<211> LENGTH: 33
<212> TYPE: DNA
<213> ORGANISM: Artificial
<220> FEATURE:
<223> OTHER INFORMATION: PCR primer
```

```
<400> SEQUENCE: 152
attataggta cctacaaaac ctccttgctt gag                                    33

<210> SEQ ID NO 153
<211> LENGTH: 24
<212> TYPE: DNA
<213> ORGANISM: Artificial
<220> FEATURE:
<223> OTHER INFORMATION: PCR primer

<400> SEQUENCE: 153
ttaataggcc ctttgggccg tcgc                                              24

<210> SEQ ID NO 154
<211> LENGTH: 25
<212> TYPE: DNA
<213> ORGANISM: Artificial
<220> FEATURE:
<223> OTHER INFORMATION: PCR primer

<400> SEQUENCE: 154
ttaataggcc caaagggccg tcgtc                                             25

<210> SEQ ID NO 155
<211> LENGTH: 35
<212> TYPE: DNA
<213> ORGANISM: Artificial
<220> FEATURE:
<223> OTHER INFORMATION: PCR primer

<400> SEQUENCE: 155
tataataagc tttacaaaac ctccttgctt gagag                                  35
```

RESTRICTIVE INVERTED TERMINAL REPEATS FOR VIRAL VECTORS

RELATED APPLICATIONS

This application is a divisional of U.S. patent application Ser. No. 13/521,448, filed Jul. 11, 2012, now U.S. Pat. No. 9,169,494 which claims priority to and is a 35 U.S.C. § 371 national phase application of PCT Application PCT/US2011/020939, filed Jan. 12, 2011 which claims priority to U.S. Provisional Application No. 61/294,181, filed Jan. 12, 2010. The entire content of each of these applications is incorporated herein by reference.

STATEMENT OF FEDERAL SUPPORT

This invention was made with government support under GM059299, HL066973, HL051818, AI072176 awarded by the National Institutes of Health and AI007419 awarded by the National Institute of Allergy and Infection Diseases. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-547_ST25.txt, 454,116 bytes in size, generated on Nov. 7, 2012 and filed via EFS-Web, is provided in lieu of a paper copy. This Sequence Listing is hereby incorporated by reference into the specification for its disclosures.

FIELD OF THE INVENTION

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that may limit vector mobilization, increasing the safety of viral vectors.

BACKGROUND OF THE INVENTION

The adeno-associated viruses (AAV) are members of the family Parvoviridae and the genera *Dependoviruses*. Serotypes 1 through 4 were originally identified as contaminates of adenovirus preparations (Carter and Laughlin (1984) in, The Parvoviruses p. 67-152 New York, N.Y.) whereas type 5 was isolated from a patient wart that was HPV positive. To date, twelve molecular clones have been generated representing the serotypes of human/primate AAV (Bantel-Schaal et al. (1999) *J. Virol.* 73: 939; Chiorini at al. (1997) *J. Virol.* 71:6823; Chiorini et al. (1999) *J. Virol.* 73:1309; Gao et al. (2002) *Proc. Nat. Acad. Sci. USA* 99:11854; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Srivastava et al. (1983) *J. Virol.* 45:555; Xiao et al. (1999) *J. Virol.* 73:3994). These clones have provided valuable reagents for studying the molecular biology of serotype specific infection. Transduction of these viruses naturally results in latent infections, with completion of the life cycle generally requiring helper functions not associated with AAV viral gene products. As a result, all of these serotypes are classified as non-pathogenic and are believed to share a safety profile similar to the more extensively studied AAV type 2 (Carter and Laughlin (1984) in, The Parvoviruses p. 67-152 New York, N.Y.).

General understanding of the mechanisms required for function at origins of replication has grown immensely since the first prokaryotic origins were characterized. While the DNA-protein interactions necessary for replication in prokaryotes, lower eukaryotes, and bacteriophages are generally well understood, mechanisms employed in the majority of higher eukaryotes and vertebrate viruses, such as AAV, are still being determined. The inverted terminal repeats (ITRs) of AAV and other Parvoviruses act as the origin of replication. These elements flank the short, single stranded genome and typically possess a T-shaped secondary structure. The replication strategies of the genus *Dependovirus*, including those of AAV, have been well characterized. The viral non-structural or Replication proteins (Rep) are the only factors required to interact with the ITR in order to catalyze replication (Im and Muzyczka (1990) *Cell* 61:447). The majority of AAV serotypes possess highly conserved origins of replication with interchangeable DNA-protein interactions. However, the Rep proteins of several serotypes interact exclusively with their cognate ITR. Discovering the mechanisms which drive Rep-ITR specificity promises to advance our understanding of DNA-protein interactions at viral origins of replication. These findings also promise to shed light on how eukaryotic and prokaryotic proteins achieve selectivity to DNA substrates.

The AAV rep gene encodes four multifunctional proteins (Hermonat et al. (1984) *J. Virol.* 51:329; Tratschin et al. (1984) *J. Virol.* 51:611; Mendelson et al. (1986) *J. Virol.* 60:823; Trempe et al. (1987) *Virol.* 161:18) that are expressed from two promoters at map units 5 (p5) and 19 (p19). The larger Rep proteins transcribed from the p5 promoter (Rep78 and Rep68), are essentially identical except for unique carboxy termini generated from unspliced (Rep78) and spliced (Rep68) transcripts, respectively (Srivastava et al, (1983) *J. Virol.* 45:555). The two smaller Rep proteins, Rep52 and Rep40, are transcribed from the p19 promoter and represent amino terminal truncations of Rep78 and Rep68, respectively.

Several biochemical activities of Rep78 and Rep68 have been characterized as involved in AAV replication. These include specific binding to the AAV ITR (Ashktorab et al. (1989) *J. Virol.* 63:3034; Im et al. (1989) *J. Virol.* 63:3095; Snyder et al. (1993) *J. Virol.* 67:6096) and site-specific endonuclease cleavage at the terminal resolution site (trs) (Im et al. (1990) *J. Virol.* 63:447; Im et al. (1992) *J. Virol.* 66:1119; Snyder et al., (1990) *Cell* 60:105; Snyder et al. (1990) *J. Virol.* 64:6204). Rep78/68 also possess ATP dependent DNA-DNA helicase (Im et al., (1990) *J. Virol.* 63:447; Im et al. (1992) *J. Virol.* 66:1119) and DNA-RNA helicase as well as ATPase activities (Wonderling et al. (1995) *J. Virol.* 69:3542). In addition to these activities involved in replication, Rep78/68 also regulate transcription from the viral promoters (Beaton et al. (1989) *J. Virol.* 63:4450; Labow et al. (1986) *J. Virol.* 60:251; Tratschin et al. (1986) *Mol. Cell. Biol.* 6:2884; Kyostio et al. (1994) *J. Virol.* 68:2947; Pereira et al. (1997) *J. Virol.* 71:1079), and have been shown to mediate viral targeted integration (Xiao, W., (1996), "Characterization of cis and trans elements essential for the targeted integration of recombinant adeno-associated virus plasmid vectors", Ph.D. Dissertation, University of North Carolina-Chapel Hill; Balague et al. (1997) *J. Virol.* 71:3299; LaMartina et al. (1998) *J. Virol.* 72:7653; Pieroni et al. (1998) *Virol.* 249:249).

Like Rep proteins, the AAV ITRs are involved in nearly every aspect of the viral life-cycle. The secondary structure of the ITR is necessary to prime synthesis of the second strand to allow transcription of the viral genes (Hauswirth and Berns (1977) *J. Virol.* 78:488). The full length Rep proteins contain a unique N-terminal DNA binding region which specifically recognizes the ITR at the 16 nt Rep-binding element (RBE) and at the tip of one of the hairpin stems known as the RBE' (FIG. 1A) (Ryan et al. (1996) *J. Virol.* 70:1542; Brister and Muzyczka (2000) *J. Virol.* 74:7762). Rep molecules multimerize on the ITR allowing the C-terminus of Rep, acting as an ATP-dependent SF3 helicase, to unwind the ITR and form a putative internal hairpin (Im and Muzyczka (1990) *Cell* 61:447; Hermonat and Batchu (1997) *FEBS Lett.* 20:180). This hairpin, (here, termed 'nicking stem') contains the terminal resolution site (trs) where Rep nicks the ITR in a site-specific manner (Brister and Muzyczka (1999) *J. Virol.* 73:9325). This DNA cleavage is important for replication of the closed ITR and to initiate subsequent rounds of genomic replication. Replicated genomes can undergo replication again or be encapsidated in the presence of the smaller Rep proteins (King et al. (2001) *EMBO J.* 20:3282).

The ITR sequences of twelve human/primate AAV serotypes have been published. These sequences typically display 80% or greater nucleotide conservation and segregate into two groups (Hewitt et al. (2009) *J. Virol.* 83:3919). The AAV2 Rep proteins (Rep2) are able to function on the ITR of every known AAV serotype except those of AAV5 (ITR5; Hewitt et al. (2009) *J. Virol.* 83:3919; Grimm et al. (2006) *J. Virol.* 80:426). Consistently, the AAV5 Rep proteins (Rep5) are unable to catalyze replication of the ITR of AAV2 (ITR2). Replicative specificity between these serotypes does not exist at the level of binding, as Rep2 and Rep5 can bind interchangeably to ITR2 or ITR5 (Chiorini et al. (1999) *J. Virol.* 73:4293). Instead, specificity is created by the inability of Rep to cleave the ITR of the opposite serotype. This occurs despite high conservation between the ITR2 and ITR5 sequence, secondary structure, and location of elements required for Rep interaction (RBE, RBE', trs, nicking stem).

All current AAV vectors in clinical trials utilize ITR2s. However, using ITR2s for therapeutic purposes creates a safety risk due to the ubiquity of AAV2 in the human population as well as other AAVs whose Rep proteins can replicate ITR2s. In this manner, rAAV vectors have the potential to be "mobilized" out of the target tissue into different tissues of the body or into other individuals in the population (Hewitt et al. (2009) *J. Virol.* 83:3919).

The present invention provides a solution to vector mobilization through the creation of a novel Rep-ITR interaction. A vector utilizing this novel interaction cannot be mobilized by one or more of the wild-type AAV serotypes which infect humans, nor the non-human serotypes which can potentially infect human hosts.

SUMMARY OF THE INVENTION

The present invention relates to the discovery of unique mechanisms at the DNA and protein level to achieve Rep-ITR specificity and utilizes these factors to create novel AAV origins of replication. Thus, one aspect of the invention relates to a polynucleotide comprising at least one parvovirus inverted terminal repeat (ITR), wherein said ITR comprises: (a) a first structural element that functionally interacts with a large Rep protein from a first AAV but does not functionally interact with a large Rep protein from a second AAV; and (b) a second structural element that that functionally interacts with the large Rep protein from the second AAV but does not functionally interact with the large Rep protein from the first AAV; wherein the ITR functionally interacts with a synthetic AAV large Rep protein. The invention further relates to a viral vector and a recombinant parvovirus particle comprising the polynucleotide of the invention. Further provided are pharmaceutical formulations comprising a virus particle of the invention in a pharmaceutically acceptable carrier.

Another aspect of the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV and said second structural element functionally interacts with a large Rep protein from a second AAV that is different from the first AAV. The invention further relates to polynucleotides encoding the synthetic large Rep protein and vectors and cells comprising the polynucleotide.

An additional aspect of the invention relates to a method of producing a recombinant parvovirus particle, comprising providing to a cell permissive for parvovirus replication: (a) a recombinant parvovirus template comprising (i) a heterologous nucleotide sequence, and (ii) the parvovirus terminal repeat sequence of the invention; (b) a polynucleotide encoding a Rep protein of the invention; under conditions sufficient for the replication and packaging of the recombinant parvovirus template; whereby recombinant parvovirus particles comprising the parvovirus capsid encoded by the cap coding sequences and packaging the recombinant parvovirus template are produced in the cell.

A further aspect of the invention relates to a method of delivering a nucleic acid to a cell, comprising introducing into a cell the recombinant parvovirus particle of the invention.

Another aspect of the invention relates to a method of administering a nucleic acid to a mammalian subject comprising administering to the mammalian subject a cell that has been contacted with the recombinant parvovirus particle of the invention under conditions sufficient for the parvovirus particle vector genome to enter the cell.

A further aspect of the invention relates to a method of administering a nucleic acid to a mammalian subject comprising administering to the mammalian subject the recombinant parvovirus particle of the invention.

An additional aspect of the invention relates to a parvovirus template comprising (i) a heterologous nucleotide sequence, and (ii) at least one snake AAV ITR sequence and a parvovirus particle comprising the parvovirus template.

A further aspect of the invention relates to a method of producing a parvovirus particle, comprising providing to a cell permissive for parvovirus replication: (a) a recombinant parvovirus template comprising (i) a heterologous nucleotide sequence, and (ii) at least one snake AAV ITR sequence; (b) a polynucleotide encoding snake AAV Rep protein and mammalian AAV Cap protein; (c) a polynucleotide encoding mammalian Rep52 and/or Rep40 proteins; under conditions sufficient for the replication and packaging of the recombinant parvovirus template; whereby recombinant parvovirus particles comprising a parvovirus capsid encoded by the cap coding sequences and packaging the recombinant parvovirus template are produced in the cell.

Another aspect of the invention relates to use of the recombinant parvovirus particle of the invention for delivering a nucleic acid to a cell.

An additional aspect of the invention relates to use of a cell that has been contacted with the recombinant parvovirus particle of the invention for delivering a nucleic acid to a mammalian subject.

A further aspect of the invention relates to use of the recombinant parvovirus particle of the invention for delivering a nucleic acid to a mammalian subject.

Another aspect of the invention relates to use of the recombinant parvovirus particle of the invention for the manufacture of a medicament for delivering a nucleic acid to a cell.

An additional aspect of the invention relates to use of a cell that has been contacted with the recombinant parvovirus particle of the invention for the manufacture of a medicament for delivering a nucleic acid to a mammalian subject.

A further aspect of the invention relates to use of the recombinant parvovirus particle of the invention for the manufacture of a medicament for delivering a nucleic acid to a mammalian subject.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

These and other aspects of the invention are set forth in more detail in the description of the invention below.

BRIEF DESCRIPTION OF THE DRAWINGS

(FIG. 1A) Sequence and structure of ITR2 (SEQ ID NO:17) (black) and ITR5 (SEQ ID NO:18) (italic) shown with incorporation of SfiI sites for cloning (bold). Length in nt of ITR elements indicated above brackets. RBE is boxed. RBE' is indicated by a hatched circle. Nicking stem is extruded with arrow indicating the nicking site and hatched box indicating the trs. The four initial chimeric ITRs generated (SEQ ID NOS:19-22) are shown (right). (FIG. 1B) Replication assay and quantitation of chimeric Reps. Replication products from the indicated ITR and either Rep2 or Rep5 were analyzed by Southern blot. Monomeric (m) and dimeric (d) replicating species are indicated. The level of replication of each sample was measured by densitometric analysis and compared to wt replication.

(FIG. 2A) Sequence of nicking stem in an otherwise ITR2 context (SEQ ID NOS: 17, 18, 23, 25, 30, 32, 28). Arrow indicates trs site. Brackets indicate height of putative stems in nt from the base of the stem to the putative nicking site. Predicted $\Delta G$ values for the hairpins are below. Southern blot analysis of the ITRs replicated by Rep2 or Rep5 are shown below. (FIG. 2B) Quantitation of the Southern blots relative to wt replication from FIG. 2A. (FIG. 2C) Same as FIG. 2A, except nicking stems indicated were used in an ITR5 context (SEQ ID NOS:17, 18, 24, 26, 35). (FIG. 2D) Quantitation of the Southern blots relative to wt replication from FIG. 2C.

(FIG. 3A) ITR2 mutants were synthesized with the indicated spacing between the RBE and nicking stem (SEQ ID NOS:17, 31, 33). (FIG. 3B) Southern blot analysis of the ITRs depicted in FIG. 3A replicated by either Rep2 or Rep5 (Left). Quantitation of Southern blots relative to wt replication (Right). (FIG. 3C) ITR5 mutants synthesized as in FIG. 3A (SEQ ID NOS:34, 18, 37, 38). (FIG. 3D) Southern blot analysis and quantitation of FIG. 3C.

(FIG. 4A) ITR5 mutants were synthesized with the indicated RBE and spacer sequence (SEQ ID NOS:18, 40, 39, 42). Brackets indicate individual tetranucleotide repeats bound by Rep monomers. Both strands of the wt ITR5 sequence are shown to illustrate conservation with the GAGY motif (indicated by *). Only one strand shown on others. (FIG. 4B) Southern blot analysis of the ITRs depicted in FIG. 4A replicated by either Rep2 or Rep5 (Left). Quantitation of Southern blots relative to wt replication (Right). (FIG. 4C) ITR2 mutants were generated with the RBE and spacer sequences indicated (SEQ ID NOS:17, 29, 41, 43). (FIG. 4D) Southern blot analysis and quantitation for FIG. 4C.

FIGS. 5A-5E show the cloning and characterization of chimeric Reps. (FIG. 5A) An alignment of the N-termini of Rep2 (SEQ ID NO:114) and Rep5 (SEQ ID NO:118). (*) represents conserved amino acids. (:) and (.) indicate conservative substitutions. (^) indicates residues implicated in RBE binding interactions. (') indicates residues which participate in the endonucleolytic active site. (+) indicates residues implicated in RBE' binding. (FIG. 5B) Chimeric Reps created and their ability to replicate ITR2 or ITR5 flanked vectors. Numbers indicate the amino acid (aa) position of the switch from one Rep to the other. (+) indicates the presence of replication, (−) indicates the absence. (FIG. 5C) Western blot for expression of the chimeric Reps. (FIG. 5D) Southern blot demonstrating replication of an ITR2 or an ITR5 vector by the chimeric Reps. Note that the ITR5 vector is 500 bp larger than the ITR2 vector. (FIG. 5E) Level of replication of the chimeric Reps relative to wt Rep2 or Rep5.

(FIG. 6A) Chimeric Reps and their ability to replicate ITR2 or ITR5 flanked vectors. Numbers indicate the aa position of the switch from one Rep to the other. (+) indicates the presence of replication, (−) indicates the absence. Region 1 and 2 involved in Rep-ITR specificity are indicated. (FIG. 6B) Western blot for expression of chimeric Reps. (FIG. 6C) Southern blot demonstrating replication of an ITR2 or ITR5 vector by the chimeric Reps. Note that the ITR5 vector is 500 bp larger than the ITR2 vector. (FIG. 6D) Structural model illustrating the two Rep regions. The nucleophilic tyrosine is indicated. Black hatched circle indicates the predicted structural difference of region 1 in the major groove of the ITR. (FIG. 6E) Structural model as in FIG. 6D. The nucleophilic tyrosine is indicated. (FIG. 6F) Detailed structural view of region 1. The side-chains of non-conserved residues from Rep5 and Rep2 are shown. Three Rep5 residues implicated in RBE' binding are indicated. (FIG. 6G) Detailed structural view of region 2. Side chains of active site residues are shown in black. Side chains of non-conserved residues in this region are shown for Rep2 and Rep5. The nucleophilic tyrosine is indicated, as is the adjacent Rep2 Asn-155.

(FIG. 7A) Southern blot of Hirt DNA demonstrating replication of the indicated ITR vector by the indicated Rep. (FIG. 7B) Table indicating the presence (+) or absence (−) of replication of the gel from FIG. 7A. (FIG. 7C) Model of a novel AAV origin of replication. The chimeric ITR can be replicated only by a chimeric Rep protein. Rep5 sequence in region 1 is required for the extended RBE of ITR5. Rep2 sequence in region 2 is required to function on an ITR2 nicking stem.

FIG. 8 shows an illustrative genomic DNA sequence for AAV-1; GenBank Accession No. NC 002077; SEQ ID NO:1.

FIG. 9 shows an illustrative genomic DNA sequence for AAV-2; GenBank Accession No. NC 001401; SEQ ID NO:2.

FIG. 10 shows an illustrative genomic DNA sequence for AAV-3A; GenBank Accession No. NC 001729; SEQ ID NO:3.

FIG. 11 shows an illustrative genomic DNA sequence for AAV-3B; GenBank Accession No. NC 001863; SEQ ID NO:4.

FIG. 12 shows an illustrative genomic DNA sequence for AAV-4; GenBank Accession No. NC 001829; SEQ ID NO:5.

FIG. 13 shows an illustrative genomic DNA sequence for AAV-5; GenBank Accession No. NC 006152; SEQ ID NO:6.

FIG. 14 shows an illustrative genomic DNA sequence for AAV-6; GenBank Accession No. NC 001862; SEQ ID NO:7.

FIG. 15 shows an illustrative genomic DNA sequence for AAV-7; GenBank Accession No. AF513851; SEQ ID NO:8.

FIG. 16 shows an illustrative genomic DNA sequence for AAV-8; GenBank Accession No. AF513852; SEQ ID NO:9.

FIG. 17 shows an illustrative genomic DNA sequence for AAV-9; GenBank Accession No. AX753250; SEQ ID NO:10.

FIG. 18 shows an illustrative genomic DNA sequence for AAV-11; GenBank Accession No. AY631966; SEQ ID NO:11.

FIG. 19 shows an illustrative genomic DNA sequence for AAV-13; GenBank Accession No. EU285562; SEQ ID NO:12.

FIG. 20 shows an illustrative genomic DNA sequence for B19 parvovirus; GenBank Accession No. NC 000883; SEQ ID NO:13.

FIG. 21 shows an illustrative genomic DNA sequence for Minute Virus from Mouse (MVM); GenBank Accession No. NC 001510; SEQ ID NO:14.

FIG. 22 shows an illustrative genomic DNA sequence for goose parvovirus; GenBank Accession No. NC 001701; SEQ ID NO:15.

FIG. 23 shows an illustrative genomic DNA sequence for snake parvovirus 1; GenBank Accession No. NC 006148; SEQ ID NO:16.

FIG. 24 provides an exemplary listing of the chimeric ITRs that were synthesized as part of the Examples described below: ITR2 (SEQ ID NO:17), ITR5 (SEQ ID NO:18), ITR5+2SNS (SEQ ID NO:19), ITR2+5SNS (SEQ ID NO:20), ITR5+2NS (SEQ ID NO:21), ITR2+5NS (SEQ ID NO:22), ITR2-TA (SEQ ID NO:23), ITR5+TA (SEQ ID NO:24), ITR2-GC (SEQ ID NO:25), ITR5+GC (SEQ ID NO:26), ITR2-2 nt (SEQ ID NO:27), ITR2 5 nt (SEQ ID NO:28), ITR2+7 (SEQ ID NO:29), ITR2 9 nt (SEQ ID NO:30), ITR2 10 nt (SEQ ID NO:31), ITR2 11 nt (SEQ ID NO:32), ITR2 15 nt (SEQ ID NO:33), ITR5 3 nt (SEQ ID NO:34), ITR5 6 nt (SEQ ID NO:35), ITR5 9 bp NS (SEQ ID NO:36), ITR5 21 nt (SEQ ID NO:37), ITR5 30 nt (SEQ ID NO:38), ITR5 GAGY (SEQ ID NO:39), ITR5 no GAGY (SEQ ID NO:40), ITR2+8 nt GAGY (SEQ ID NO:41), ITR5 Spacer RBE (SEQ ID NO:42), ITR2+8−8 Spacer RBE (SEQ ID NO:43), ITR5 with ITR2 hairpins (SEQ ID NO:44), ITR2 no hairpins (SEQ ID NO:45), ITR2 T1 (SEQ ID NO:46), ITR2 T2 (SEQ ID NO:47), ITR2 T2 #2 (SEQ ID NO:48), ITR2 T3 (SEQ ID NO:49), ITR2 T4 (SEQ ID NO:50), ITR5+3 nt Spacer & ITR5 NS (SEQ ID NO:51), and ITR2 pHpa8 (SEQ ID NO:52).

FIG. 25 provides an exemplary listing of the chimeric Rep proteins that were synthesized as part of the Examples described below: Rep52aa73 (SEQ ID NO:53), Rep52aa84 (SEQ ID NO:54), Rep52aa110 (SEQ ID NO:55), Rep52aa126 (SEQ ID NO:56), Rep52aa138 (SEQ ID NO:57), Rep52aa160 (SEQ ID NO:58), Rep52aa175 (SEQ ID NO:59), Rep52aa187 (SEQ ID NO:60), Rep52aa207 (SEQ ID NO:61), Rep25aa73 (SEQ ID NO:62), Rep25aa77 (SEQ ID NO:63), Rep25aa97 (SEQ ID NO:64), Rep25aa116 (SEQ ID NO:65), Rep25aa125 (SEQ ID NO:66), Rep25aa141 (SEQ ID NO:67), Rep25aa149 (SEQ ID NO:68), Rep25aa166 (SEQ ID NO:69), Rep25aa187 (SEQ ID NO:70), Rep25aa216 (SEQ ID NO:71), Rep525aa110-148 (SEQ ID NO:72), Rep525aa146-187 (SEQ ID NO:73), Rep525aa110-187 (SEQ ID NO:74), Rep252aa97-146 (SEQ ID NO:75), Rep252aa149-187 (SEQ ID NO:76), and Rep252aa97-187 (SEQ ID NO:77).

FIG. 26 shows both the nucleotide and amino acid sequences of a chimeric Rep protein of the invention: Rep52aa146 (SEQ ID NO:78 and SEQ ID NO:79, respectively).

FIG. 27 shows both the nucleotide and amino acid sequences of a chimeric Rep protein of the invention: Rep52aa147 (SEQ ID NO:80 and SEQ ID NO:81, respectively).

FIG. 28 shows both the nucleotide and amino acid sequences of a chimeric Rep protein of the invention: Rep52aa151 (SEQ ID NO:82 and SEQ ID NO:83, respectively).

FIG. 30 shows an alignment of the amino acid sequences of exemplary Rep52 proteins from AAV1 (SEQ ID NO:94), AAV2 (SEQ ID NO:95), AAV3A (SEQ ID NO:96), AAV3B (SEQ ID NO:97), AAV4 (SEQ ID NO:98), AAV5 (SEQ ID NO:99), AAV6 (SEQ ID NO:100), AAV7 (SEQ ID NO:101) and AAV8 (SEQ ID NO:102), as well as a consensus sequence (SEQ ID NO:103). Dashes indicate gaps in the sequence and shading indicates positions of sequence homology.

FIG. 31 shows an alignment of the amino acid sequences of exemplary Rep68 proteins from AAV1 (SEQ ID NO:104), AAV2 (SEQ ID NO:105), AAV3A (SEQ ID NO:106), AAV3B (SEQ ID NO:107), AAV4 (SEQ ID NO:108), AAV5 (SEQ ID NO:109), AAV6 (SEQ ID NO:110), AAV7 (SEQ ID NO:111) and AAV8 (SEQ ID NO:112). Dashes indicate gaps in the sequence and shading indicates positions of sequence homology.

FIG. 33 shows the nucleotide sequence of the snake ITR utilized in Example 9 (SEQ ID NO:123).

FIG. 34 shows the nucleotide sequence of the snake ITR eGFP vector plasmid (SEQ ID NO:124) used to synthesize the snake vector described in Example 9.

FIG. 35 shows the nucleotide sequence of the pSnRep-Cap2 plasmid (SEQ ID NO:125) used to synthesize the snake vector described in Example 9.

(FIG. 36A) The ITR was synthesized in two pieces (━━ and ━ ━ ━) overlapping across one hairpin stem holding the SfiI site (••••••••). (FIG. 36B) Each half was amplified via PCR prior to digestion and cloning. (FIG. 36C) Proper triple-ligation with pUC18-CMV GFP produced an ITR in DD format.

DETAILED DESCRIPTION OF THE INVENTION

Figure 1A:
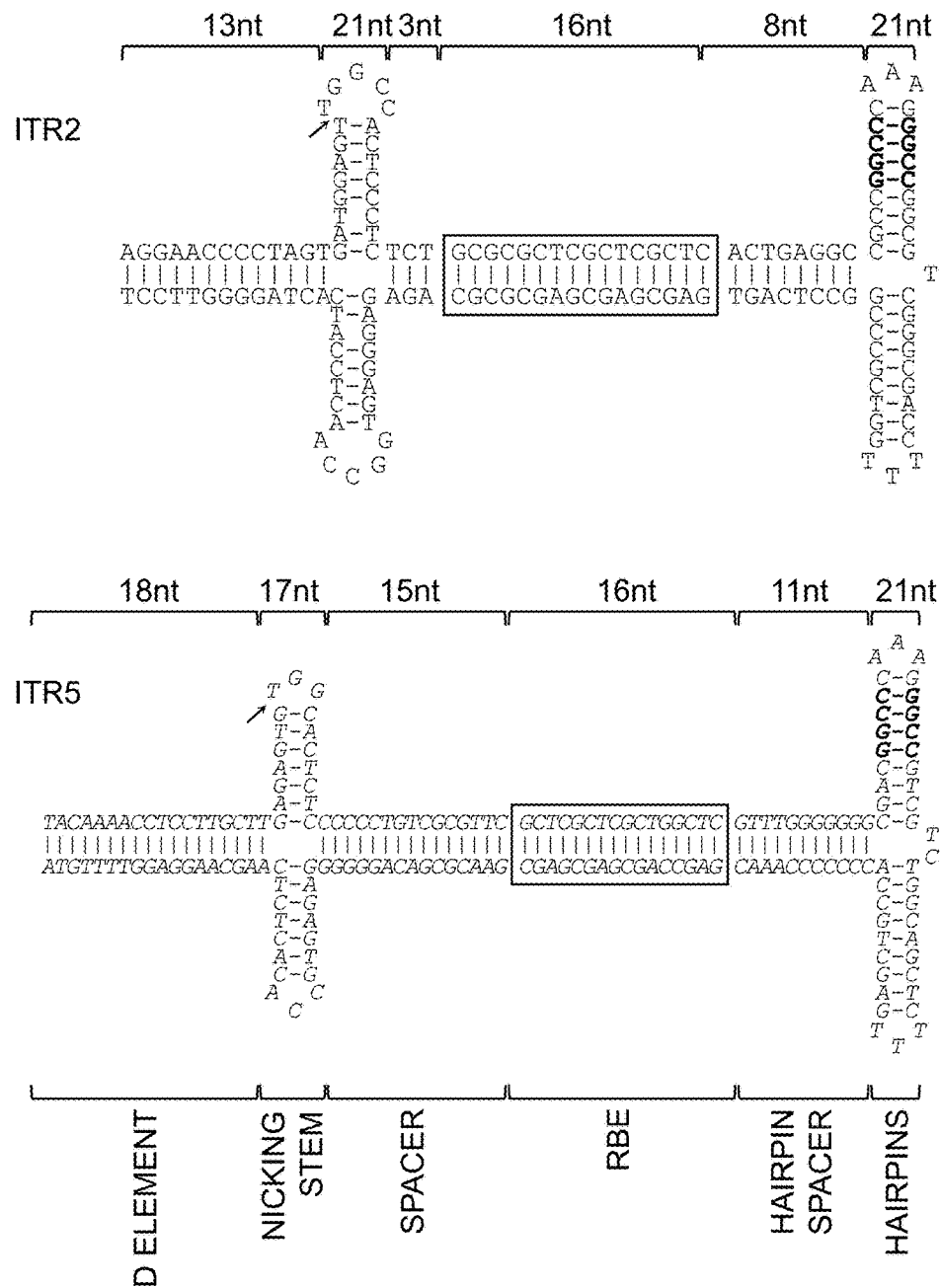
FIGS. 1A-1B show the cloning and characterization of chimeric ITRs.
Figure 1A:
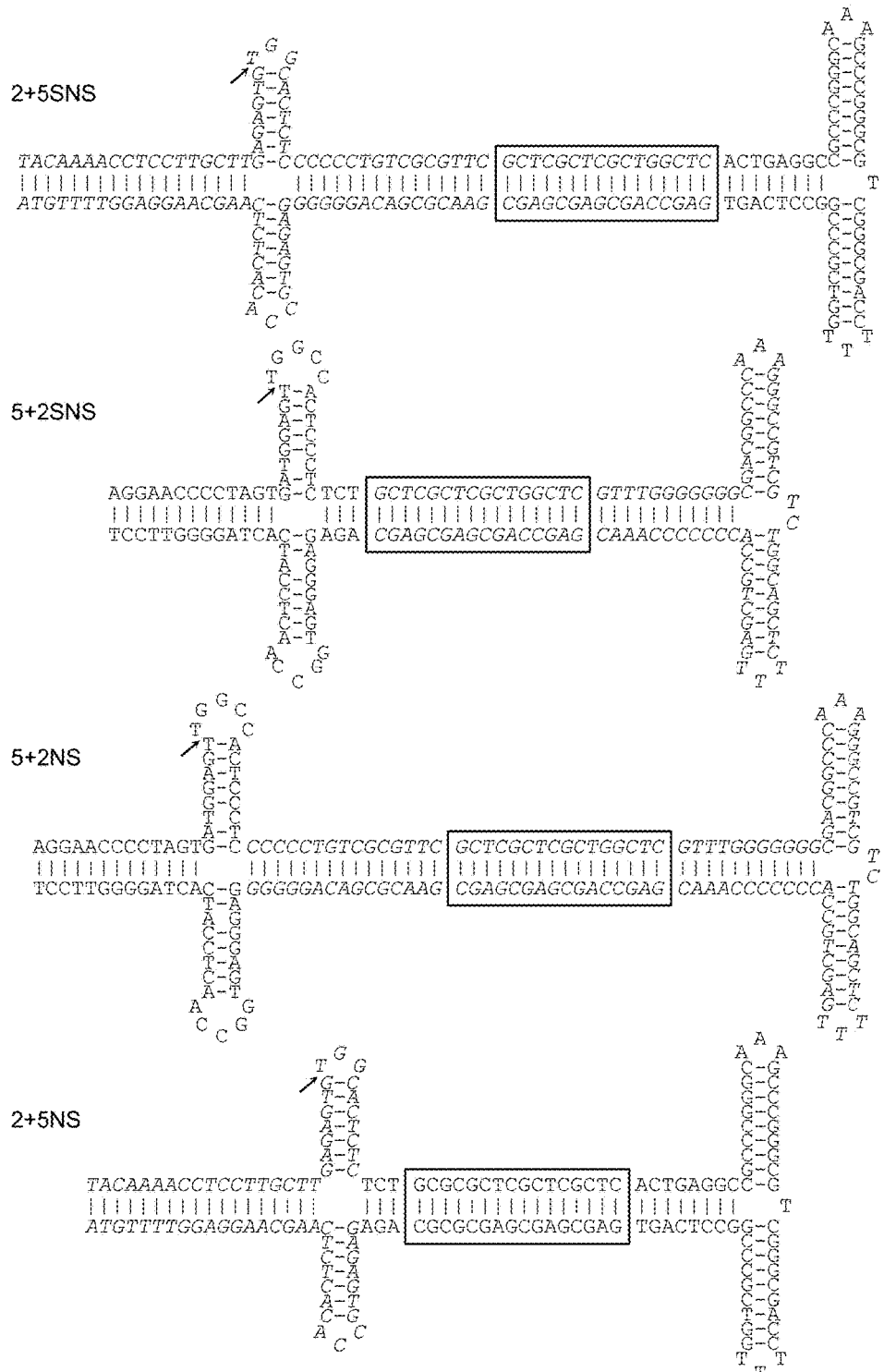

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual*, 99-102 (November 1990) (U.S. Patent and Trademark Office).

Except as otherwise indicated, standard methods known to those skilled in the art may be used for the construction of recombinant parvovirus and rAAV constructs, packaging vectors expressing the parvovirus Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York).

Definitions

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "parvovirus" as used herein encompasses the family Parvoviridae, including autonomously-replicating parvoviruses and *dependoviruses*. The autonomous parvoviruses include members of the genera *Parvovirus, Erythrovirus, Densovirus, Iteravirus,* and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus (See, e.g., FIGS. 20-23). Other autonomous parvoviruses are known to those skilled in the art. See, e.g., FIELDS et al. VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIGS. 8-19; FIELDS et al. VIROLOGY, volume 2, chapter 69 (4th ed., Lippincott-Raven Publishers); and Table 1.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |

TABLE 1-continued

| GenBank Accession Number | |
|---|---|
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) J. Virol. 78:6381; Moris et al. (2004) Virol. 33-:375; and Table 1).

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., FIGS. 8-23; GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33-:375-383; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol.* 45:555; Xiao et al. (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by a parvovirus or AAV means that the parvovirus/AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/REA DME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. FIG. 24 provides examples of synthetic ITRs contemplated by the present invention.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al. (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in e.g., FIELDS et al. VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the term "synthetic large Rep protein" refers to a large Rep protein having an amino acid sequence that differs from a wild-type large Rep protein sequence. The sequence of the synthetic large Rep protein may differ from a wild-type sequence due to one or more deletions, additions, substitutions, or any combination thereof. The difference between the synthetic and wild-type sequences may be as little as a single amino acid change, e.g., a change in 1, 2, 3, 4, 5,6, 7, 8, 9, 10, 15, 20, 25, 30, 35, 40, 45, 60, 60, 70, 80, 90, 100, 125, 150, 175, 200, 225, 250, 275, 300, 325, 350, 375, 400. 425, 450, 475, 500, 525, 550, 575, or 600 or more amino acids or any range therein. In certain embodiments, the synthetic large Rep protein is a chimeric Rep protein comprising portions of the wild-type sequence of two or more different large Rep proteins. In other embodiments, the synthetic large Rep protein is a chimeric Rep protein comprising portions of the wild-type sequence of two or more different large Rep proteins, one or more portions of which have been modified from the wild-type sequence.

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

As used herein, the term "structural element," when used with respect to a parvovirus ITR, refers to a portion of the ITR that, based on nucleotide sequence, secondary structure, or both, plays a role in the functional interaction of a large Rep protein with the ITR, e.g., a portion that, when removed from the ITR, prevents functional interaction with a large Rep protein. In some embodiments, the structural element physically interacts with the large Rep protein.

As used herein, the term "functionally interacts" refers to an interaction between an ITR and a large Rep protein (e.g., binding) that ultimately results in nicking of the ITR and replication of a polynucleotide in which the ITR is present.

As used herein, the term "nicking stem" refers to a hairpin loop structure present in a parvovirus ITR that is nicked by a large Rep protein during replication of a polynucleotide in which the ITR is present.

As used herein, the term "extended RBE" refers to the nucleotide sequence of a parvovirus ITR between the nicking stem and the RBE (the spacer sequence as shown in FIG. 1A) which, in certain parvoviruses (e.g., AAV5), functions as an extension of the RBE (i.e., is recognized and bound by a large Rep protein). The term "extended RBE" is only applicable to the spacer sequence when the sequence functions as an extension of the RBE.

Modified Parvovirus ITRs

The present invention provides modified parvovirus ITRs and synthetic Rep proteins that functionally interact with the modified ITRs. The modified ITRs are unique in that they do not functionally interact with wild-type Rep proteins and may reduce or avoid vector mobilization.

One aspect of the invention relates to a polynucleotide comprising at least one parvovirus ITR, wherein the ITR comprises: (a) a first structural element that functionally interacts with a large Rep protein from a AAV but does not functionally interact with a large Rep protein from a second AAV; and (b) a second structural element that functionally interacts with the large Rep protein from the second AAV but does not functionally interact with the large Rep protein from the first AAV; wherein the ITR functionally interacts with a synthetic AAV large Rep protein. In one embodiment, the ITR does not functionally interact with any wild-type large Rep protein, e.g., AAV2 Rep, AAV5 Rep, or any other known Rep protein. In particular embodiments, the synthetic large Rep protein comprises an amino acid sequence selected from the group consisting of SEQ ID NOS:79, 81, and 83 or an amino acid sequence having at least 80% identity to one of SEQ ID NOS: 79, 81, and 83, e.g., at least 85%, 90%, 95%, 96%, 97%, 98%, or 99% identity. In one embodiment, the ITR further comprises a third structural element that functionally interacts with a large Rep protein from an AAV that is the same as or different from the first and/or second AAV.

In one embodiment of the invention, the parvovirus ITR is from an autonomous parvovirus. In another embodiment, the parvovirus ITR is from an AAV, e.g., an AAV selected from the group consisting of AAV1, AAV2, AAV3, AAV4, AAV5, AAV6, AAV7, AAV8, AAV9, AAV10, AAV11, AAV12, and AAV13. In a further embodiment, the parvovirus ITR is from a non-human AAV such as snake AAV, avian AAV, bovine AAV, canine AAV, equine AAV, ovine AAV, goat AAV, or shrimp AAV.

The structural element of the ITR can be any structural element that is involved in the functional interaction of the ITR with a large Rep protein. In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of a nicking stem, a spacer, a RBE, an extended RBE, and any combination thereof. In a particular embodiment, the first structural element is a nicking stem. In another embodiment, the second structural element is a RBE. In a further embodiment, the second structural element is an extended RBE. In an additional embodiment, the second structural element is a spacer.

The ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., the nicking stem, spacer, RBE, and/or extended RBE) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the nicking stem or RBE can be replaced with a structural element from AAV5. In another example, the ITR can be an AAV5 ITR and the nicking stem, RBE, or extended RBE can be replaced with a structural element from AAV2. In one example, the ITR can be an AAV2 ITR with the nicking stem replaced with the AAV5 ITR nicking stem, e.g., the ITR of SEQ ID NO:22 or a modified sequence thereof. In another example, the AAV ITR can be an AAV5 ITR with the nicking stem replaced with the AAV2 ITR nicking stem, e.g., the ITR of SEQ ID NO:21 or a modified sequence thereof.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a synthetic structural element. In certain embodiments, the specific ITRs exemplified herein (SEQ ID NOS:17-52) can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80% identity with one of the ITRs of SEQ ID NOS:17-52, e.g., at least 85%, 90%, 95%, 96%, 97%, 98%, or 99% identity. In one embodiment, the structural element is a nicking stem and the modified sequence is a modified terminal resolution site (trs) sequence. For example, a nicking stem can be modified to comprise the ITR2 trs (GGT/TGG) or the ITR5 trs (AGTG/TGG). In another embodiment, the structural element is a RBE or an extended RBE and the sequence is a modified at the nucleotides responsible for binding specificity. For example, the sequence of a RBE or an extended RBE can be modified to make the sequence closer to or further from the consensus GAGY binding sites recognized by Rep. In one example, the spacer or extended RBE can be modified to comprise one or more exact GAGY repeats (e.g., the ITR of SEQ ID NO:39 or a modified sequence thereof), e.g., 1, 2, 3, or 4 or more exact GAGY repeats.

In a different embodiment, the structure of the structural element can be modified. For example, the structural element can be a nicking stem and the modification can be a change in the height of the stem and/or the number of nucleotides in the loop. For example, the height of the stem can be about 2, 3, 4, 5, 6, 7, 8, or 9 nucleotides or more or any range therein. In one embodiment, the nicking stem height can be about 5 nucleotides to about 9 nucleotides and functionally interacts with Rep2. In another embodiment, the nicking stem height can be about 7 nucleotides and functionally interacts with Rep5. In another example, the loop can have 3, 4, 5, 6, 7, 8, 9, or 10 nucleotides or more or any range therein. In another example, the structural element can be a RBE or an extended RBE and the number of GAGY binding sites or GAGY-related binding sites within the RBE or extended RBE can be increased or decreased. In one example, the RBE or extended RBE, can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as the nicking stem and the RBE or the RBE and a hairpin) can be altered (e.g., increased or decreased) to alter functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein. In one embodiment, the spacer between the nicking stem and the RBE is about 3 nucleotides in length and functionally interacts with Rep2. In another embodiment, the spacer between the nicking stem and the RBE is about 3 nucleotides (e.g., the ITR of SEQ ID NO:34 or a modified sequence thereof) to about 21 nucleotides in length (e.g., the ITR of SEQ ID NO:37 or a modified sequence thereof) and functionally interacts with Rep5. In one embodiment, the spacer is the 15 nucleotide spacer of the AAV5 ITR or a sequence having at least 80% identity thereto, e.g., at least 85%, 90%, 95%, 96%, 97%, 98%, or 99% identity.

In a representative embodiment, the polynucleotide comprises at least one parvovirus ITR, wherein said ITR comprises: (a) a first structural element that functionally interacts with a large Rep protein from one or more of AAV1, AAV2, AAV3, AAV4, AAV6, AAV7, AAV8, AAV9, AAV10, AAV11, AAV12, and AAV13 but does not functionally interact with a large Rep protein from AAV5; and (b) a second structural element that functionally interacts with the large Rep protein from AAV5 but does not functionally interact with the large Rep protein from one or more of AAV1, AAV2, AAV3, AAV4, AAV6, AAV7, AAV8, AAV9, AAV10, AAV11, AAV12, and AAV13; wherein the ITR functionally interacts with a synthetic AAV large Rep protein comprising an amino acid sequence selected from SEQ ID NOS: 79, 81, and 83.

In one aspect of the invention the polynucleotide comprising the modified ITR of the invention further comprises a second ITR which may be the same as or different from the first ITR. In one embodiment, the polynucleotide further comprises a heterologous nucleic acid, e.g., a sequence encoding a protein or a functional RNA. In some embodiments, the second ITR cannot be resolved by the Rep protein, i.e., resulting in a double stranded viral DNA.

The invention also provides a viral vector comprising the polynucleotide comprising the modified ITR of the invention. The viral vector can be a parvovirus vector, e.g., an AAV vector. The invention further provides a recombinant parvovirus particle (e.g., a recombinant AAV particle) comprising the modified ITR of the invention. Viral vectors and viral particles are discussed further below.

Synthetic Rep Proteins

One aspect of the invention relates to synthetic large Rep proteins that functionally interact with the modified ITRs of the invention. Thus, in one aspect, the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV. In one embodiment, the protein comprises a third portion that functionally interacts with a third structural element that functionally interacts with a large Rep protein from an AAV that is the same as or different from the first and/or second AAV. In one embodiment, the first structural element is a nicking stem and the first portion of the synthetic large Rep protein functional interacts with the nicking stem. In another embodiment, the second structural element is a spacer, RBE, or extended RBE and the second portion of the synthetic large Rep protein functional interacts with the spacer, RBE, or extended RBE.

In one embodiment, one or more portions of the synthetic large Rep protein comprise a wild-type amino acid sequence from a parvovirus Rep protein. In another embodiment, one or more portions of the synthetic large Rep protein comprise an amino acid sequence that is modified as compared to the wild-type sequence of a parvovirus Rep protein. The modification can be an addition, deletion, substitution, or any combination thereof. The synthetic large Rep protein can comprise one or more modified amino acids, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 150, 175, 200, 225, 250, 275, 300, 325, 350, 375, 400, 425, 450, 475, 500, 525, 550, 575, or 600 or more amino acids or any range therein.

In one embodiment of the invention, the first and second portions (and/or the third portion) are directly linked to each other. In another embodiment, the portions are connected by a linker, e.g., 1, 2, 3, 4, 5, or 6 or more amino acids. The synthetic large Rep protein can comprise further portions (e.g., from Rep or another protein or synthetic sequences) that are not involved in the functional interaction with an ITR. Examples of other sequences can include, without limitation, localization signals, tags for improved isolation, etc.

In one embodiment, the first portion of the synthetic large Rep protein comprises, consists essentially of, or consists of an amino acid sequence from about residue 97 to about residues 146-151 of a wild-type AAV5 Rep sequence, e.g., SEQ ID NO:118. For example the first portion can comprise, consist essentially of, or consist of an amino acid sequence from about residue 1, 5, 10, 15, 20, 25, 30, 35, 40, 45, 50, 55, 60, 65, 70, 75, 80, 85, 90, or 95 to about residue 146, 147, 148, 149, 151, or 151 of a wild-type AAV5 Rep sequence or any range therein. In certain embodiments, the first portion comprises, consists essentially of, or consists of an amino acid sequence having at least 80% identity to a sequence from about residue 97 to about residues 146-151 of a wild-type AAV5 Rep sequence, e.g., at least 85%, 90%, 95%, 96%, 97%, 98%, or 99% identity.

In one embodiment, the second portion of the synthetic large Rep protein comprises, consists essentially of, or consists of an amino acid sequence from about residue 149 to about residue 187 of a wild-type AAV2 Rep sequence, e.g., SEQ ID NO:114. For example, the second portion can comprise, consist essentially of, or consist of an amino acid sequence from about residue 149 to about residue 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, or 620 of a wild-type AAV2 Rep sequence or any range therein. In certain embodiments, the second portion comprises, consists essentially of, or consists of an amino acid sequence having at least 80% identity to a sequence from about residue 149 to about residue 187 of a wild-type AAV5 Rep sequence, e.g., at least 85%, 90%, 95%, 96%, 97%, 98%, or 99% identity.

In a representative embodiment of the synthetic large Rep protein, the first portion comprises, consists essentially of, or consists of an amino acid sequence from about residue 97 to about residues 146-151 of a wild-type AAV5 Rep sequence and the second portion comprises, consists essentially of, or consists of an amino acid sequence from about residue 149 to about residue 187 of a wild-type AAV2 Rep sequence. In another representative embodiment, the first portion comprises, consists essentially of, or consists of an amino acid sequence from about residue 1 to about residues 146-151 of a wild-type AAV5 Rep sequence and the second portion comprises, consists essentially of, or consists of an amino acid sequence from about residue 149 to about residue 621 of a wild-type AAV2 Rep sequence. In certain embodiments, the synthetic large Rep protein comprises, consists essentially of, or consists of an amino acid sequence of SEQ ID NOS: 79, 81, and 83. In other embodiments, the synthetic large Rep protein comprises, consists essentially of, or consists of an amino acid sequence having at least 80% identity to an amino acid sequence of SEQ ID NOS: 79, 81, and 83, e.g., at least 85%, 90%, 95%, 96%, 97%, 98%, or 99% identity.

Figures 30, 31:
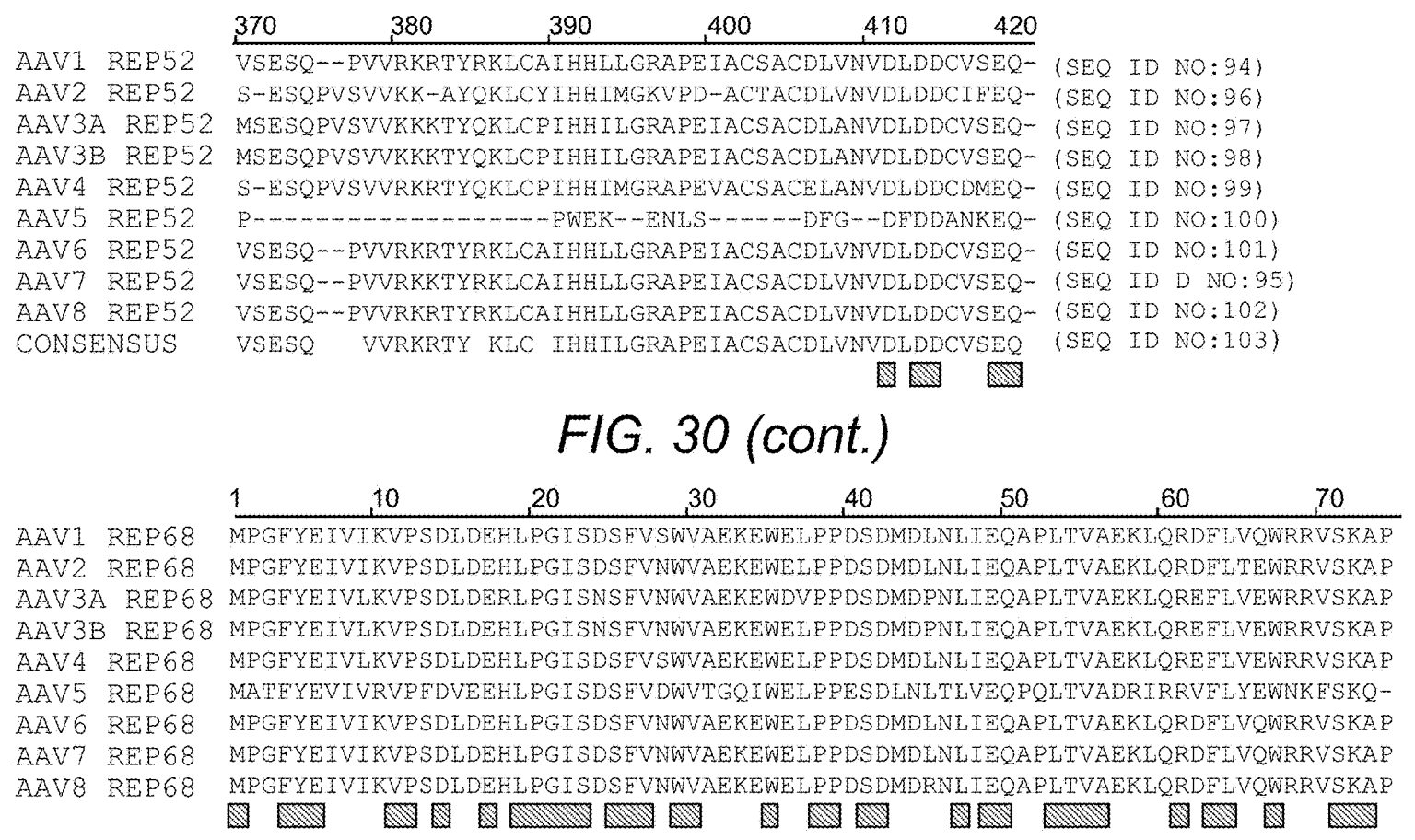
Figure 32:
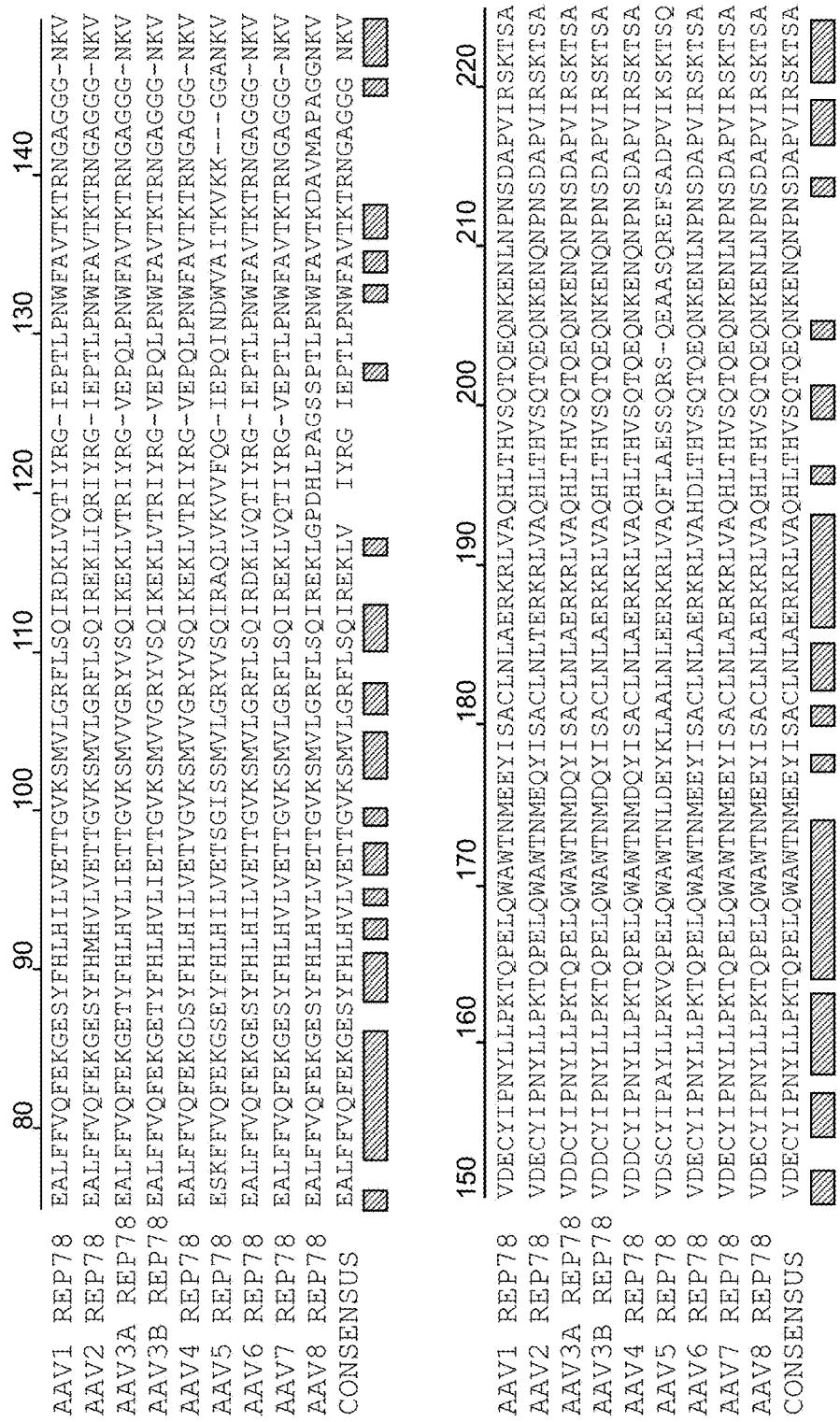
FIG. 32 shows an alignment of the amino acid sequences of exemplary Rep78 proteins from AAV1 (SEQ ID NO:113), AAV2 (SEQ ID NO:114), AAV3A (SEQ ID NO:115), AAV3B (SEQ ID NO:116), AAV4 (SEQ ID NO:117), AAV5 (SEQ ID NO:118), AAV6 (SEQ ID NO:119), AAV7 (SEQ ID NO:120) and AAV8 (SEQ ID NO:121), as well as a consensus sequence (SEQ ID NO:122). Dashes indicate gaps in the sequence and shading indicates positions of sequence homology.

In certain embodiments, the portion of the synthetic large Rep protein from a wild-type AAV2 Rep sequence as described above can be replaced with the corresponding portion from another human AAV serotype Rep protein other than AAV5, e.g., AAV1, AAV3, AAV4, AAV6, AAV7, AAV8, AAV9, AAV10, AAV11, AAV12, or AAV13. The structural and functional similarity between the Rep proteins of AAV2 and other human serotypes (with the exception of AAV5) may allow substitution of Rep sequences between the serotypes (see FIGS. 31 and 32).

In certain embodiments, one or more of the portions the synthetic Rep proteins can be modified to differ from the wild-type sequence (e.g., by modifying 1, 2, 3, 4, 5, 6, 7, 8, 9, 10, 11, 12, 13, 14, 15, 16, 17, 18, 19, or 20 or more aa or any range therein). In other embodiments, the synthetic Rep proteins exemplified herein can be modified (e.g., by modifying 1, 2, 3, 4, 5, 6, 7, 8, 9, 10, 11, 12, 13, 14, 15, 16, 17, 18, 19, or 20 or more aa or any range therein). In some embodiments, the modified synthetic Rep proteins retain amino acid Y156 (numbering according to Rep2). In other embodiments, modified synthetic Rep proteins retain amino acids C151, N155, and/or T161 (numbering according to Rep2). In other embodiments, modified synthetic Rep proteins retain amino acids G148, A152, and/or V158 (numbering according to Rep5). These specific amino acids may be important for activity and/or specificity.

The invention also provides polynucleotides (optionally, isolated polynucleotides) encoding the synthetic Rep proteins of the invention. In some embodiments, the polynucleotides further encode one or more parvovirus Cap proteins. Further provided are vectors comprising the polynucleotides, and cells (in vivo or in culture) comprising the polynucleotides and/or vectors of the invention. Suitable vectors include, without limitation, viral vectors (e.g., adenovirus, AAV, herpesvirus, vaccinia, poxviruses, baculoviruses, Epstein-Barr virus, and the like), plasmids, phage, YACs, BACs, and the like. In some embodiments, the polynucleotide is stably integrated into the genome of a cell. Such polynucleotides, vectors and cells can be used, for example, as reagents (e.g., helper packaging constructs or packaging cells) for the production of virus vectors as described herein.

Snake AAV ITRs

One aspect of the invention relates to the discovery that a snake AAV ITR sequence can function as a part of a parvovirus vector yet is not recognized by the Rep proteins of mammalian (e.g., human or primate) parvoviruses. Vector mobilization may therefore be reduced or avoided. Thus, one aspect of the invention relates to a parvovirus template comprising (i) a heterologous nucleotide sequence, and (ii) at least one snake AAV ITR sequence. The snake AAV ITR sequence can be from a royal python AAV. In one embodiment, the snake AAV ITR sequence comprises the nucleotide sequence of SEQ ID NO:123. In a further embodiment, the snake AAV ITR sequence comprises the nucleotide sequence of SEQ ID NO:123 that has been modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the parvovirus template comprises at least a portion of a snake AAV ITR, e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 or more contiguous nucleotides of a snake AAV ITR or any range therein. In certain embodiments, the parvovirus template comprises two snake AAV ITR sequences.

The invention further relates to a parvovirus particle comprising the snake parvovirus template of the invention. In certain embodiments, the parvovirus particle comprises a mammalian capsid, e.g., a human or primate capsid.

In one aspect, the invention relates to the discovery of methods for producing parvovirus particles comprising a snake AAV ITR, including the requirement for a mammalian small Rep protein. Thus, one aspect of the invention relates to a method of producing a parvovirus particle, comprising providing to a cell (e.g., a mammalian cell such as a human or primate cell) permissive for parvovirus replication: (a) a recombinant parvovirus template comprising (i) a heterologous nucleotide sequence, and (ii) at least one snake AAV ITR sequence; (b) a polynucleotide encoding one or more snake AAV Rep proteins and mammalian AAV Cap protein(s); and (c) a polynucleotide encoding mammalian Rep52 and/or Rep40 proteins; under conditions sufficient for the replication and packaging of the recombinant parvovirus template; whereby recombinant parvovirus particles packaging the recombinant parvovirus template are produced in the cell. In one embodiment, the mammalian AAV Cap protein is a human or primate AAV Cap protein. In another embodiment, the mammalian AAV Rep 52 and/or Rep 40 proteins are human or primate Rep52 and/or Rep40 proteins (including modified forms thereof), e.g., from AAV2. In some embodiments, the polynucleotide encoding snake AAV Rep protein and mammalian AAV Cap protein also encodes the mammalian Rep52 and/or Rep40 proteins. In other embodiments, the polynucleotide encoding snake AAV Rep protein and mammalian AAV Cap protein is separate from the polynucleotide encoding the mammalian Rep52 and/or Rep40 proteins. In some embodiments, the polynucleotide encoding snake AAV Rep protein and mammalian AAV Cap protein is the plasmid pSnRepCap2 (SEQ ID NO:125).

In other embodiments, other non-human AAV ITR sequences not recognized by the Rep proteins of human or primate parvoviruses may be used. Examples include, without limitation, sequences from shrimp, insect, goat, bovine, equine, canine, and equine AAVs.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a heterologous nucleotide sequence, and (ii) the modified parvovirus ITR of the invention; (b) a polynucleotide encoding a synthetic large Rep protein of the invention; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvovirus viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into parvovirus virions, e.g., are not flanked by TRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the parvovirus rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the parvovirus template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by TRs so that these sequences are not packaged into the parvovirus virions.

Zhang et al., ((2001) Gene Ther. 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) Gene Ther. 6:986 and WO 00/17377.

As a further alternative, the virus vectors of the invention can be produced in insect cells using baculovirus vectors to deliver the rep/cap genes and parvovirus template as described, for example, by Urabe et al., (2002) Human Gene Ther. 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g, Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factorα soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. Parvovirus vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. No. 6,013,487; U.S. Pat. No. 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are as are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intraocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

Example 1

Materials and Methods

Rep Cloning— pXR2 (Rep2Cap2) and pRep5Cap2 AAV helper plasmids served as templates for Rep cloning. The primer sequences used are indicated in Table 4. Two cloning strategies were used. Existing restriction sites were incorporated into primers for PCR (PCR-RD in Table 4) utilizing either pXR out fw or pXR out rev primers. PfuTurbo DNA Polymerase (Stratagene, La Jolla, Calif.) was used at the manufacturer's recommendations for all PCR reactions. PCR-RD products were digested with the enzymes indicated in Table 4 (NEB, Ipswich, Mass.) prior to ligation with T4 DNA Ligase (Invitrogen, Carlsbad, Calif.) according to the manufacturer's instructions. Alternately, an overlap-extension mediated PCR (OE-PCR) approach was used to produce Rep chimeras (Higuchi et al. (1988) *Nucleic Acids Res.* 16:7351). The Rep2 and Rep5 junction was incorporated into forward and reverse primers which were used in separate PCR reactions with the pXR out fw and rev primers (Table 4, only fw oligos indicated, rev oligos complimentary to fw). These overlapping PCR products were combined into a single PCR reaction and cycled as follows: 1 cycle at 94° C. for 30 seconds, 18 cycles of 30 seconds at 94° C., 30 seconds at 65° C., and 4 minutes at 72° C., 1 cycle of 10 minutes at 72° C. 1 μl of this reaction was used as template for a nested PCR with the pXR in fw and rev primers. Chimeras with the N-terminus of Rep2 and C-terminus of Rep5 were cloned into the Rep25aa166 construct between the PpuMI and MfeI sites. Chimeras with the N-terminus of Rep5 and C-terminus of Rep2 were cloned into the 52aa160 construct between the PpuMI and BstBI sites. All constructs were verified by DNA sequencing at the UNC-CH Genome Analysis Facility.

TABLE 4

| Clone/Primer | Cloning Method | Orientation | Sequence | SEQ ID NO |
|---|---|---|---|---|
| pXR out fw | | Forward | 5' CGAAAAGTGCCACCTGACGTCTAAGAAACC | 126 |
| pXR in fw | | Forward | 5' TCGAATTCGACGGCCAGTGAATTGTAATACGACTC | 127 |
| pXR out rev | | Reverse | 5' CCATGATTACGCCAAGCTCGGAATTAACCGCATGCGA | 128 |
| pXR in rev | | Reverse | 5' CCATGGCCGGGCCCGGATTCACC | 129 |
| Rep52aa84 | PCR-RD AleI | Reverse | 5' TTCACCCCGGTGGTTTCCACGAGCACGTGCATGTGGAAGTAGCTCT CTCCCTTTTCAAACTGCACAAAG | 130 |
| Rep52aa110 | PCR-RD EagI | Forward | 5' CCTCGGCCGCTACGTGAGTCAGATTCGCGAAAAACTGATTCAGAG | 131 |
| Rep52aa126 | OE PCR | Forward | 5' GTGGTCTTCCAGGGAATTGAACCCACTTTGCCAAACTGGTTCGCGGTC | 132 |
| Rep52aa138 | OE PCR | Forward | 5' CTGGGTCGCCATCACCAAGGTAAAGAAGGGAGGCGGGAACAAGGTGGT GGATGAG | 133 |
| Rep52aa146 | OE PCR | Forward | 5' GCGGAGCCAATAAGGTGGTGGATGAGTGCTACATCCCCAATTACTTGCTC | 134 |
| Rep52aa160 | PCR-RD Bpu10I | Reverse | 5' ACTGGAGCTCAGGTTGGACCTTCGGCAGCAGGTAG | 135 |
| Rep52aa175 | OE PCR | Forward | 5' CGTGGACAAACCTGGACGAGTATAAATTGGCCTGTTTGAATCTCACGGAG CGTAAAC | 136 |
| Rep52aa187 | OE PCR | Forward | 5' CTGAATCTGGAGGAGCGCAAACGGTTGGTGGCGCAGCATCTGACGCAC | 137 |
| Rep52aa207 | PCR-RD SgrAI | Reverse | 5' GATCACCGGCGCATCCGAGAACTCACGCTGCGAAGC | 138 |
| Rep25aa77 | OE PCR | Forward | 5' TAAGGCCCCGGAGGCCCTTTTCTTTGTGCAGTTTGAAAAGGGATCTG | 139 |
| Rep25aa97 | OE PCR | Forward | 5' CCACATGCACGTGCTCGTGGAAACCTCCGGCATCTCTTCCATGGTCCTCG | 140 |
| Rep25aa116 | PCR-RD NruI | Forward | 5' TCAGATTCGCGAAAAACTGGTGAAAGTGGTCTTCCAGG | 141 |
| Rep25aa125 | OE PCR | Forward | 5' GAATTTACCGCGGGATCGAGCCG CAGATCAACGACTGGGTCGCCATC | 142 |
| Rep25aa141 | OE PCR | Forward | 5' GGTCACAAAGACCAGAAATGGCGCCGGCGGAGCCAATAAGGTGGTGGATT CTGG | 143 |
| Rep25aa149 | OE PCR | Forward | 5' GAGGCGGGAACAAGGTGGTGGATTCTGGGTATATTCCCGCCTACTGC | 144 |
| Rep25aa166 | PCR-RD Bpu10I | Forward | 5' CCAGCCTGAGCTCCAGTGGGCGTGGACAAACCTG | 145 |
| Rep25aa187 | OE PCR | Forward | 5' GTTTGAATCTCACGGAGCGTAAACGGCTCGTCGCGCAGTTTCTGGCAG | 146 |
| Rep25aa216 | PCR-RD SgrAI | Forward | 5' ATGCGCCGGTGATCAAAAGCAAGACTTCCCAGAAATACATGG | 147 |
| ITR2 Half1 Kpn | | Forward | 5' ATTATAGGTACCAGGAACCCCTAGTGATG | 148 |
| ITR2 Half 1 Sfi | | Reverse | 5' TAATAGGGCCCAAAGGGCCGGG | 149 |
| ITR2 Half2 Sfi | | Forward | 5' TTAATAGGCCCTTTGGGCCGGG | 150 |
| ITR2 Half2 Hind | | Reverse | 5' TATAATAAGCTTAGGAACCCCTAGTGATGGAG | 151 |
| ITR5 Halt1 Kpn | | Forward | 5' ATTATAGGTACCTACAAAACCTCCTTGCTTGAG | 152 |
| ITR5 Half1 Sfi | | Reverse | 5' TTAATAGGCCCTTTGGGCCGTCGC | 153 |

TABLE 4-continued

| Clone/Primer | Cloning Method | Orientation | Sequence | SEQ ID NO |
|---|---|---|---|---|
| ITR5 Half2 Sfi | | Forward | 5' TTAATAGGCCCAAAGGGCCGTCGTC | 154 |
| ITR5 Half2 Hind | | Reverse | 5' TATAATAAGCTTTACAAAACCTCCTTGCTTGAGAG | 155 |

ITR Cloning—

ITRs were cloned into a pUC-18 plasmid with a GFP cassette (CMV promoter, SV40 polyA) cloned between the KpnI and EcoRI restriction sites. The ITRs were synthesized in two halves as 4 nmol Ultramer DNA oligos (Integrated DNA Technologies, Coralville, Iowa). SfiI restriction sites were incorporated into one hairpin arm the ITR for cloning (FIG. 1A). Due to inconsistencies of the reported sequence at the tip of the ITR5 hairpins between Chiorini et al. (1999), the published GenBank sequence (accession number NC_006152), and restriction mapping, an ITR2 hairpin was utilized for the ITR5 construct (FIG. 1A). 200 pg of each oligo was amplified in a PCR reaction using the ITR primers listed in Table 4. 2.5 U of PfuTurbo DNA Polymerase (Stratagene, La Jolla, Calif.) was used to amplify each half of the ITR as follows: 1 cycle at 94° C. for 4 minutes, 35 cycles of 45 seconds at 94° C., 30 seconds at 50° C., and 30 seconds at 72° C., 1 cycle of 10 minutes at 72° C. PCR reactions were purified and subject to digestion by KpnI and SfiI or HindIII and SfiI (NEB, Ipswich, Mass.). A triple ligation with the pUC-18 GFP plasmid and each half of the ITR was performed with T4 DNA Ligase (Invitrogen, Carlsbad, Calif.) for 1.5 hours at room temperature. All constructs were verified by DNA sequencing at the UNC-CH Genome Analysis Facility after linearization of the plasmid and ablation of the ITR secondary structure by SfiI digestion.

Western Blot Analysis—

Samples for Western blot analysis were harvested 48-72 hours after transfection of Ad-helper plasmid and the appropriate AAV helper construct. Cells were washed and resuspended in 100 µl PBS prior to addition of 100 µl 2× Laemmli Sample Buffer (100 mM Tris pH 6.8, 4% SDS, 200 mM DTT, 20% glycerol, 0.1% Bromophenol Blue). Samples were briefly sonicated and boiled for 10 minutes. Samples were run on NUPAGE 4-12% Bis-Tris gels (Invitrogen, Carlsbad, Calif.) at 160 volts for 90 minutes. Protein was transferred to a Nitrocellulose membrane (Invitrogen, Carlsbad, Calif.) via a wet transfer for 60 minutes at 30 volts. Gels were blocked overnight in 10% nonfat dry milk in 1× PBS/Tween (0.05%). Detection of both Rep2 and Rep5 proteins (all four sizes) was achieved with a monoclonal Anti-Adeno-Associated Virus Rep Protein antibody (clone 259.5, American Research Products, Belmont, Mass.) at a 1:20 dilution in PBS/Tween for 60 minutes at room temperature. After washing, a secondary HRP anti-mouse antibody was added at a 1:5,000 dilution in PBS/Tween for one hour at room temperature. After washing, SuperSignal West Femto Maximum Sensitivity Substrate (Pierce, Rockford, Ill.) was added and blots were exposed to X-ray film.

Cell Culture and rAAV Production—

HEK 293 cells were obtained from ATCC and cultured in Dulbecco Modified Eagle Medium (DMEM) supplemented with 10% Fetal Bovine Serum (Sigma, St. Louis, Mo.) and 100 units/ml penicillin and 100 µg/ml streptomycin and grown at 37° C. with 5% $CO_2$ saturation. Transfections were performed in six-well cell culture plates. 0.75 µg each of Ad-helper plasmid, AAV helper plasmid (either Rep2Cap2, Rep5Cap2, or the Rep mutant described), and the GFP plasmid containing the ITR (mutant or wt ITR as specified in text) were triple-transfected with polyethyleneimine (PEI) (25,000 linear molecular weight) as described (Xiao et al. (1998) J. Virol. 72:2224). Cells were harvested 48-72 hours post-transfection.

Hirt DNA Purification and Southern Blot Analysis—

Hirt DNA purification was performed as described (Hirt (1967) J. Mol. Biol. 26:365). Cells were harvested 48-72 hours post-transfection, washed in PBS, and resuspended in 370 µl Hirt Solution (0.01M Tris-HCl pH 7.5 and 0.1M EDTA) prior to addition of 25 µl 10% SDS and 165 µl 5M NaCl. Samples were incubated at 4° C. overnight prior to centrifugation. DNA was purified by phenol chloroform extraction and precipitated by an equal volume of isopropanol prior to resuspension in 50 µl sterile $ddH_2O$. 5 ul of each sample was digested with 4 U DpnI (NEB, Ipswich, Mass.) 2-4 hours at 37° C. prior to gel electrophoresis and Southern blot analysis to remove non-replicated transfected plasmid (Chomczynski (1992) Anal. Biochem. 201:134). The nylon membrane (Hybond-XL; GE Healthcare Life Sciences, Piscataway, N.J.) was hybridized to a probe corresponding to the GFP open reading frame labeled with the Random Primed DNA Labeling Kit (Roche, Indianapolis, Ind.) and d-CTP $P^{32}$. Blots were visualized after exposure to a phosphorimager screen (GE Healthcare Life Sciences, Piscataway, N.J.).

Densitometry—

Densitometry was performed using the public domain NIH Image program (developed at the U.S. National Institutes of Health available on the Internet at the NIH website). Densitometry analysis of a DpnI resistant band on the agarose gel prior to transfer was used as a loading control to normalize values obtained from the Southern blot. The lowest value (absence of any vector replication) was subtracted from all values to account for background. In order to gauge relative replication efficiency, values for ITR2 vectors were divided by the value obtained from the Rep2-ITR2 control. ITR5 vectors were compared to the Rep5-ITR5 control. All values were obtained in triplicate (n=3). Error bars represent standard error (standard deviation divided by the root of 3). All samples were compared to controls on the same blot.

Molecular Modeling—

Molecular models were generated using Swiss-Model (available at the expasy.org website). The published crystal structure of the N-terminus of Rep5 complexed with the RBE (PDB accession #1rz9) was used as a template for all models. Visualization of protein structure rendering of images were performed with PyMOL (available at pymol.org). DNA folding was performed using the DNA mfold server (available at mfold.bioinfo.rpi.edu).

Example 2

Construction and Characterization of Chimeric ITRs

Previously, AAV replicative specificity was postulated to be driven by the trs sequence (Chiorini et al. (1999) J. Virol.

73:4293; Chiorini et al. (1999) *J. Virol.* 73:1309). Rep2 can nick the ITR2 trs (AGT/TGG) and the AAVS1 trs of human chromosome 19 (GGT/TGG) (Wu et al. (2001) *Arch. Biochem. Biophys.* 389:271). Rep5 nicks only the ITR5 trs (AGTG/TGG). However, alignment of the ITR2 and ITR5 sequences revealed several significant sequence and structural differences outside the trs sequence (FIG. 1A). The spacing between the putative RBE and the nicking stem was significantly different; three nucleotides (nt) for ITR2 and 15 nt for ITR5. Additionally, while the trs sequence is not tightly conserved between ITR2 and ITR5, neither is the height or overall length of the putative nicking stem.

A novel method was used to generate mutant ITRs in order to determine which portions of the ITR were responsible for replicative specificity. Previous studies have investigated Rep-ITR interactions in vitro largely due to the difficulty of synthesizing full length ITRs for in vivo assays. PCR through the secondary structure of the ITR is inefficient and sequencing through these elements typically requires radiolabeled chain-terminator sequencing (Young et al. (2000) *J. Virol.* 74:3953). The AAV ITRs are highly recombinogenic and are frequently mutated even in a plasmid context (Samulski et al. (1983) *Cell* 33:135).

Figure 36A:
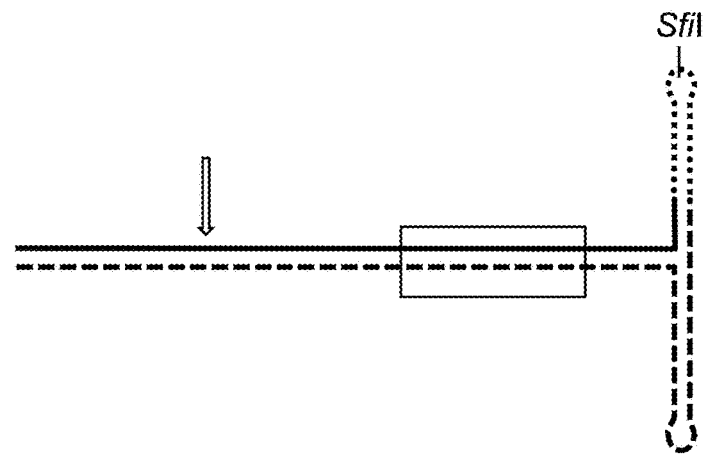
FIGS. 36A-36C shows a diagram of ITR synthesis.
Figure 36B:
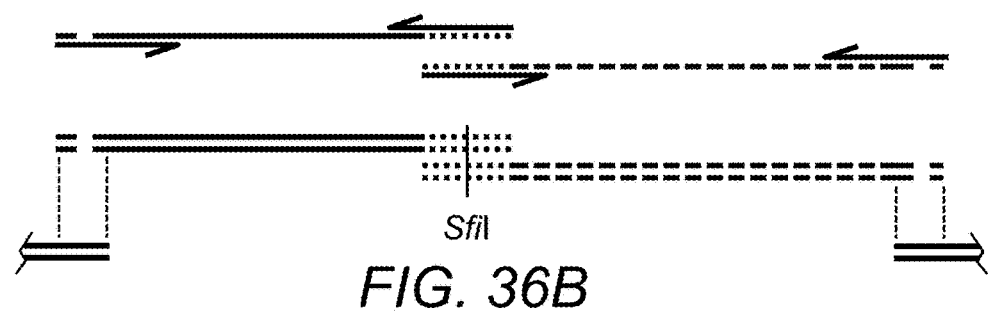
Figure 36C:
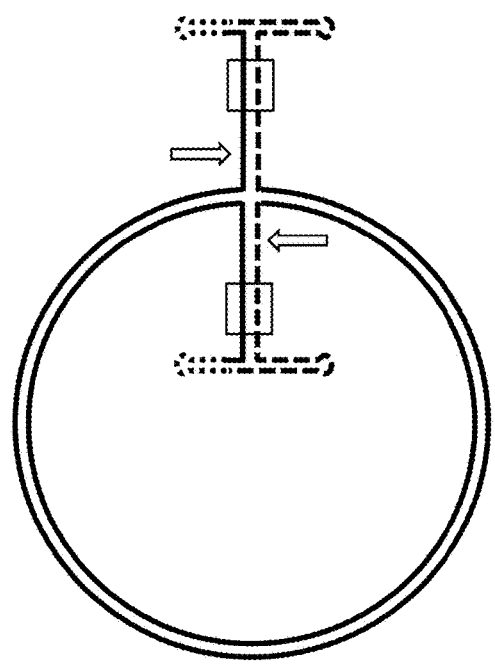

In order to address these concerns, the ITRs were synthesized and amplified in halves (FIGS. 36A-36C). To assemble the halves, a SfiI site was included in one of the hairpin arms of the ITR. SfiI allowed the conservation of the RBE' sequence (Brister and Muzyczka (2000) *J. Virol.* 74:7762). Cloning the ITR in a double D element (DD) format required only one ITR per plasmid for replication (Xiao et al. (1997) *J. Virol.* 71:941). The three core Rep functions necessary for AAV replication (Rep binding, helicase, and nicking) were analyzed by the presence or absence of intracellular replication of the plasmid. This assay provided the ability to quantitate Rep-ITR function in a physiological setting, removing the concern that highly purified Rep protein might take on aberrant function in vitro. This system also avoided concerns that previous in vitro assays used only a fragment of the ITR or that oligos used to recapitulate the ITR might not fold correctly.

An alignment of ITR2 (SEQ ID NO:17) and ITR5 (SEQ ID NO:18) (FIG. 1A) revealed several divergent elements which might confer Rep specificity. The spacer and nicking stem elements appeared to be the most likely candidates for unique interactions with their cognate Rep protein. This hypothesis was supported by low homology of these elements between AAV2 and AAV5.

Figure 1B:
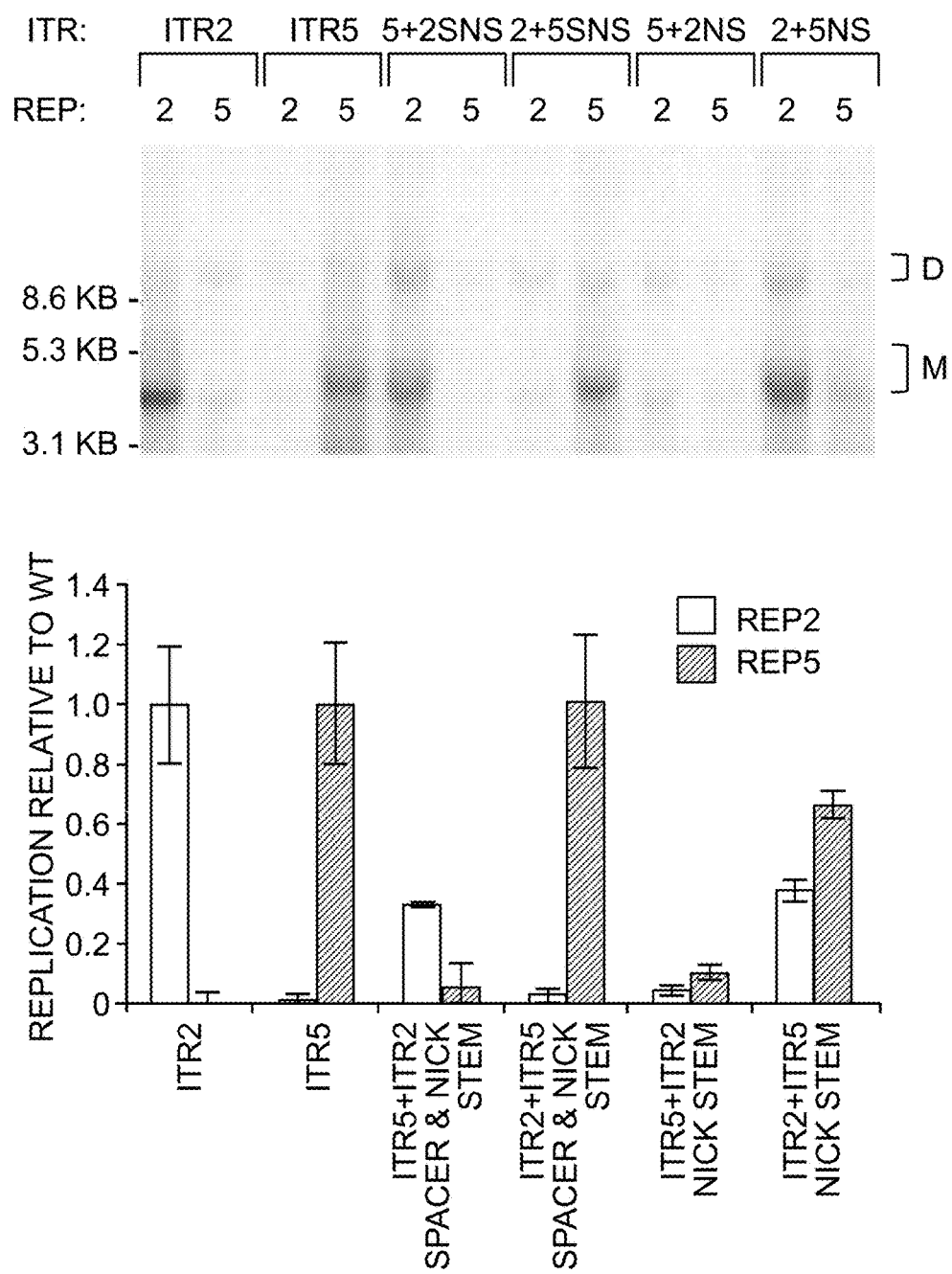

Wt ITRs containing the SfiI site functioned as expected with Rep2 specific to ITR2 and Rep5 specific to ITR5 (FIG. 1B). Rep2-ITR2 replicated approximately 2-fold better than Rep5-ITR5, potentially due to the lower folding energy of ITR5 resulting in reduced plasmid stability prior to replication. Due to this minor difference in replicative fidelity, all ITRs replicated with Rep2 were normalized to Rep2-ITR2, while ITRs replicated with Rep5 were normalized to Rep5-ITR5 (FIG. 1B).

In order to confirm that the RBE and hairpin arms played no role in Rep specificity, we generated a chimeric ITR with ITR5 binding elements and an ITR2 spacer and nicking stem (ITR5+2SNS, SEQ ID NO:19). Only Rep2 replicated this ITR, confirming the determinants of replicative specificity lie in the spacer/nicking stem elements (FIG. 1B). While ITR5+2SNS replication was not as efficient as ITR2-Rep2, it was replicated at ITR5-Rep5 levels. Conversely, Rep5 specifically replicated an ITR comprised of ITR2 hairpins and hairpin spacer and the ITR5 spacer and nicking stem (ITR2+5SNS, SEQ ID NO:20, FIG. 1B). Rep5 replicated this ITR at wt levels. These data demonstrated that Rep-ITR specificity lies outside of the ITR binding regions.

Next, chimeric ITRs were created to explore whether the nicking stem or the spacing between the RBE and nicking stem harbored unique interactions with the Rep protein. An ITR with the ITR5 binding elements and spacer and the ITR2 nicking stem could not be replicated by either Rep2 or Rep5 (ITR5+2NS, SEQ ID NO:21, FIG. 1B). The corresponding chimeric ITR (ITR2 binding elements and spacer with an ITR5 nicking stem) was replicated by both Rep2 and Rep5 (ITR2+5NS, SEQ ID NO:22, FIG. 1B). This disparity suggested that the spacer and nicking stem play different roles in Rep-ITR specificity between AAV2 and AAV5.

Example 3

The Nicking Stem is Important for ITR5 Specificity

Figure 2A:
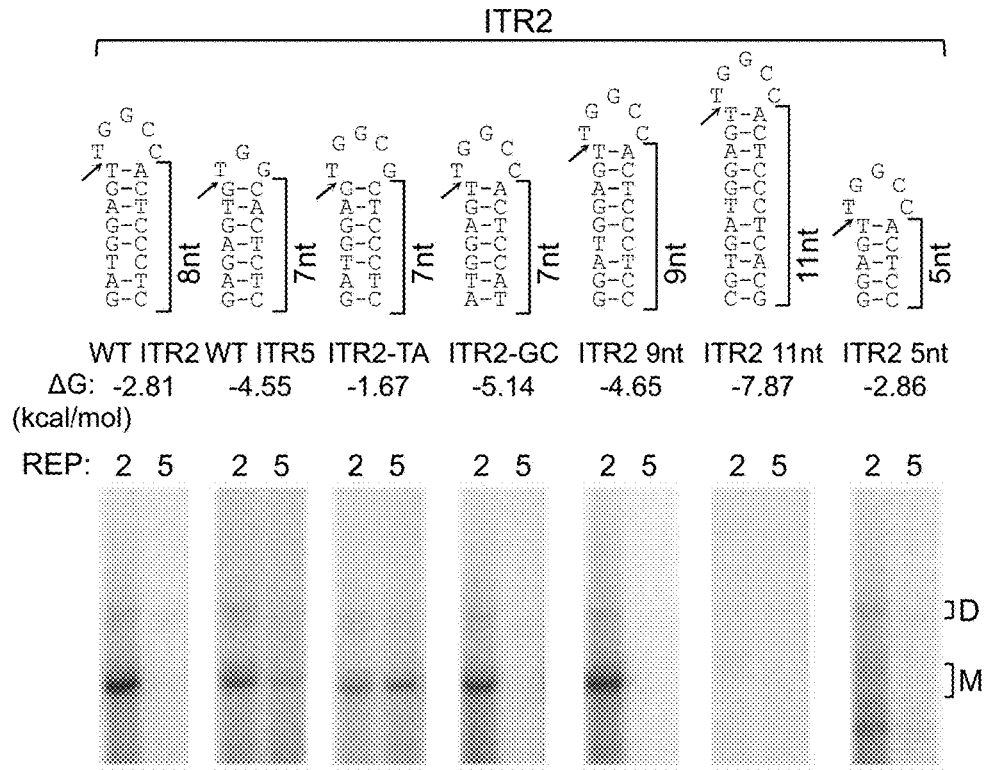
FIGS. 2A-2D show the relation of nicking stem height and sequence to Rep-ITR specificity.

ITR2+5NS (SEQ ID NO:22) established that Rep2 is capable of nicking an ITR with an ITR5 nicking stem and that Rep-ITR specificity is not driven exclusively by the trs sequence (FIG. 1B). In order to determine the flexibility of Rep2 toward mutant nicking stems, ITR2s containing altered forms of the hairpin were generated (FIG. 2A). Rep2 is able to replicate an ITR with an ITR5 nicking stem even though the ITR5 nicking stem contains a different trs sequence, is one bp shorter, and has two fewer unpaired nucleotides at its tip (FIG. 2A). The substitution of the ITR5 nicking stem into ITR2 also allowed replication by Rep5.

To determine which element of the ITR2 nicking stem prevented Rep5 activity, specific portions of the ITR2 stem were altered. First, one bp at the top of the putative ITR2 nicking stem was removed to lower the height to that of ITR5 (ITR2-TA, SEQ ID NO:23). Removing the T-A bp also resulted in a trs resembling ITR5, nicking between G/T opposed to T/T. Rep2 continued to function on this ITR as did Rep5, demonstrating that Rep5 can tolerate five unpaired nucleotides at the tip of the stem as long as the stem height and nt sequence are correct. A similar deletion from the base of the ITR2 nicking stem reduced the height to that of ITR5 while retaining the ITR2 nicking site (ITR2-GC, SEQ ID NO:25). Rep2 continued to function efficiently on this ITR while Rep5 activity was ablated. This data suggested that the inability of Rep5 to function on ITR2 is primarily the sequence of the trs, specifically the requirement for a nick to be generated between G/T.

To determine the extent of Rep2 flexibility for different nicking stems, three additional ITR2 mutants were created. Extending the nicking stem by one bp at the base had no effect on replication by Rep2 (ITR2 9 nt, SEQ ID NO:30). However, a three bp extension was sufficient to ablate Rep2 function on the ITR (ITR2 11 nt, SEQ ID NO:32). Surprisingly, Rep2 was able to tolerate a three bp deletion from the base of the stem, underlining the flexibility of Rep2 with respect to nicking stem substrates (ITR2 5 nt, SEQ ID NO:28).

Figure 2B:
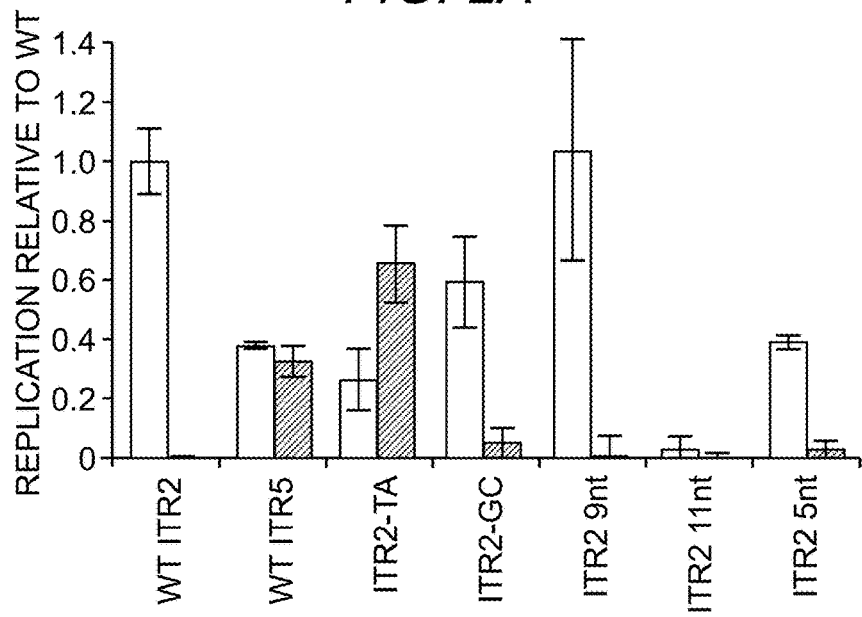
Figure 2C:
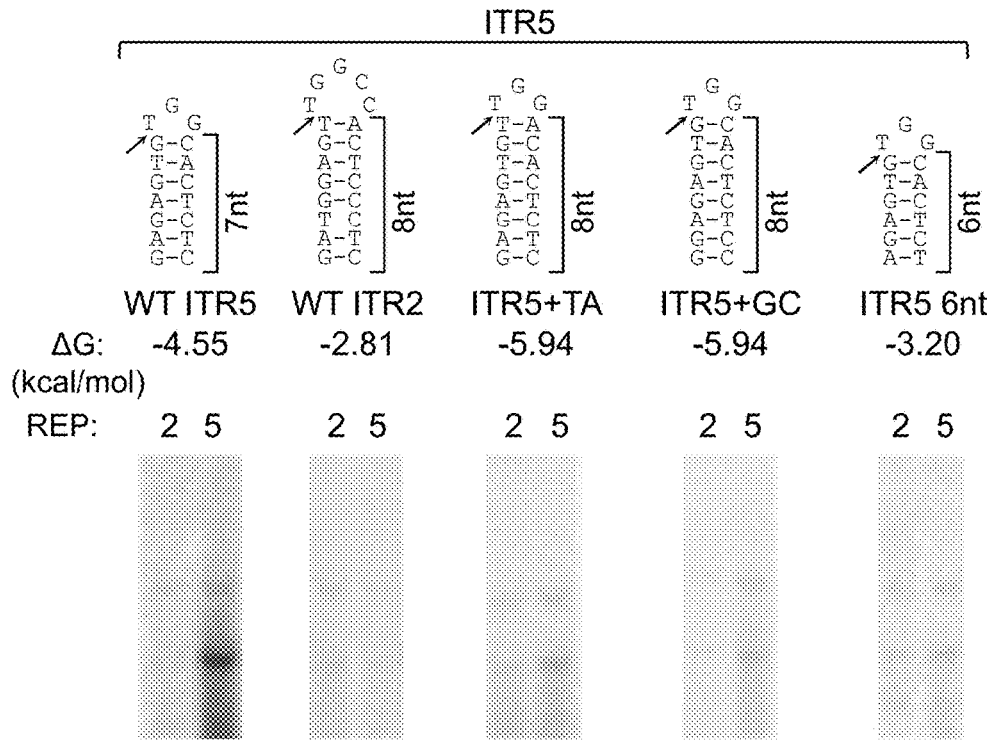
Figure 2D:
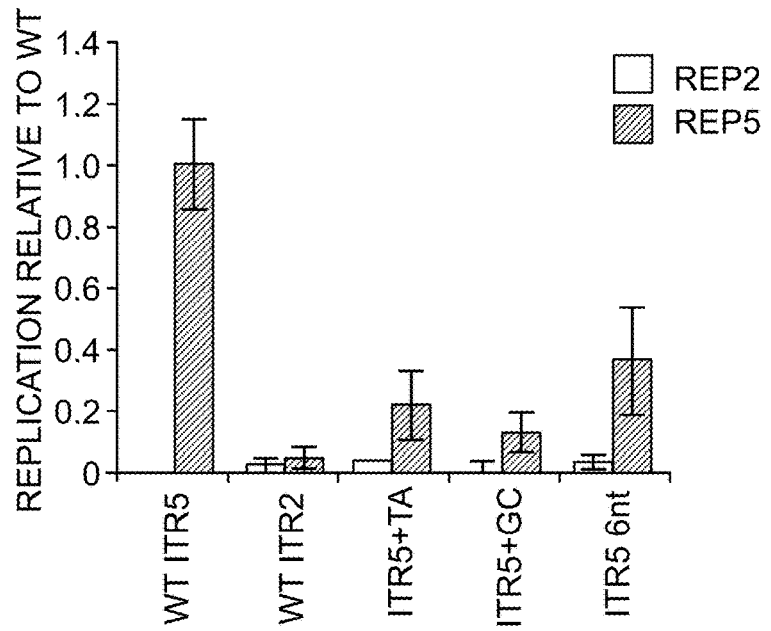

In order to explore the level of flexibility Rep5 possessed toward non-wt nicking stems, a panel of mutant ITR5s harboring altered nicking stems were created (FIG. 2C). Curiously, Rep2 replicated none of these ITRs, suggesting an element outside the ITR5 nicking stem is responsible for preventing Rep2 function. As in FIG. 1B, replacement of the ITR5 nicking stem with that of ITR2 resulted in the ablation of replication by Rep5, attributable to the incompatible trs sequence. The addition of one bp at the top of the ITR5 nicking stem severely decreased the ability of Rep5 to replicate the ITR (ITR5+TA, SEQ ID NO:24, FIG. 2D). This insertion disrupted the ITR5 trs sequence and increased the size of the stem one bp. However, the low level of replication by Rep5 on ITR5+TA suggests that the entire trs site of ITR2 is necessary to confer Rep2 specificity, not just the presence of a T/T nick site.

The addition of one bp to the base of the ITR5 nicking stem, preserving the ITR5 trs at the tip, nearly eliminated replication by Rep5 (ITR5+GC, SEQ ID NO:26). Likewise, the removal of one bp from the base of the ITR5 nicking stem strongly decreased replication by Rep5 (ITR5 6 nt, SEQ ID NO:35, FIG. 2D). This data suggests that Rep5 is sensitive both to the height of the nicking stem as well as to the sequence of the trs. Thus, Rep5 is unable to replicate ITR2 because the ITR2 nicking stem is one bp too tall and has an incompatible trs sequence.

Example 4

Spacer Length is Important for ITR2, not ITR5

While Rep2 can replicate a vector with an ITR5 nicking stem, it can not replicate wt ITR5 (FIG. 1B). The only difference between ITR5+2SNS (which Rep2 can replicate) and ITR5+2NS (which Rep2 cannot replicate) is the ITR5 spacer (FIG. 1B). The wt Rep2 spacer is three nt long while the wt Rep5 spacer is 15 nt long. Thus, we hypothesized that Rep2 may be sensitive to spacer length.

Figure 3A:
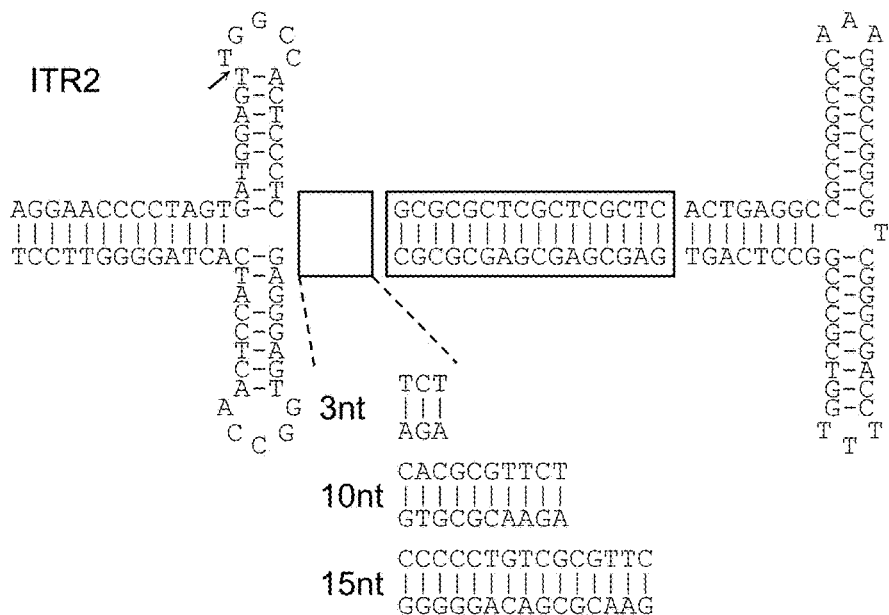
FIGS. 3A-3D show the effect of RBE-nicking stem spacing on Rep-ITR specificity.
Figure 3B:
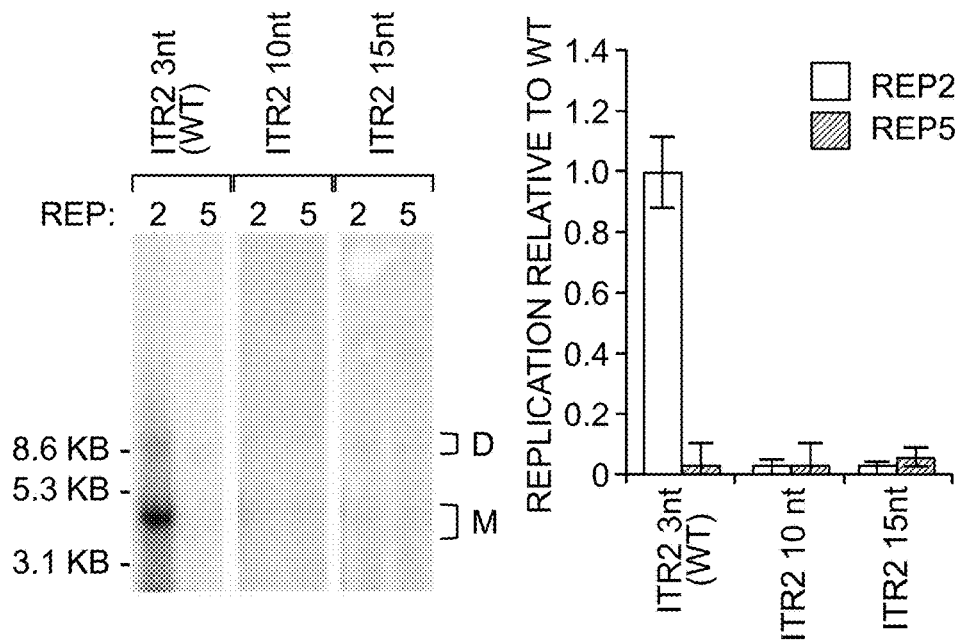
Figure 3C:
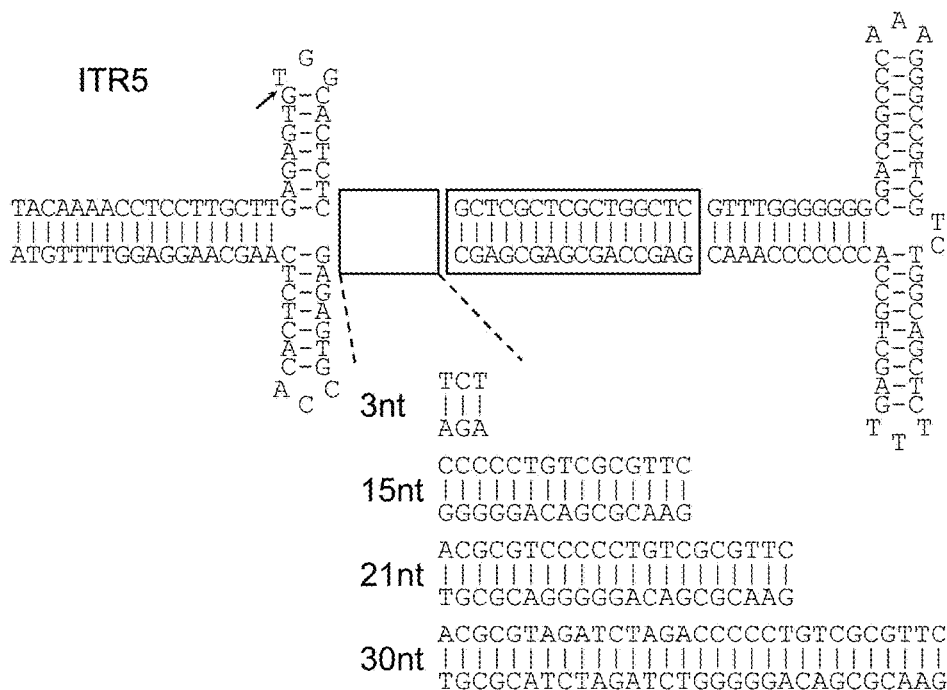

To explore the effect of spacer length on ITR2 and ITR5, a series of mutant ITR2s and ITR5s with differing spacer lengths were generated (FIGS. 3A and 3C). An insertion extending the ITR2 spacer to 10 nt ablated replication by Rep2 (ITR2 10 nt, SEQ ID NO:31, FIG. 3B). Similarly, substitution of the ITR2 spacer with the 15 nt spacer of ITR5 also ablated replication by Rep2 (ITR2 15 nt, SEQ ID NO:33, FIG. 3B). Rep5 was unable to replicate any of these vectors due to the presence of the ITR2 stem loop.

Figure 3D:
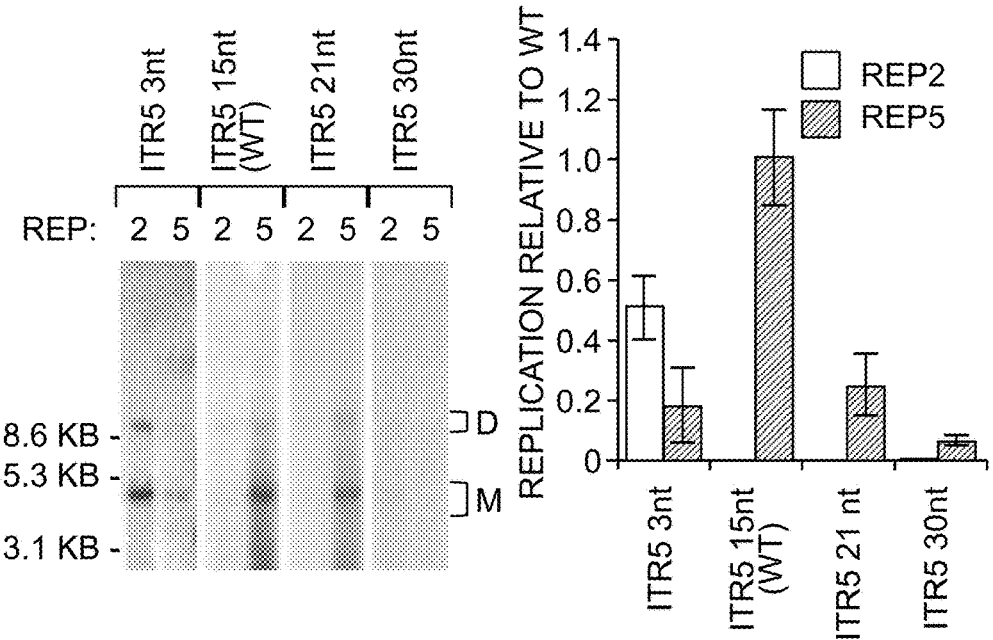

Rep5 displayed greater flexibility toward spacer elements of differing lengths. Replacing the 15 nt ITR5 spacer with that of ITR2 resulted in an ITR in which Rep5 retained the ability to replicate at a reduced level (ITR5 3 nt, SEQ ID NO:34, FIG. 3D). Additionally, the presence of the three nt spacer allowed Rep2 to function on this ITR. The addition of six nt to the ITR5 spacer (for a total spacer length of 21 nt) resulted in an ITR capable of being replicated by Rep5 at an efficient level (ITR5 21 nt, SEQ ID NO:37, FIG. 3D). Replication by Rep5 was effectively abolished only after the insertion of 15 nt into the spacer (ITR5 30 nt, SEQ ID NO:38, FIG. 3D). This panel of mutant ITR5s demonstrates the importance of a three nt spacer element for Rep2 function.

This data confirmed that the length of the ITR5 spacer was important to block Rep2 function. Even small insertions into the ITR2 spacer were not tolerated by Rep2. Meanwhile, Rep5 is flexible in regard to spacer length, demonstrating the ability to function on ITRs with spacers from 3-21 nt.

Example 5

The ITR5 Spacer Acts as a RBE for Rep5

Figure 4A:
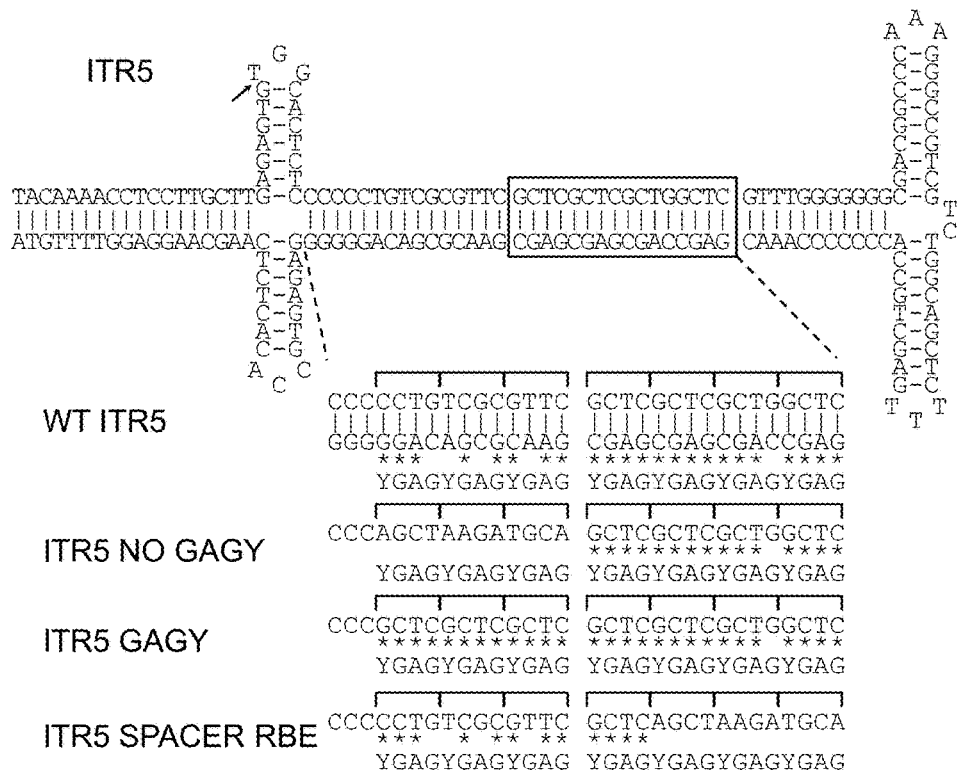
FIGS. 4A-4D demonstrate that the ITR5 spacer acts as a RBE for Rep5.

The inability of Rep2 to function on ITRs with spacers longer than three nt led to the question of why Rep5 was so flexible in this regard. It was hypothesized that Rep5 might specifically bind the ITR5 spacer just as it binds the RBE. The inability of Rep2 to bind this sequence would preclude its function on ITR5. Supporting this hypothesis was a moderately conserved GAGY Rep binding motif extending throughout the ITR5 spacer (FIG. 4A). Additionally, as Rep monomers bind every four nt, the binding of three Rep5 monomers to the 15 nt spacer element would result in a three nt spacer, similar to that of ITR2 (Hickman et al. (2004) *Mol. Cell* 13:403).

Figure 4B:
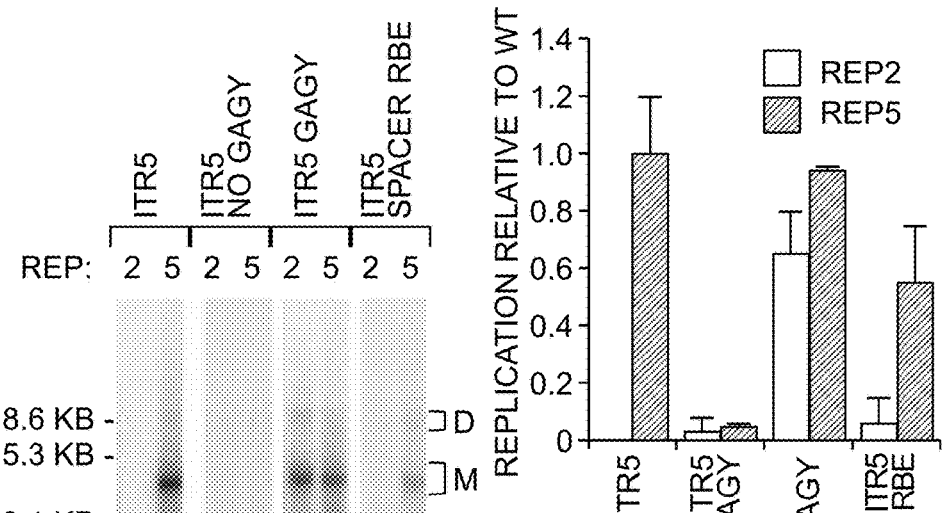

If Rep5 does bind the loosely conserved GAGY motif, the removal of that motif from the spacer should abolish Rep5 function. Indeed, the ITR5 No GAGY mutant (SEQ ID NO:40) could not be replicated by Rep2 or Rep5 (FIG. 4B). This suggested that the specific sequence of the ITR5 spacer plays an active role in the Rep5-ITR5 interaction. Conversely, a spacer with a pure GAGY repeat should not disrupt the ability of Rep5 to function on the ITR. Indeed, Rep5 was able to replicate this ITR at wt levels (ITR5 GAGY, SEQ ID NO:39, FIG. 4B). Rep2 was also able to replicate this ITR efficiently, suggesting the poorly conserved nature of the GAGY repeat within the ITR5 spacer prevents an important DNA-protein interaction with Rep2 necessary for replication.

To explore how the ITR5 spacer functioned as an RBE, we removed three GAGY repeats from the hairpin side of the RBE (ITR5 Spacer RBE, SEQ ID NO:42, FIG. 4A). This essentially shifted the 16 nt RBE 12 nt closer to the nicking stem. Rep5 replicated this ITR efficiently, confirming the ITR5 spacer acts as a RBE (FIG. 4B). The slight reduction in replication fidelity of this ITR, as compared with that of wt ITR5, may signal the inability of Rep to properly interact with the RBE' (Brister and Muzyczka (2000) *J. Virol.* 74:7762). Rep2 was again unable to replicate ITR5 Spacer RBE due to its inability to interact with the ITR5 spacer.

Figure 4C:
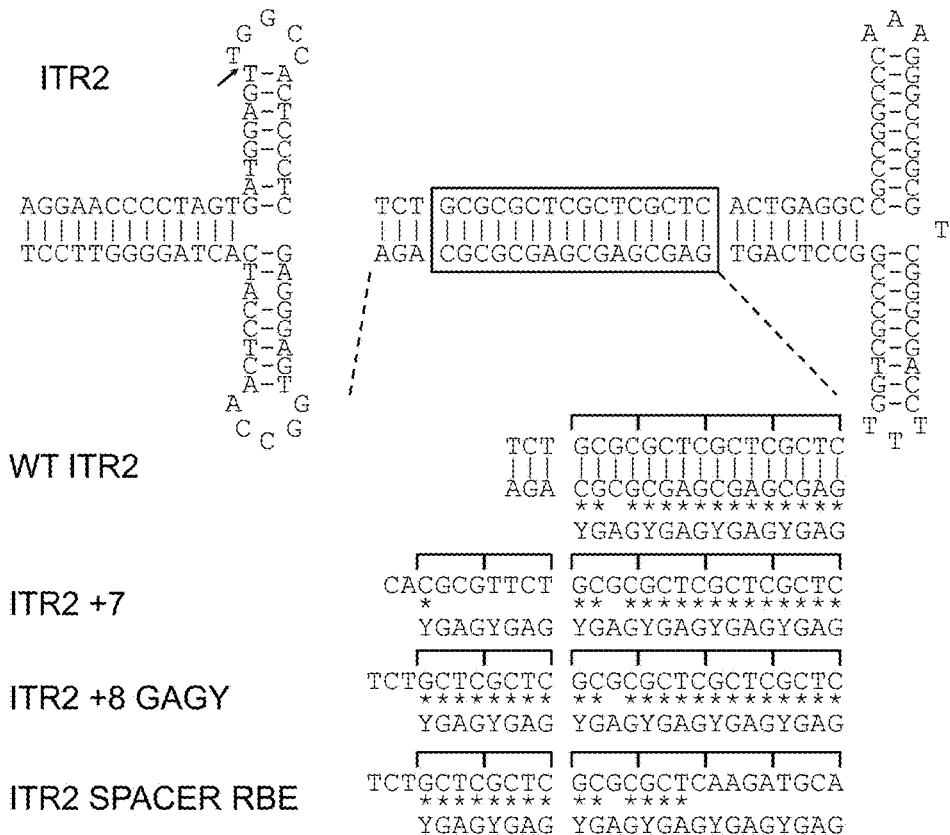
Figure 4D:
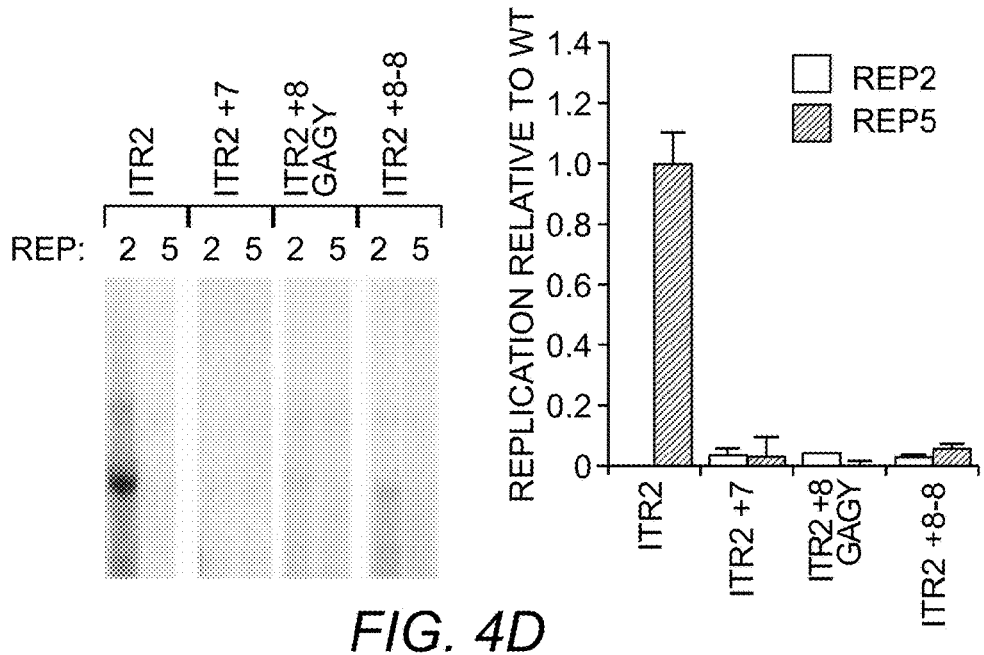

Next, we sought to extend the ITR2 spacer element to function as an extended RBE (FIG. 4C). The seven nt insertion attempted in FIG. 3A possessed essentially no GAGY homology (ITR2+7, SEQ ID NO:29, FIG. 4C). As a result, Rep2 could not replicate this ITR (FIG. 4D). Eight nt (two four nt GAGY repeats) inserted into the ITR2 spacer between the RBE and the existing spacer (ITR2+8 GAGY, SEQ ID NO:41) prevented replication by Rep2, demonstrating that the ITR2 RBE cannot be extended. This suggests that Rep2 may be dependent on RBE' binding or a specific spacer length for proper oligomerization to function on its cognate ITR. Curiously, this requirement does not apply to Rep2 function on ITR5 GAGY (FIG. 4A).

Similar to ITR5 Spacer RBE, we retained the eight nt GAGY insertion into ITR2 while removing eight nt of GAGY from the hairpin side of the RBE (ITR2+8–8 Spacer RBE, SEQ ID NO:43, FIG. 4C). This shifted the RBE eight nt closer to the nicking stem. Rep2 replicated this ITR very inefficiently at a level below the detection threshold of densitometric analysis (FIG. 4D, Southern).

Example 6

Identification of Regions in Rep Responsible for ITR Specificity

Identifying the two elements of the ITR responsible for Rep specificity allowed us to map the regions of Rep2 and Rep5 involved in ITR specificity. We focused exclusively on the N-terminal 208 aa of the large Rep proteins as this region encompasses the DNA binding and endonucleolytic activity of the protein (Yoon et al. (2001) *J. Virol.* 75:3230). This region displays approximately 60% sequence conservation evenly distributed across the protein sequence (FIG. 5A). Residues involved in the active site of the protein are 100% conserved between Rep2 and Rep5 (Hickman et al. (2002) *Mol. Cell* 10:327). Residues implicated in binding the RBE' are highly conserved (Hickman et al. (2004) *Mol. Cell* 13:403). Residues which bind the RBE display nearly perfect conservation except for two conservative substitutions near aa 140.

Figure 5C:
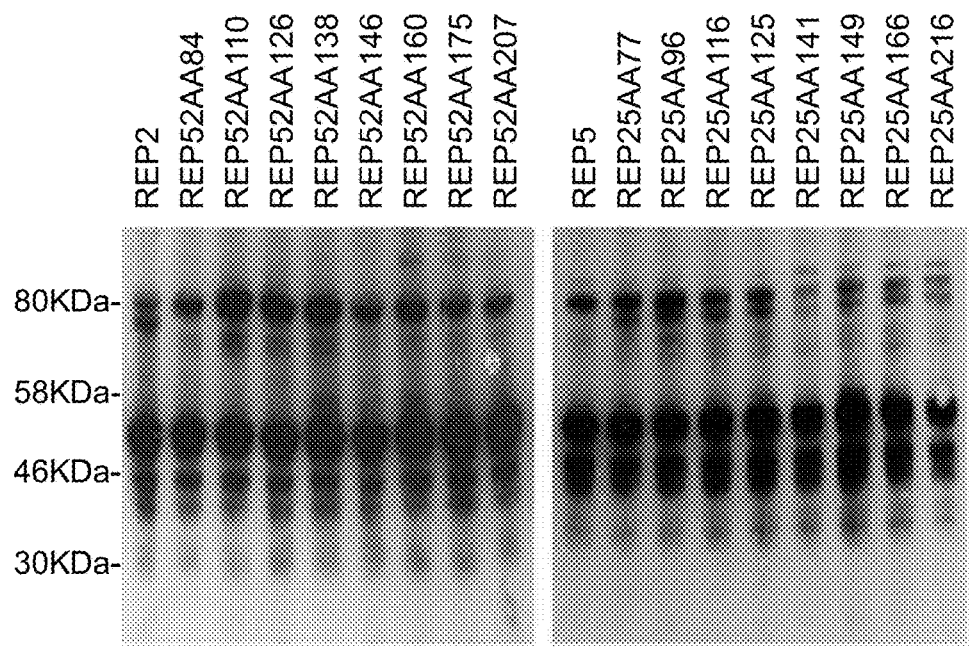
Figure 5D:
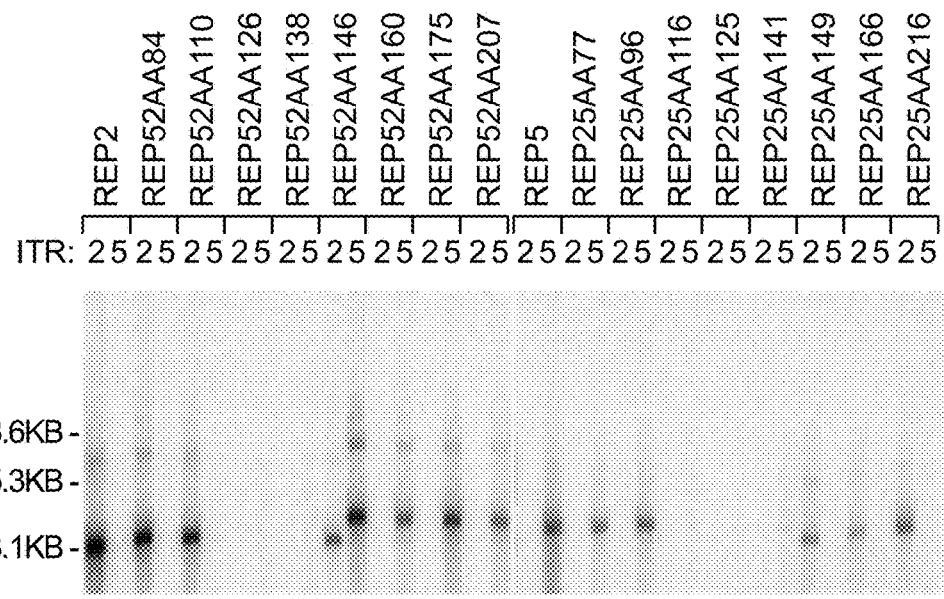
Figure 5E:
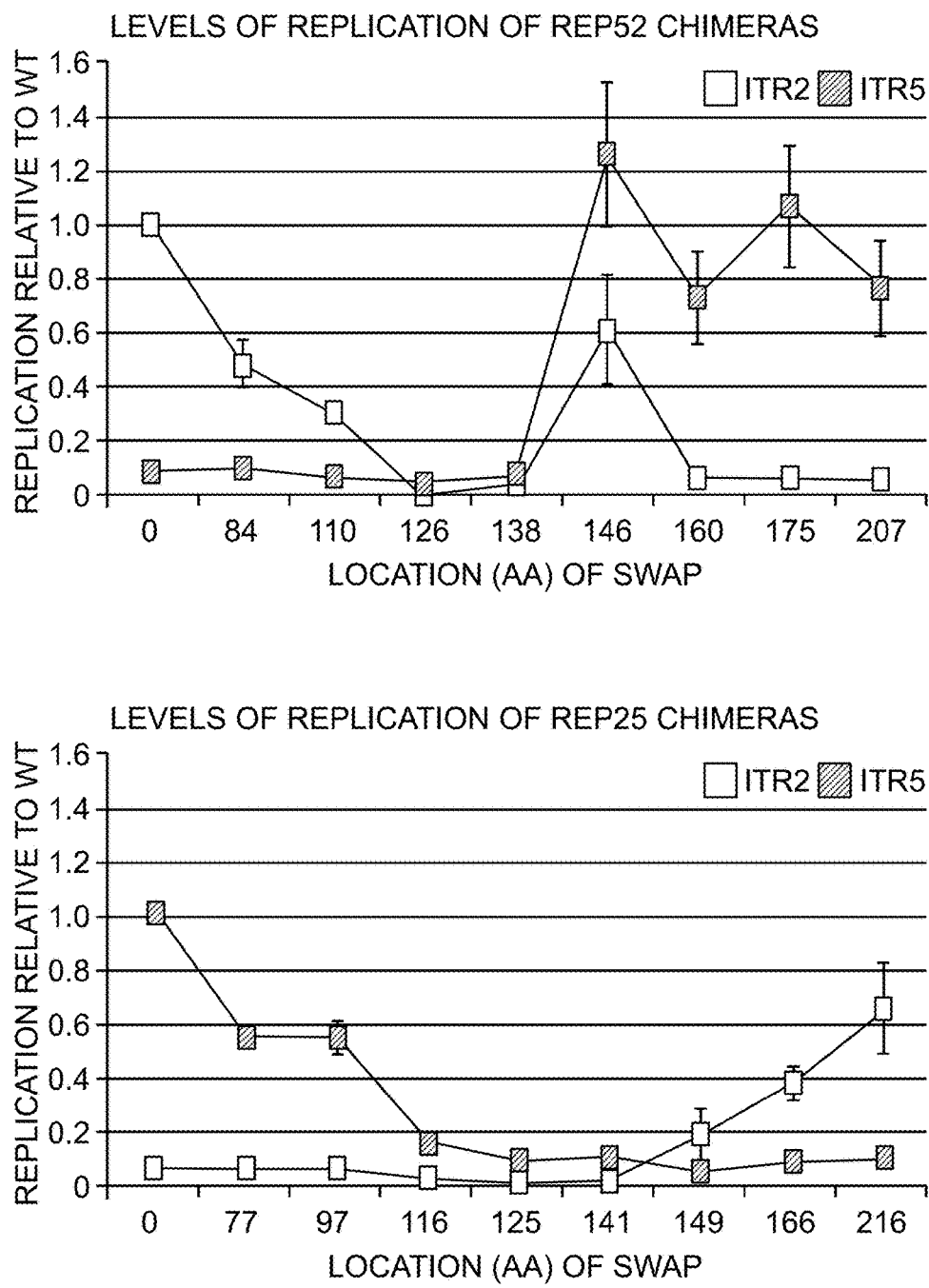

In order to map the regions of Rep involved in ITR specificity, a panel of chimeric Reps derived from Rep2 and Rep5 were generated (FIG. 5B). The ability of each chimeric Rep to replicate an ITR2- or ITR5-flanked vector in HEK 293 cells was determined by Southern blot (FIGS. 5B and 5D). Each Rep in the panel was verified by DNA sequencing and Western blot analysis (FIG. 5C). Every chimeric Rep showed similar protein expression profiles compared to wt. Densitometric analysis provided a comparison of the replication efficiency of each chimeric Rep with that of wt Rep2 or Rep5 (FIG. 5E). Chimeric Reps were named according to the aa location of the swap between serotypes; for instance, Rep25aa77 (SEQ ID NO:63) possesses the N-terminal 76 aa of Rep2 and the C-terminus of Rep5.

In the case of Rep5, replacement of the N-terminal 77 or 97 aa with Rep2 had no effect on ITR specificity nor a significant impact on replicative fidelity (FIGS. 5D and 5E). Larger pieces of Rep2 substituted onto the N-terminus of Rep5 were sufficient to prevent efficient replication of ITR5s (Rep25aa116, SEQ ID NO:65; Rep25aa125, SEQ ID NO:66; Rep25aa141, SEQ ID NO:67). This suggested that these chimeras possessed interruptions of a critical region of Rep5 for ITR5 specificity.

Rep2-based chimeras were unable to replicate ITR5s without the inclusion of the N-terminal 146 aa of Rep5 (Rep52aa146, SEQ ID NO:79, FIG. 5D). Rep52aa146 replicated ITR5 at wt levels, as did the three chimeras with larger portions of Rep5 on the N-terminus (Rep52aa160, SEQ ID NO:58; Rep52aa175, SEQ ID NO:59; Rep52aa207, SEQ ID NO:61). This mapping reveals that the critical region for ITR specificity in Rep5 lies between aa 97-146. Surprisingly, the Rep52aa146 clone also functioned efficiently on ITR2, constituting a Rep capable of replicating ITR2 and ITR5. This suggested that ITR specificity existed in two different regions of Rep.

For Rep2, the N-terminal 83 or 109 aa of Rep5 could be substituted with no effect on ITR specificity or major influence on replicative fidelity (Rep52aa84, SEQ ID NO:54; Rep52aa110, SEQ ID NO:55; FIGS. 5D and 5E). Chimeras including slightly larger portions of Rep5 were unable to replicate either ITR, again suggesting the interruption of a domain critical for ITR specificity (Rep52aa126, SEQ ID NO:56; Rep52aa138, SEQ ID NO:57).

Rep5-based chimeras were unable to replicate ITR2s without the inclusion of the N-terminal 149 aa of Rep2. However, ITR2 replication was inefficient (Rep25aa149, SEQ ID NO:68, FIGS. 5D and 5E). The inclusion of larger portions of Rep2 allowed replication of ITR2s to increase to wt levels (Rep25aa166, SEQ ID NO:69; Rep25aa216, SEQ ID NO:71). This data maps the Rep2 region involved in ITR specificity to aa 110-149. However, unlike Rep5, this was not the only region which played a role in ITR specificity. The ability of the Rep52aa146 chimera to replicate ITR2 and ITR5 vectors demonstrated a second region of Rep2 between aa 138-160 sufficient to allow replication of ITR2s even when the other critical region (aa 110-149) was Rep5. The isolation of two different Rep regions involved in ITR specificity was consistent with the discovery of two independent elements governing specificity within the ITR.

Example 7

Characterization of Rep Regions Involved in ITR Specificity

Figure 6A:
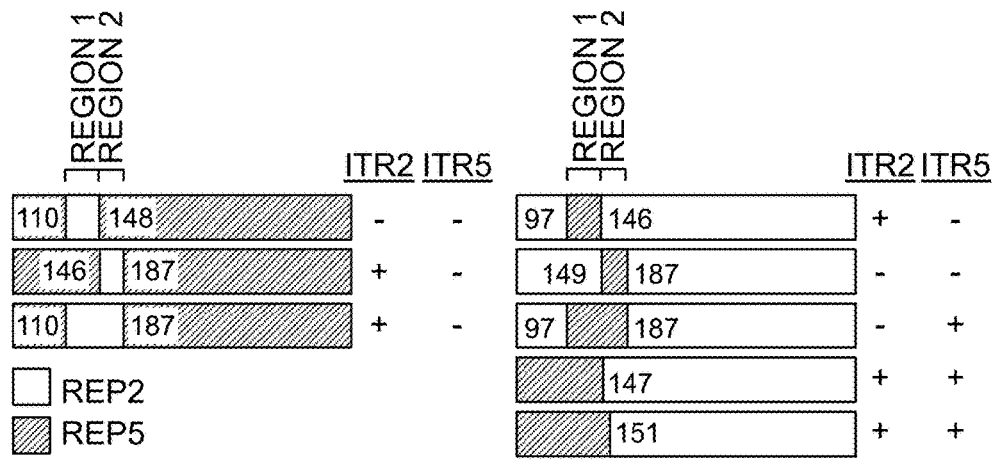
FIGS. 6A-6G show the characterization of Rep regions involved in ITR specificity.
Figure 6B:
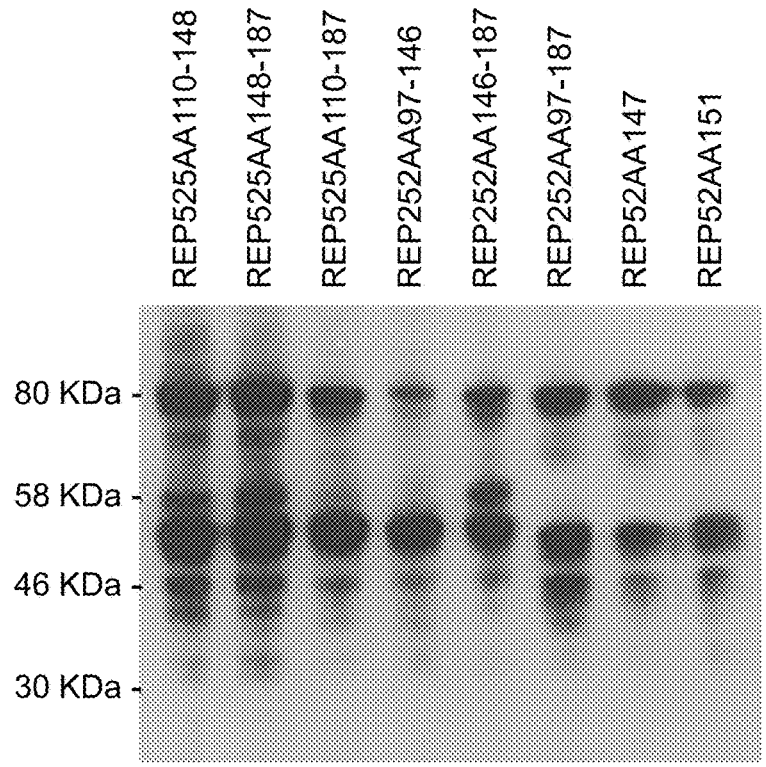

To characterize the Rep domains identified in FIGS. 5A-5E, chimeric Rep proteins which specifically exchanged the regions implicated in ITR specificity were created (FIG. 6A). Region 1 existed in Rep2 from aa 110-149 and in Rep5 from aa 97-146. Region 2 lay within Rep2 from aa 149-187 and Rep5 from aa 146-187. As in FIGS. 5A-5E, all chimeras were verified by DNA sequencing and Western blot analysis (FIG. 6B). Chimeras were then assayed for the ability to replicate ITR2- or ITR5-flanked vectors (FIG. 6C).

Figure 6C:
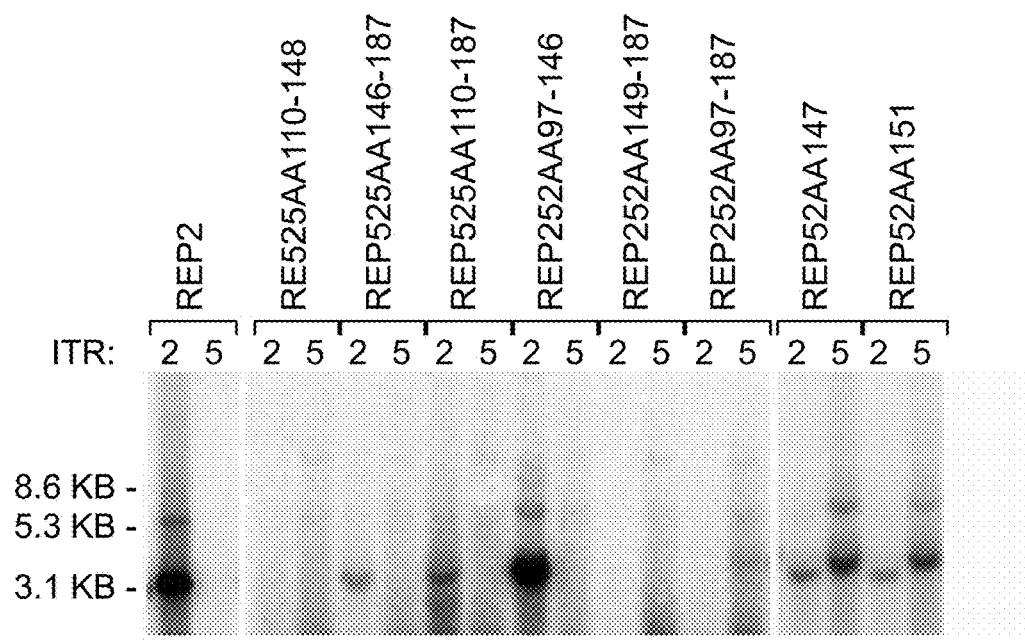

Replacing Rep5 region 1 with Rep2 yielded a clone unable to replicate either vector, suggesting the chimera lacked the ability to bind the ITR5 spacer or nick the ITR2 nicking stem (Rep525aa110-148, SEQ ID NO:72, FIG. 6C). Replacing Rep5 region 2 with that of Rep2 allowed this chimera to replicate an ITR2 vector, suggesting region 2 of Rep2 was critical to nick the ITR2 nicking stem (Rep525aa146-187, SEQ ID NO:73). The inability of this chimera to recognize ITR5 is harder to explain as Rep52aa146 could replicate ITR2 and ITR5 efficiently (FIG. 5B). This result suggests that Rep2 region 2 makes specific contacts within Rep2 aa 188-208 which are necessary in order to function on the ITR5 nicking stem. Replacing regions 1 and 2 of Rep5 with Rep2 resulted in a Rep chimera which replicated only ITR2s (Rep525aa110-187, SEQ ID NO:74).

Replacing Rep2 region 1 with Rep5 resulted in replication of only ITR2s, again demonstrating a connection between Rep2 region 2 and the ITR2 nicking stem (Rep252aa97-146, SEQ ID NO:75). The lack of ITR5 replication by Rep252aa97-146 is difficult to explain based on the Rep52aa146 chimera which replicates ITR2s and ITR5s efficiently (FIG. 5B). This result suggests that Rep5 region 1 makes specific contacts within the preceding 96 aa of Rep5 in order to replicate ITR5. Replacing Rep2 region 2 with Rep5 resulted in a chimera unable to replicate either ITR (Rep252aa149-187, SEQ ID NO:76). This chimeric Rep possesses neither Rep2 region 2 (required to nick the ITR2 nicking stem) nor Rep5 region 1 which appears to interact with the ITR5 spacer. Finally, replacing both Rep2 regions 1 and 2 with Rep5 resulted in a chimera capable of replicating only ITR5 vectors (Rep252aa97-187, SEQ ID NO:77).

Figure 6D:
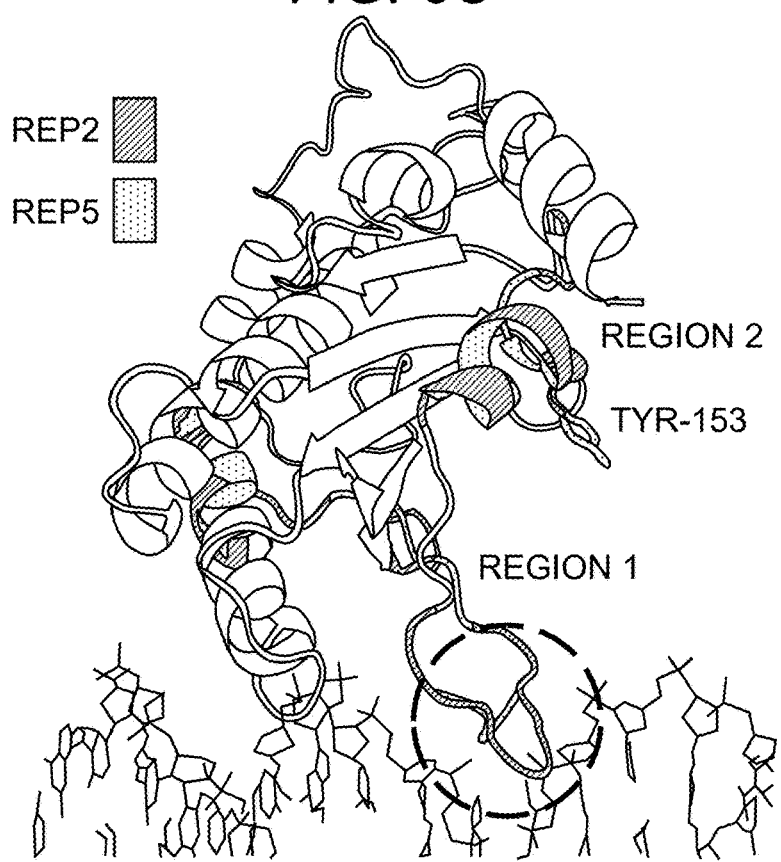

The crystal structure of the N-terminal 193 aa of Rep5 complexed to the RBE allowed the location of these two critical regions to be modeled (Hickman et al. (2004) *Mol. Cell* 13:403). The structure of the N-terminus of Rep2 was modeled with Swiss-Model software using Rep5 as a template. The location of region 1 supports its involvement with the spacer/RBE (FIG. 6D). This region interacts with the major groove of the ITR where one of the most apparent structural differences between Rep2 and Rep5 is predicted (FIG. 6D, hatched circle). Rep2 contains a two aa insertion in this loop with respect to Rep5. This insertion and other non-conservative substitutions are likely responsible for the inability of Rep2 to interact with the ITR5 spacer.

Figure 6E:
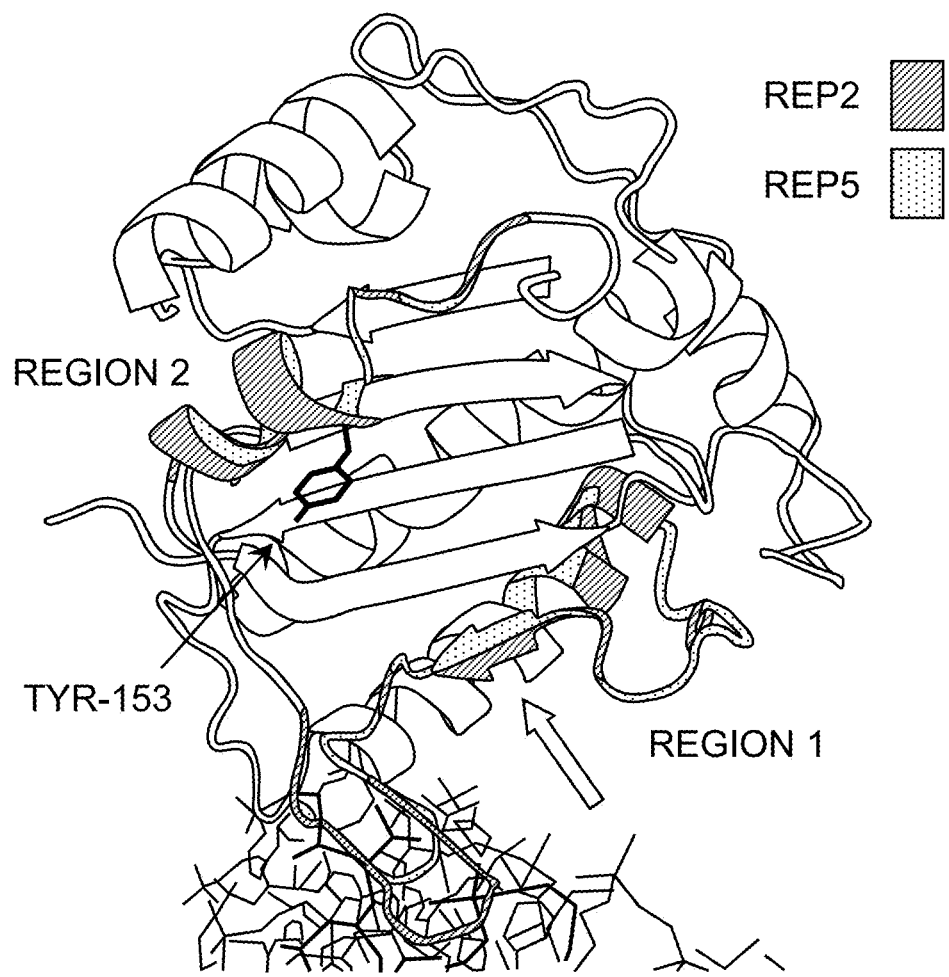
Figure 6F:
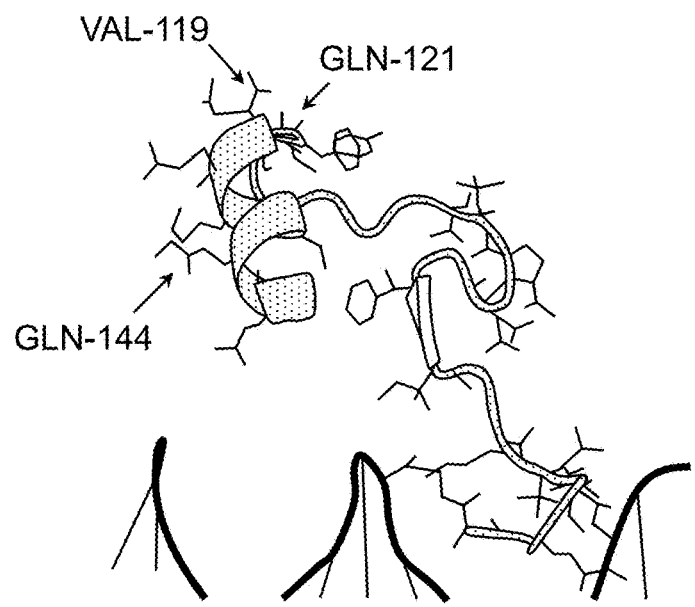

Viewing Rep along the length of the ITR illustrates that region 1 constitutes much of the base of the protein (FIG. 6E). Both Reps are predicted to participate in a β-sheet motif in the center of this region, while areas of reduced homology exist toward either side (the loop interacting with the major groove of the ITR on one side, RBE' interactions on the other). A more detailed look at region 1 reveals the greatest disparity between Rep2 and Rep5 occurs at the RBE binding interface in the major groove of the ITR (FIG. 6F).

Figure 6G:
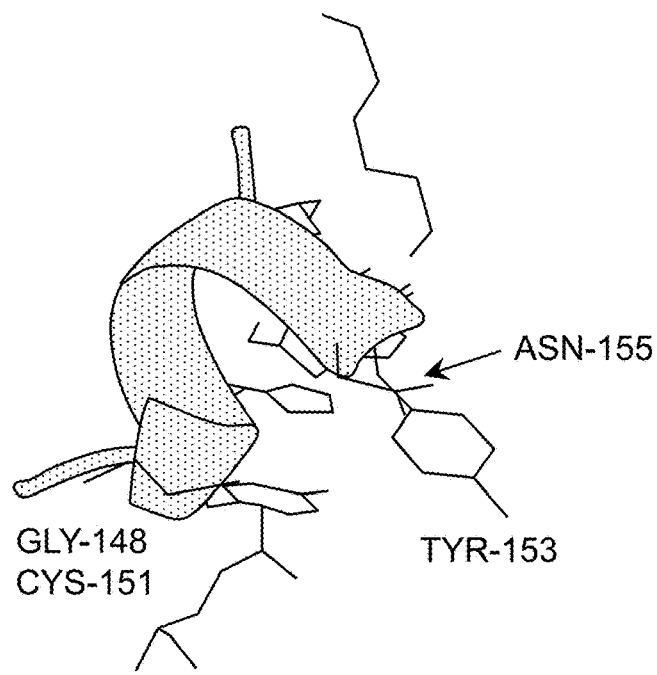

There is very little predicted structural difference between region 2 of Rep2 and Rep5 (FIGS. 6D and 6E). In an effort to dissect this region, we created two additional clones: Rep52aa147 (SEQ ID NO:81) and Rep52aa151 (SEQ ID NO:83) (FIG. 6A). Like Rep52aa146, both of these Reps were able to replicate ITR2 and ITR5 vectors (FIG. 6C). Rep52aa146 and Rep52 aa147 replicated ITR2 and ITR5 vectors with equivalent efficiency, suggesting E147 of Rep2 is not involved in ITR specificity. Rep52aa151 did display a modest reduction in ITR2 replication compared to Rep52aa146, suggesting that C151 of Rep2 plays a role in ITR2 specificity. Because Rep52aa160 cannot replicate ITR2, this leaves only two other non-conserved residues between Rep2 and Rep5 in this region (N155 and T161). Both of these residues lie near the active site and are likely to interact with the nicking stem or active site. N155 lies directly adjacent to Y156, the nucleophilic tyrosine, and may play a major role in ITR2 specificity (FIG. 6G).

Example 8

Structure-Function Model of Rep-ITR Specificity

In order to unify the ITR and Rep elements involved in specificity into a single model, the chimeric Reps separating region 1 and region 2 along with the chimeric ITRs separating the nicking stem and spacer were utilized. Rep2, Rep5, Rep52aa146 (which divides region 1 and 2 of Rep and can replicate ITR2 and ITR5), and Rep25aa149 (essentially no ITR2 or ITR5 replication) were selected. These Reps were tested for their ability to replicate ITR2, ITR5, ITR2+5NS (which is replicated by both Rep2 and Rep5), and ITR5+2NS (which is replicated by neither Rep2 nor Rep5).

Figures 7A, 7B:
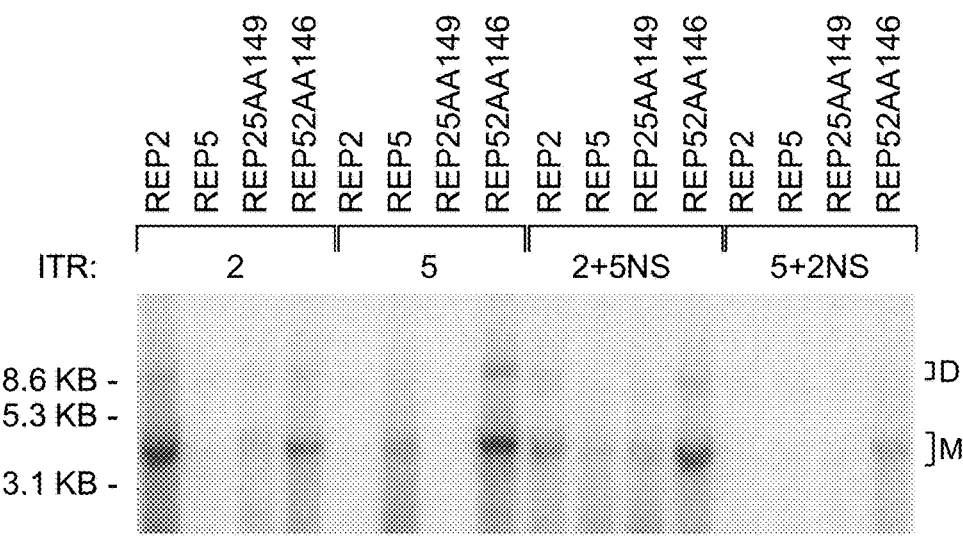
FIGS. 7A-7C show a model of Rep-ITR specificity.

Only Rep2 and Rep52aa146 efficiently replicated ITR2 (FIGS. 7A and 7B). Only Rep5 and Rep52aa146 replicated ITR5. As in FIGS. 1A and 1B, Rep2 and Rep5 replicated ITR2+5NS. Additionally, Rep25aa149 (SEQ ID NO:68) and Rep52aa146 (SEQ ID NO:79) replicated ITR2+5NS. This ITR appears to be universally replicated by every Rep in this assay due to the exclusion of DNA elements involved in protein specificity. The three nt ITR2 spacer is amenable to the DNA binding region 1 of Rep2 and Rep5. The seven bp tall ITR5 nicking stem functions with region 2 of Rep2 and Rep5. Thus, any combination of these regions constitutes a Rep protein capable of replicating ITR2+5NS.

Figure 7C:
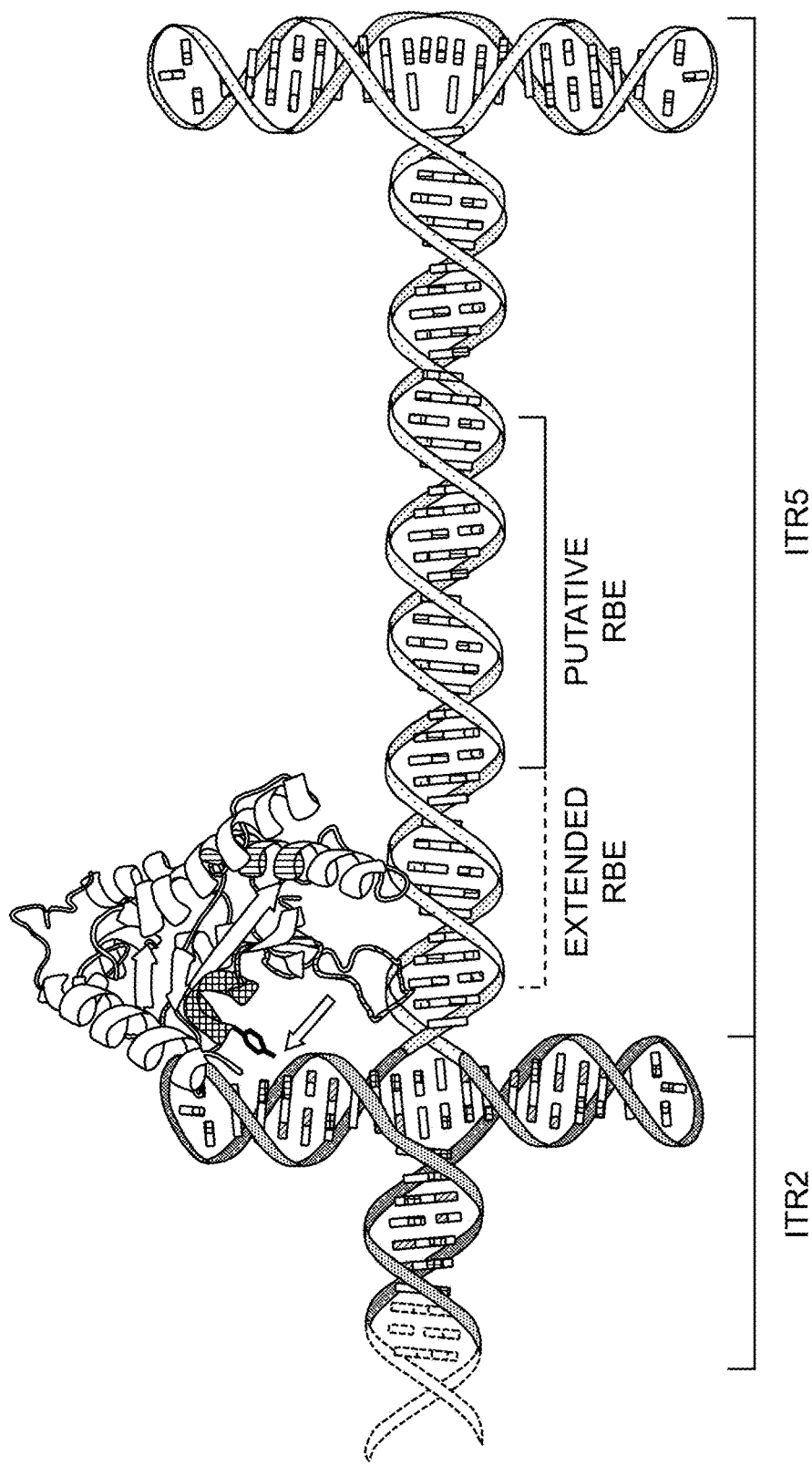
Figure 29:
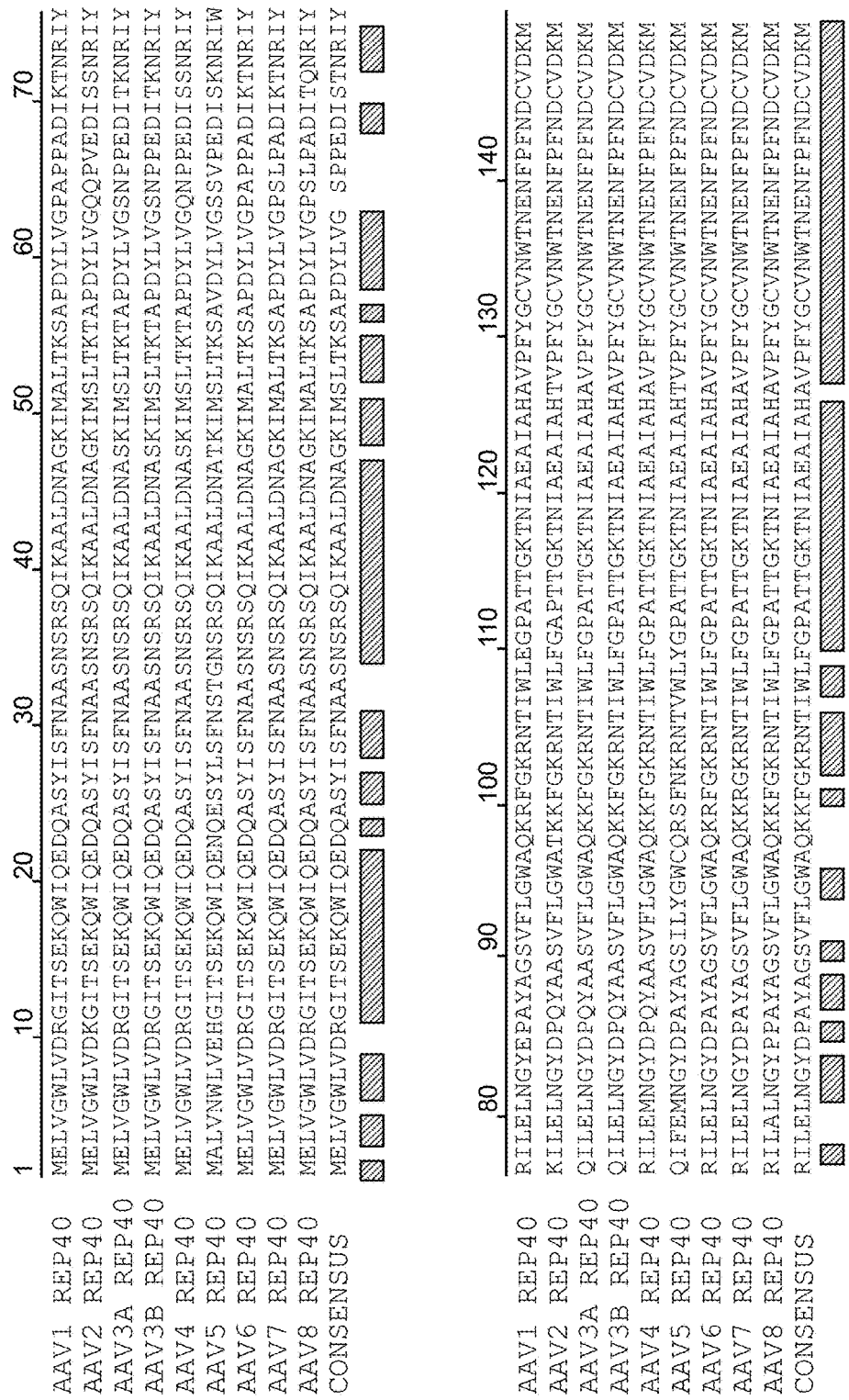
FIG. 29 shows an alignment of the amino acid sequences of exemplary Rep40 proteins from AAV1 (SEQ ID NO:84), AAV2 (SEQ ID NO:85), AAV3A (SEQ ID NO:86), AAV3B (SEQ ID NO:87), AAV4 (SEQ ID NO:88), AAV5 (SEQ ID NO:89), AAV6 (SEQ ID NO:90), AAV7 (SEQ ID NO:91) and AAV8 (SEQ ID NO:92), as well as a consensus sequence (SEQ ID NO:93). Dashes indicate gaps in the sequence and shading indicates positions of sequence homology.

Finally, neither Rep2 nor Rep5 replicated ITR5+2NS. Rep2 is unable to interact properly with the 15 nt ITR5 spacer. Rep5 is unable to function on the ITR2 nicking stem. For these reasons, Rep25aa149 was also unable to catalyze replication. However, Rep52aa146 was able to replicate this ITR due to the proper combination of Rep regions (FIG. 7C). Rep52aa146 possesses Rep5 region 1 which interacts with the 15 nt ITR5 spacer. This chimera also possesses Rep2 region 2, which functions on the ITR2 nicking stem. This recombinant DNA-protein interaction is unique from either AAV2 or AAV5 and constitutes a novel Parvovirus origin of replication.

Taken as a whole, this work illustrates two specific mechanisms of DNA-protein specificity at the Parvovirus origin of replication. Chimeric ITRs narrowed the DNA elements involved in specificity to the spacer and nicking stem sequences (FIG. 1B). These results contradicted previous assertions that Rep-ITR specificity were driven solely by the nicking sequence as Rep2 efficiently nicked an ITR harboring the ITR5 nicking stem (Chiorini et al. (1999) *J. Virol.* 73:4293). Rep2 is highly flexible in the sequence and height of its nicking stem while Rep5 is highly specific to its cognate stem (FIGS. 2A-2D).

Three residues of Rep2 are important to cleave the ITR2 nicking stem (FIGS. 5A-5E and 6A-6G). Residues C151, N155, and T161 all lie in the active site of the protein in a predicted alpha helix along with the nucleophilic tyrosine Y156. How these residues (termed Rep region 2) grant Rep2 flexibility toward mutant nicking stems remains unclear. The corresponding Rep5 residues (G148, A152, and V158) may participate in highly specific interactions which require specific height and sequence considerations for the ITR5 nicking stem.

AAV5 Rep-ITR specificity is mediated by the ITR5 spacer. Replacement of the three nt ITR2 spacer with the 15 nt ITR5 spacer ablated replication by Rep2 (FIG. 2B). A poorly conserved Rep binding element allows Rep5 to interact with the elongated ITR5 spacer (FIG. 4B). Mutating the spacer to include a strong Rep binding element allowed Rep2 and Rep5 to replicate the ITR. However, insertion of a Rep binding element into the ITR2 spacer still largely decreased Rep2 function. While this data might suggest that additional Rep5 molecules bind to ITR5, previous in vitro experiments have not come to this conclusion, although those studies were performed in the absence of hairpins on the ITRs (Chiorini et al. (1999) *J. Virol.* 73:4293).

A 49 aa region of Rep5 interacts with the ITR5 spacer (aa 97-146, FIGS. 5A-5E and 6A-6G). The crystal structure of the N-terminus of Rep5 reveals that this region (region 1) possesses residues which specifically bind to the RBE and RBE' of the ITR. Major structural differences in the Rep5 loop which binds the major groove of the RBE likely account for the majority of ITR5 spacer specificity. While FIG. 1B predicts RBE' binding should not play a role in Rep-ITR specificity, it is possible that RBE' contacts alter the secondary structure of region 1 as it interacts with the RBE.

Because the regions of Rep conferring ITR specificity were separate (region 1 of Rep5 from aa97-146 and region 2 of Rep2 from aa151-161), a chimeric Rep possessing both regions was able to efficiently replicate ITR2 and ITR5. An ITR which could be replicated by any wt or chimeric Rep was constructed by excluding the DNA elements required for specificity; the ITR5 spacer and the ITR2 nicking stem. Most significantly, a novel origin of replication was generated. This ITR contained both of the elements for Rep specificity; the ITR5 spacer and the ITR2 nicking stem. As a result, only a chimeric Rep protein made up of Rep5 region 1 and Rep2 region 2 was able to replicate the ITR. The creation of a unique origin of replication highlights the power of studying the DNA-protein interactions of a viral origin of replication.

The creation of a unique DNA-protein interaction was possible because of the separation of the specific Rep-ITR interactions in AAV2 and AAV5. How and why these two different DNA-protein interactions evolved is unclear. It is likely due to evolutionary divergence in the ITR sequence which may have occurred in different hosts (AAV2 is related to other primate AAVs, AAV5 is related to non-primate AAVs such as goat and bovine). This model of replicative specificity can likely be extended to other parvoviruses such as snake AAV which has a highly conserved T-shaped ITR structure but different spacer and nicking stem lengths (Farkas et al. (2004) *J. Gen. Virol.* 85:555).

These results also stand to improve the safety of future AAV therapeutic vectors. The danger of AAV vector mobilization by wt AAV could be averted if therapeutic vectors harbored ITRs which no wt Rep could replicate (Hewitt et al. (2009) *J. Virol.* 83:3919).

Example 9

Snake ITR Vector Production

Figure 34:
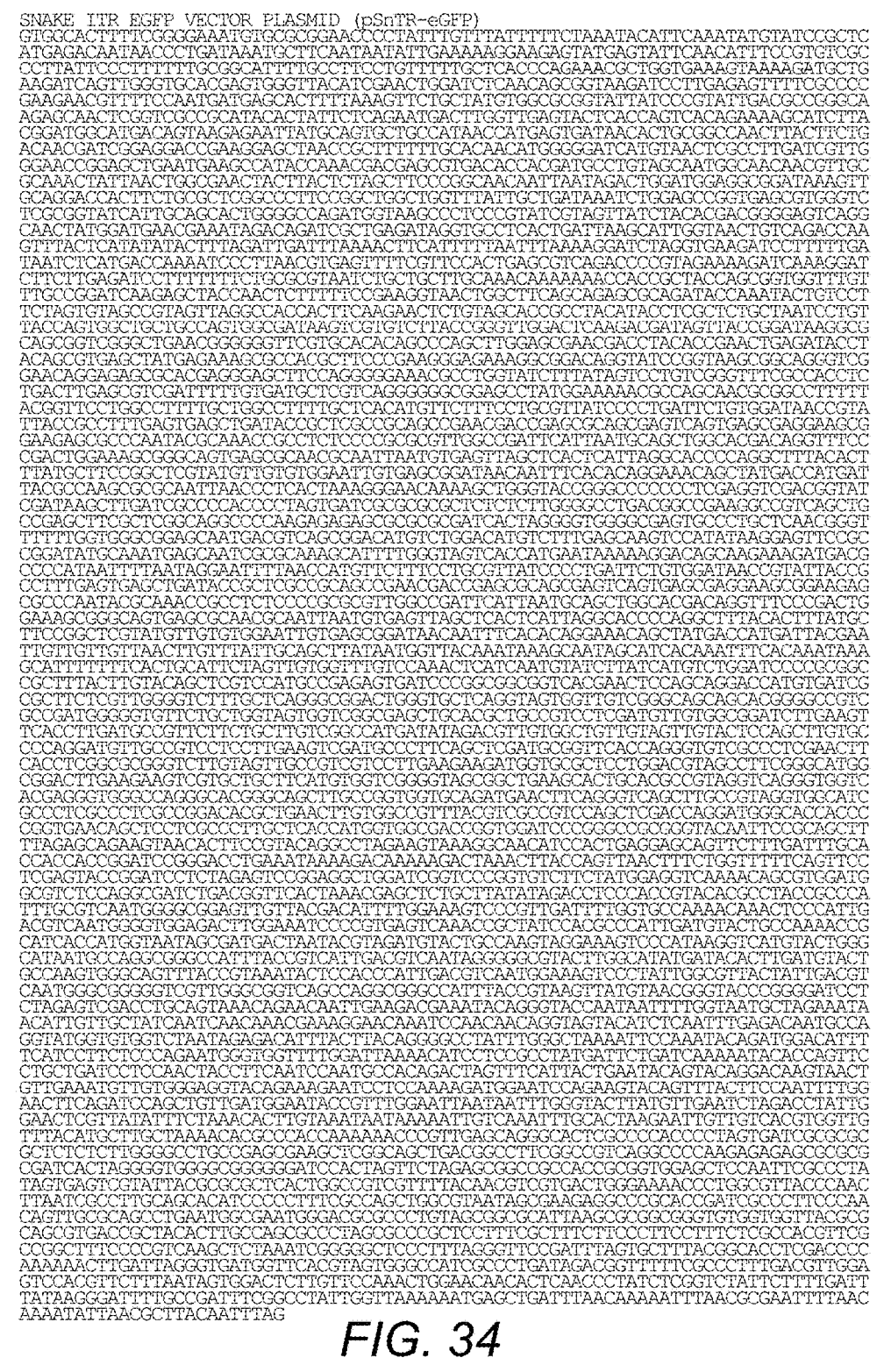

HEK 293 cells were cultured in Dulbecco Modified Eagle Medium (DMEM) supplemented with 10% Fetal Bovine Serum (Sigma, St. Louis, Mo.) and 100 units/ml penicillin and 100 µg/ml streptomycin and grown at 37° C. with 5% $CO_2$ saturation. To produce snake (royal python) ITR vectors, 10 µg of each of the following plasmids were transfected by PEI into HEK 293 cells in a 15 cm culture dish: pXX680 (Ad helper plasmid), pSnTR-eGFP (the ITR containing plasmid, SEQ ID NO:124), pSnRepCap2 (AAV helper plasmid containing the snake Rep genes and AAV2 Cap genes, SEQ ID NO:125), and pXR2 (AAV helper plasmid containing the AAV2 Rep and Cap genes). See FIGS. 33-35. Alternately, a plasmid expressing only the small AAV2 Rep proteins (Rep52 and Rep40) could be used in place of pXR2. 48 hours post-transfection, the cells were harvested and vector was purified by CsCl gradient centrifugation as previously described for other AAV vectors.

The foregoing is illustrative of the present invention, and is not to be construed as limiting thereof. The invention is defined by the following claims, with equivalents of the claims to be included therein.

That which is claimed is:

1. A synthetic large Rep protein comprising a first portion from a first adeno-associated virus (AAV) and a second portion from a second AAV;
   wherein one of the first AAV and the second AAV is AAV5 and the other is an AAV other than AAV5;
   wherein the synthetic large Rep protein functionally interacts with a synthetic inverted terminal repeat (ITR) comprising a first structural element from the first AAV and a second structural element from the second AAV; and
   wherein the synthetic large Rep protein does not functionally interact with a wild-type ITR from the first AAV or with a wild-type ITR from the second AAV; and
   wherein said first and second structural element is a nicking stem, a spacer or an RBE.

2. The protein of claim 1, wherein said protein comprises a third portion and wherein the synthetic large Rep protein functionally interacts with a synthetic ITR comprising the first structural element, the second structural element, and a third structural element.

3. The protein of claim 1, wherein said first portion comprises an amino acid sequence from about residue 97 to about residues 146-151 of a wild-type AAV5 Rep sequence.

4. The protein of claim 1, wherein said second portion comprises an amino acid sequence from about residue 149 to about residue 187 of a wild-type AAV2 Rep sequence.

5. The protein of claim 1, wherein said first portion comprises an amino acid sequence from about residue 97 to about residues 146-151 of a wild-type AAV5 Rep sequence and said second portion comprises an amino acid sequence from about residue 149 to about residue 187 of a wild-type AAV2 Rep sequence.

6. The protein of claim 1, wherein said first portion comprises an amino acid sequence from about residue 1 to about residues 146-151 of a wild-type AAV5 Rep sequence and said second portion comprises an amino acid sequence from about residue 149 to about residue 621 of a wild-type AAV2 Rep sequence.

7. The synthetic large Rep protein of claim 1, wherein the AAV other than AAV5 is selected from the group consisting of AAV1, AAV2, AAV3a, AAV3b, AAV4, AAV6, AAV7, AAV8, AAV9, AAV10, AAV11, AAV12, and AAV13.

8. The synthetic large Rep protein of claim 1, wherein the first AAV is AAV5.

9. The synthetic large Rep protein of claim 8, wherein the second AAV is AAV2.

10. The synthetic large Rep protein of claim 1, wherein the first AAV is AAV2.

11. The synthetic large Rep protein of claim 10, wherein the second AAV is AAV5.

* * * * *

UNITED STATES PATENT AND TRADEMARK OFFICE
CERTIFICATE OF CORRECTION

PATENT NO. : 10,233,428 B2
APPLICATION NO. : 14/922935
DATED : March 19, 2019
INVENTOR(S) : Hewitt et al.

Page 1 of 1

It is certified that error appears in the above-identified patent and that said Letters Patent is hereby corrected as shown below:

On the Title Page

Item (56) References Cited, U.S. PATENT DOCUMENTS, Column 1, 3rd cite:
Please correct "2604/0197895" to read -- 2004/0197895 --

Signed and Sealed this
Ninth Day of July, 2019

Andrei Iancu
*Director of the United States Patent and Trademark Office*